United States Patent [19]

Dean et al.

[11] Patent Number: 5,349,127
[45] Date of Patent: Sep. 20, 1994

[54] EXPRESSION OF HERBICIDE METABOLIZING CYTOCHROMES P450

[75] Inventors: Caroline Dean, Norwich, United Kingdom; Patricia A. Harder, Wilmington, Del.; Kenneth J. Leto, Wilmington, Del.; Daniel P. O'Keefe, Ridley Park, Pa.; Charles A. Omer, Downingtown, Pa.; James A. Romesser, Wilmington, Del.; James M. Tepperman, Oakland, Calif.

[73] Assignee: E. I. Du Pont de Nemours and Company, Wilmington, Del.

[21] Appl. No.: 967,093

[22] Filed: Oct. 26, 1992

Related U.S. Application Data

[60] Division of Ser. No. 569,781, Aug. 23, 1990, Pat. No. 5,212,296, which is a continuation-in-part of Ser. No. 464,499, Jan. 12, 1990, abandoned, which is a continuation-in-part of Ser. No. 405,605, Sep. 11, 1989, abandoned.

[51] Int. Cl.$^5$ .................... A01H 4/00; C12N 15/82
[52] U.S. Cl. .................... 800/205; 800/250; 800/255; 800/DIG. 71; 435/320.1; 435/172.3; 935/64; 935/67
[58] Field of Search ....... 800/205, 250, 255, DIG. 71; 435/320.1, 172.3; 935/64, 67

[56] References Cited

U.S. PATENT DOCUMENTS 4,346,227  8/1982  Terahara et al. .................... 560/119

FOREIGN PATENT DOCUMENTS 215665  3/1987  European Pat. Off. .
273711  7/1988  European Pat. Off. .
281245  9/1988  European Pat. Off. .
12686  12/1989  PCT Int'l Appl. .

OTHER PUBLICATIONS

J. A. Romesser et al., Biochem. Biophys. Res. Comm., vol. 140, No. 2, pp. 650–659, Oct. 30, 1986.
D. P. O'Keefe et al., Recent Adv. in Phytochem., vol. 21, pp. 151–173 (1987).
J. A. Saunders et al., Phytochemical Effects of Environmental Compounds, Ed., pp. 151–173, Plenum Pub. Cp.
J. A. Romesser et al., Abstract Ann. Mtg. Am. Soc. Microbiol., p. 248 (1985) (Abstract).
K. Leto et al., Plant Physiology, vol. 80, & 347, (1986) (Abstract).
D. P. O'Keefe et al., Plant Physiology, vol. 80, & 348 (1985) (Abstract).
D. P. O'Keefe et al., Arch. of Microbiol., vol. 149 pp. 406–412 (1988).
C. A. Omer et al., J. Bacteriology, vol. 170, No. 5, pp. 2174–2184, (May 1988).
D. M. Stalker et al., Science, vol. 242, pp. 419–422, (Oct. 1988).
W. R. Streber et al., Biol Technology, vol. 7, pp. 811–816 (Aug. 1989).
M. M. Joshi et al., Weed Science, vol. 33, pp. 888–893 (1985).

*Primary Examiner*—Che S. Chereskin

[57] ABSTRACT

DNA sequences encoding herbicide metabolizing cytochrome P450 enzymes and iron-sulfur proteins that donate electrons to these enzymes, were introduced into plants and microorganisms rendering them able to produce the encoded gene products and to metabolize herbicides.

66 Claims, 45 Drawing Sheets

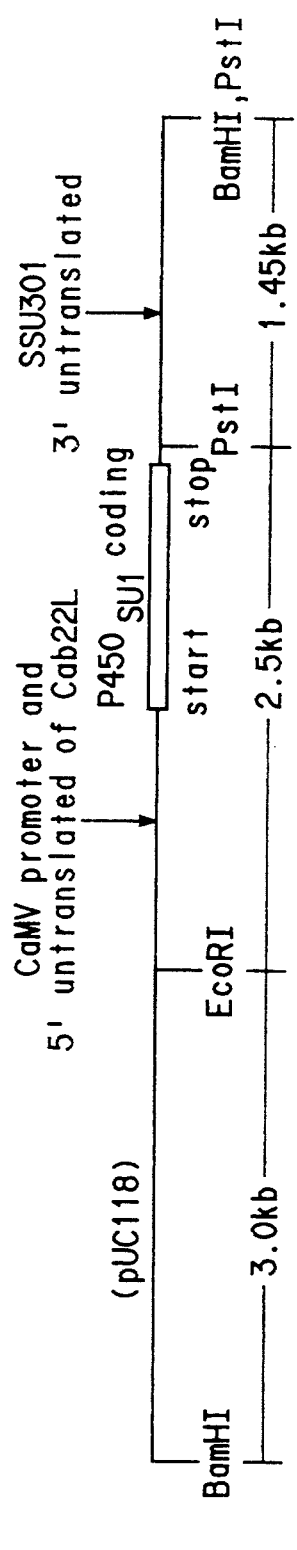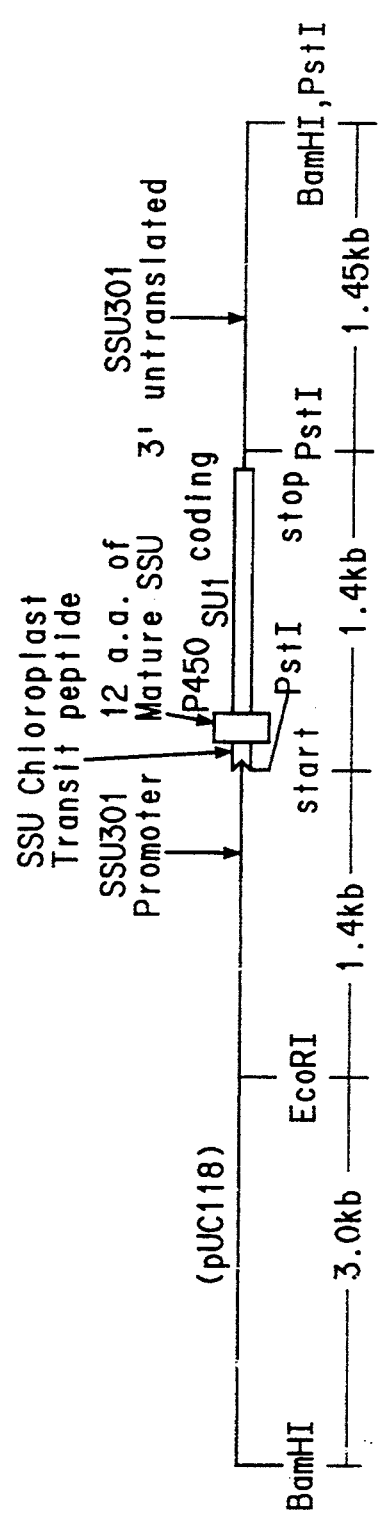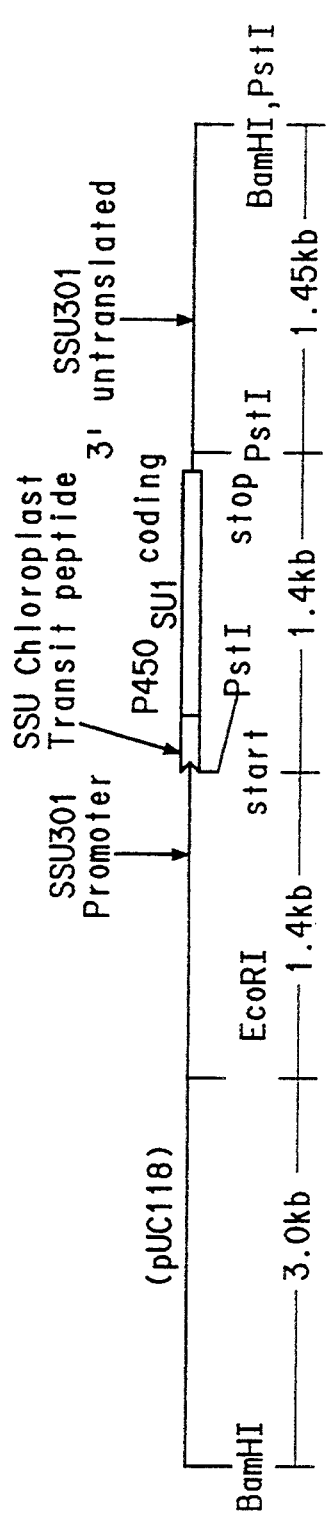

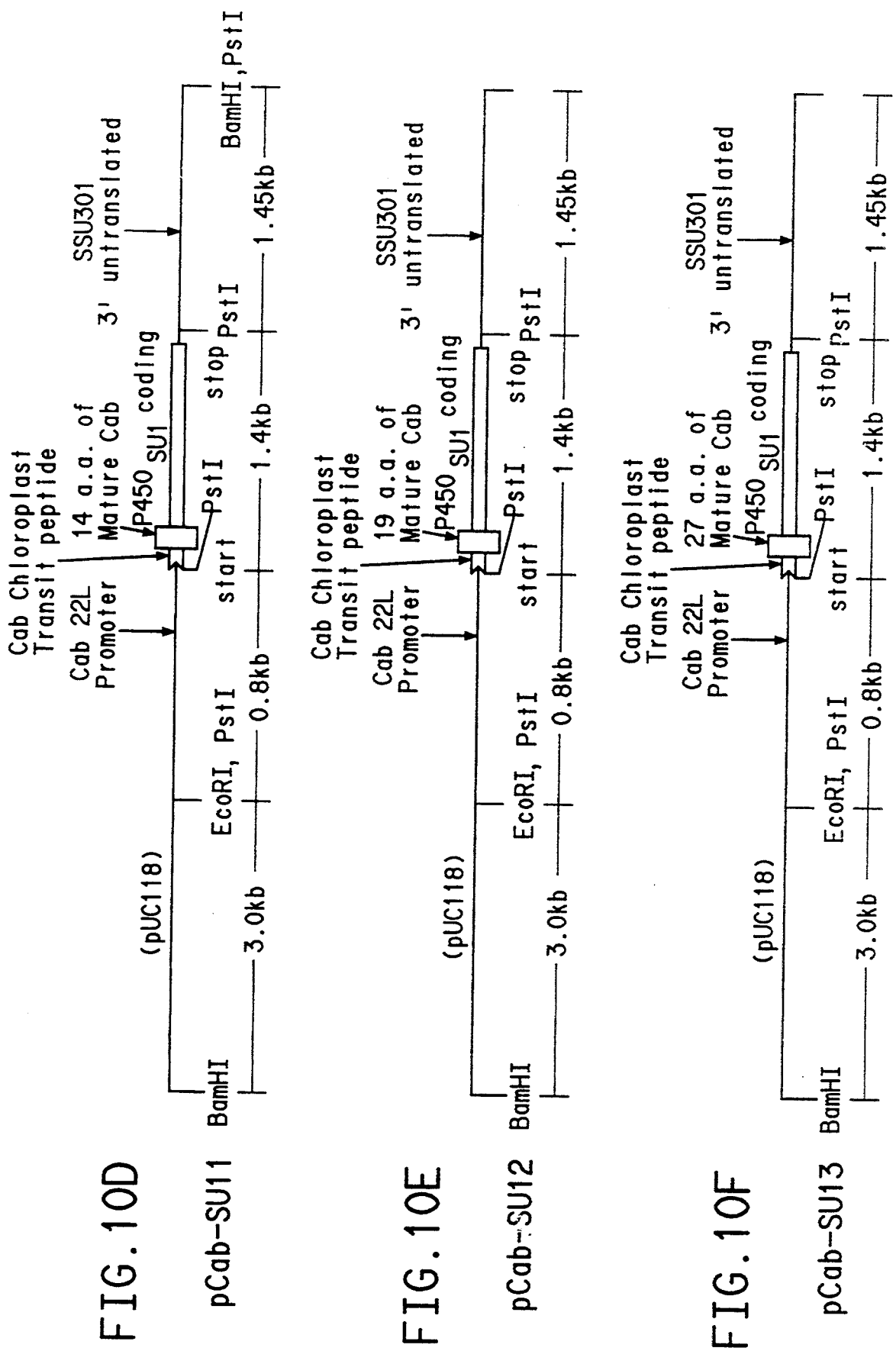

FIG.11
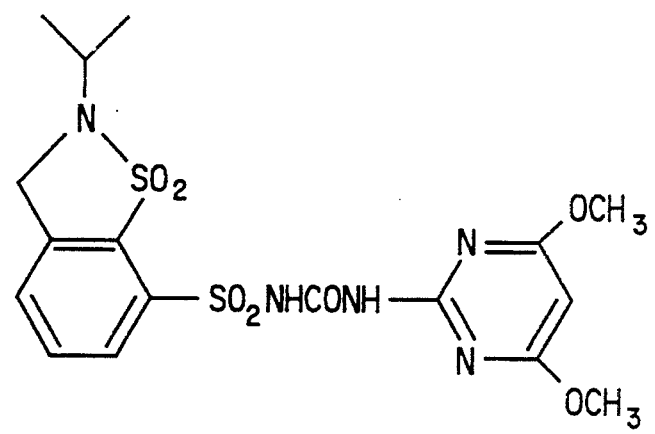
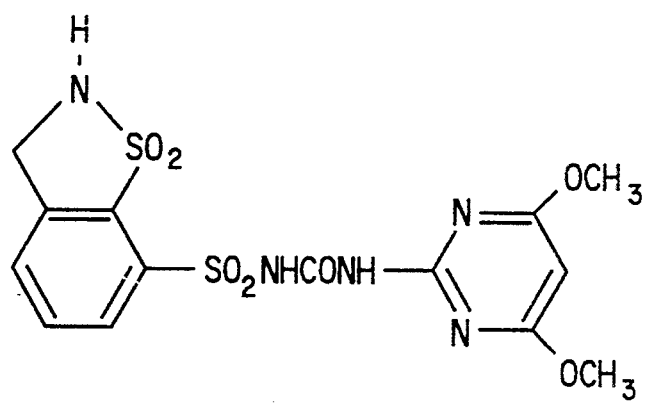

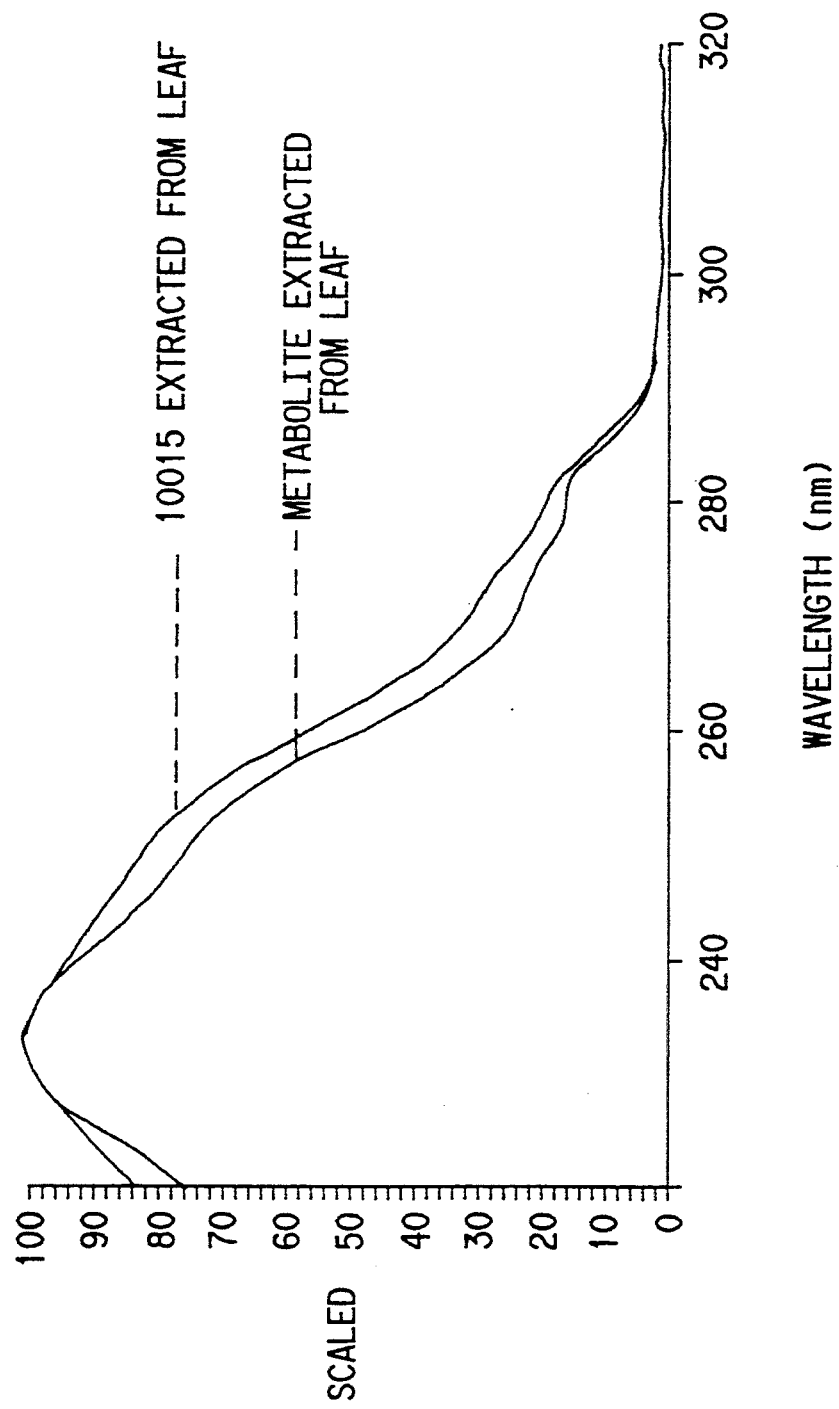

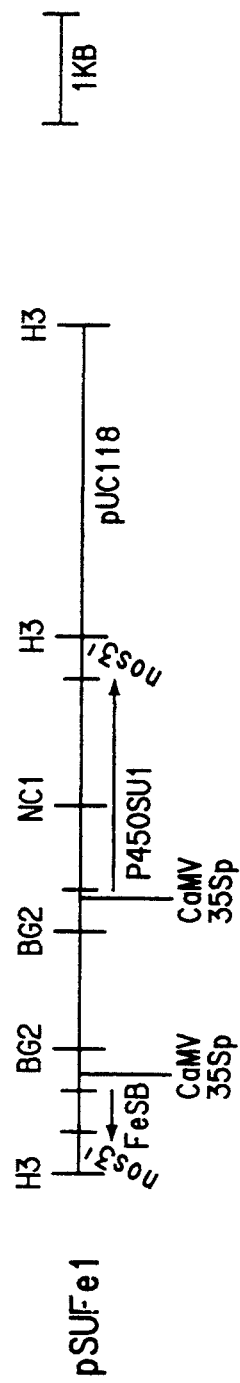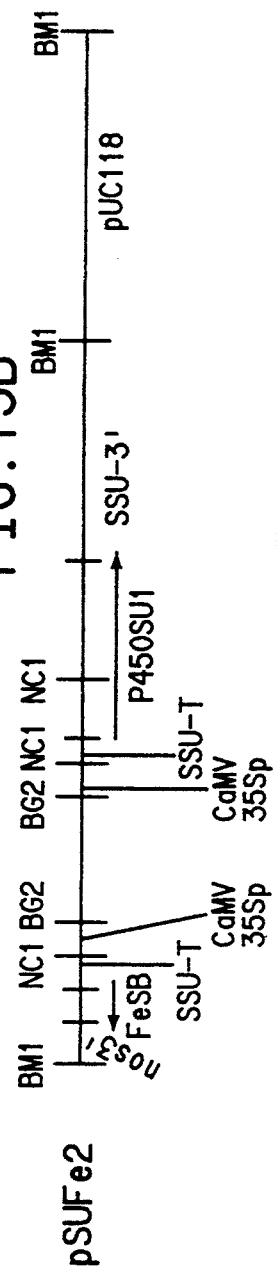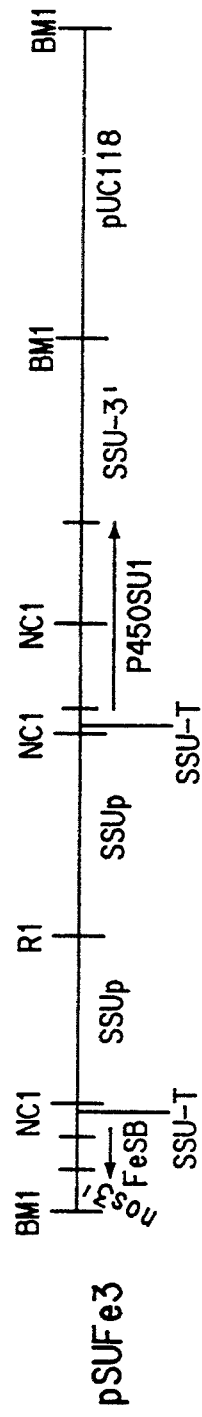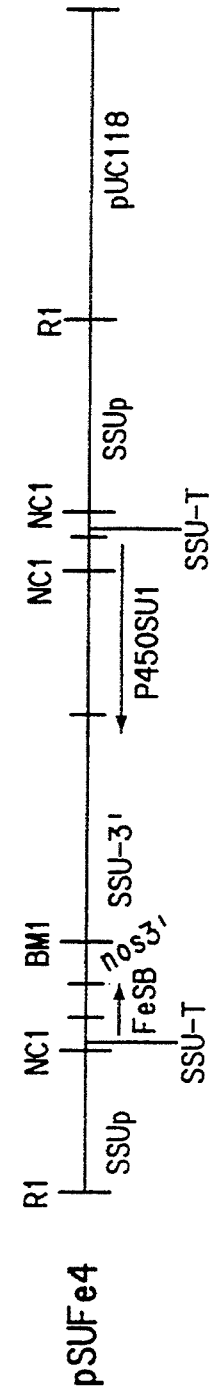

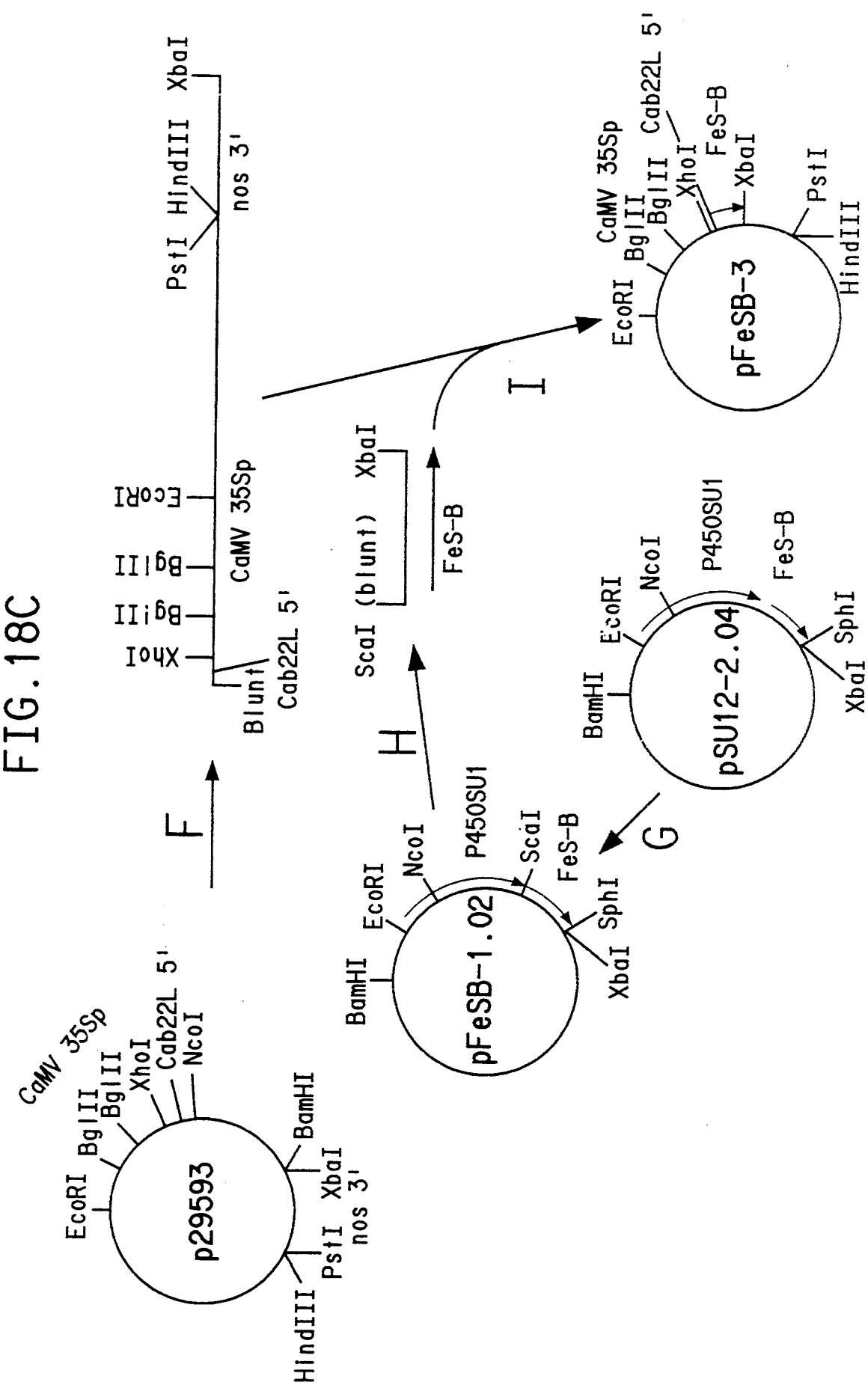

EXPRESSION OF HERBICIDE METABOLIZING CYTOCHROMES P450

CROSS-REFERENCE TO RELATED APPLICATIONS

This is a division of application Ser. No. 07/569,781, now abandoned, which is a continuation in part of Ser. No. 07/464,499, filed on Jan. 12, 1990, now abandoned, which is a continuation in part of Ser. No. 07/405,605, filed on Sep. 11, 1989, now abandoned.

FIELD OF THE INVENTION

The invention relates to the introduction of DNA sequences from Streptomyces griseolus into plants and microorganisms so that the recipient organisms produce the protein products of those genes and are thereby rendered capable of metabolizing the herbicide. These DNA sequences comprise those encoding herbicide metabolizing cytochromes P450 and iron-sulfur proteins that donate electrons to these cytochromes P450.

BACKGROUND OF THE INVENTION

The use of herbicides in weed control is a widely accepted agricultural practice. Our understanding of herbicide metabolism and degradation is still in its infancy and is being actively investigated. Soil microorganisms were implicated in the degradation of herbicides by Joshi et al., Weed Sci. 33: 888–893, 1985. Sulfonylurea herbicides were shown to be co-metabolized by the soil bacterium Streptomyces griseolus by Romesser et al., Abstr. Ann. Mtg. Am. Soc. Microbiol. p. 248, 1985. Further study, as disclosed by Leto et al., Plant Physiol. 805: 5347 (1986) and Romesser et al., Biochem. Biophys. Res. Comm. 140: 650–659 (1986) showed that two cytochrome P450 enzymes designated P450SU1 and P450SU2, heme containing proteins of about 45,000 molecular weight, are synthesized in cells of the bacterium Streptomyces griseolus when they are grown in a medium containing any of several herbicides. The synthesis of these proteins by S. griseolus is detectable by UV/vis difference spectroscopy as described by Romesser, et al., Biochem. Biophys. Res. Comm. 140: 650–659 (1986), analytical anion exchange and gel filtration chromatography as described by O'Keefe et al., Plant Physiol. 805: 5347 (1986) and LDS gel electrophoresis as described by Leto et al., Plant Physiol. 805: 5348 (1986). Romesser et al., Biochem. Biophys. Res. Comm. 140: 650–659 (1986) and O'Keefe et al., Recent Advances in Phytochemistry 21: 151–173 (1987), correlated the presence of P450 enzymes with the ability of this organism to carry out a variety of metabolic reactions on a number of sulfonylurea herbicides. Further, as discussed by Romesser et al., Biochem. Biophys. Res. Comm. 140: 650–659, 1986, crude cell-free extracts from S. griseolus exhibit sulfometuron methyl (10010) hydroxylase activity only when they are from cells grown in the presence of certain sulfonylureas, and difference spectra of the extracts resulting when chlorsulfuron (10013) or sulfometuron methyl (10010) is added suggest that the newly appearing cytochromes P450 bind to these compounds in a manner similar to substrate binding to cytochrome P450.

Additionally, genes that cause the breakdown of the active moieties of herbicidal compounds may be incorporated in plants and cause said plants to become resistant to the affected herbicide. Stalker et al., Science 242: 419–422 (1988) describe the transfer of the gene from Klebsiella ozaenae encoding a specific nitrilase that converts the herbicide bromoxynil to metabolite 3,5-dibromo-4-hydroxybenzoic acid into tobacco plants with the result that the tobacco plants became resistant to bromoxynil.

The major objects of the invention described here are the DNA sequences encoding the two cytochromes P450. Other objects are the sequences encoding their iron-sulfur protein electron donors. These sequences of this invention are from the bacterium Streptomyces griseolus ATCC11796. These two cytochromes P450 are capable of metabolizing sulfonylurea compounds and other herbicides. The two cytochromes P450 have been designated P450SU1 and P450SU2, and the two iron-sulfur proteins have been designated FeS-A and FeS-B.

In wild type Streptomyces griseolus, expression of cytochromes P450SU1, P450SU2, and iron-sulfur proteins FeS-A and FeS-B is induced by the addition of sulfonylurea compounds. Although many sulfonylurea compounds may be metabolized by these cytochromes P450, not all are good inducers of these proteins. Thus optimal metabolism of many sulfonylurea compounds by wild type organisms can only be achieved by first inducing the cytochromes P450 and iron-sulfur proteins with a sulfonylurea known to be a good inducer. Organisms producing the P450 enzymes constitutively or as a result of exposure to light would obviate the need for inducing organisms with sulfonylureas to make them capable of metabolizing said sulfonylureas.

Thus, another object of this invention is to obviate the need to induce the herbicide metabolizing cytochromes P450 and their iron-sulfur protein electron donors in organisms (bacteria and plants) by transforming said organisms with the genes of the herbicide metabolizing cytochromes P450 and where necessary, their iron-sulfur protein electron donors contained in plasmids which permit the constitutive or light induced expression of the P450 enzymes and, where necessary, the iron sulfur proteins in the transformed organisms. Said transformed organisms are able to metabolize herbicides, both good and poor inducers, whenever they encounter them.

Typical cytochrome P-450 monooygenase systems from bacteria are similar to the P-450 CAM system from Pseudomonas putida (Sligar et al. in: Cytochrome P-450 Structure, Mechanism and Biochemistry, Ortiz de Montellano, ed. Plenum Press, N.Y. (1986) pp. 429–504). This system is comprised of a flavoprotein reductase (putidaredoxin reductase), a low molecular weight iron-sulfur protein (putidaredoxin) and the cytochrome P-450 (P-450 CAM). This system of proteins functions to transfer reducing equivalents from a reduced pyridine nucleotide sequentially from putidaredoxin reductase, to putidaredoxin and then to P-450 CAM. It is important to note, however, that the specificity of the enzyme system for substrate resides solely on the P-450 protein, and that the reductase and iron sulfur proteins are only important insofar as they provide the reducing equivalents to the P-450 necessary for catalysis. Thus, another object of this invention is to place the genes for sulfonylurea or herbicide metabolism in other organisms in such a way as to utilize existing sources of reducing equivalents in these organisms to facilitate the function of the cytochrome P-450.

SUMMARY OF THE INVENTION

The bacterium, *Streptomyces griseolus*, contains two inducible genes which produce certain P450 enzymes which metabolize herbicidal compounds. The two enzymes are called P450SU1 and P450SU2. It is known that these enzymes operate effectively only when certain iron sulfur proteins are available and when reductase proteins capable of donating electrons to the iron-sulfur proteins are available. Genes for iron sulfur proteins in *Streptomyces griseolus* are located adjacent to and downstream of those for the P450 enzymes. The applicants have isolated the DNA sequences from *S. griseolus* which encode the P450 enzymes P450SU1 and P450SU2 and adjacent iron sulfur proteins, FeS-B and FeS-A. It has been found that either iron-sulfur protein FeS-A or FeS-B can transfer reducing equivalents to either enzyme. The DNA sequence comprising that for P450SU1 plus adjacent iron sulfur protein FeS-B is as detailed on pages 27 to 31 hereinafter starting at base pair number 128 and ending at base pair number 1578. The DNA sequence comprising that for P450SU2 plus its adjacent iron sulfur protein FeS-A is as detailed on pages 32 to 36 hereinafter starting at base pair number 195 and ending at base pair number 1646. The applicants have constructed novel plasmids comprising the DNA sequences for P450SU1 plus FeS-B (i.e., pCAO400, pCAO401, pCAO200SU#112, pCAO200SU1-FeS-B#9 or pPAT108) and P450SU2 plus FeS-A (i.e., pCAO200-SU2-FeS-A#11 or pCS325) which can transform bacteria. Bacteria, preferably bacteria of the genus Streptomyces and most preferably *Streptomyces lividans* transformed with a plasmid selected from pCAO400, pCAO401, pCAO200SU1-FeS-B#9, or pPAT108 all comprising the DNA sequence encoding P450SU1 plus FeS-B produce the P450SU1 constitutively and metabolize herbicidal sulfonylurea compounds even though no iron-sulfur protein reductase gene has been introduced into these cells. Bacteria transformed with the plasmid pCAO200SU2-FeS-A#11 or pCS325, comprising the DNA sequence encoding P450SU2 plus the iron sulfur protein FeS-A produce P450SU2 constitutively and can also metabolize herbicidal sulfonylurea compounds even though no iron-sulfur protein reductase gene has been added.

Another embodiment of this invention is a method for the preparation of metabolites of herbicide compounds comprising incubating sulfonylurea or other herbicide compounds with cultures of bacteria, preferably bacteria of the genus Streptomyces transformed with a plasmid selected from pCAO400, pCAO401, pCAO20-0SU1-FeS-B#9, pCAO200SU2-FeS-A#11, pPAT108 or pCS325.

Still another embodiment of this invention is a method for protecting plants in soil containing inhibitory amounts of herbicidal compounds comps of herbicidal compounds comprising soaking seedlings of plants in cultures of bacteria, preferably bacteria of the genus Streptomyces and most preferably *Streptomyces lividans* transformed with a plasmid selected from pCAO400, pCAO401, pCAO200SU1-FeS-B#9 or pCAO200SU2-FeS-A#11 prior to transplanting the seedlings in the soil. A further embodiment of this invention is the bacteria coated seeds.

And another embodiment of this invention is the transformation of plants, in particular those of horticultural or agronomic utility, with these genes to make them capable of metabolizing sulfonylurea herbicides. For this purpose plasmids (i.e., pSU18, pSSU-SU111, pSSU-SU121, pCab-SU111, pCab-SU121, and pCab-SU131, pSuFe11, pSuFe21, pSuFe31 and pSuFe41) utilizing a fragment comprising sequences encoding P450SU1 and/or FeS-B with certain other DNA sequences preceding and following the P450SU1 and/or FeS-B sequence have been engineered to transform plants with these genes. This may result in making said transformed plants susceptible to chemicals which lack, or contain only weakly, herbicidal activity by means of metabolizing the chemicals to compounds exhibiting greater plant toxicity.

Metabolism of herbicides by transformed plants can make them resistant to said herbicides and reduce the buildup of herbicide residues in the plant. Cytochrome P450-mediated metabolism of sulfonylureas from a less toxic to a more toxic form results in conditionally lethal phenotype and could possibly be used for applications of tissue specific killing or for selection of events which disrupt gene expression.

Such transformed plants can include plants containing other mutant genes prior to their transformation with the P450SU1 or P450SU2 genes. Of particular interest are plants containing a mutant acetolactate synthase enzyme which prevents or decreases inhibition. This enzyme catalyses the first reaction in the synthesis of the amino acids valine, leucine, and isoleucine in plants and microorganisms. It is known that this enzyme in a variety of plants and microorganisms is quite sensitive to inhibition by sulfonylureas. It is theorized that transformed plants containing both mutant acetolactate synthase enzymes which decrease or prevent inhibition of the enzyme by sulfonylureas or other herbicides and P450 cytochrome enzymes enabling plants to metabolize herbicides would possibly result in plants showing even greater resistance to a wider variety of sulfonylurea compounds than that seen in plants containing mutant acetolactate synthase alone.

Figure 1:
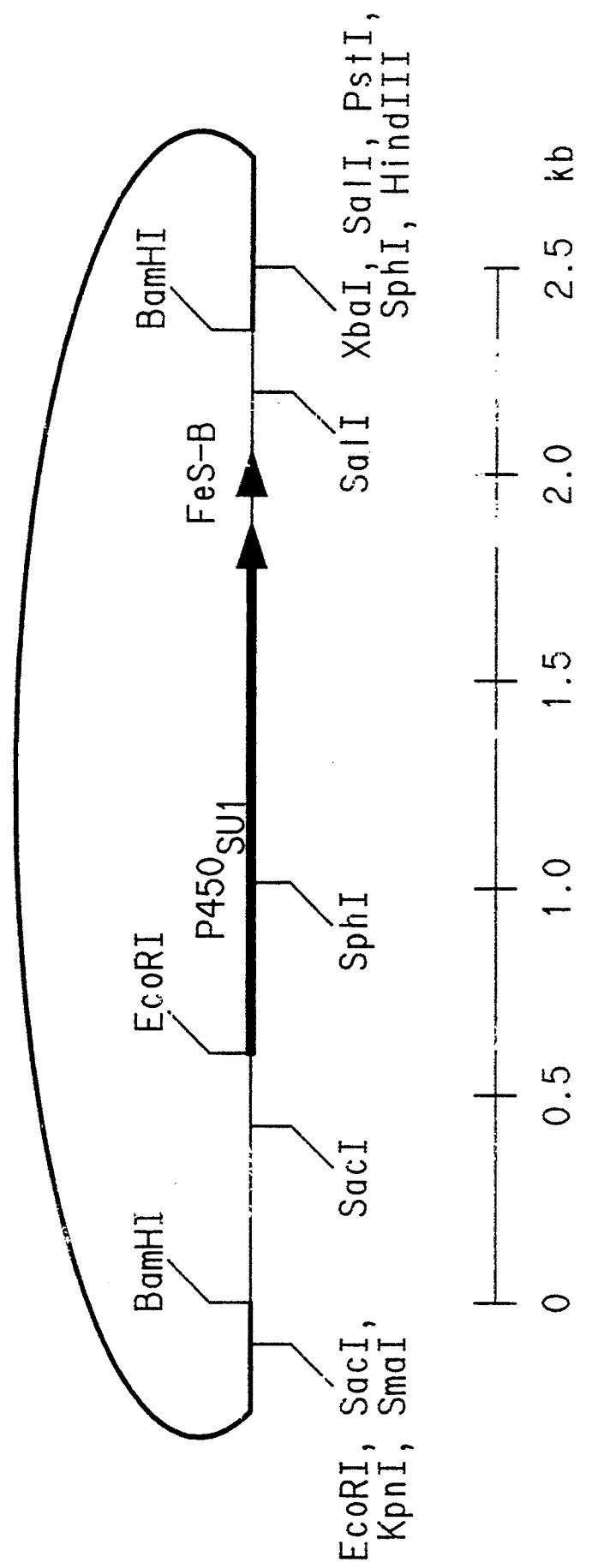
FIG. 1 is a physical map, showing restriction endonuclease sites, of plasmid pUC18-SU1-BamHI.
Figure 2A:
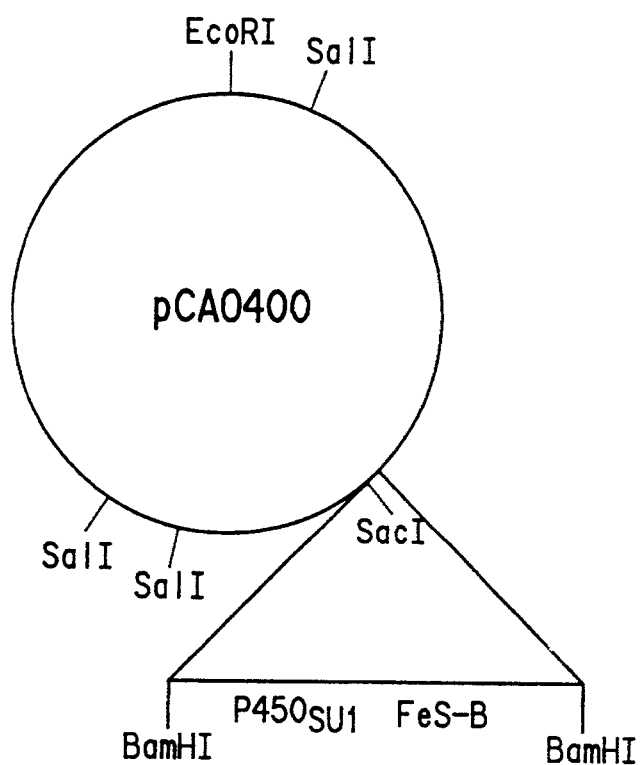
FIG. 2A is a physical map, showing the restriction endonuclease site, of plasmid pCAO400.
Figure 2B:
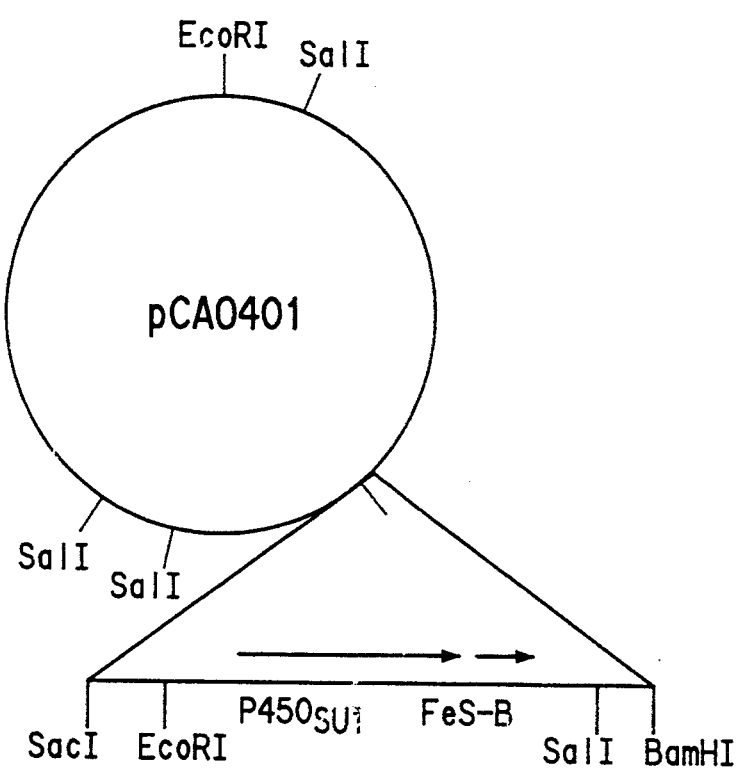
FIG. 2B is a physical map, showing the restriction endonuclease site, of plasmit pCAO401.

lane 2, protein extract of *S. lividans* transformed with pCAO401 and induced with 120 ppm of 10001 for 6 hours;

lane 3, protein extract of *S. lividans* transformed with pCAO401 and induced with 120 ppm of 10001 for 3 hours;

lane 4, protein extract of *S. lividans* transformed with pCAO401 and grown for 24 hours;

lane 5, protein extract from *S. lividans* transformed with pCAO400 and induced with 120 ppm of 10001 for 24 hours;

lane 6, protein extract of *S. lividans* transformed with pCAO400 and induced with 120 ppm of 10001 for 6 hours;

lane 7, protein extract of *S. lividans* transformed with pCAO400 and induced with 120 ppm of 10001 for 3 hours;

lane 8, protein extract of *S. lividans* transformed with pCAO400 and grown for 24 hours;

lane 9, 100 ng of purified cytochrome P450SU1.

Figure 7:
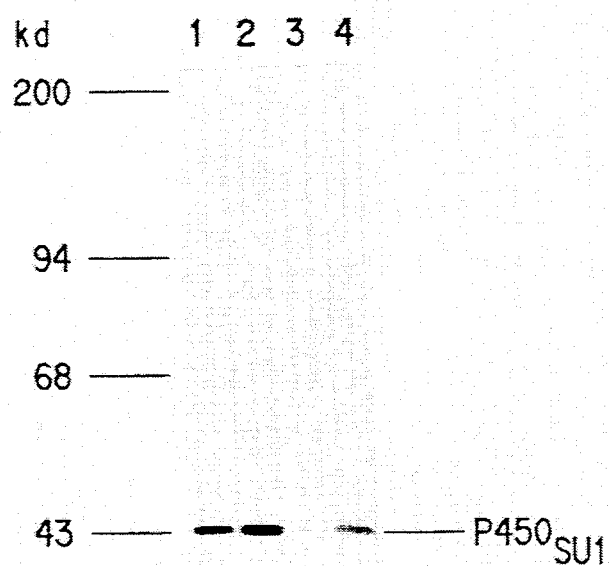

FIG. 7 shows Western blots as follows:

lane 1, 100 ng of purified cytochrome P450SU1;

lane 2, 200 ng of purified cytochrome P450SU1;

lane 3, extracts of *S. lividans* transformed with pCAO200SU1#12;

lane 4, extracts of *S. lividans* transformed with pCAO200SU1-FeS-B#9.

Figure 8:
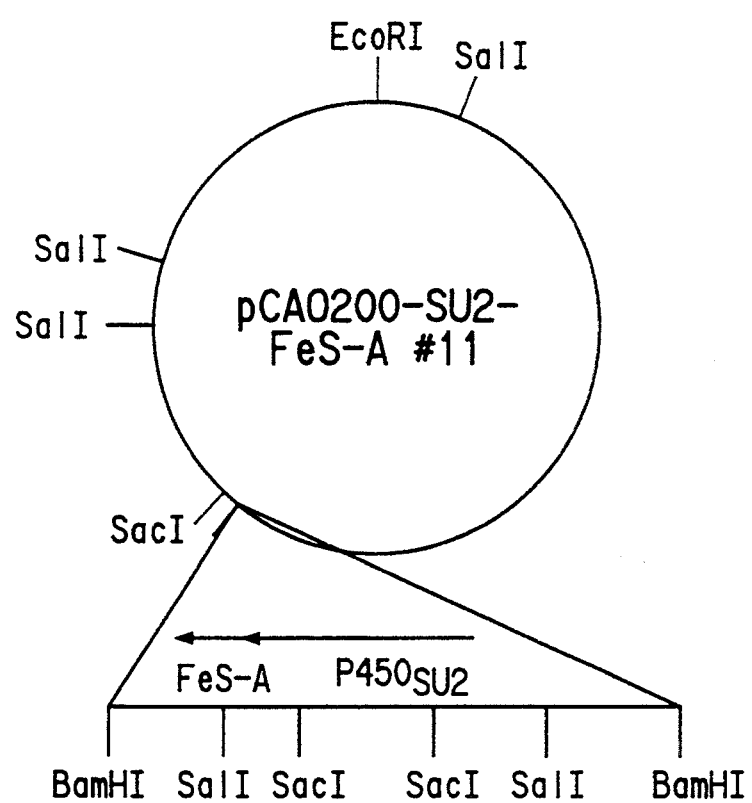

FIG. 8 is a physical map, showing restriction endonuclease sites, of pCAO200SU2-FeS-A#11.

Figure 9:
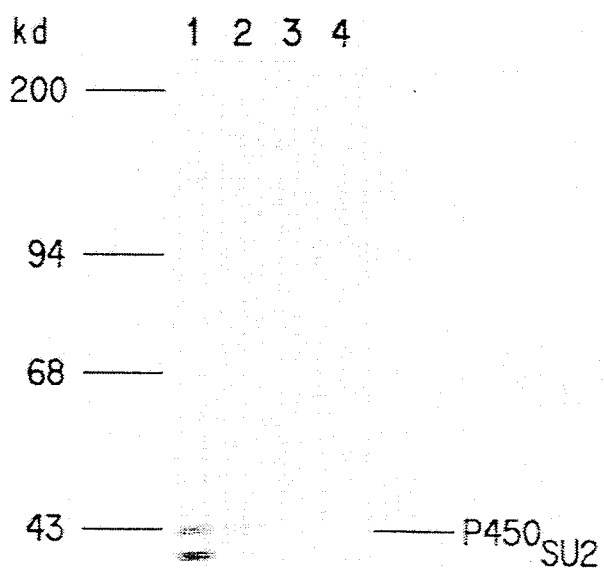

-FIG. 9 shows Western blots as follows:

lane 1, 100 ng of purified cytochrome P450SU2;

lane 2, extract (30 μg of protein) of *S. lividans* transformed with pCAO200SU2-FeS-A#11 grown without sulfonylurea;

lane 3 extract (30 μg of protein) of *S. lividans* transformed with-pCAO200SU1#12 grown without sulfonylurea;

lane 4 extract (30 μg of protein) of *S. lividans* transformed with pCAO200SU1-FeS-B#9 grown without sulfonylurea.

FIG. 10A is a physical map showing restriction endonuclease sites of pSU17.

FIG. 10B is a physical map showing restriction endonuclease sites of pSSU-SU11.

FIG. 10C is a physical map showing restriction endonuclease sites of pSSU-SU12.

FIG. 10D is a physical map showing restriction endonuclease sites of pCab-SU11.

FIG. 10E is a physical map showing restriction endonuclease sites of pCab-SU12.

FIG. 10F is a physical map showing restriction endonuclease sites of pCab-SU13.

FIG. 11 depicts the N-dealkylation of 10015 to 10014.

Figure 12A:
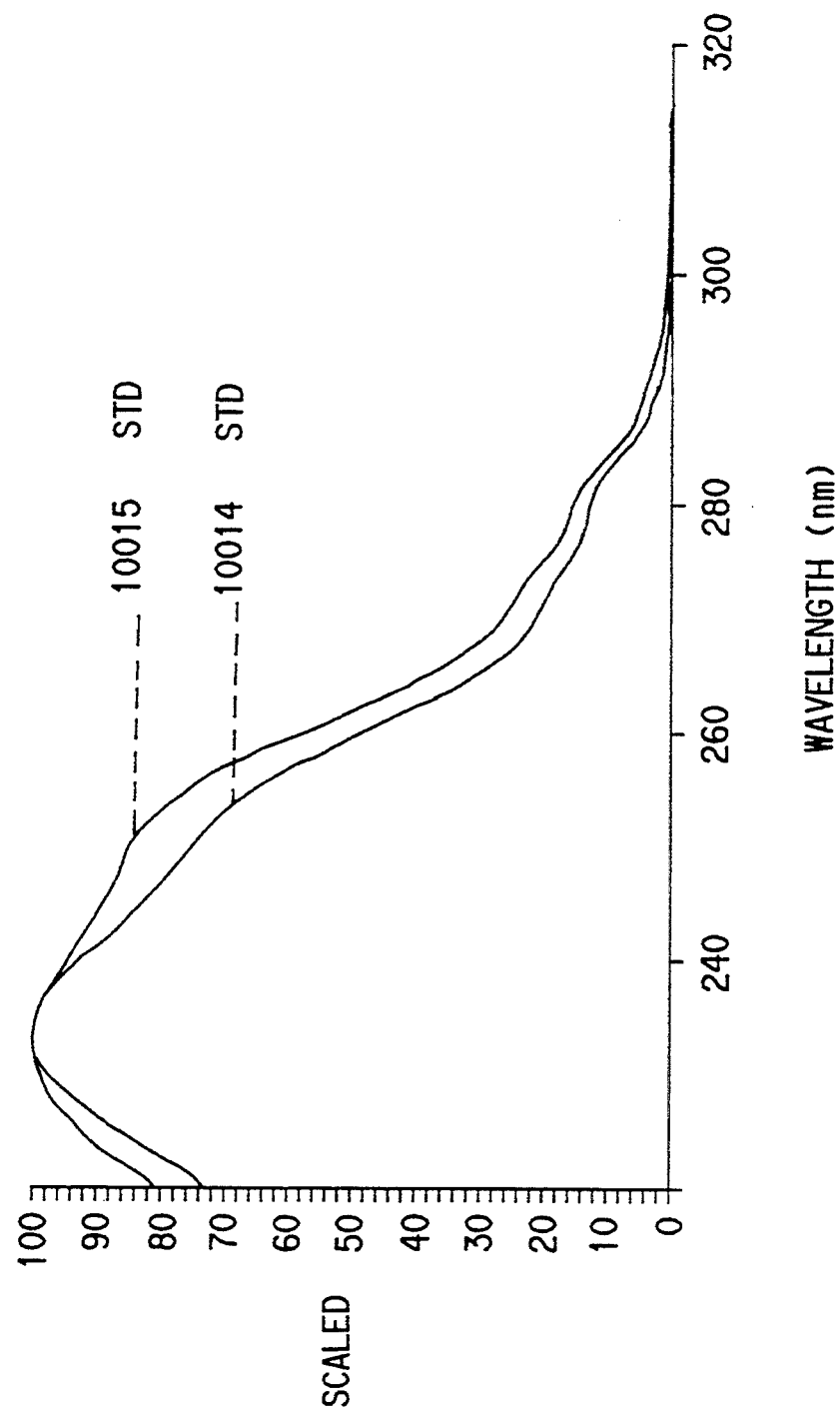

FIG. 12A is the UV Absorbance Spectra for 10015 and 10014 standards.

FIG. 12B is the UV Absorbance Spectra for 10015 extracted from leaf and metabolite extracted from leaf.

Figure 13D:
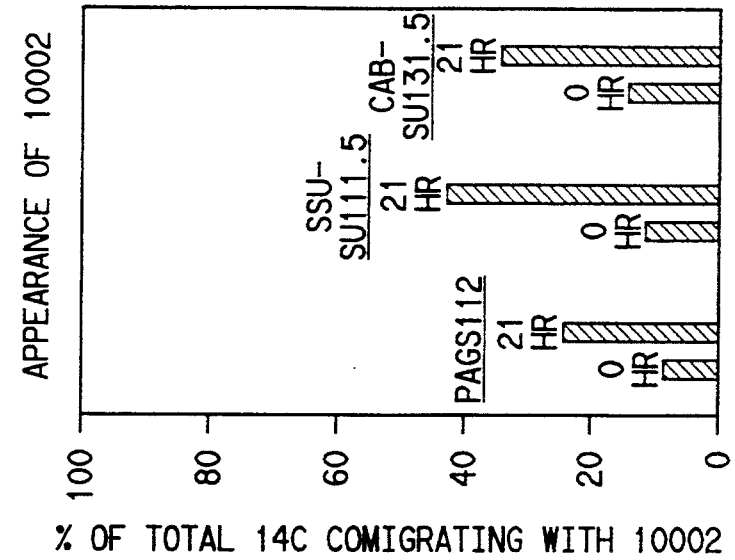
Figure 13C:
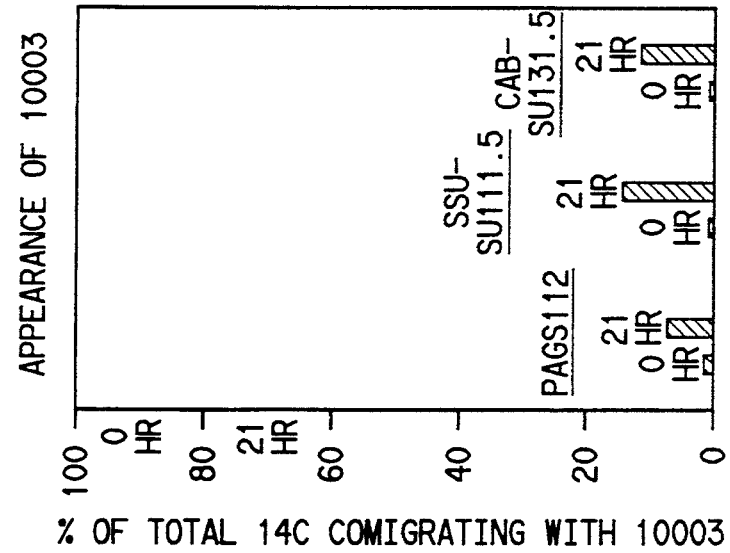
Figure 13B:
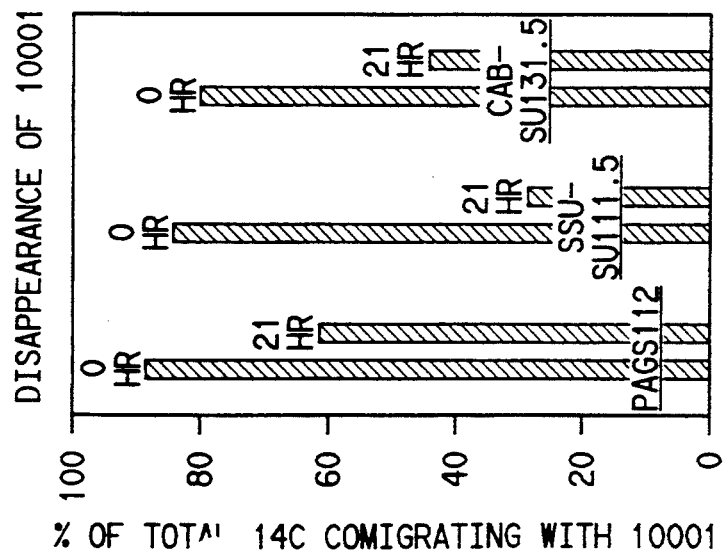
Figure 13A:
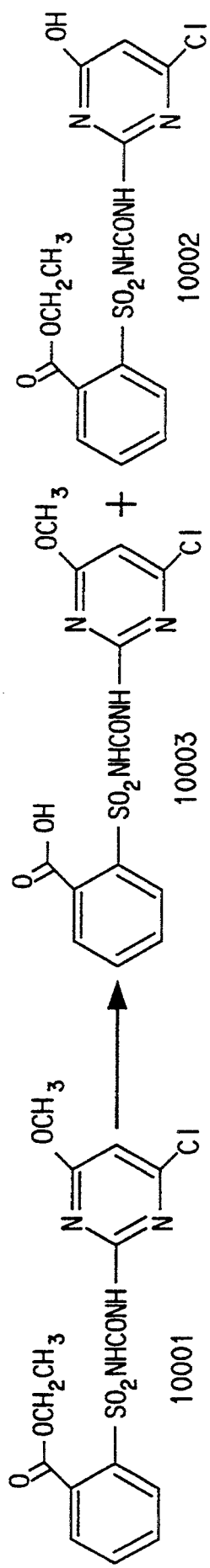

FIG. 13A depicts the metabolism of 10001 by tissues of transformed tobacco leaves to 10003 and 10002.

FIG. 13B depicts the disappearance over time of 10001.

FIG. 13C depicts the appearance over time of 0003.

FIG. 13D depicts the appearance over time of 0002.

Figure 14:
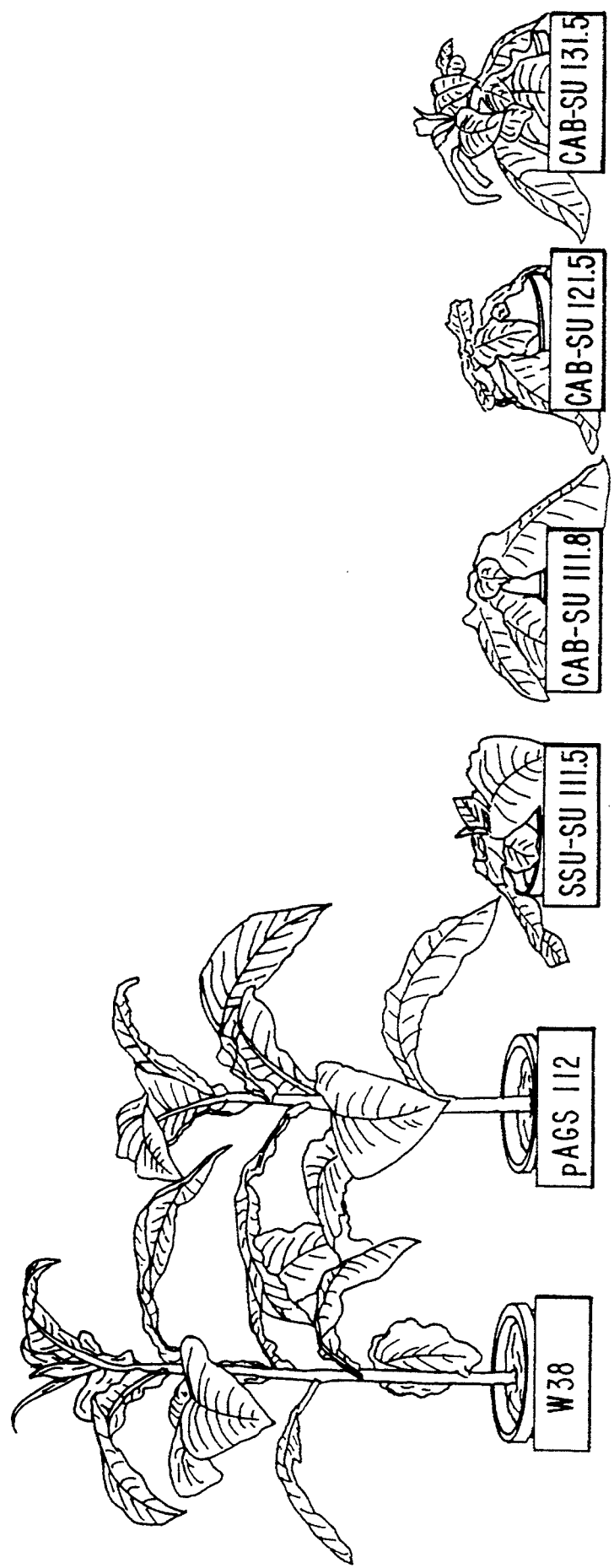

FIG. 14 depicts the appearance of transformed and nontransformed tobacco plants 22 days after spraying with 10015.

FIG. 15A is a physical map showing restriction endonuclease sites of plasmid pSuFe1.

FIG. 15B is a physical map showing restriction endonuclease sites of plasmid pSuFe2.

FIG. 15C is a physical map showing restriction endonuclease sites of plasmid pSuFe3.

FIG. 15D is a physical map showing restriction endonuclease sites of plasmid pSuFe4.

In FIGS. 15A through 15D, H3 represents HindIII, BMI represents BamHI, NCl represents NcoI, RI represents EcoRI, and BG2 represents BglII.

Figure 16A:
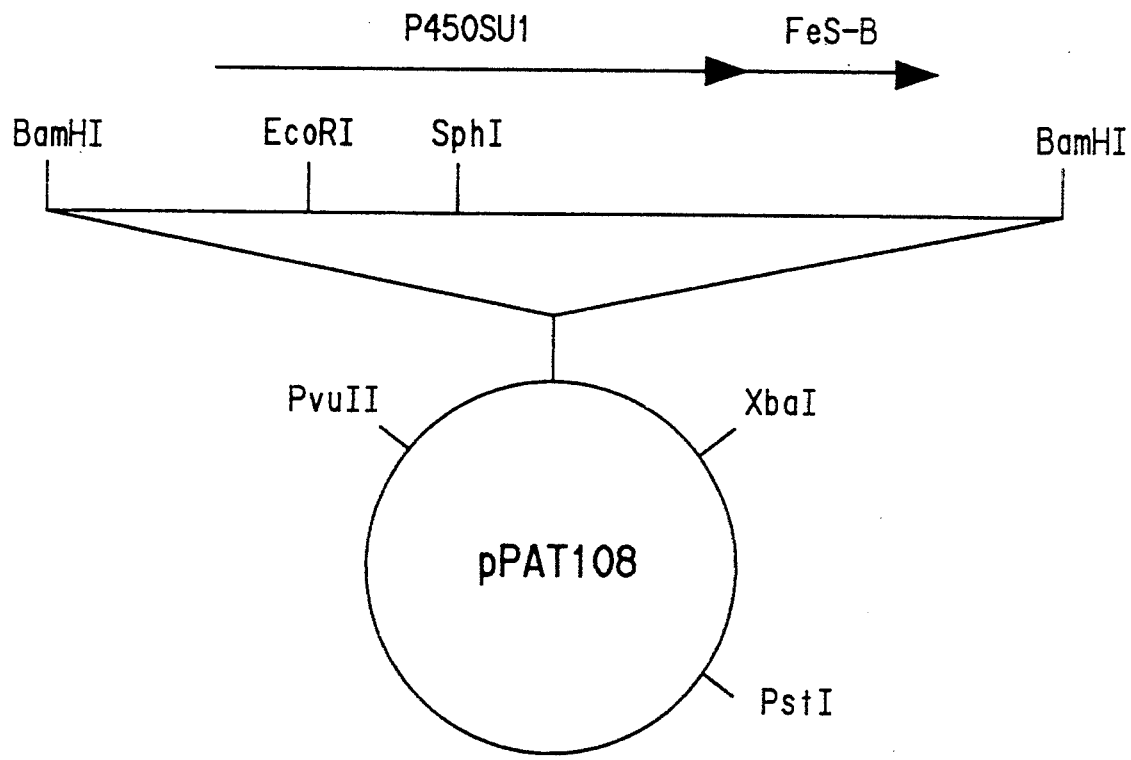

FIG. 16A is a physical map showing restriction endonuclease sites of plasmid pPAT108.

Figure 16B:
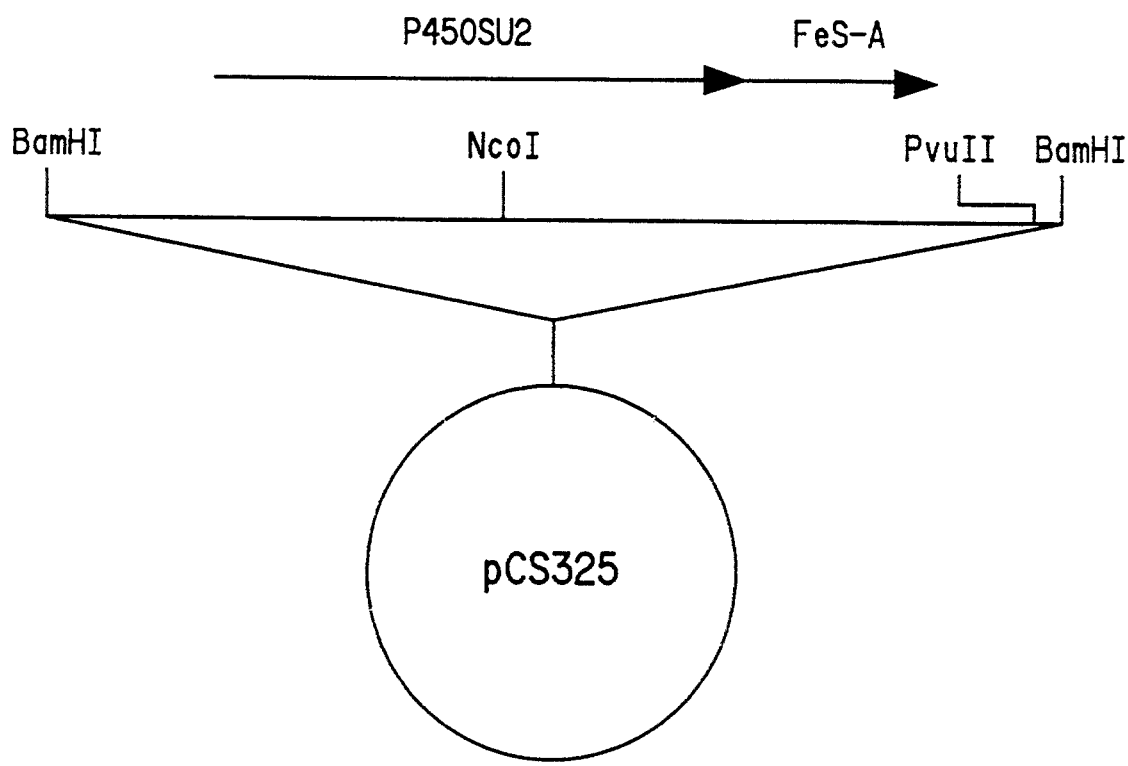

FIG. 16B is a physical map showing restriction endonuclease sites of plasmid pCS325.

FIGS. 17A to 17D are diagrams showing the construction of plasmid pSU17.

Figure 17A:
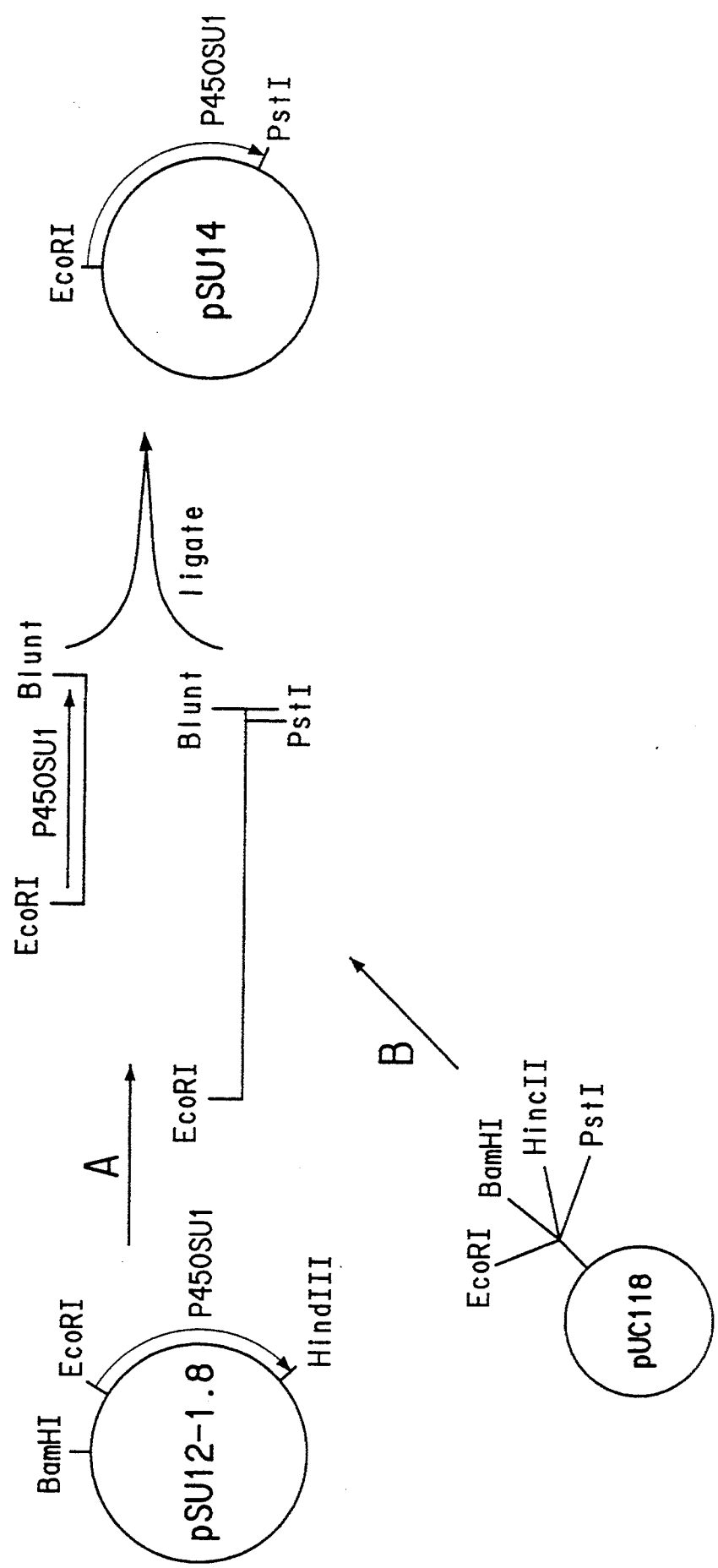
Figure 17B:
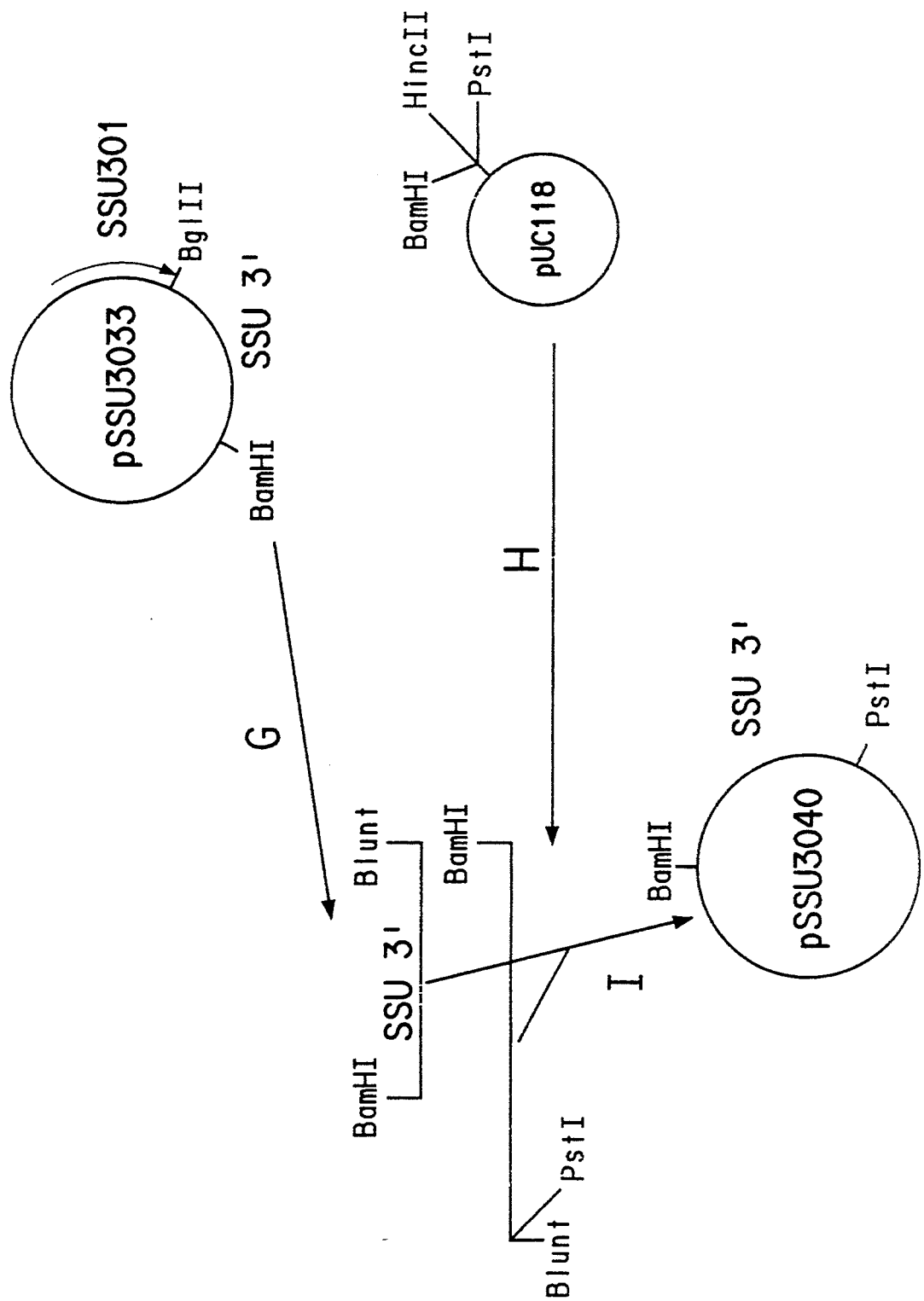
Figure 17C:
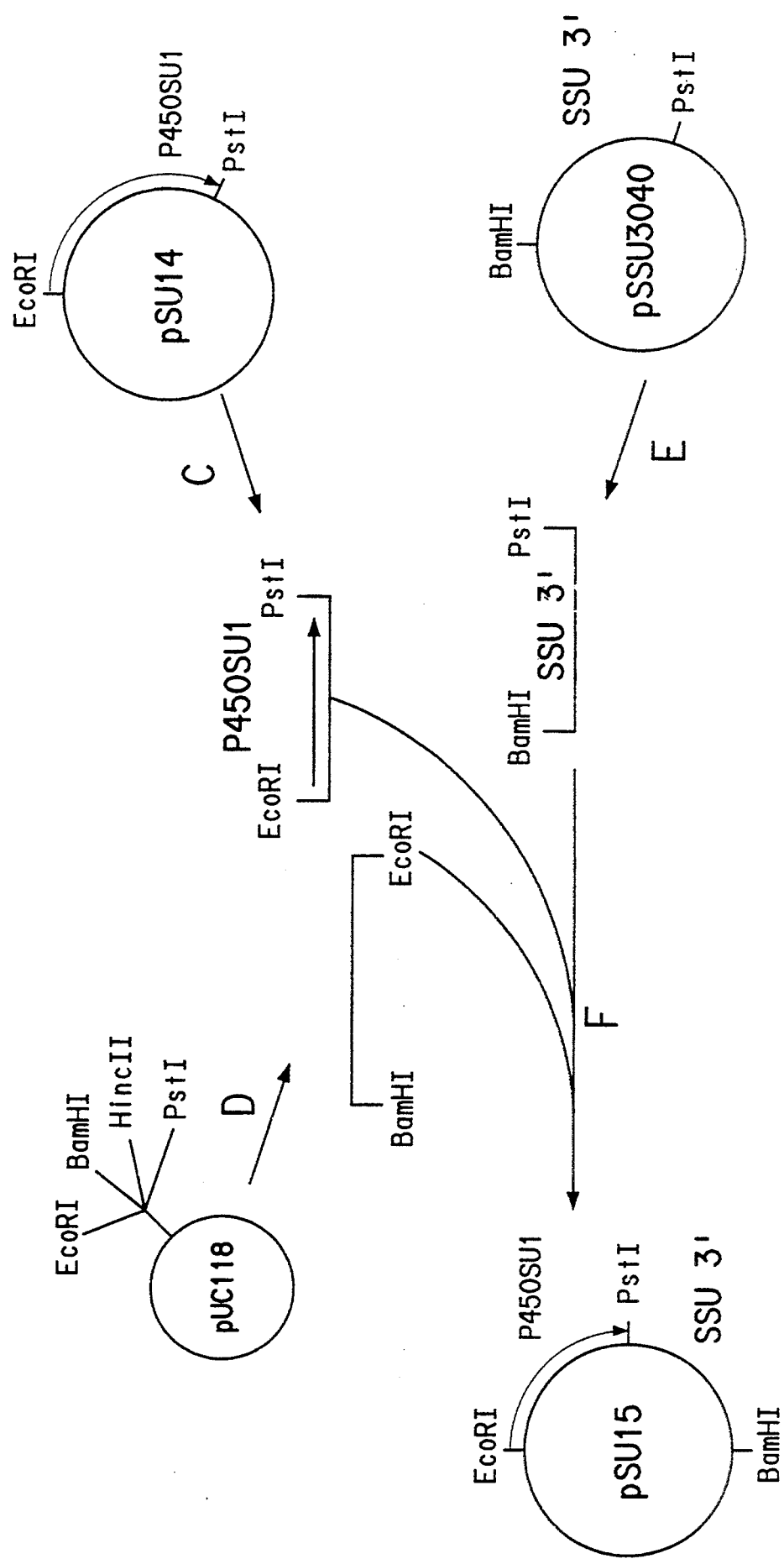
Figure 17D:
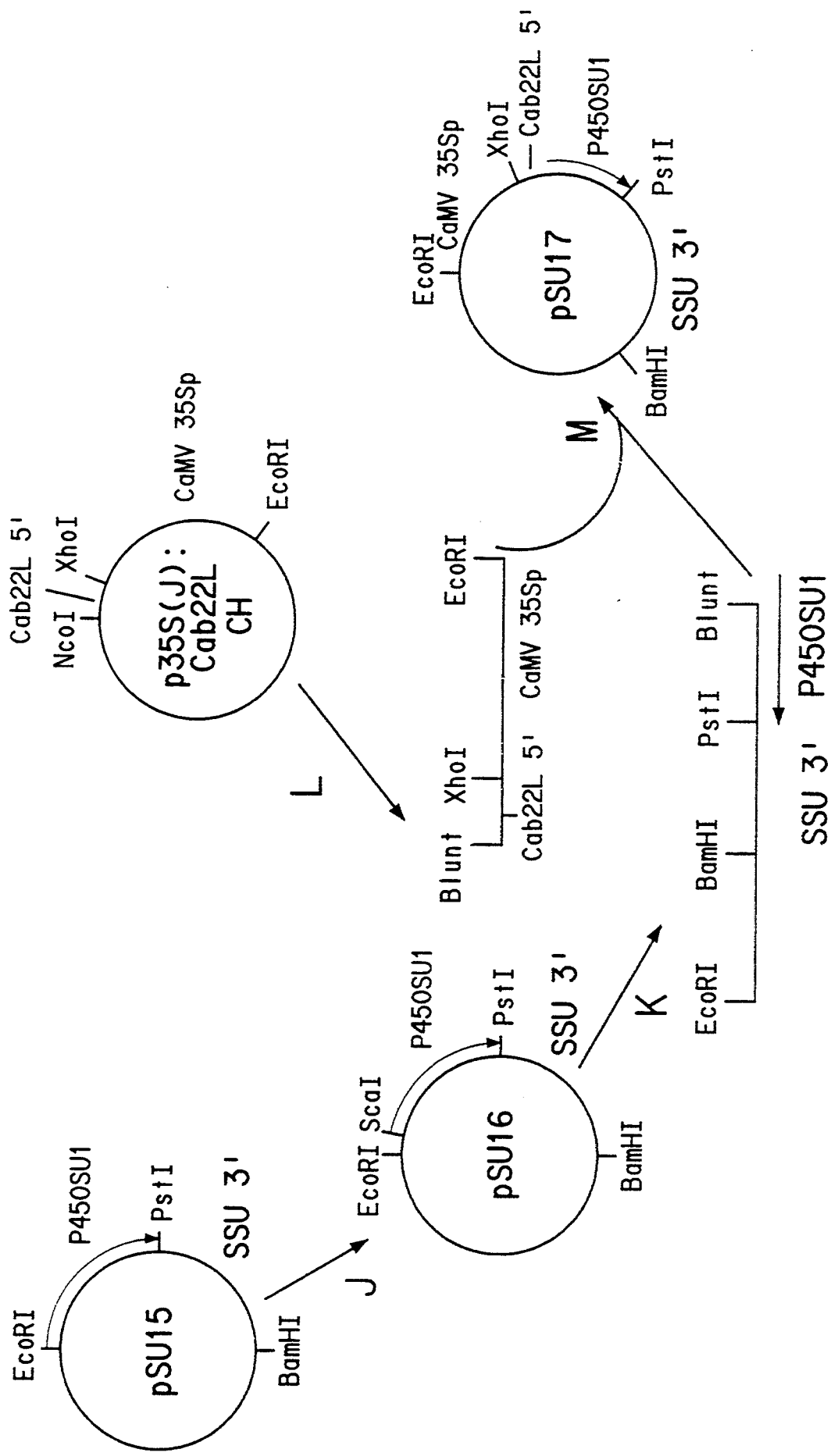

FIG. 17A shows the construction of pSU14. FIG. 17B shows the construction of pSSU3040. FIG. 17C shows the construction of pSU15. FIG. 17D shows final steps in the construction of pSU17.

FIGS. 18A to 18D are diagrams showing the construction of plasmid pSUFe1.

Figure 18A:
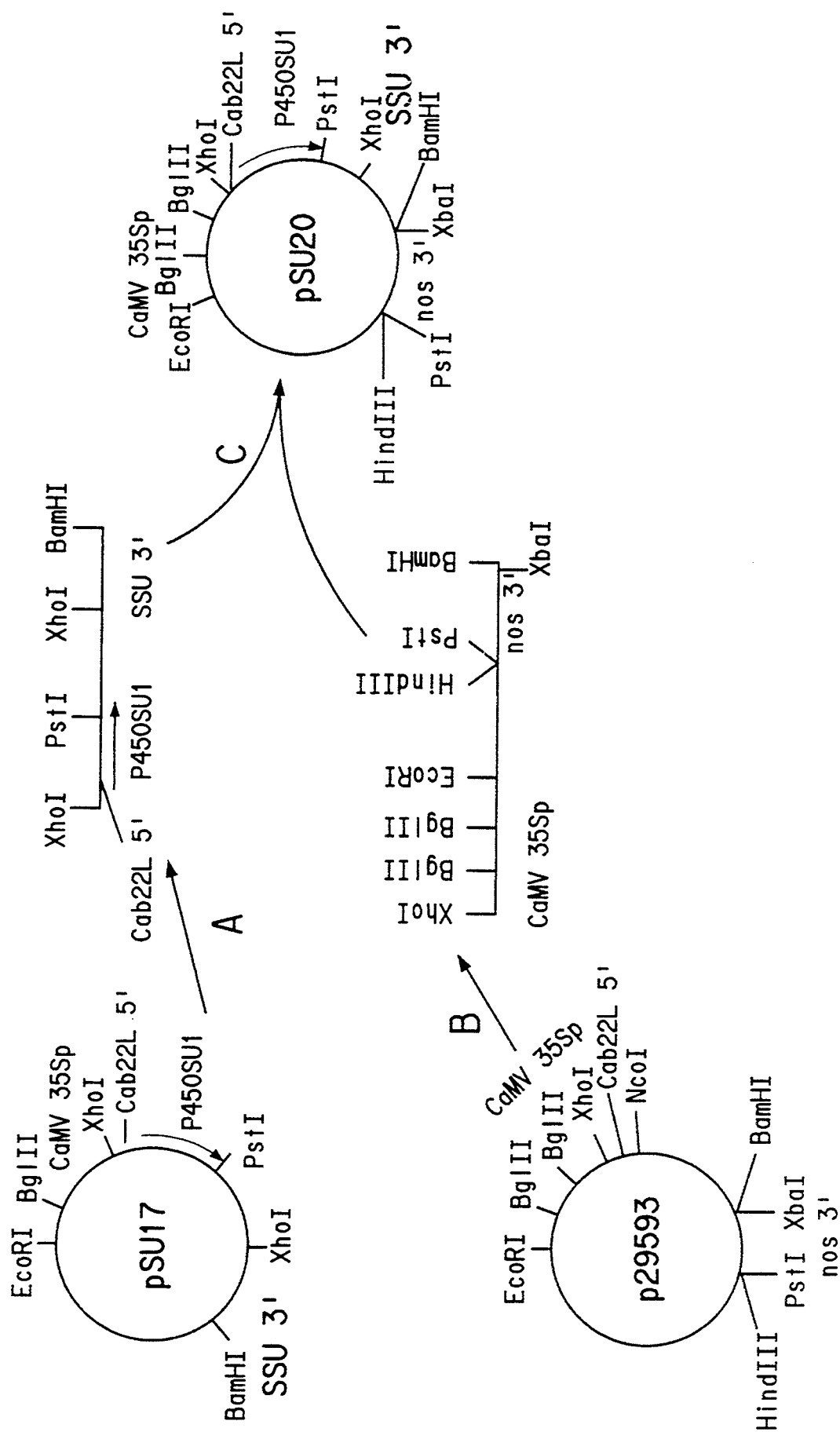
Figure 18B:
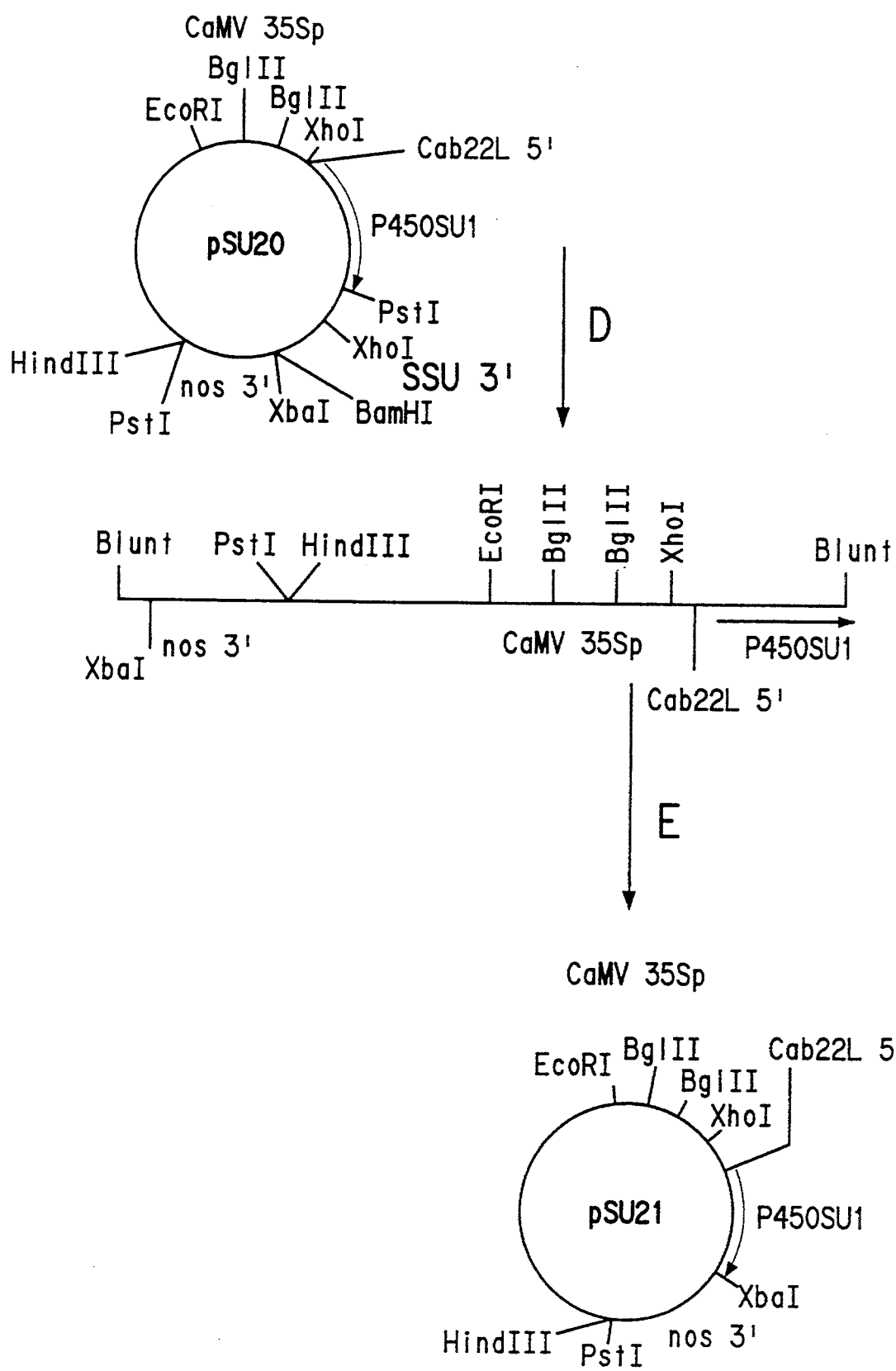
Figure 18D:
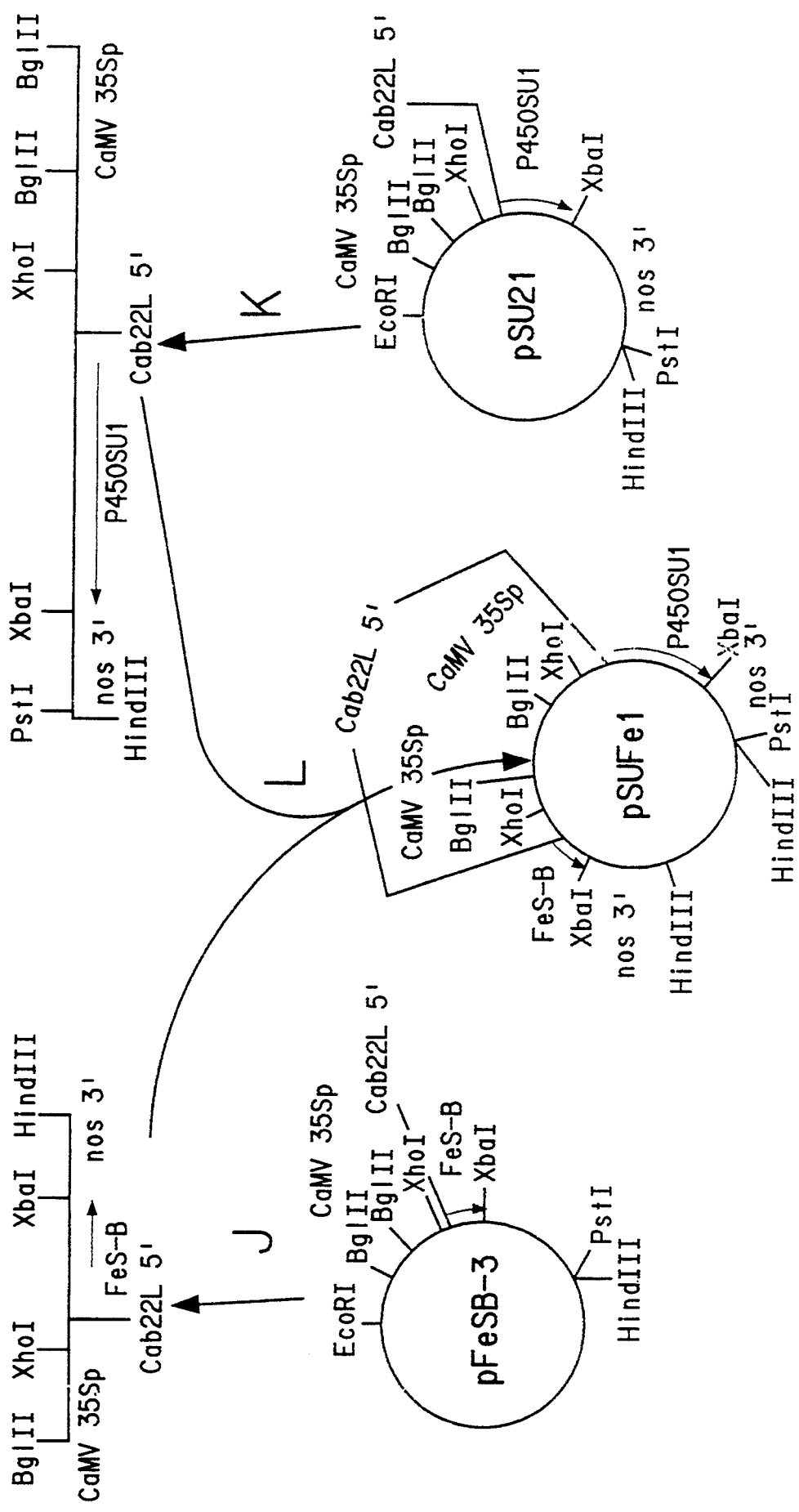

FIG. 18A shows the construction of pSU20. FIG. 18B shows the construction of pSU21. FIG. 18C shows the construction of pFESB-3. FIG. 18D shows the final steps in the construction of pSUFe1.

Figure 19A:
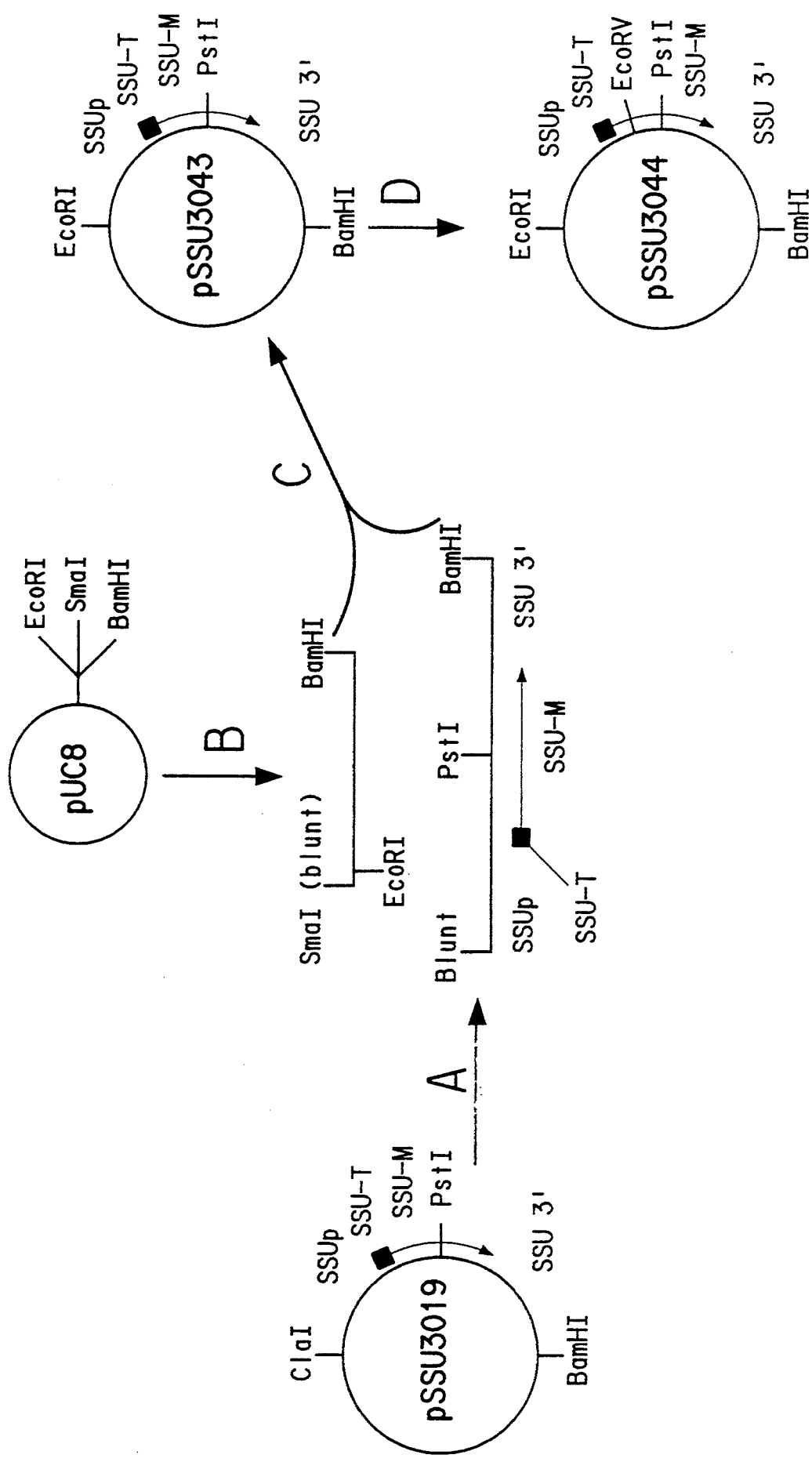
Figure 19B:
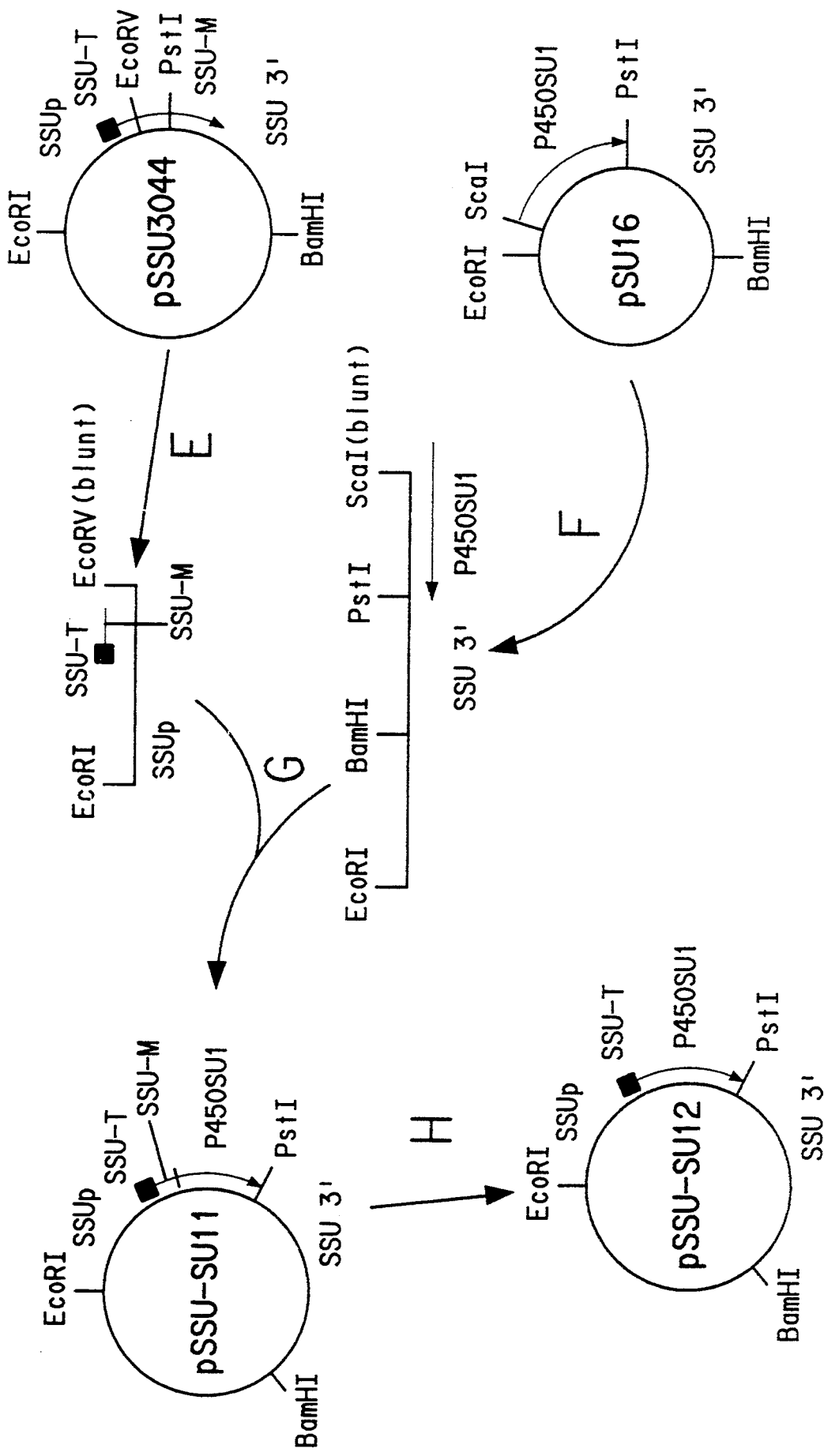

FIGS. 19A and 19B are diagrams showing the construction of plasmids pSSU-SU11 and pSSU-SU12.

FIG. 19A is a diagram showing the construction of pSSU3044. FIG. 19B is a diagram showing the finale steps in the construction of pSSU-SU11 and pSSU-SU12.

Figure 20A:
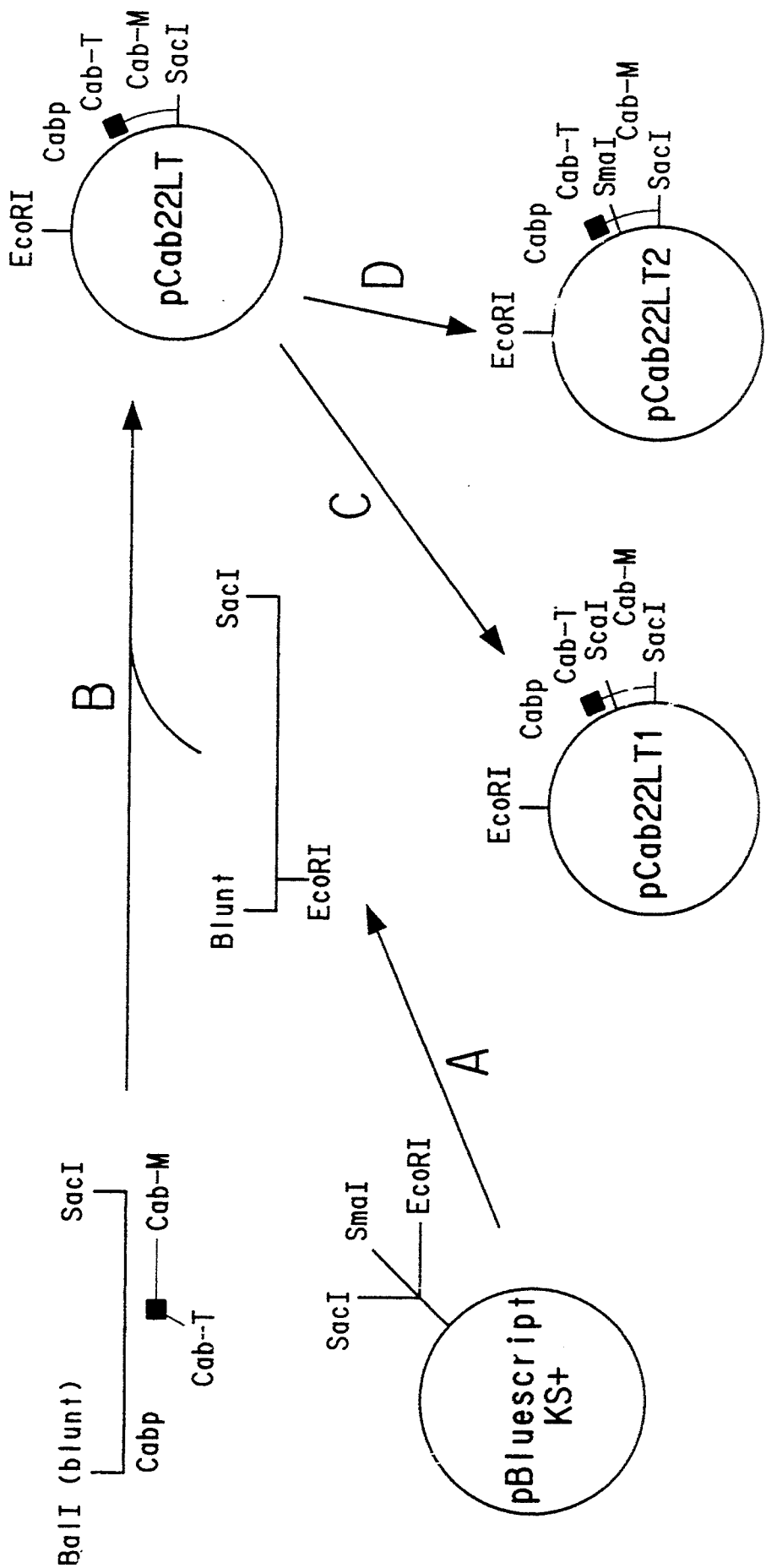
Figure 20B:
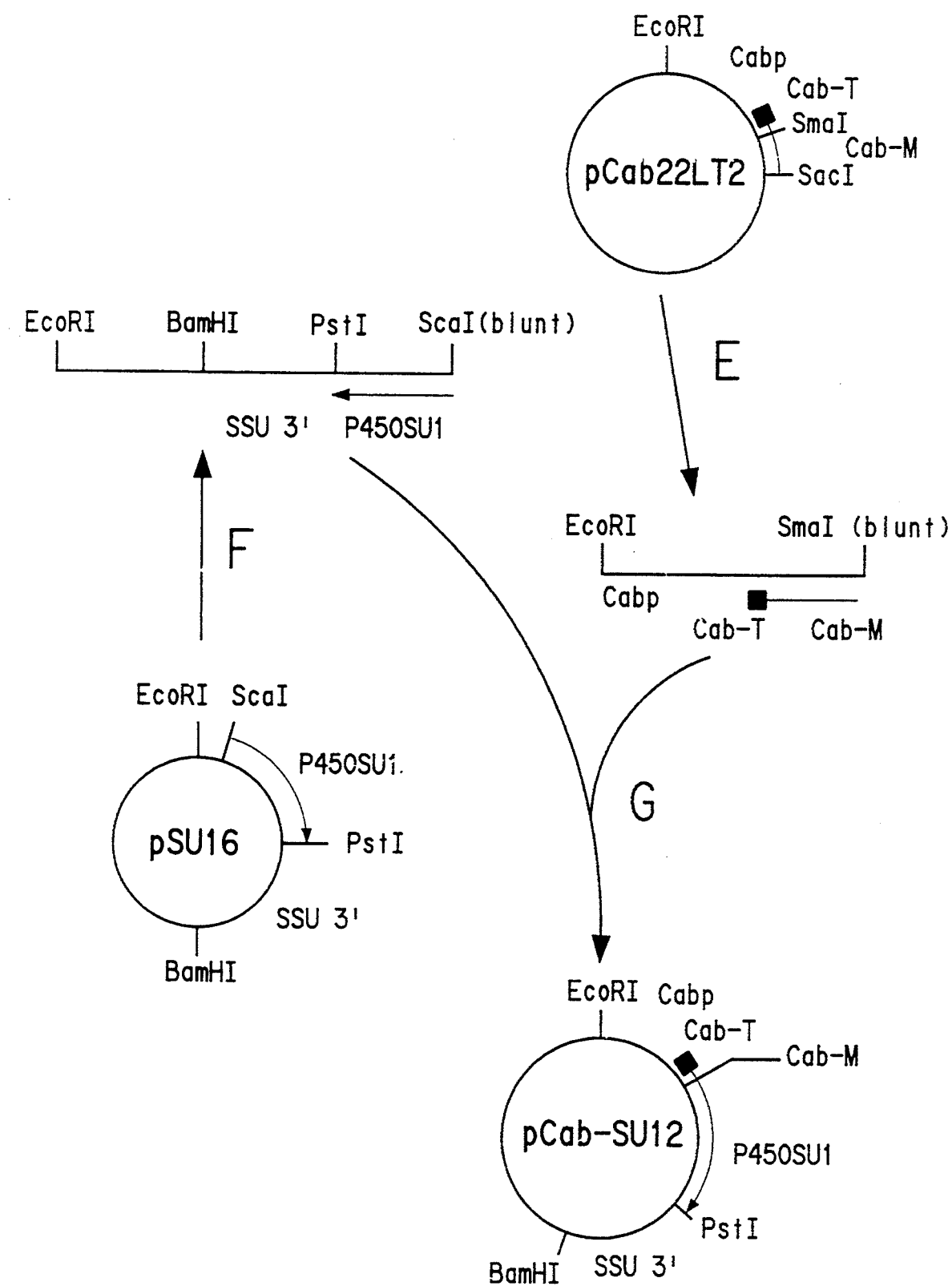
Figure 20C:
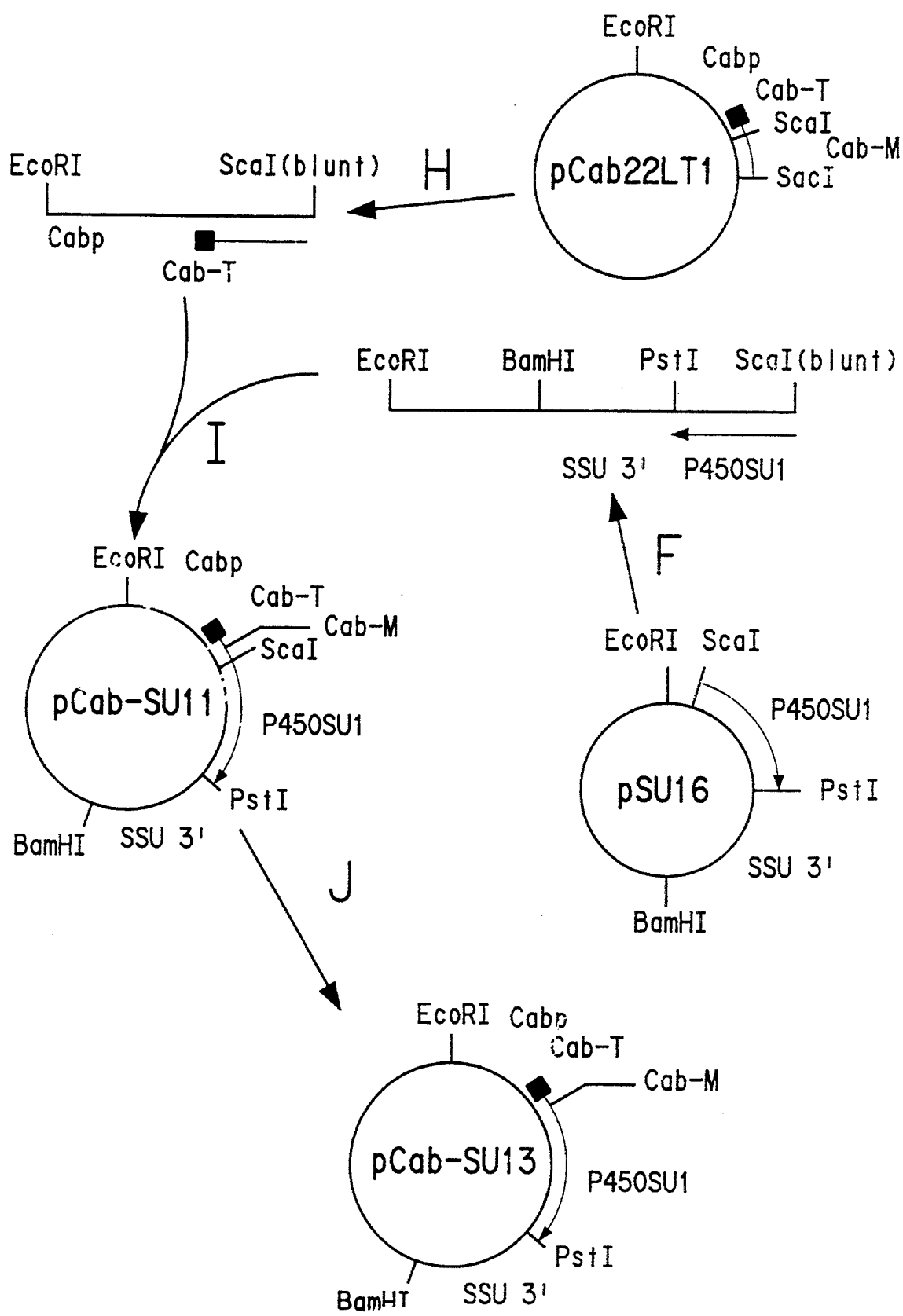

FIGS. 20A to 20C are diagrams showing the construction of plasmids PCab-SU11, pCab-SU12 and pCab-SU13.

FIG. 20A shows the construction of pCab22LT1 and pCab22LT2. FIG. 20B shows the construction of pCab-SU12. FIG. 20C shows the construction of pCab-SU11 and pCab-SU13.

Figure 21A:
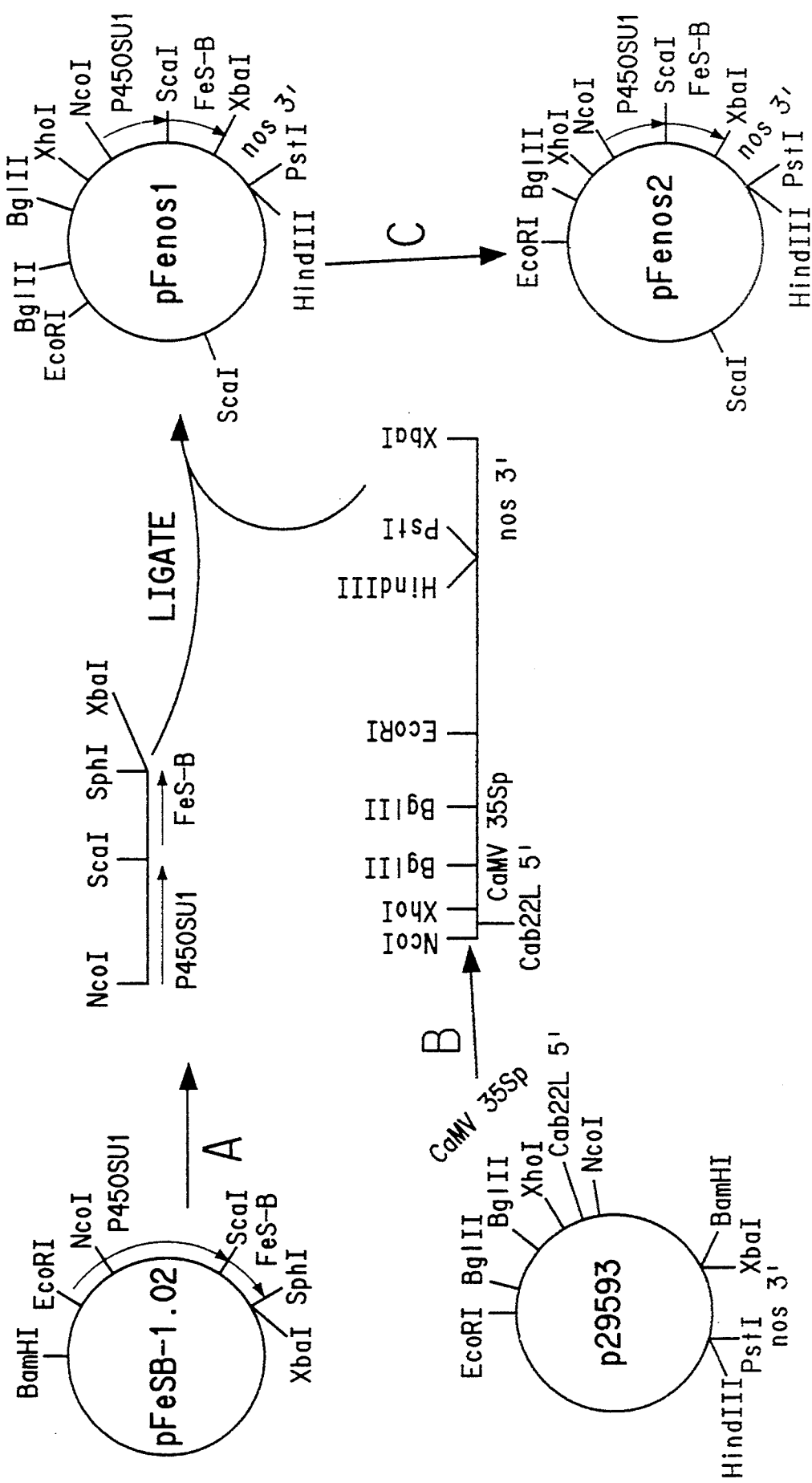
Figure 21B:
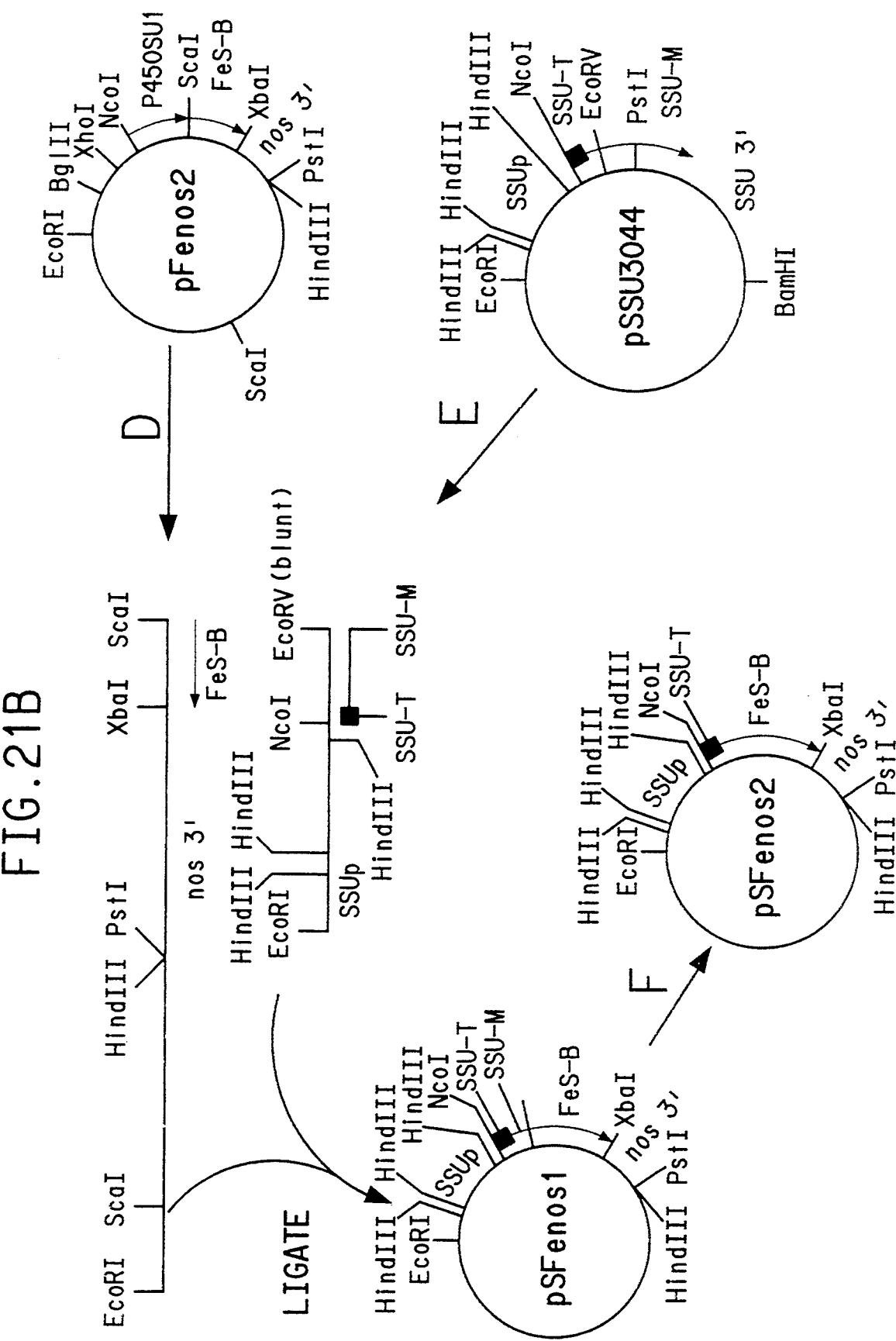

FIGS. 21A to 21B are diagrams showing the construction of plasmids pSUFe3 and pSUFe4.

Figure 21C:
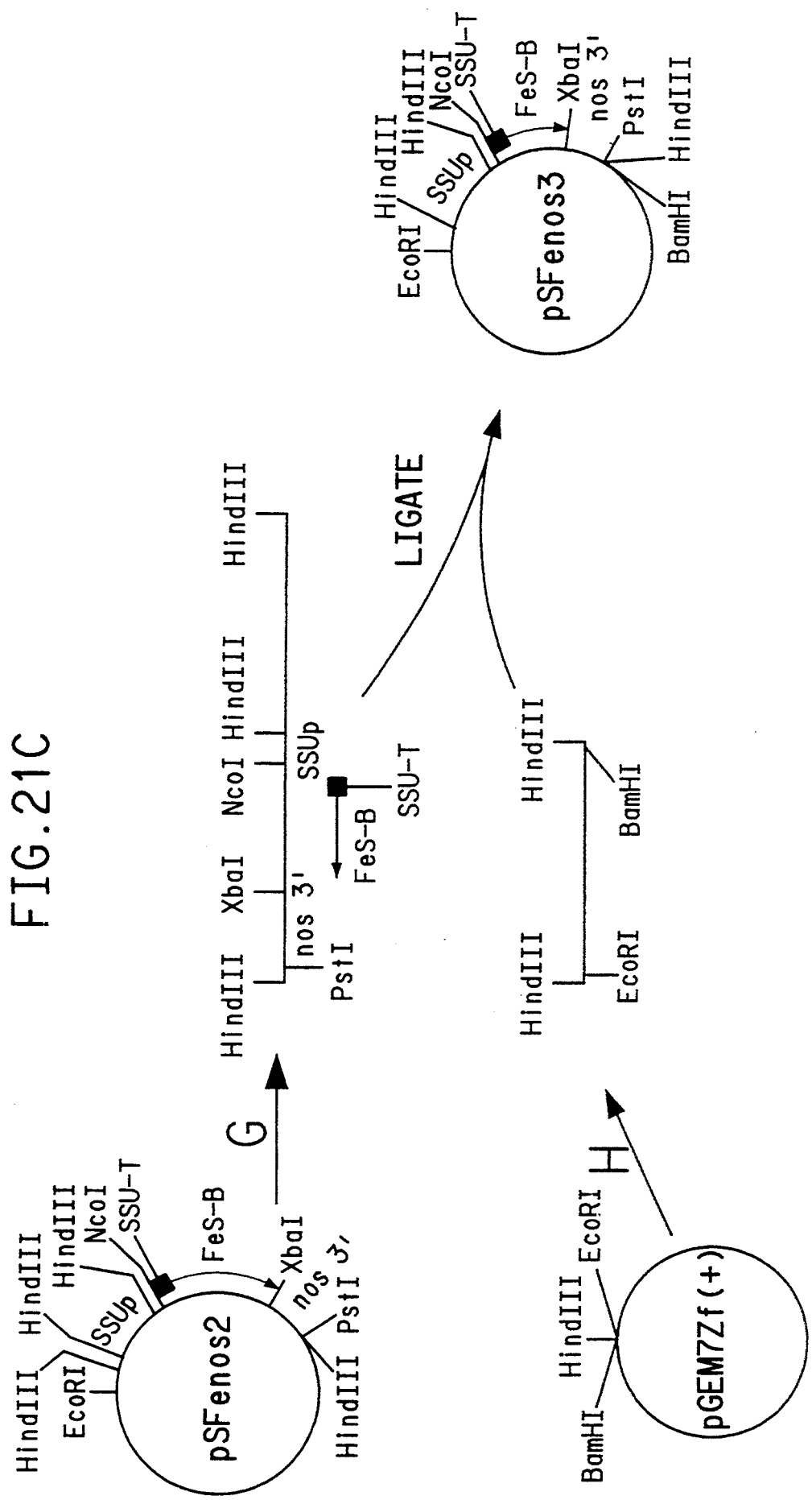
Figure 21D:
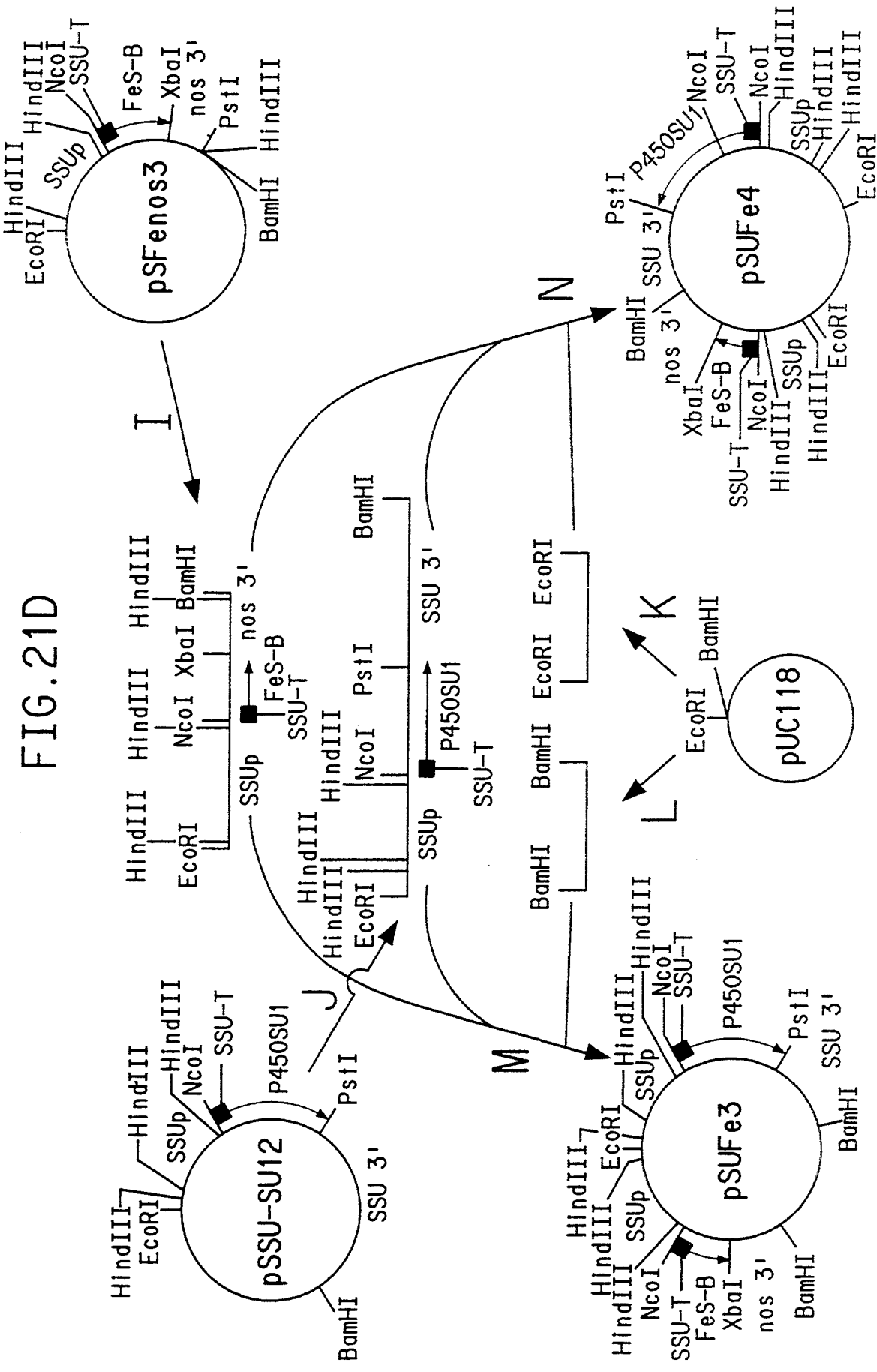

FIG. 21A shows the construction of pFenos2. FIG. 21B shows the construction of pSFenos2. FIG. 21C shows the construction of pSfenos3. FIG. 21D shows the final steps in the construction of pSUFe3 and pSUFe4.

Figure 22A:
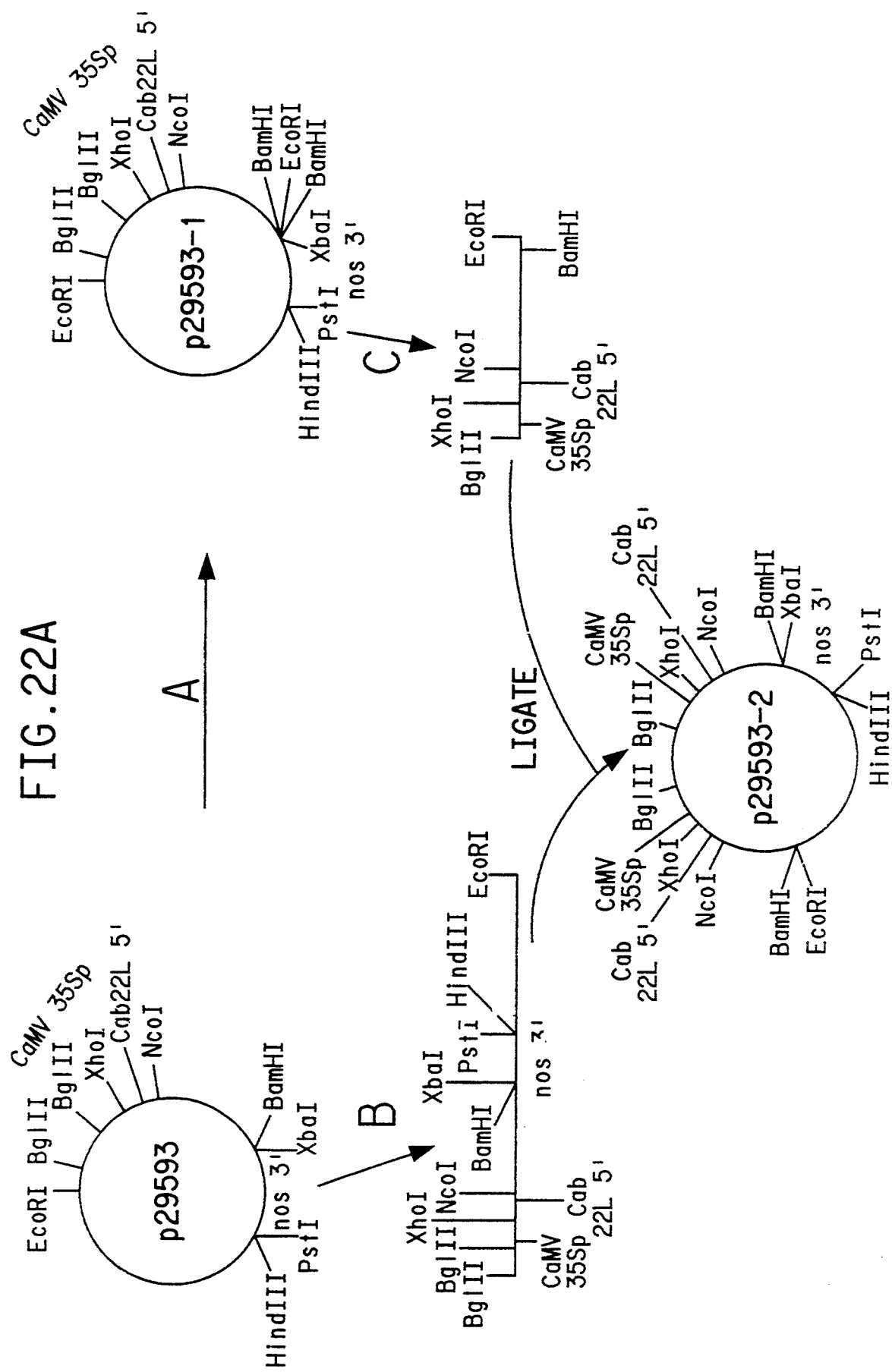
Figure 22B:
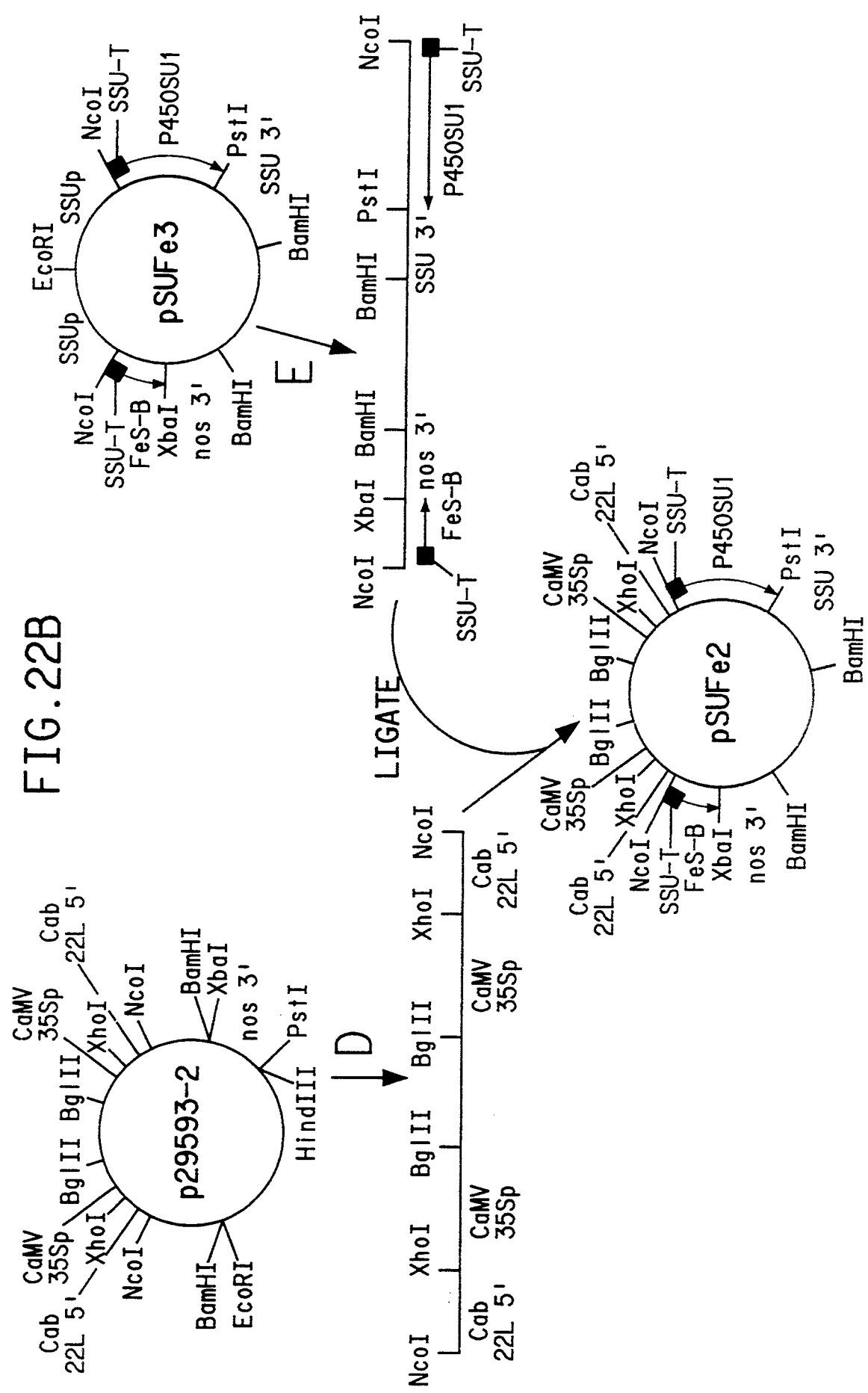

FIGS. 22A and 22B are diagrams showing the construction of plasmid pSUFe2.

FIG. 22A shows the construction of p29593-2. FIG. 22B shows the final steps of the construction of pSUFe2.

Figure 23A:
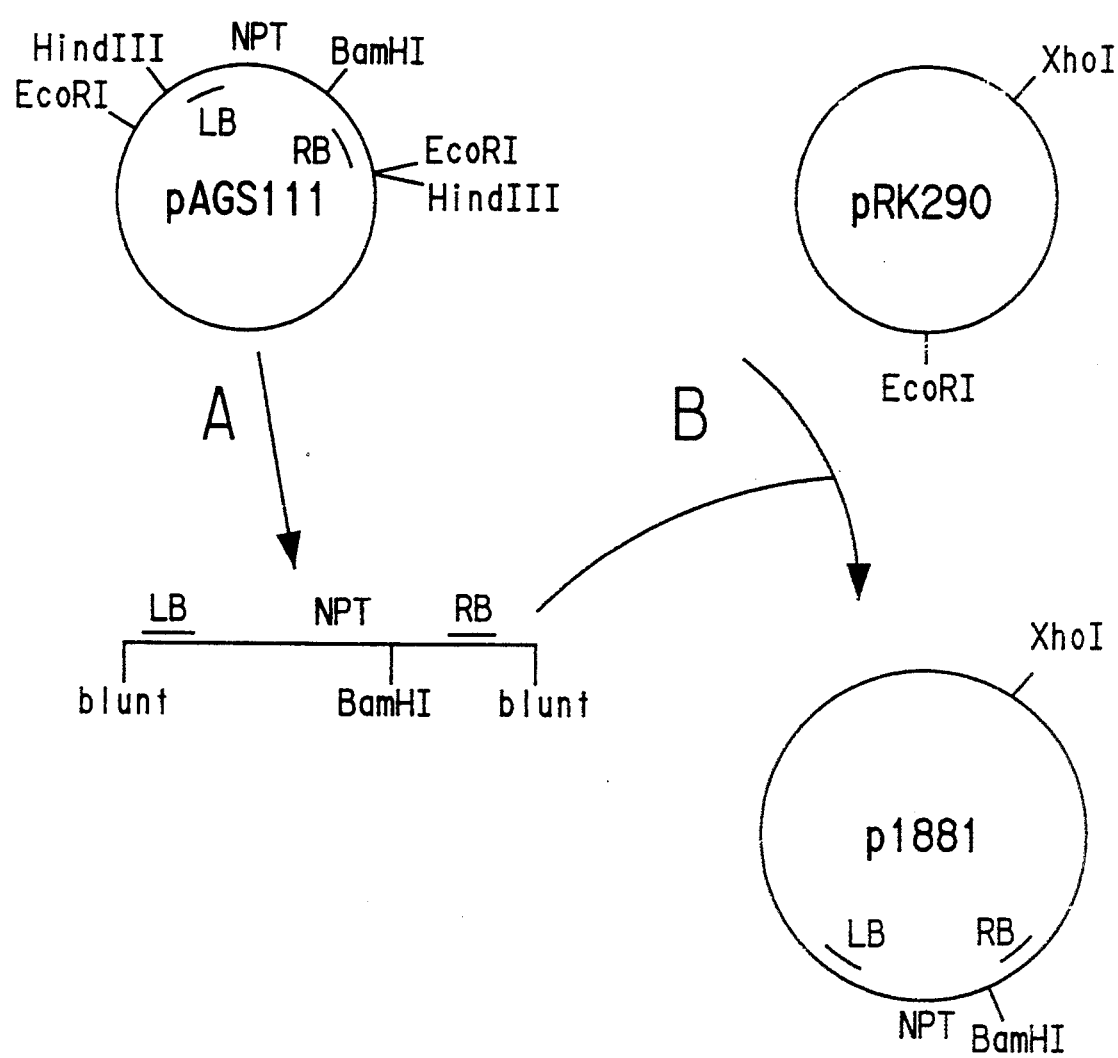
Figure 23B:
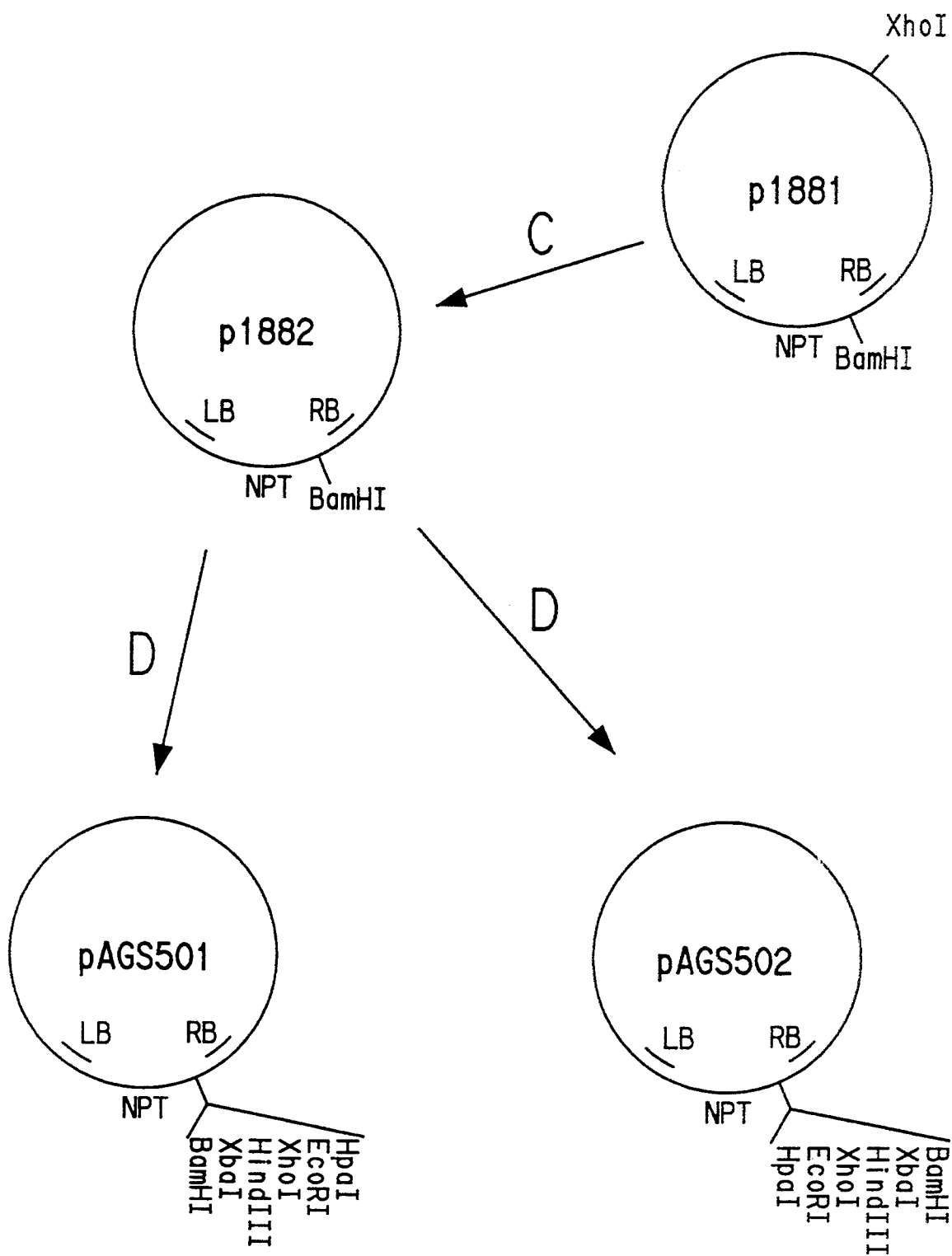

FIGS. 23A and 23B are diagrams showing the construction of plasmids pAGS501 and pAGS502.

FIG. 23A shows the construction of p1881. FIG. 23B shows the final steps of the construction of pAGS501 and pAGS502.

Figure 24A:
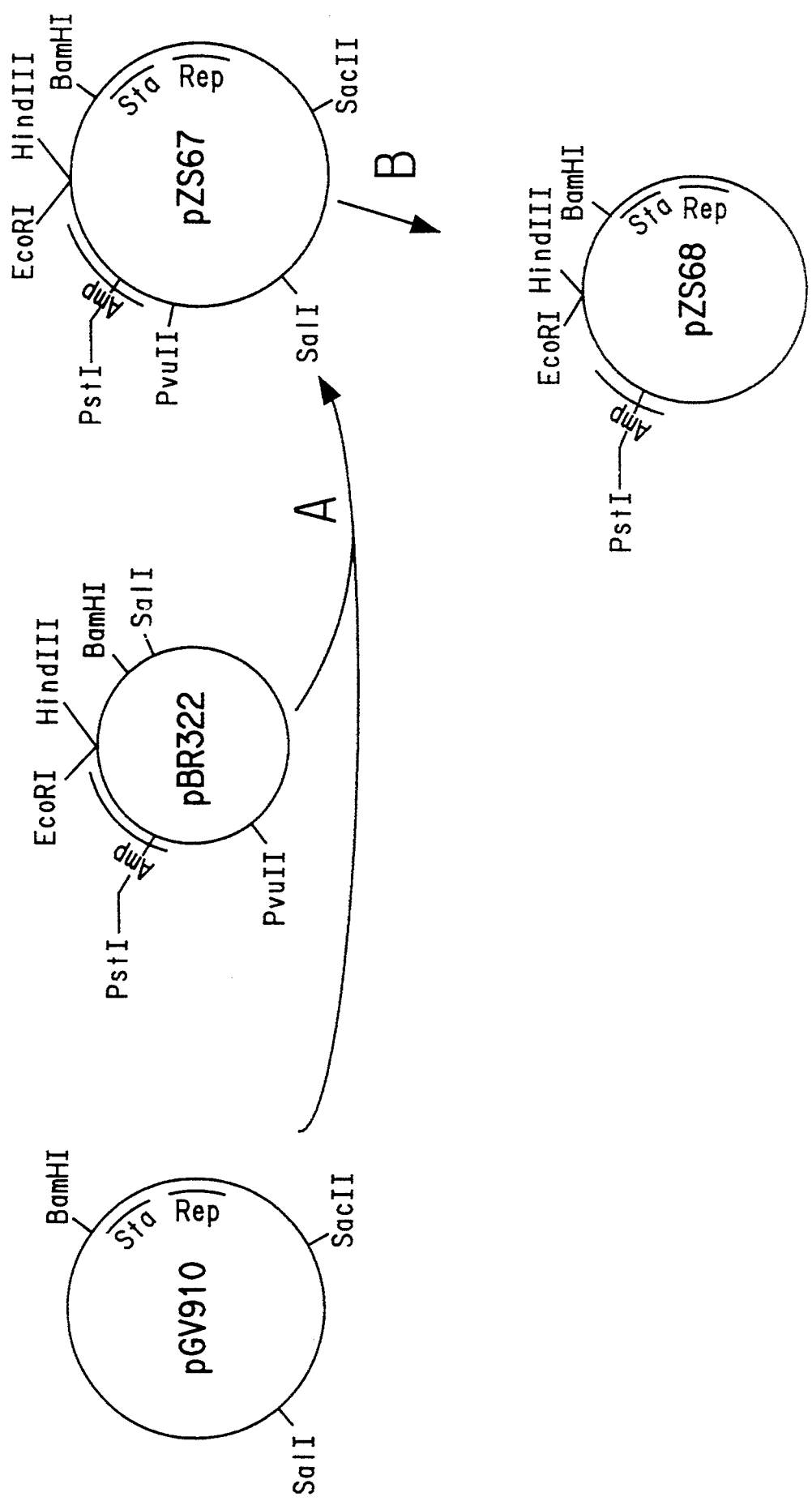
Figure 24B:
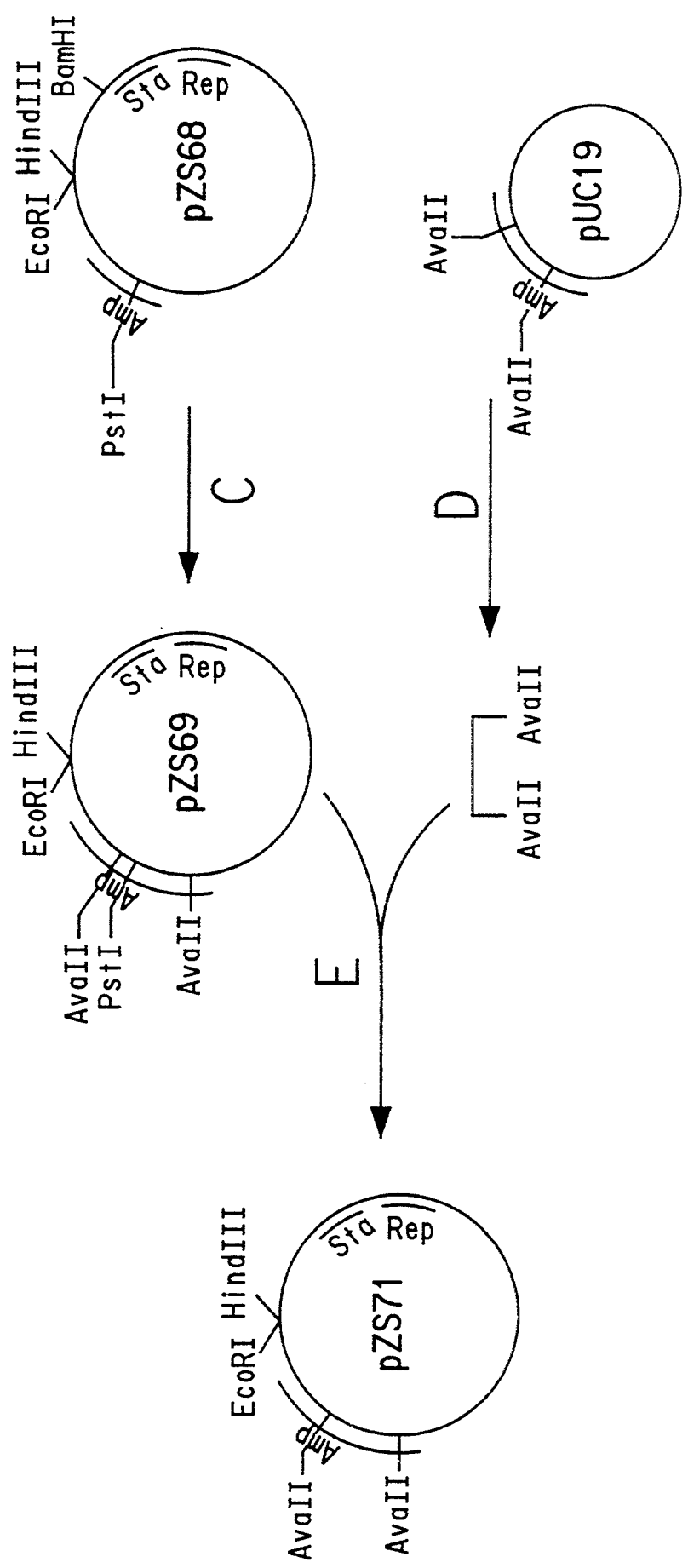

FIGS. 24A through 24B are diagrams showing the construction of plasmid pZ596.

Figure 24C:
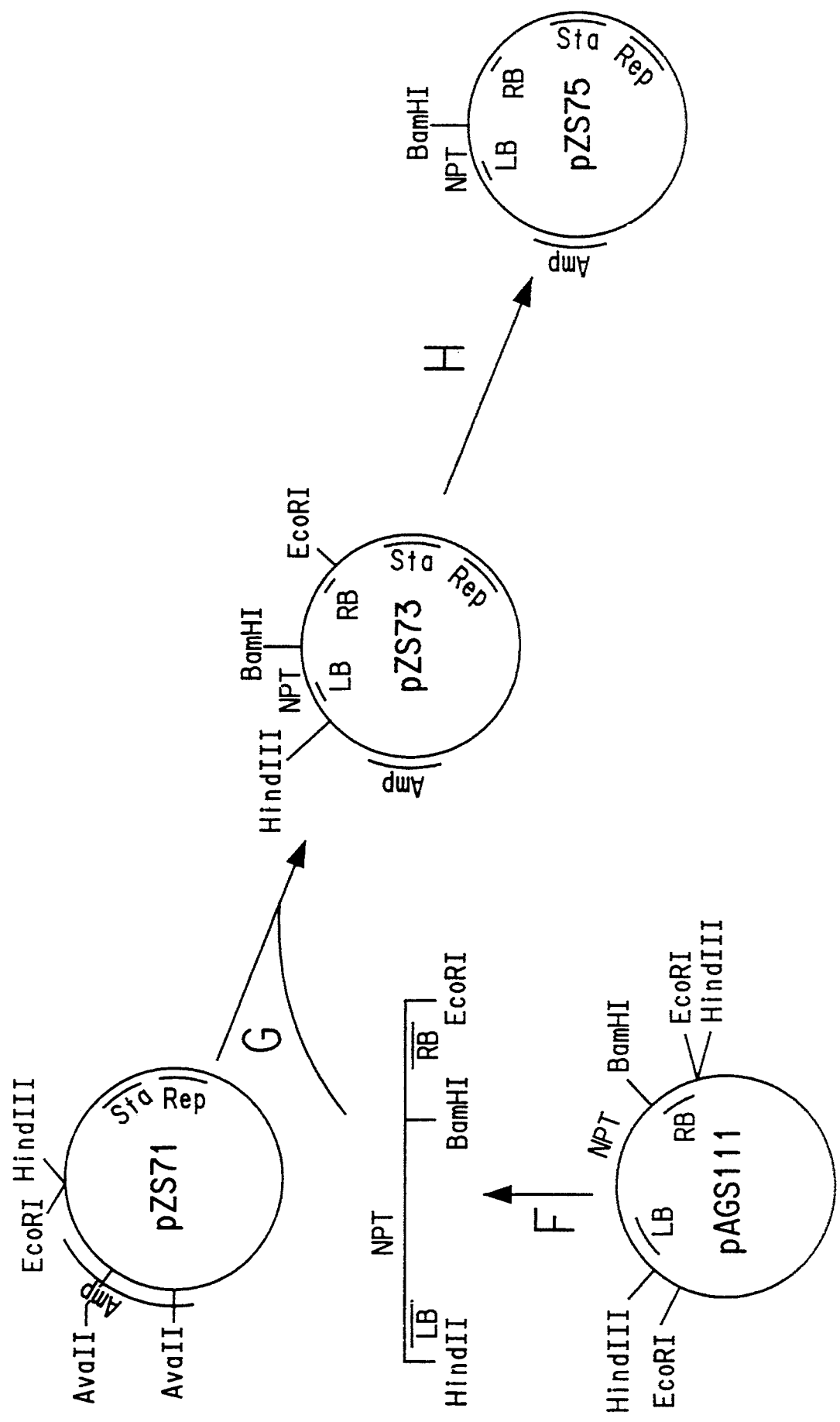
Figure 24D:
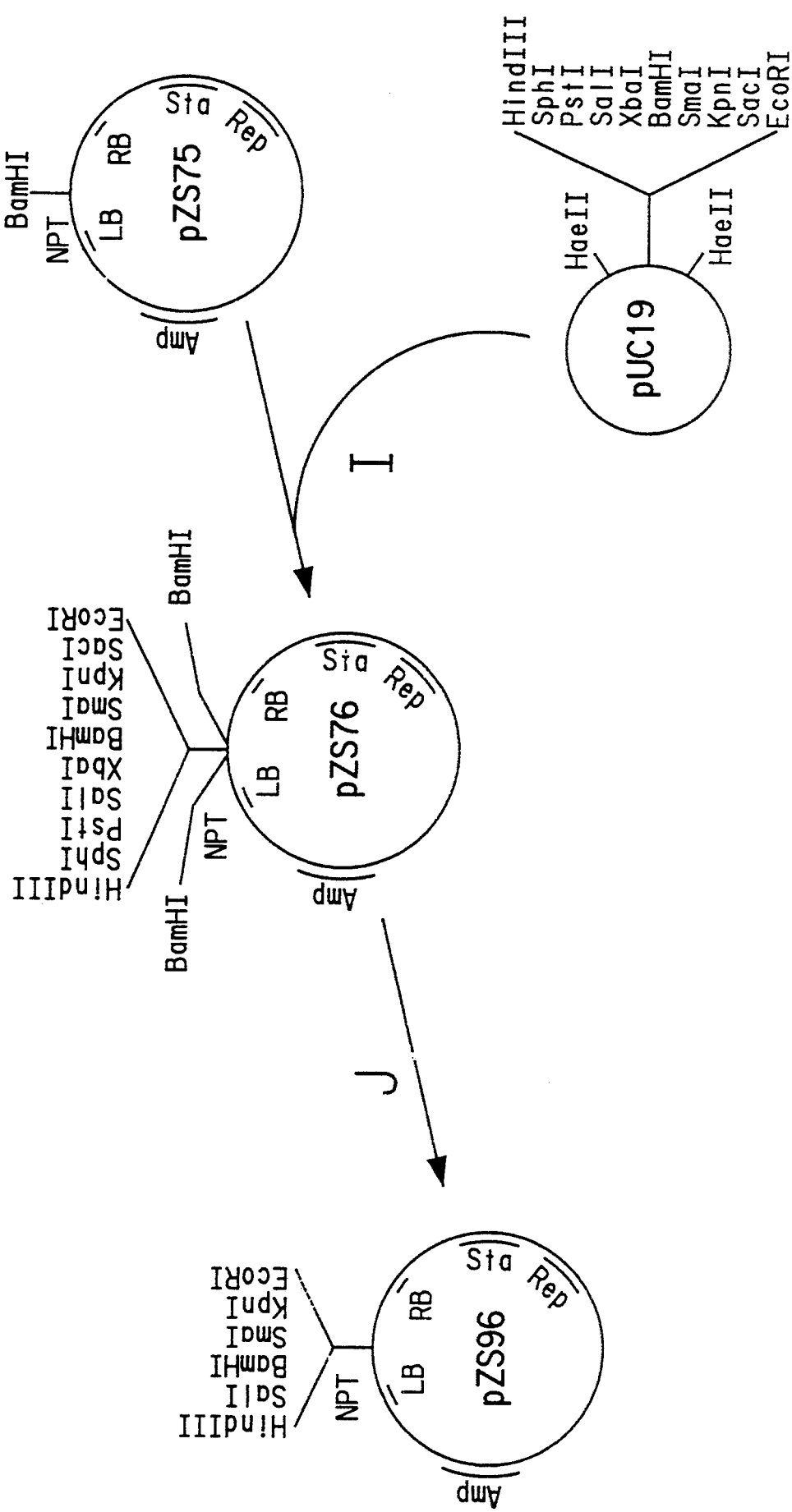

FIG. 24A shows the construction of pZS68. FIG. 24B shows the construction of pZS71. FIG. 24C shows the construction of pZS75. FIG. 24D shows the final step in the construction of pZS96.

Figure 25A:
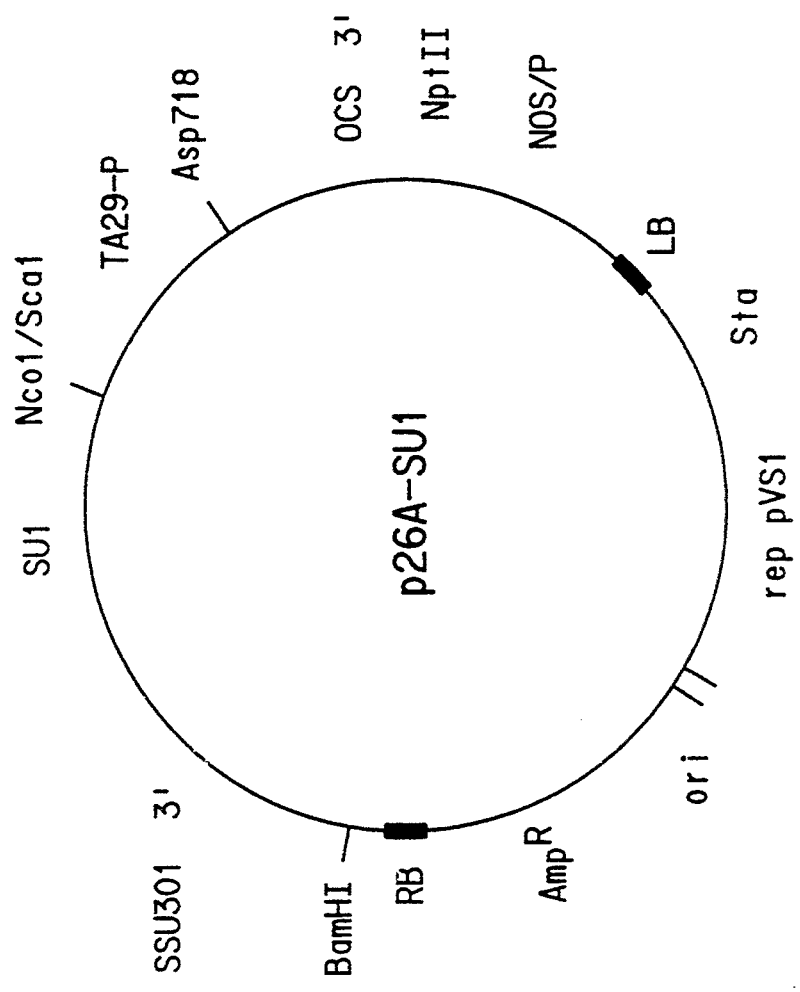

FIG. 25A is a physical map showing restriction endonuclease sites of plasmid pZ6A-SU1.

Figure 25B:
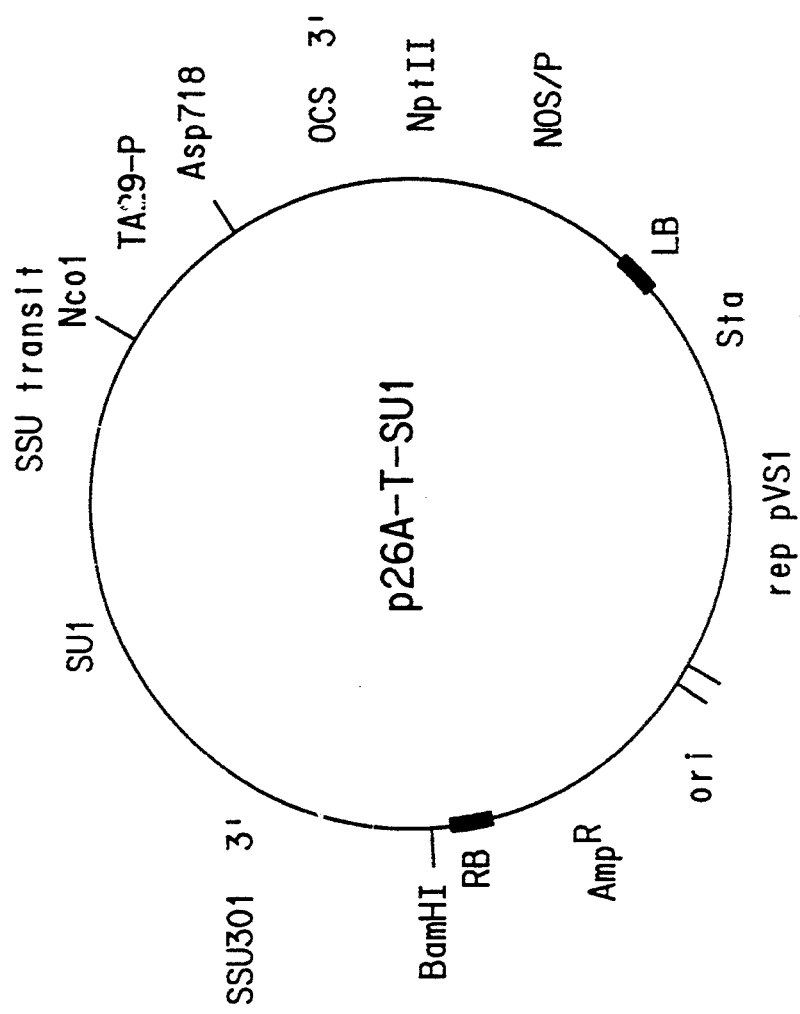

FIG. 25B is a physical map showing restriction endonuclease sites of plasmid pZ6AT-SU1.

In FIGS. 17 through 22, P450SU1 represents the coding sequence for the cytochrome P450SU1 enzyme; CaMV35Sp is the 35S promoter of CaMV; Cab2215' is the 5' untranslated sequence of petunia gene for Cab22L; SSU301 is the coding sequence for the petunia gene for SSU; SSU3' is the 3' untranslated sequence of the petunia gene for SSU301; SSUp is the promoter of the petunia SSU301 gene; SSU-T is the sequence coding for the chloroplast transit peptide of the petunia SSU301 protein; SSU-M is the sequence coding for the mature petunia SSU301 protein; Cabp is the promoter of the petunia Cab22L gene; CabT is the sequence coding chloroplast transit; CabM is the sequence coding mature protein of petunia Cab22L protein; FeS-B is the sequence coding for FeS-B; and nos 3' is the 3' untranslated region from nopaline synthase gene. In FIGS. 23A and 23B, AMP means ampicillin resistance in bacteria, LB means left border of T-DNA, RB denotes right border of T-DNA, and NPT denotes kanamycin resistance in plants.

DETAILS OF THE INVENTION

Definitions

PIPES:piperazine-N, N'-bis(2-ethanesulfonic acid)

MOPS: 3-(N-morpholino)propanesulfonic acid

ATCC: American Type Culture Collection depository located at 12301 Parklawn Drive, Rockville, Md. 20852.

HPLC: high performance liquid chromatography

UV: ultraviolet light

Cytochromes P450SU1 and P450SU2: the names assigned to the two cytochrome P450 enzymes of this invention.

FeS-A and FeS-B: the names assigned to the two iron-sulfur proteins of this invention.

10001: N-[(4-chloro-6-methoxy-pyrimidin-2-yl)aminocarbonyl]-2-ethoxycarbonylbenzenesulfonamide 10002: N-[(4-chloro-6-hydroxy-pyrimidin-2-yl)aminocarbonyl]-2-ethoxycarbonylbenzenesulfonamide 10003: N-[(4-chloro-6-methoxy-pyrimidin-2-yol)aminocarbonyl]-2-carboxybenzenesulfonamide 10004: 2-butyl-2,3-dihydro-N-[(4,6-dimethoxypyrimidin-2-yl)aminocarbonyl-1,2-benzisothiazole-7-sulfonamide-1,1-dioxide 10005: 2-(3-hydroxybutyl)-2,3-dihydro-N-[(4,6-dimethoxypyrimidin-2-yl)aminocarbonyl]1,2-benzisothiazole-7-sulfonamide-1,1-dioxide 10006: N-[(4-methoxy-6-methyl-1,3,5-triazinyl-)aminocarbonyl ]-2-methoxycarbonylbenzenesulfonamide 10007: N-[(4-hydroxy-6-methyl-1,3,5-triazinyl-)aminocarbonyl ]-2-methoxycarbonylbenzenesulfonamide 10008: N-[(4-methoxy-6-methyl-1,3,5-triazinyl-)aminocarbonyl ]-2-carboxybenzenesulfonamide 10009: N-[(4-methoxy-6-hydroxymethyl-1,3,5-triazinyl) aminocarbonyl]-2-methoxycarbonylbenzenesulfonamide 10010: N-[(4,6-dimethylpyrimidin-2-yl)aminocarbonyl]-2 -methoxycarbonylbenzenesulfonamide 10011: N-[(4-hydroxymethyl-6-methyl-pyrimidin-2-yl)aminocarbonyl]-2-methoxycarbonylbenzenesulfonamide 10012: N-[(4-carboxy-6-methylpyrimidin-2yl-)aminocarbonyl]-2-methoxycarbonylbenzenesulfonamide 10013: N-[(4-methoxy-6-methyl-1,3,5 triazinyl-)aminocarbonyl]-2-chlorobenzenesulfonamide 10014: 2,3-dihydro-N-[(4,6-dimethoxypyrimidin-yl)aminocarbonyl]-1,2-benzisothiazol-7-sulfonamide-1,1-dioxide 10015: 2-methylethyl-2,3-dihydro-N-[(4,6-dimethoxypyrimidin-2-yl)aminocarbonyl]-1,2-benzisothiazole-7-sulfonamide-1,1-dioxide 10016: N-[(4-methoxy-6-methylpyrimidin-2-yl)aminocarbonyl]-5-dimethylamino-1-napthalenesulfonamide 10017: 3-cyclohexyl-1-methyl-6-dimethylamino-S-triazine-2,4(1H,3H)dione 10018: 4-amino-6-tert-butyl-3-(methylthio)-AS-triazin-5(4H)-one 10019: 3-(3-chloro-p-tolyl)-1,1-dimethylurea 10020: 7-chloro-5-fluoro-4-(2,3,4,5,6,7-hexahydro-1,3-dioxo-1H-isoindol-2-yl)-2,3-dihydro-2-benzofurancarboxylic acid, methyl ester 10021: 2-[4-chloro-6-(ethylamino-1,3,5-triazin-2-yl)amino]-2-methylpropanenitrile 10022: 1-methyl-2(1H)-pyrimidinone 10023: 3,5-dibromo-4-hydroxybenzonitrile 10024: N-[(4,6-dimethoxypyrimidin-2-yl)aminocarbonyl]-2-ethyl-2,3-dihydro-1,2-benzisothiazole-7-sulfonamide-1,1-dioxide 10025: N-[(4,6-dimethoxypyrimidin-2-yl)aminocarbonyl]2,3-dihydro-2-(phenylmethyl)-1,2-benzisothiazole-7-sulfonamide-1,1-dioxide 10026: N-[(4,6-dimethoxypyrimidin-2-yl)aminocarbonyl]-2-(2 -fluoroethyl)-2,3-dihydro-1,2-benzisothiazole-7-sul fonamide-1,1-dioxide 10027: N-[(4,6-dimethoxypyrimidin-2-yl)aminocarbonyl]-2,3- dihydro-2-propyl-1,2-benzisothiazole-7-sulfonamide-1,1-dioxide 10028: N-[(4,6-dimethoxypyrimidin-2-yl)aminocarbonyl]-2,3-dihydro-2-(2-propenyl)-1,2-benzisothiazole-7-sulfonamide-1,1-dioxide 10029: N-[(4,6-dimethoxypyrimidin-2-yl)aminocarbonyl]-2-methyl-1,2-benzisothiazole-7-sulfonamide-1,1-dioxide 10030: N-[(4,6-dimethoxypyrimidin-2-yl)aminocarbonyl]-2,3-dihydro-2-(2-methylpropyl)-1,2-benzisothiazole-7-sulfonamide-1,1-dioxide 10031: 2-acetyl-N-[(4,6-dimethoxypyrimidin-2yl-)aminocarbonyl]-2,3-dihydro-1,2-benzisothiazole-7-sulfonamide-1,1-dioxide 10032: N-[(4,6-dimethoxypyrimidin-2-yl)aminocarbonyl]-2,3-dihydro-2-(trimethylsilylmethyl)-1,2-benzisothiazole-7-sulfonamide-1,1-dioxide 10033: N-(2-chloro-6-methylphenyl)-5,7-dimethyl-1,2,4-triazolo-1,5A-pyrimidine-2-sulfonamide 10034: 2-[(4,5-dihydro-4-methyl-4-(1-methylethyl)-1H-imidazol-2-yl)1-5-ethyl-3-pyridinecarboxylic acid 10035: 2-[4,5-dihydro-4-methyl-4-(1-methylethyl)-5-oxo-1H-imidazol-2-yl]-3-quinolinecarboxylic acid 10036: N-(2,6-dichlorophenyl)-4,6-dimethyl-2-pyrimidinesulfonamide In the context of this disclosure, a number of terms shall be utilized. As used herein, the terms "promoter" and "promoter region" refer to a sequence of DNA, usually upstream (5') to the protein coding sequence of a structural gene, which controls the expression of the coding region by providing the recognition for RNA polymerase and/or other factors required for transcription to start at the correct site. Promoter sequences are necessary but not always sufficient to drive the expression of the gene.

A "fragment" constitutes a fraction of the DNA sequence of the particular region.

"Nucleic acid" refers to a molecule which can be single stranded or double stranded, composed of monomers (nucleotides) containing a sugar, phosphate and either a purine or pyfimidine. In bacteria in higher plants, "deoxyribonucleic acid" (DNA) refers to the genetic material while "ribonucleic acid" (RNA) is involved in the translation of the information from DNA into proteins.

"Regulation" and "regulate" refer to the modulation of gene expression controlled by DNA sequence elements located primarily, but not exclusively upstream of (5' to) the transcription start of a gene. Regulation may result in an all or none response to a stimulation, or it may result in variations in the level of gene expression.

The term "coding sequence" refers to that portion of a gene encoding a protein, polypeptide, or a portion thereof, and excluding the regulatory sequences which drive the initiation of transcription. A coding sequence may be one normally found in the cell or it may be one not normally found in a cellular location wherein it is introduced, in which case it is termed a heterologous gene. A heterologous gene may be derived in whole or in part from any source known to the art, including a bacterial genome or episode, eukaryotic nuclear or plasmid DNA, cDNA, or chemically synthesized DNA. The coding sequence may constitute an uninterrupted coding region or it may include one or more introns bounded by appropriate splice junctions. The coding sequence may be a composite of segments derived from different sources, naturally occurring or synthetic.

A "3' downstream region" (or "3' end") refers to that portion of a gene comprising a DNA segment, excluding the 5' sequence, which drives the initiation of transcription and the coding sequence of the gene, that contain a polyadenylation signal in eukaryotes and any other regulatory Signals capable of affecting mRNA processing or gene expression. The polyadenylation signal in eukaryotes is usually characterized by affecting the addition of polyadenylic acid tracts to the 3' end of the mRNA precursor. Polyadenylation signals are commonly recognized by the presence of homology to the canonical form 5'-AATAAA-3', although variations are not uncommon.

The term "construction" or "construct" refers to a plasmid, virus, autonomously replicating sequence, phage or nucleotide sequence, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a plant cell.

As used herein, "plant" refers to whole plants and plant-derived tissues.

As used herein, "transformation" is the acquisition of new genes in a cell after the incorporation of nucleic acid (usually double stranded DNA).

The term, "operably linked" refers to the chemical fusion of two fragments of DNA in a proper orientation and reading frame to be transcribed into functional RNA.

The term "expression" as used herein is intended to mean the transcription and translation to gene product from a gene coding for the sequence of the gene product. In the expression, a DNA chain coding for the sequence of gene product is first transcribed to a complementary RNA which is often a messenger RNA and, then, the thus transcribed messenger RNA is translated into the above-mentioned gene product if the gene product is a protein.

The "translation initiation signal" refers to a unit of three nucleotides (codon) in a nucleic acid that specifies the initiation of protein synthesis.

The term "plasmid" as used herein refers to an extra chromosomal element often carrying genes which are not part of the central metabolism of the cell, and usually in the form of circular double-stranded DNA molecules.

The term "restriction endonuclease" refers to an enzyme which binds and cuts within a specific nucleotide sequence within double-stranded DNA.

The term "T-DNA" is the segment of DNA from a plasmid transferred from soil bacterium Agrobacterium to the genome of its plant host.

The techniques of DNA recombination used throughout this invention are known to those skilled in the art and are generally described in Maniatis et al., *Molecular Cloning.: A Laboratory Manual,* Cold Spring Harbor Laboratory, Cold Spring Harbor, N.Y., 1982).

Materials and General Methods

Restriction endonucleases, DNA polymerases, DNA ligase and other DNA modification enzymes were purchased from Bethesda Research Laboratories, Gaithersburg, MD 20877; New England Biolabs, Beverly, Mass. 01915; and Boehringer-Mannheim Biochemicals, Indianapolis, IN 46250.

Media

Media for growth of StreDtomvCeS cultures are YEME broth, sporulation broth, trypticase soy broth and minimal medium.

YEME broth consists of 340 g sucrose, 3.0 g yeast extract (Difco), 5.0 g peptone (Difco), 3.0 g malt extract broth (Oxoid) and 10 g glucose dissolved in water to 1 liter.

Sporulation broth consists of 1.0 g yeast extract (Difco), 1.0 g beef extract (Difco), 2.0 g tryptose (Difco), 10 g glucese and approximately 1 mg $FeSO_4$ dissolved in water to 1 liter.

Trypticase soy broth consists of 17.0 g pancreatic digest of casein, 3.0 g papaic digest of soybean meal, 5.0 g NaCl, 5.0 g $K_2HPO_4$, and 2.5 g glucose per liter of water.

Minimal medium consists of 0.5 g $K_2HPO_4$, 0.6 g L-asparagine, 0.3 g KOH, 0.4 g $MgSO_4.7H_2O$, 0.01 g $FeSO_4.7H_2O$, 3.07 g glycerol per liter of $H_2O$. To make solid medium, 15 g of agar is added per liter of medium.

Culturing of Streptomyces

Streptomyces cultures are grown in sporulation, YEME or trypticase soy broth at 30° C. with shaking at 150–300 rpm in an orbital shaker.

Harvesting bacterial cells

Bacterial cells are harvested by centrifuging them at 6,000–12,000×g for 10–20 minutes at 4° C. Cells are washed in 0.1M PIPES buffer pH 7.0 or 0.1M MOPS pH 7.2 and collected by again centrifuging them at 6,000–12,000×g for 10–20 minutes at 4° C.

Cell extracts

Cell extracts from Streptomyces are obtained by resuspending harvested cells in 1 to 3 cell volumes of 0.1M PIPES buffer pH 6.8–7.0 and disrupting them by means of a French pressure cell (20,000 psi). The cell debris is removed by centrifugation at 10,000–12,000×g for 10–20 minutes in a microcentrifuge at 4° C. The protein concentrations of each extract is quantitated using the method of Bradford (Anal. Biochem. 72: 247–254 (1976)).

Western blot analyses

Western blot analysis of proteins is performed by separating the proteins by SDS polyacrylamide gel electrophoresis (Laemmli, Nature 227: 680, 1970, herein incorporated by reference) and then transferring the proteins to nitrocellulose and detecting the protein of interest with antibody specific for the protein as described by Towbin et al., Proc. Natl. Acad. Sci. U.S.A. 76: 4350–4354 (1979) and Bio-Rad bulletin 885 85-0335. (Bio-Rad Laboratories, Richmond, CA 94804), each herein incorporated by reference. Antiserum to cytochrome P450SU1 was that described by O'Keefe et al., Recent Advances in Phytochemistry 21: 151–173 (1987), herein incorporated by reference. Antiserum to cytochrome P450SU2 was prepared as was that for P450SU1 except that cytochrome P450SU2 was isolated from S. griseolus PH2042, a mutant that does not make cytochrome P450SU1.

HPLC analysis of herbicide compounds

Herbicides and their metabolites are measured by HPLC as described by Romesser et al., BBRC 140: 650–659 (1986), herein incorporated by reference, except that 0.1% $H_3PO_4$ is used in both solvents. Chromatographic identity and quantitation of the herbicides and their resulting metabolites is determined by comparing them chromatographically with authentic standard compounds. Identity of the resulting metabolites is also confirmed by UV spectroscopy.

Isolation of S. griseolus mutants without P450SU1

Mutants of S. griseolus that do not make cytochrome P450SU1, but do make cytochrome P450SU2 were isolated by treating spores of S. griseolus ATCC 11796 with 2 mg/ml nitrosoguanidine for 30 minutes at room temperature. The mutagehized spores were diluted and plated on a rich medium and incubated at 30° C. until mature colonies had formed. Single colonies from these plates were then patched onto minimal medium. The colonies were incubated for several days, then, a soft agar overlay containing 20 mg/ml of the fluorescent sulfonylurea 10016 was poured over the plate followed by further incubation at 30° C. The plates were then viewed under short wave UV light. Large non-fluorescent zones were observed around a majority of the colonies that had metabolized the sulfonylurea. Those colonies which showed a reduced ability to metabolize 10016 (i.e., smaller non-fluorescent zones were observed) were considered potential mutants. A number of such colonies were isolated and found to make cytochrome P450SU2 but not cytochrome P450SU1. Three of these mutants, S. griseolus PH2001, PH2003 and PH2042, were used in the examples described below. These mutants have similar properties.

Amino acid sequencing

Cytochromes P450SU1 and P450SU2 were purified using the methods described by O'Keefe et al., Arch. Microbiol. 149: 406–412 (1988), herein incorporated by reference. Purified, native cytochromes P450SU1 and P450SU2 were reacted with iodoacetic acid to make the carboxymethyl-derivatives of each protein which were subsequently subjected to amino acid analysis and automated Edman degradation amino acid sequencing using methods well known to those skilled in the art (Methods of Protein Microcharacterization (1986), Humana Press, Inc., Clifton, N.J., J. E. Shively, ed., herein incorporated by reference). Two iron-sulfur proteins, FeS-A and FeS-B, which can be used in the reconstitution of cytochrome P450 enzymatic activity in the presence of cytochrome P450SU1 or P450SU2 and spinach ferredoxin:NADP oxidoreductase (commercially available) were purified from the same extracts of sulfonylurea induced S. griseolus cells used to purify cytochromes P450SU1 and P450SU2. The iron-sulfur proteins were collected as a single peak from the anion exchange column used in the P450 purification (O'Keefe et al., Arch Microbiol. 149: 406–412 (1988), herein incorporated by reference, and were detected by their spectral property of having nearly equal absorbance at both 460 nm and 420 nm. The iron-sulfur proteins isolated in this way were subsequently concentrated by ultrafiltration. Determination of the acid labile iron and sulfide content confirmed the proteins to be iron-sulfur proteins. Carboxymethylation of the iron sulfur proteins and reverse phase chromatography separated the iron-sulfur protein preparation into two separate apoproteins designated FeS-A and FeS-B which were subjected to amino acid analysis and automated Edman degradation amino acid sequencing using methods well known to those skilled in the art (Methods of Protein Microcharacterization (1986), Humana Press, Inc., Clifton, N.J., J. E. Shively, ed.). The amino terminal amino acid sequences and amino acid compositions of P450SU1, P450SU2, FeS-A, and FeS-B are shown below.

Amino terminal amino acid sequence of P450SU1

```
                          5                           10
NH2—Thr—Asp—Thr —Ala—Thr—Thr—Pro—Gln—Thr—Thr—Asp—Ala—Pro—
       15                     20                      25
   Ala—Phe—Pro—Val—Asn—Arg—Ser—Cys—Pro—Tyr—Gln—Leu—X—Asp—
                 30
   Gly—Tyr—Ala—Gln    (amino acid 17 may be serine)
```

Amino terminal amino acid sequence of P450SU2

```
                          5                           10
NH2—Thr—Thr—Ala—Glu—X—Thr—Ala—Pro—Pro—Asp—Ala—Leu—Thr—
       15                     20                      25
   Val—Pro—Ala—Ser—Arg—Ala—Pro—Gly—Cys—Pro—Phe—Asp—Pro—Ala—
                 30
   Pro—Asp—Val—Thr—Glu
```

Amino terminal amino acid sequence of FeS-A

```
                          5                           10
NH2—Met—Arg—Ile—His—Val—Asp—Gln—Asp—Lys—Cys—Cys—Gly—Ala—
       15                     20                      25
   Gly—Ser—Cys—Val—Leu—Ala—Ala—Pro—Asp—Val—Phe—Asp—Gln—Arg—
```

-continued

```
         30              35              40
Glu—Glu—Asp—Gly—Ile—Val—Val—Leu—Leu—Asp—Thr—Ala—Pro—Pro—
         43
Ala—Ala—
```

Amino terminal amino acid sequence of FeS-B

```
                          5                              10
NH2—Thr—Met—Arg—Val—Ser—Ala—Asp—Arg—Thr—Val—Cys—Val—Gly—
         15                      20                      25
Ala—Gly—Leu—Cys—Ala—Leu—Thr—Ala—Pro—Gly—Val—Phe—Asp—Gln—
         30                      35                      40
Asp—Asp—Asp—Gly—Ile—Val—Thr—Val—Leu—Thr—Ala—Glu—Pro—Ala—
         43
Ala—Asp—
```

| Amino acid compositions of cytochromes P450SU1, P450SU2, FeS-A, and FeS-B | | | | |
|---|---|---|---|---|
| | Mole % of each Amino Acid | | | |
| Amino Acid | P450SU1 | P450SU2 | FeS-A | FeS-B |
| Cys | 0.7 | 1.3 | 4.7 | 3.4 |
| Asx | 9.5 | 9.0 | 12.5 | 13.2 |
| Thr | 6.7 | 7.3 | 6.0 | 9.8 |
| Ser | 4.3 | 3.3 | 1.6 | 2.9 |
| Glx | 11.4 | 9.2 | 8.2 | 7.9 |
| Pro | 6.7 | 6.9 | 6.5 | 4.3 |
| Gly | 7.8 | 7.1 | 4.9 | 9.0 |
| Ala | 11.4 | 12.3 | 18.9 | 14.7 |
| Val | 7.8 | 6.9 | 10.8 | 12.3 |
| Met | 1.7 | 1.9 | 1.2 | 1.2 |
| Ile | 3.1 | 3.3 | 5.7 | 1.1 |
| Leu | 11.4 | 11.8 | 6.7 | 6.2 |
| Tyr | 1.9 | 0.9 | 0 | 0 |
| Phe | 3.1 | 3.1 | 1.6 | 1.5 |
| His | 2.6 | 2.4 | 3.0 | 1.4 |
| Lys | 1.4 | 1.2 | 1.7 | 0.3 |
| Trp | 0.5 | 0.5 | 0 | 0 |
| Arg | 8.1 | 11.6 | 6.1 | 10.9 |

Cloning the genes for cytochrome P450SU1, cytochrome P450SU2, FeS-A and FeS-B from Streptomyces griseolus ATCC11796

DNA encoding the gene for cytochrome P450SU1 was cloned from S. griseolus DNA. Bacteriophages containing the proper sequences of DNA were obtained by first identifying clones of transformed E. coli that expressed the SU1 protein. This was done by using antibody specific for cytochrome P450SU1 as described by O'Keefe et al., Recent Advances in Phytochemistry 21: 151–173 (1987), using methods well known to those skilled in the art (Young et el., Proc. Natl. Acad. Sci. U.S.A. 80: 1194–1198 (1983) and Young et al., Science 222: 778–782 (1983)), each of which is herein incorporated by reference). Restriction endonuclease maps (Maniatis et al., Molecular Cloning: a Laboratory Manual, Cold Spring Harbor Press, Cold Spring Harbor, N.Y.) were made of the isolated S. griseolus DNA and they indicated that a 2.4 kb BamHI restriction endonuclease fragment should contain the complete cytochrome P450SU1 coding sequence. This 2.4 kb restriction endonuclease fragment was cloned from S. griseolus DNA into the plasmid pUC18 using methods well known to those skilled in the art (Maniatis et al., Molecular Cloning: a Laboratory Manual, Cold Spring Harbor Press, Cold Spring Harbor, N.Y.; Frischauf et al.,J. Mol. Biol. 170: 827–842 (1983), each herein incorporated by reference), to make the plasmid pUC18-SU1-BamHI. Subsequent DNA sequence analysis, shown below, indicated that the coding sequence for the FeS-B protein is also encoded on this 2.4 kb BamHI fragment, being just downstream from the sequence for SU1. The plasmid pUC18-SU1-BamHI has been deposited in the American Type Culture collection and has ATCC accession number 67780. A restriction endonuclease map of pUC18-SU1-BamHI is shown in FIG. 1.

Figure 4:
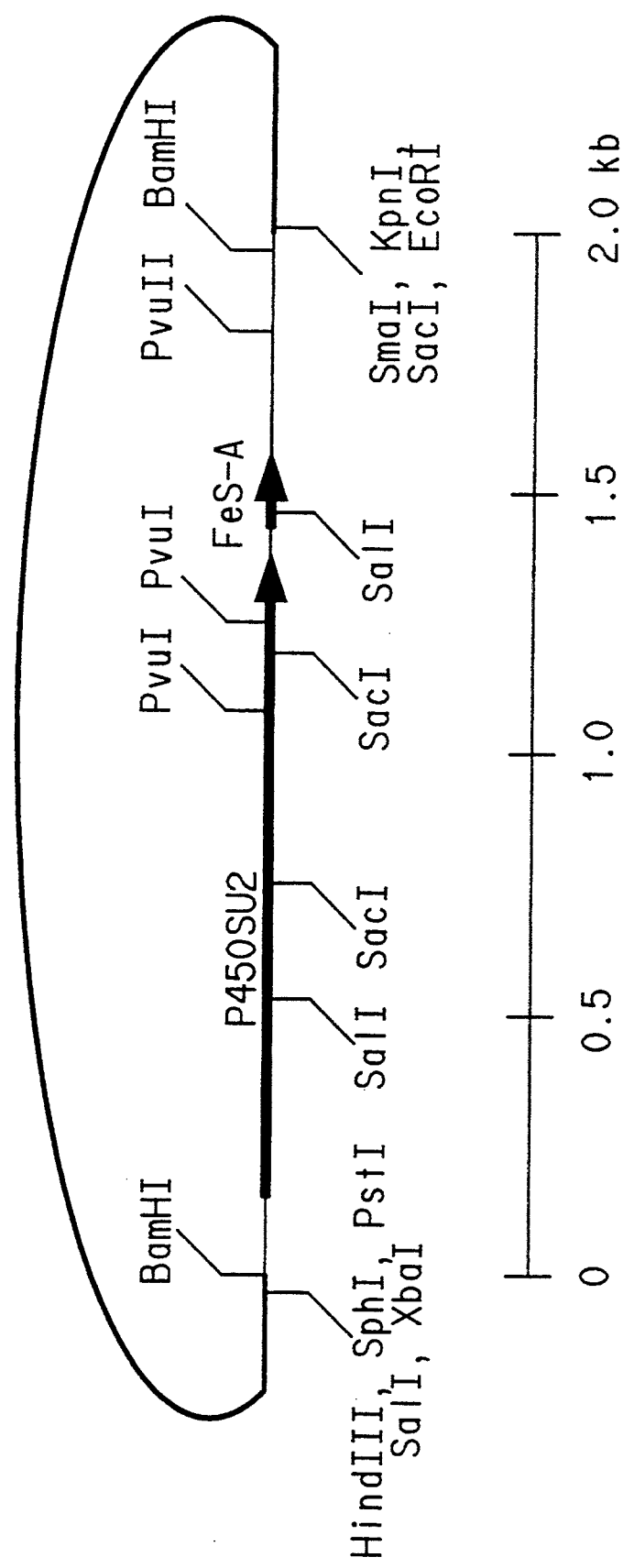
FIG. 4 is a physical map, showing restriction endonuclease sites, of plasmid pUC19-SU2-8.

A 2.0 kb BamHI restriction endonuclease DNA fragment that cross-hybridized to the 2.4 kb BamHI fragment encoding cytochrome P450SU1 and FeS-B and which encodes cytochrome P450SU2 and FeS-A was obtained from S. griseolus mutant PH2001 and cloned using methods well known to those skilled in the art (Maniatis et al., Molecular Cloning: a Laboratory Manual, Cold Spring Harbor Press, Cold Spring Harbor, N.Y.). The 2.0 kb BamHI fragment was shown to encode both cytochrome P450SU2 and FeS-A as determined by DNA sequence analysis of the DNA. The 2.0 kb BamHI DNA fragment was subcloned into the plasmid pUC19 in E. coli and is called pUC19-SU2-8 and has been deposited in the American Type Culture collection and has ATCC accession number 67781. A restriction endonuclease map of pUC19-SU2-8 is shown in FIG. 4.

The DNA sequence of cytochrome P450SU1 and FeS-B protein genes

By further restriction endonuclease mapping, it was determined that a 2.0 kb SacI-BamHI fragment of DNA derived from the 2.4 kb BamHI fragment in pUC18-SU1-BamHI contains the complete DNA coding sequence for the cytochrome P450SU1 and FeS-B proteins. That the 2.0 kb fragment contains the complete DNA coding sequence for the cytochrome P450SU1 and FeS-B proteins was determined by comparing all possible proteins encoded by the DNA sequence of the fragment with the molecular weight, amino acid composition, and N-terminal amino acid sequences of P-450SU 1 and the amino acid composition of N-terminal amino acid sequence of FeS-B, as shown above. The DNA sequence of the 2.0 kb SacI-BamHI fragment was determined from about 100 bp downstream of the SacI site through the BamHI site using methods well known to those skilled-in the art (Messing, Methods in Enzymology 101: 20–78 (1983), herein incorporated by reference), and is shown as follows with the coding sequences of cytochrome P450SU1 and FeS-B, which start at base no. 128 and end at base no. 1578, indicated.

DNA Sequence of the DNA Containing the Coding Sequences for Cytochrome P450SU1 and FeS-B

```
              10                      30
GCGGACAGGGGGACTCCTGAAGATGTCTGATAGAGGCCGTTGCGTTCTCTACGGGGGCAA
----------+---------+---------+---------+---------+---------+
```

-continued

```
          CGCCTGTCCCCCTGAGGACTTCTACAGACTATCTCCGGCAACGCAAGAGATGCCCCCGTT 70                  90                 110
    GTCTATGCTCCGAAATAGAGAACATGGCGTTCTTTAAAGGTGAGAATTCTTGAATCGGAG
    ---------+---------+---------+---------+---------+---------+
    CAGATACGAGGCTTTATCTCTTGTACCGCAAGAAATTTCCACTCTTAAGAACTTAGCCTC
                                    EcoRI 130                 150                170
    TGGACCGATGACCGATACCGCCACGACGCCCCAGACCACGGACGCACCCGCCTTCCCGAG
    ---------+---------+---------+---------+---------+---------+
    ACCTGGCTACTGGCTATGGCGGTGCTGCGGGGTCTGGTGCCTGCGTGGGCGGAAGGGCTC
P450SU1    Met Thr Asp Thr Ala Thr Thr Pro Gln Thr Thr Asp Ala Pro Ala Phe Pro Se
Start 190                 210                230
    CAACCGGAGCTGTCCCTACCAGTTACCGGACGGCTACGCCCAGCTCCGGGACACCCCCGG
    ---------+---------+---------+---------+---------+---------+
    GTTGGCCTCGACAGGGATGGTCAATGGCCTGCCGATGCGGGTCGAGGCCCTGTGGGGGCC
    r Asn Arg Ser Cys Pro Tyr Gln Leu Pro Asp Gly Tyr Ala Gln Leu Arg Asp Thr Pro Gl 250                 270                290
    CCCCCTGCACCGGGTGACGCTCTACGACGGCCGTCAGGCGTGGGTGGTGACCAAGCACGA
    ---------+---------+---------+---------+---------+---------+
    GGGGGACGTGGCCCACTGCGAGATGCTGCCGGCAGTCCGCACCCACCACTGGTTCGTGCT
    y Pro Leu His Arg Val Thr Leu Tyr Asp Gly Arg Gln Ala Trp Val Val Thr Lys His Gl 310                 330                350
    GGCCGCGCGCAAACTGCTCGGCGACCCCCGGCTGTCCTCCAACCGGACGGACGACAACTT
    ---------+---------+---------+---------+---------+---------+
    CCGGCGCGCGTTTGACGAGCCGCTGGGGGCCGACAGGAGGTTGGCCTGCCTGCTGTTGAA
    u Ala Ala Arg Lys Leu Leu Gly Asp Pro Arg Leu Ser Ser Asn Arg Thr Asp Asp Asn Ph 370                 390                410
    CCCCGCCACGTCACCGCGCTTCGAGGCCGTCCGGGAGAGCCCGCAGGCGTTCATCGGCCT
    ---------+---------+---------+---------+---------+---------+
    GGGGCGGTGCAGTGGCGCGAAGCTCCGGCAGGCCCTCTCGGGCGTCCGCAAGTAGCCGGA
    e Pro Ala Thr Ser Pro Arg Phe Glu Ala Val Arg Glu Ser Pro Gln Ala Phe Ile Gly Le 430                 450                470
    GGACCCGCCCGAGCACGGCACCCGGCGGATGACGATCAGCGAGTTCACCGTCAAGCG
    ---------+---------+---------+---------+---------+---------+
    CCTGGGCGGGCTCGTGCCGTGGGCCGCCGCCTACTGCTAGTCGCTCAAGTGGCAGTTCGC
    u Asp Pro Pro Glu His Gly Thr Arg Arg Arg Met Thr Ile Ser Glu Phe Thr Val Lys Ar 490                 510                530
    GATCAAGGGCATGCGCCCCGAGGTCGAGGAGGTGGTGCACGGCTTCCTCGACGAGATGCT
    ---------+---------+---------+---------+---------+---------+
    CTAGTTCCCGTACGCGGGGCTCCAGCTCCTCCACCACGTGCCGAAGGAGCTGCTCTACGA
    g Ile Lys Gly Met Arg Pro Glu Val Glu Glu Val Val His Gly Phe Leu Asp Glu Met Le 550                 570                590
    GGCCGCCGGCCCGACCGCCGACCTGGTCAGTCAGTTCGCGCTGCCGGTGCCCTCCATGGT
    ---------+---------+---------+---------+---------+---------+
    CCGGCGGCCGGGCTGGCGGCTGGACCAGTCAGTCAAGCGCGACGGCCACGGGAGGTACCA
    u Ala Ala Gly Pro Thr Ala Asp Leu Val Ser Gln Phe Ala Leu Pro Val Pro Ser Met Va 610                 630                650
    GATCTGCCGACTCCTCGGCGTGCCCTACGCCGACCACGAGTTCTTCCAGGACGCGAGCAA
    ---------+---------+---------+---------+---------+---------+
    CTAGACGGCTGAGGAGCCGCACGGGATGCGGCTGGTGCTCAAGAAGGTCCTGCGCTCGTT
    l Ile Cys Arg Leu Leu Gly Val Pro Tyr Ala Asp His Glu Phe Phe Gln Asp Ala Ser Ly 670                 690                710
    GCGGCTGGTGCAGTCCACGGACGCGCAGAGCGCGCTCACCGCGCGGAACGACCTCGCGGG
    ---------+---------+---------+---------+---------+---------+
    CGCCGACCACGTCAGGTGCCTGCGCGTCTCGCGCGAGTGGCGCGCCTTGCTGGAGCGCCC
    s Arg Leu Val Gln Ser Thr Asp Ala Gln Ser Ala Leu Thr Ala Arg Asn Asp Leu Ala Gl 730                 750                770
    TTACCTGGACGGCCTCATCACCCAGTTCCAGACCGAACCGGGCGCGGGCCTGGTGGGCGC
    ---------+---------+---------+---------+---------+---------+
    AATGGACCTGCCGGAGTAGTGGGTCAAGGTCTGGCTTGGCCCGCGCCCGGACCACCCGCG
    y Tyr Leu Asp Gly Leu Ile Thr Gln Phe Gln Thr Glu Pro Gly Ala Gly Leu Val Gly Al 790                 810                830
    TCTGGTCGCCGACCAGCTGGCCAACGGCGAGATCGACCGTGAGGAACTGATCTCCACCGC
    ---------+---------+---------+---------+---------+---------+
    AGACCAGCGGCTGGTCGACCGGTTGCCGCTCTAGCTGGCACTCCTTGACTAGAGGTGGCG
    a Leu Val Ala Asp Gln Leu Ala Asn Gly Glu Ile Asp Arg Glu Glu Leu Ile Ser Thr Al
```

-continued

```
                  850                          870                           890
GATGCTGCTCCTCATCGCCGGCCACGAGACCACGGCCTCGATGACCTCCCTCAGCGTGAT
---------+---------+---------+---------+---------+---------+
CTACGACGAGGAGTAGCGGCCGGTGCTCTGGTGCCGGAGCTACTGGAGGGAGTCGCACTA
a Met Leu Leu Leu Ile Ala Gly His Glu Thr Thr Ala Ser Met Thr Ser Leu Ser Val Il 910                          930                           950
CACCCTGCTGGACCACCCCGAGCAGTACGCCGCCCTGCGCGCCGACCGCAGCCTCGTGCC
---------+---------+---------+---------+---------+---------+
GTGGGACGACCTGGTGGGGCTCGTCATGCGGCGGGACGCGCGGCTGGCGTCGGAGCACGG
e Thr Leu Leu Asp His Pro Glu Gln Tyr Ala Ala Leu Arg Ala Asp Arg Ser Leu Val Pr 970                          990                          1010
CGGCGCGGTGGAGGAACTGCTCCGCTACCTCGCCATCGCCGACATCGCGGGCGGCCGCGT
---------+---------+---------+---------+---------+---------+
GCCGCGCCACCTCCTTGACGAGGCGATGGAGCGGTAGCGGCTGTAGCGCCCGCCGGCGCA
o Gly Ala Val Glu Glu Leu Leu Arg Tyr Leu Ala Ile Ala Asp Ile Ala Gly Gly Arg Va 1030                         1050                          1070
CGCCACGGCGGACATCGAGGTCGAGGGGCACCTCATCCGGGCCGGCGAGGGCGTGATCGT
---------+---------+---------+---------+---------+---------+
GCGGTGCCGCCTGTAGCTCCAGCTCCCCGTGGAGTAGGCCCGGCCGCTCCCGCACTAGCA
l Ala Thr Ala Asp Ile Glu Val Glu Gly His Leu Ile Arg Ala Gly Glu Gly Val Ile Va 1090                         1110                          1130
CGTCAACTCGATAGCCAACCGGGACGGCACGGTGTACGAGGACCCGGACGCCCTCGACAT
---------+---------+---------+---------+---------+---------+
GCAGTTGAGCTATCGGTTGGCCCTGCCGTGCCACATGCTCCTGGGCCTGCGGGAGCTGTA
l Val Asn Ser Ile Ala Asn Arg Asp Gly Thr Val Tyr Glu Asp Pro Asp Ala Leu Asp Il 1150                         1170                          1190
CCACCGCTCCGCGCGCCACCACCTCGCCTTCGGCTTCGGCGTGCACCAGTGCCTGGGCCA
---------+---------+---------+---------+---------+---------+
GGTGGCGAGGCGCGCGGTGGTGGAGCGGAAGCCGAAGCCGCACGTGGTCACGGACCCGGT
e His Arg Ser Ala Arg His His Leu Ala Phe Gly Phe Gly Val His Gln Cys Leu Gly Gl 1210                         1230                          1250
GAACCTCGCCCGGCTGGAGCTGGAGGTCATCCTCAACGCCCTCATGGACCGCGTCCCGAC
---------+---------+---------+---------+---------+---------+
CTTGGAGCGGGCCGACCTCGACCTCCAGTAGGAGTTGCGGGAGTACCTGGCGCAGGGCTG
n Asn Leu Ala Arg Leu Glu Leu Glu Val Ile Leu Asn Ala Leu Met Asp Arg Val Pro Th 1270                         1290                          1310
GCTGCGACTGGCCGTCCCCGTCGAGCAGTTGGTGCTGCGGCCGGGTACGACGATCCAGGG
---------+---------+---------+---------+---------+---------+
CGACGCTGACCGGCAGGGGCAGCTCGTCAACCACGACGCCGGCCCATGCTGCTAGGTCCC
r Leu Arg Leu Ala Val Pro Val Glu Gln Leu Val Leu Arg Pro Gly Thr Thr Ile Gln Gl 1330                         1350                          1370
CGTCAACGAACTCCCGGTCACCTGGTGACGGGGGAGAGGGGCAAGGACATGACCATGCGG
---------+---------+---------+---------+---------+---------+
GCAGTTGCTTGAGGGCCAGTGGACCACTGCCCCCTCTCCCCGTTCCTGTACTGGTAGGCC
y Val Asn Glu Leu Pro Val Thr Trp End      FeS-B    Start    Met Thr Met Arg 1390                         1410                          1430
GTGAGTGCGGATCGGACGGTCTGCGTCGGTGCCGGGCTGTGTGCGCTGACGGCGCCGGGC
---------+---------+---------+---------+---------+---------+
CACTCACGCCTAGCCTGCCAGACGCAGCCACGGCCCGACACACGCGACTGCCGCGGCCCG
Val Ser Ala Asp Arg Thr Val Cys Val Gly Ala Gly Leu Cys Ala Leu Thr Ala Pro Gly 1450                         1470                          1490
GTCTTCGACCAGGACGACGACGGGATCGTCACGGTGCTGACGGCCGAACCCGCCGCCGAC
---------+---------+---------+---------+---------+---------+
CAGAAGCTGGTCCTGCTGCTGCCCTAGCAGTGCCACGACTGCCGGCTTGGGCGGCGGCTG
Val Phe Asp Gln Asp Asp Asp Gly Ile Val Thr Val Leu Thr Ala Glu Pro Ala Ala Asp 1510                         1530                          1550
GACGACCGGCGCACCGCGCGCGAGGCCGGCCATCTCTGTCCGTCCGGTGCGGTCCGCGTC
---------+---------+---------+---------+---------+---------+
CTGCTGGCCGCGTGGCGCGCGCTCCGGCCGGTAGAGACAGGCAGGCCACGCCAGGCGCAG
Asp Asp Arg Arg Thr Ala Arg Glu Ala Gly His Leu Cys Pro Ser Gly Ala Val Arg Val 1570                         1590                          1610
GTCGAGGACACGGAATAGGGTCAAGGACACGGAACAGGCGAGCGGGGATTCCGGCCGTCG
---------+---------+---------+---------+---------+---------+
CAGCTCCTGTGCCTTATCCCAGTTCCTGTGCCTTGTCCGCTCGCCCCTAAGGCCGGCAGC
Val Glu Asp Thr Glu End 1630                         1650                          1670
GCCGGGGCGGTCTCCGGCCGACGGGCTGGGGCCGCCCGCGGTGCCGCCGCGCAGGCGAGG
```

```
                                                                                                    -continued
- - - - - - - - +- - - - - - - - - +- - - - - - - - - +- - - - - - - - - +- - - - - - - - - +- - - - - - - - - +
CGGCCCCGCCAGAGGCCGGCTGCCCGACCCCGGCGGGCGCCACGGCGGCGCGTCCGCTCC 1690                1710                1730
CCGCCGGTGGCGCCCGGCACCCGCGGCGGCCGTCAGATCCACCCCTTCCGCGCCGCGTAC
- - - - - - - - +- - - - - - - - - +- - - - - - - - - +- - - - - - - - - +- - - - - - - - - +- - - - - - - - - +
GGCGGCCACCGCGGGCCGTGGGCGCCGCCGGCAGTCTAGGTGGGGAAGGCGCGGCGCATG 1750                1770                1790
AGAGCGAGTTGGAAACGGGTGGTGGCGTCGGCGGCGCGGTTGAGCTGCTCCAACTGGCGG
- - - - - - - - +- - - - - - - - - +- - - - - - - - - +- - - - - - - - - +- - - - - - - - - +- - - - - - - - - +
TCTCGCTCAACCTTTGCCCACCACCGCAGCCGCCGCGCCAACTCGACGAGGTTGACCGCC 1810                1830                1850
GAGAGGGTGCGTCGACTGATGCCGAGCAGTTCGGCGATGGTCTCGTCCGTGACGCCGCTC
- - - - - - - - +- - - - - - - - - +- - - - - - - - - +- - - - - - - - - +- - - - - - - - - +- - - - - - - - - +
CTCTCCCACGCAGCTGACTACGGCTCGTCAAGCCGCTACCAGAGCAGGCACTGCGGCGAG 1870
CCCAGCAGCTCCAGGATCC
- - - - - - - - +- - - - - - - - -
GGGTCGTCGAGGTCCTAGG
                 BamHI
```

DNA Sequence of the cytochrome P450SU2 and FeS-A protein genes

The DNA sequence of the 2.0 kb BamHI fragment isolated from *S. griseolus* transformed with the plasmid pUC19-SU2-8 that contains the genes for cytochrome P450SU2 and the iron sulfur protein FeS-A was determined by methods well known to those skilled in the art and described by Messing, Methods in Enzymology 101: 20–78 (1983). That the 2.0 kb BamHI DNA fragment encodes cytochrome P450SU2 and FeS-A was determined by comparing all possible proteins encoded by the DNA sequence to the known size, amino acid composition, and amino terminal amino acid sequence of P450SU2 and the known amino acid composition and amino terminal amino acid sequence of FeS-A. The DNA sequence of the fragment ts shown as follows and the locations of the coding sequence for cytochrome P450SU2 and FeS-A, which start at base no. 195 and end at base no. 1646 are indicated.

DNA Sequence of the 2.0 kilobase BamHI DNA Fragment Containing the Coding Sequences for Cytochrome P450SU2 and FeS-A

```
             10                  30                  50
GGATCCGGCCACCGCCCGACCCGTCCGCACTCCGCCCCGCCGACCGTCGTCCATCCGCCC
- - - - - - - - +- - - - - - - - - +- - - - - - - - - +- - - - - - - - - +- - - - - - - - - +- - - - - - - - - +
CCTAGGCCGGTGGCGGGCTGGGCAGGCGTGAGGCGGGGCGGCTGGCAGCAGGTAGGCGGG
BamHI 70                  90                  110
CTGCGGCCATGCGGTTTGAGCCAACCTCGGTGCTGCCGCGATCTGCCCTTCCCTCCCCCG
- - - - - - - - +- - - - - - - - - +- - - - - - - - - +- - - - - - - - - +- - - - - - - - - +- - - - - - - - - +
GACGCCGGTACGCCAAACTCGGTTGGAGCCACGACGGCGCTAGACGGGAAGGGAGGGGGC 130                 150                 170
CCGGGCCTGCGTTAGCGTGACGACATCTTAATTACCTAAGTTAGGTAATTAGCTCACGCG
- - - - - - - - +- - - - - - - - - +- - - - - - - - - +- - - - - - - - - +- - - - - - - - - +- - - - - - - - - +
GGCCCGGACGCAATCGCACTGCTGTAGAATTAATGGATTCAATCCATTAATCGAGTGCGC 190                 210                 230
GAAGGACCGGCCGCATGACGACCGCAGAACGCACCGCTCCCCCCGACGCCCTCACCGTCC
- - - - - - - - +- - - - - - - - - +- - - - - - - - - +- - - - - - - - - +- - - - - - - - - +- - - - - - - - - +
CTTCCTGGCCGGCGTACTGCTGGCGTCTTGCGTGGCGAGGGGGGCTGCGGGAGTGGCAGG
P450SU2            Met Thr Thr Ala Glu Arg Thr Ala Pro Pro Asp Ala Leu Thr Val P
Start 250                 270                 290
CGGCCAGCCGCGCCCCCGGCTGCCCCTTCGACCCCGCGCCCGACGTCACCGAGGCGGCCC
- - - - - - - - +- - - - - - - - - +- - - - - - - - - +- - - - - - - - - +- - - - - - - - - +- - - - - - - - - +
GCCGGTCGGCGCGGGGGCCGACGGGGAAGCTGGGGCGCGGGCTGCAGTGGCTCCGCCGGG
or Ala Ser Arg Ala Pro Gly Cys Pro Phe Asp Pro Ala Pro Asp Val Thr Glu Ala Ala A 310                 330                 350
GCACCGAACCGGTCACCCGGGCCACCCTCTGGGACGGCTCCTCCTGCTGGCTGGTGACGC
- - - - - - - - +- - - - - - - - - +- - - - - - - - - +- - - - - - - - - +- - - - - - - - - +- - - - - - - - - +
CGTGGCTTGGCCAGTGGGCCCGGTGGGAGACCCTGCCGAGGAGGACGACCGACCACTGCG
rg Thr Glu Pro Val Thr Arg Ala Thr Leu Trp Asp Gly Ser Ser Cys Trp Leu Val Thr A 370                 390                 410
GCCATCAGGACGTCCGCGCGGTCCTCGGCGACCCGCGCTTCAGCGCCGACGCCCACCGCA
```

-continued

```

CGGT AGT CCT GCA GGC GCG CCA GGA GCC GCT GGG CGC GAA GTC GCG GCT GCG GGT GGC GT
 rg  His Gln Asp Val Arg Ala Val Leu Gly Asp Pro Arg Phe Ser Ala Asp Ala His Arg  T 430                    450                    470
CCG GCT TCC CCT TCC TGA CCG CCG GCG GCC GCG AGA TCA TCG GCA CCA ACC CGA CCT TCC

GGC CGA AGG GGA AGG ACT GGC GGC CGC CGG CGC TCT AGT AGC CGT GGT TGG GCT GGA AGG
 hr Gly Phe Pro Phe Leu Thr Ala Gly Gly Arg Glu Ile Ile Gly Thr Asn Pro Thr Phe  L 490                    510                    530
TGC GCA TGG ACG ACC CGG AGC ACG CCC GAC TGC GCC GGA TGC TCA CCG CCG ACT TCA TCG

ACG CGT ACC TGC TGG GCC TCG TGC GGG CTG ACG CGG CCT ACG AGT GGC GGC TGA AGT AGC
 eu Arg Met Asp Asp Pro Glu His Ala Arg Leu Arg Arg Met Leu Thr Ala Asp Phe Ile  V 550                    570                    590
TCA AGA AGG TCG AGG CGA TGC GCC CCG AGG TGC AGC GCC TCG CCG ACG ACC TGG TCG ACC

AGT TCT TCC AGC TCC GCT ACG CGG GGC TCC ACG TCG CGG AGC GGC TGC TGG ACC AGC TGG
 al Lys Lys Val Glu Ala Met Arg Pro Glu Val Gln Arg Leu Ala Asp Asp Leu Val Asp  A 610                    630                    650
GGA TGA CCA CCG GAC GCA CCT CCG CCG ACC TGG TCA CCG AGT TCG CGC TGC CGC TGC CGT

CCT ACT GGT GGC CTG CGT GGA GGC GGC TGG ACC AGT GGC TCA AGC GCG ACG GCG ACG GCA
 rg Met Thr Thr Gly Arg Thr Ser Ala Asp Leu Val Thr Glu Phe Ala Leu Pro Leu Pro  S 670                    690                    710
CCC TGG TGA TCT GCC TGC TGC TCG GCG TCC CCT ACG AGG ACC ACG CGT TCT TCC AGG AGC

GGG ACC ACT AGA CGG ACG ACG AGC CGC AGG GGA TGC TCC TGG TGC GCA AGA AGG TCC TCG
 er Leu Val Ile Cys Leu Leu Leu Gly Val Pro Tyr Glu Asp His Ala Phe Phe Gln Glu  A 730                    750                    770
GCA GCC GGG TCC TGC TCA CCC TGC GGT CCA CTC CCG AGG AAG TCC GGG CCG CCC AGG ACG

CGT CGG CCC AGG ACG AGT GGG ACG CCA GGT GAG GGC TCC TTC AGG CCC GGC GGG TCC TGC
 rg Ser Arg Val Leu Leu Thr Leu Arg Ser Thr Pro Glu Glu Val Arg Ala Ala Gln Asp  G 790                    810                    830
AGT TGC TGG AGT ACC TCG CCC GGC TCG CCC GGA CCA AGC GGG AGC GGC CGG ACG ACG CCA

TCA ACG ACC TCA TGG AGC GGG CCG AGC GGG CCT GGT TCG CCC TCG CCG GCC TGC TGC GGT
 lu Leu Leu Glu Tyr Leu Ala Arg Leu Ala Arg Thr Lys Arg Glu Arg Pro Asp Asp Ala  I 850                    870                    890
TCA TCA GCC GCC TGG TCG CCC GCG GCG AGC TCG ACG ACA CCC AGA TCG CCA CCA TGG GAC

AGT AGT CGG CGG ACC AGC GGG CGC CGC TCG AGC TGC TGT GGG TCT AGC GGT GGT ACC CTG
 le Ile Ser Arg Leu Val Ala Arg Gly Glu Leu Asp Asp Thr Gln Ile Ala Thr Met Gly  A 910                    930                    950
GCC TGT TGC TGG TCG CCG GCC ACG AGA CGA CCG CCA ACA TGA CCG CGC TCT CCA CCC TCG

CGG ACA ACG ACC AGC GGC CGG TGC TCT GCT GGC GGT TGT ACT GGC GCG AGA GGT GGG AGC
 rg Leu Leu Leu Val Ala Gly His Glu Thr Thr Ala Asn Met Thr Ala Leu Ser Thr Leu  V 970                    990                    1010
TGC TGC TGC GCA ACC CCG ACC AAC TCG CCC GGC TGC GCG CCG AAC CCG CGC TCG TCA AGG

ACG ACG ACG CGT TGG GGC TGG TTG AGC GGG CCG ACG CGC GGC TTG GGC GCG AGC AGT TCC
 al Leu Leu Arg Asn Pro Asp Gln Leu Ala Arg Leu Arg Ala Glu Pro Ala Leu Val Lys  G 1030                   1050                   1070
GCG CCG TCG AGG AGC TGC TGC GCT ACC TGA CGA TCG TGC ACA ACG GCG TTC CCC GGA TCG

CGC GGC AGC TCC TCG ACG ACG CGA TGG ACT GCT AGC ACG TGT TGC CGC AAG GGG CCT AGC
 ly Ala Val Glu Glu Leu Leu Arg Tyr Leu Thr Ile Val His Asn Gly Val Pro Arg Ile  A 1090                   1110                   1130
```

-continued

```

CCACCGAGGACGTGCTCATCGGCGGCCGCACCATCGCCGCCGGCGAGGGCGTCCTGTGCA
---------+---------+---------+---------+---------+---------+
GGTGGCTCCTGCACGAGTAGCCGCCGGCGTGGTAGCGGCGGCCGCTCCCGCAGGACACGT
la  Thr Glu Asp Val Leu Ile Gly Gly Arg Thr Ile Ala Ala Gly Glu Gly Val Leu Cys M 1150                1170                1190
TGATCAGCTCCGCCAACCGGGACGCCGAGGTGTTCCCCGGCGGCGACGACCTCGACGTGG
---------+---------+---------+---------+---------+---------+
ACTAGTCGAGGCGGTTGGCCCTGCGGCTCCACAAGGGGCCGCCGCTGCTGGAGCTGCACC
et  Ile Ser Ser Ala Asn Arg Asp Ala Glu Val Phe Pro Gly Gly Asp Asp Leu Asp Val A 1210                1230                1250
CCCGCGACGCCCGCCGCCACGTGGCCTTCGGCTTCGGCGTCCACCAGTGCCTGGGACAGC
---------+---------+---------+---------+---------+---------+
GGGCGCTGCGGGCGGCGGTGCACCGGAAGCCGAAGCCGCAGGTGGTCACGGACCCTGTCG
la  Arg Asp Ala Arg Arg His Val ALa Phe Gly Phe Gly Val His Gln CYs Leu Gly Gln P 1270                1290                1310
CGTTGGCCAGGGTGGAGCTCCAGATCGCCATCGAAACGCTGCTGCGCCGCCTGCCGGACC
---------+---------+---------+---------+---------+---------+
GCAACCGGTCCCACCTCGAGGTCTAGCGGTAGCTTTGCGACGACGCGGCGGACGGCCTGG
ro  Leu Ala Arg Val Glu Leu Gln Ile Ala Ile Glu Thr Leu Leu Arg Arg Leu Pro Asp L 1330                1350                1370
TGCGGCTGGCCGTGCCCCACGAGGAGATCCCGTTCCGCGGCGACATGGCGATCTACGGGG
---------+---------+---------+---------+---------+---------+
GCAACCGGTCCCACCTCGAGGTCTAGCGGTAGCTTTGCGACGACGCGGCGGACGGCCTGG
eu  Arg Leu Ala Val Pro His Glu Glu Ile Pro Phe Arg Gly Asp Met Ala Ile Tyr Gly V 1390                1410                1430
TGCGGCTGGCCGTGCCCCACGAGGAGATCCCGTTCCGCGGCGACATGGCGATCTACGGGG
---------+---------+---------+---------+---------+---------+
ACGCCGACCGGCACGGGGTGCTCCTCTAGGGCAAGGCGCCGCTGTACCGCTAGATGCCCC
al  His Ser Leu Pro Ile Ala Trp End 1450                1470                1490
TCCACTCGCTGCCGATCGCCTGGTAGCCCGGGCGCCCCCACCACCGACCACCACGCACCC
---------+---------+---------+---------+---------+---------+
AGGTGAGCGACGGCTAGCGGACCATCGGGCCCGCGGGGGTGGTGGCTGGTGGTGCGTGGG
FeS-A           Met Arg Ile His Val Asp Gln Asp Lys Cys Cys Gly Ala Gly Ser Cys V 1510                1530                1550
TTGGGAGCACCATGCGCATCCACGTCGACCAGGACAAGTGCTGCGGCGCCGGCAGTTGCG
---------+---------+---------+---------+---------+---------+
AACCCTCGTGGTACGCGTAGGTGCAGCTGGTCCTGTTCACGACGCCGCGGCCGTCAACGC
al  Leu Ala Ala Pro Asp Val Phe Asp Gln Arg Glu Glu Asp Gly Ile Val Val Leu Leu A 1570                1590                1610
TCCTCGCCGCGCCCGACGTCTTCGACCAGCGGGAGGAGGACGGCATCGTGGTCCTCCTCG
---------+---------+---------+---------+---------+---------+
AGGAGCGGCGCGGGCTGCAGAAGCTGGTCGCCCTCCTCCTGCCGTAGCACCAGGAGGAGC
sp  Thr Ala Pro Pro Ala Ala Leu His Asp Ala Val Arg Glu Ala Ala Thr Ile Cys Pro A 1630                1650                1670
ACACCGCGCCGCCCGCCGCGCTGCACGACGCGGTCCGTGAGGCGGCGACCATCTGCCCCG
---------+---------+---------+---------+---------+---------+
TGTGGCGCGGCGGGCGGCGCGACGTGCTGCGCCAGGCACTCCGCCGCTGGTAGACGGGGC
la  Ala Ala Ile Thr Val Thr Asp End 1690                1710                1730
CCGCCGCGATCACGGTGACCGACTGAGCCACCGGCCGCCCCGCCCGCCCGCGCCCCGGTC
---------+---------+---------+---------+---------+---------+
GGCGGCGCTAGTGCCACTGGCTGACTCGGTGGCCGGCGGGGCGGGCGGGCGCGGGGCCAG 1750                1770                1790
CCCGCATCCCCCCGCGGCCCGGGGCGCGCCCCTAACCCGCCGCCCCGCACGCCGTCGCGC
---------+---------+---------+---------+---------+---------+
GGGCGTAGGGGGGCGCCGGGCCCCGCGCGGGGATTGGGCGGCGGGGCGTGCGGCAGCGCG 1810                1830                1850
GCGCCGCCAGTGCCCGCAGCGCCGCCTCGGACGACGAACCCGGCACGGCGTGGTGGGTCA
```

```
                                                                1870                         1890                        1910
CCAGCGTCTGCCCCGGTTCGGCCGCCACGCGCAGCGTCCCGTAGGTCAGGGTCAGCGGGC
---------+---------+---------+---------+---------+---------+
GGTCGCAGACGGGGCCAAGCCGGCGGTGCGCGTCGCAGGGCATCCAGTCCCAGTCGCCCG 1930                         1950                        1970
CCACCACCGGGTGGTCCAGCTGCTTCGTCCCGAAACCCTTGTCCTTGATGTCGTGCCGGG
---------+---------+---------+---------+---------+---------+
GGTGGTGGCCCACCAGGTCGACGAAGCAGGGCTTTGGGAACAGGAACTACAGCACGGCCC

1990
CCCAGAAGCGCCGGAACTCCTCGCTCTGCACGGTCAGTTCGGTGATCCGCGCGGTCAGCG
---------+---------+---------+---------+---------+---------+
GGGTCTTCGCGGCCTTGAGGAGCGAGACGTGCCAGTCAAGCCACTAGGCGCGCCAGTCGC
                                                             BamHI
```

Plasmids for the constitutive expression of cytochrome P450SU1 in other organisms Plasmids with which to transform other organisms to constitutively express cytochrome P4505U1 alone and P4505U1 and FeS-B together may be made as follows. Expression of the two genes (i.e., the DNA sequences) may be driven by the promoter and transcription signal of the genes from S. griseolus, or by any plasmid promoter(s) and translation signals that allow constitutive expression of exogenous coding sequences in the organism to be transformed. The non-regulated expression of the genes from these promoters in other organisms as exemplified by the example herein, in S. lividans, and as opposed to their regulated expression in S. griseolus is presumably due to the absence of the regulatory factors (genes) in the other organisms that normally regulate the expression of cytochrome P450SU1 and FeS-B in S. griseolus.

pCAO400

This plasmid was made in E. coli by inserting the 2.4 kb BamHI fragment from pUC18-SU1-BamHI that contains the genes for both cytochrome P450SU1 and FeS-B into the unique BamHI site of pCAO170 (Omer et al., J. Bacteriol. 170:2174–2184, (1988)), using methods described in Manjarls et al., Molecular Cloning: a Laboratory Manual, Cold Spring Harbor Press, Cold Spring Harbor, N.Y., pp. 390–400. The plasmid pCAO170 in E. coli CE170 has been deposited in the American Type Culture Collection and has the ATCC accession number 68085. The resulting plasmid is called pCAO400.

pCAO401

This plasmid was made in E. coli by inserting the 2.0 kb BamHI-SacI fragment from pUC18-SU1-BamHI that contains the genes for both cytochrome P450SU1 and FeS-B into pCAO170 that had been digested with BamHI and SacI restriction endonucleases using methods as described by Maniatis et al., Molecular Cloning: a Laboratory Manual, Cold Spring Harbor Press, Cold Spring Harbor, N.Y. The resulting plasmid is called pCAO401.

pCAO200SU1-FeS-B #9

This plasmid was made similarly to the way pCAO400 above was made except that pCAO200 which can be made from pCAO170 (Omer et al., J. Bacteriol. 170:2174–2184, (1988)), was used instead of pCAO170 as the recipient of the 2.4 kb BamHI fragment.

pCAO200SU1#12

This plasmid was made by deleting the complete FeS-B protein coding sequence from the 2.4 kb BamHI DNA fragment. The deletion was made as described (Henikoff, Gene, 28:351–359 (1984); Messing, Methods in Enzymology 101: 20–78 (1983)). The resulting 1.8 kb DNA fragment still contains the sequences upstream of SU1, the complete cytochrome P450SU1 coding sequence, and 6 bp downstream of SU1. It is designated pUC118-SU-1.8. A BamHI site containing linker was inserted at the HindIII site downstream of the P450SU1 coding region and the resulting fragment was inserted in pUC118 creating pUC118-SU1-1.8(B). The 1.8 kb BamHI DNA fragment was isolated from pUC118-SU1-1.8(B) and inserted into the BarnHi site of pCAO200 using methods well known to those skilled in the art (Maniatis et al., Molecular Cloning: a Laboratory Manual, Cold Spring Harbor Press, Cold Spring Harbor, N.Y., Pp 390–400) creating the plasmid pCAO200SU1#12.

Plasmid for the constitutive expression of cytochrome P450SU2 in other organisms A plasmid for introducing the genes for cytochrome P450SU2 and FeS-A into S. lividans may be constructed as follows. The 2.0 kb BamHI fragment from pUC19-SU2-8 containing the genes for cytochrome P450SU2 and FeS-A can be cloned into the BamHI site of pCAO200 using methods well known to those skilled in the art creating PCAO200SU2-FeS-A#11 (Maniatis et al., Molecular Cloning: a Laboratory Manual, Cold Spring Harbor Press, Cold Spring Harbor, N.Y., pp. 390–400). This fragment may also be cloned in other vectors.

Figure 3A:
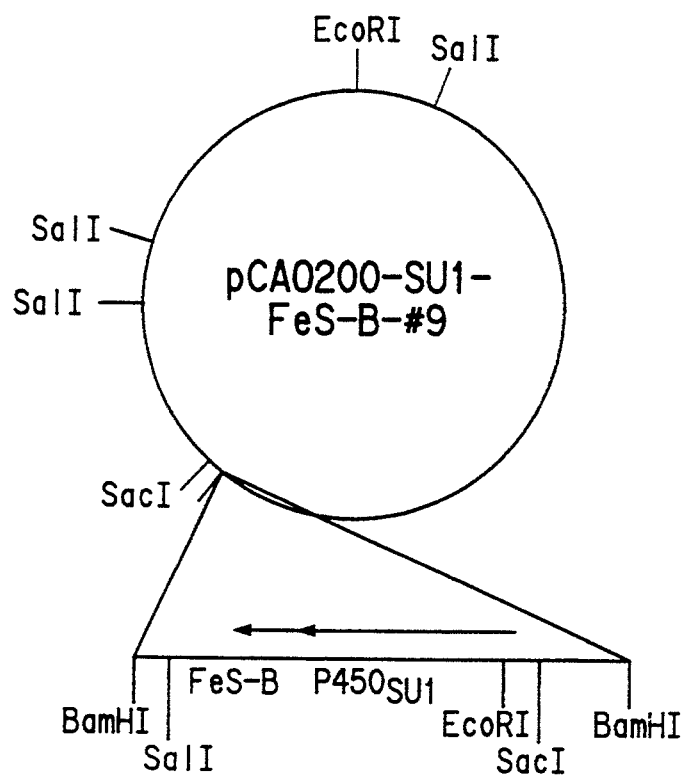
FIG. 3A is a physical map, showing the restriction endonuclease site, of plasmid pCAO200SU1-FeS-B#9.
Figure 3B:
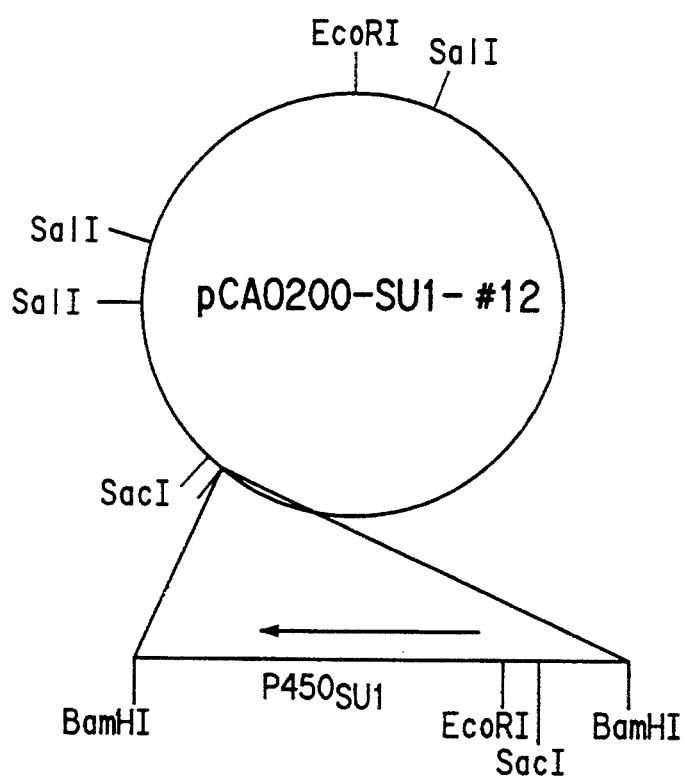
FIG. 3B is a physical map, showing the restriction endonuclease site, of plasmid pCAO200SU1#12.

The five plasmids, pCAO400, pCAO401 (FIGS. 3A and 3B), pCAO200SU1-FeS-B-#9, pCAO200SU1#12 (FIGS. 4A and 4B), and pCAOSU2-FeS-A (FIG. 8) were introduced into S. lividans JI1326 as described by Hopwood et al., Genetic Manipulation of Streptomyces. A Laboratory Manual, John Innes Foundation, Norwich, U. K., pp 108–109. S. lividans JI1326 has been deposited in the American Type Culture Collection and has the ATCC accession number 53939. Transformants were selected for thiostrepton resistance which is encoded on the plasmids. These plasmids, which are based upon the SLP1 plasmid, site-specifically integrate into a unique locus in the S. lividans chromosome and are present in 1–2 copies per chromosome (Omer et al., J. Bacteriol. 170:2174–2184, (1988)).

While *S. lividans* can be transformed by the plasmids described above (including pCAO200SU1-FeS-B#9, pCAOSU2-FeS-A#11, pCAO400 and pCAO401) the host range of these SLP1-derived plasmids is limited (Kieser et al., 1982, Mol. Gen. Genet. 185:223–238). Broad host range plasmids such as those derived from the plasmids SPC2 or pIJ101 can be used to introduce into and allow expression of these genes in other Streptomyces species (Lydiate et al., 1985, Gene 35:223–235, Kieser et al., 1982, Mol. Gen. Genet. 185:223–238, Ward et al., 1986, Mol. Gen. Genet. 203:468–478). The 2.4 kb BamHI DNA fragment from pUC18-SU1 BamHI that contains the genes for P450SU1 and FeS-B can be cloned into the BamHI site of pIJ922 using methods well known to those skilled in the art (Maniatis et al., 1982, A Guide to Molecular Cloning:A Laboratory Manual) creating pPAT108 (FIG. 16A). The 2.0 kb BamHI DNA fragment from pUC19-SU2-8 can be cloned into the BglII site of pIJ425 using methods well-known to those skilled in the art (Maniatis et al., 1982, A Guide to Molecular Cloning:A Laboratory Manual) creating pCS325 (FIG. 16B). The plasmids pPAT108 and pCS325 can be transformed into various Streptomyces species and will enable the transformed strains to constitutively metabolize herbicide chemicals.

Engineering plasmids with P450SU1 for the transformation of plants

For transcription and translation in plants, additional sequences must be added to the 5′-end and 3′-end of the DNA fragment comprising the cytochrome P450SU1 coding sequence. This yields a recombinant plasmid comprising A) a DNA fragment of the 2.4 kb BamHI fragment encoding enzyme P450SU1, a DNA fragment of the 2.0 kb SacI-BamHI fragment encoding enzyme P450SU1, a DNA fragment of the 1.8 kb BamHI fragment encoding enzyme P450SU1, or the 2.0 kb BamHI fragment encoding P450SU2 isolated from *S. griseolus* mutant PH2001; B) a DNA sequence of a plant promoter upstream and operably linked to said fragment; C) a 5′-untranslated sequence including a ribosomal binding site upstream and operably linked to said fragment; D) a DNA sequence downstream and operably linked to said fragment of a 3′-untranslated sequence which enables the mRNA transcribed from the plasmids to be polyadenylated on its 3′end.

This can be done using standard genetic engineering techniques as described in Maniatis et al., Molecular Cloning: a Laboratory Manual, Cold Spring Harbor Press, Cold Spring Harbor, N.Y. and Kunkel, T. A. et al. Proc. Natl. Acad. Sci. U.S.A., 82:488–492 (1985).

Sources for a DNA fragment encoding the P450SU1 gene product include a 2.4 kb BamHI DNA fragment or a 2.0 kb BamHI-SacI DNA fragment from pUC18-SU1-BamHI. A source for a DNA fragment encoding the P450SU2 gene product is a 2.0 kb BamHI fragment in pUC19-SU2-8 isolated from *S. griseolus* mutant PH2001. A preferred source of a DNA fragment comprising the sequences encoding the P450SU1 gene product is the 2.4 kb BamHI DNA fragment from pUC18-SU1-BamHI. An alternative source for a similar cytochrome P450 gene would be the P450SU2 gene contained on a 2.0 kb BamHI fragment in pUC19-SU2-8.

Addition of promoter and 5′-untranslated sequences to the P450SU1 coding sequence A plant promoter and 5′-untranslated sequence including a ribosomal binding site must be added upstream of the DNA encoding cytochrome P450SU1 to permit the transcription and translation of the P450SU1 gene in plants. Among the promoters and 5′-untranslated sequences that will suffice for this purpose are those of the 35S promoter from the Cauliflower Mosaic Virus (CaMV) (Harpster et al. Mol. Gen. Genet. 212:182–190 (1988)), the light induced and tissue specific SSU301 gene from petunia (Dean et al. Mol. Gen. Genet. 206:465–474 (1987)), the light induced and tissue specific Cab22L gene from petunia (Dunsmuir, Nucleic Acids Res. 13:2503–2518 (1985) and Harpster et al. Mol. Gen. Genet. 212:182–190 (1988)), and the chemically inducible absicic acid-regulated Em promoter from wheat (Marcotte et al., The Plant Cell 1:969–976 (1989)). Other plant promoters and 5′-untranslated regions from plant genes could also be used.

Addition of 3′-untranslated sequences to the P450 SU1 coding sequence

Sequences must be added downstream of the DNA encoding cytochrome P450SU1 to enable the mRNA transcribed from the vectors to be polyadenylated on its 3′-end. A preferred source of such DNA is from the SSU301 gene from petunia (SSU301 encodes the small subunit of ribulose bisphosphate carboxylase) (Dean et al. Mol. Gen. Genet. 206:465–474 (1987)). This provides a poly A addition site on the P450SU1 encoding mRNA transcript when the 3′-tail region from the SSU301 gene is cotranscribed along with the p450SU1 coding sequence. Other plant genes could be used as sources of these 3′-untranslated sequences.

Addition to the cytochrome P450SU1 coding sequence of sequences encoding peptides that can facilitate the transport of cytochrome P450SU1 into the chloroplast of the plant cell Plasmids consisting of the plant promoter, plant 5′-untranslated sequences, P450SU1 coding sequence, and plant 3′-untranslated sequences will express cytochrome P450SU1 in the cytoplasm of the plant cell. Localization of P450SU1 in chloroplasts instead of the cytoplasm may give better metabolism of herbicides because in chloroplasts there are electrons and iron-sulfur proteins that could deliver electrons to P450SU1 that might not be present in the cytoplasm. In order to express the cytochrome P450SU1 protein in the chloroplasts of plants, constructions require in addition to the above mentioned components a transit peptide encoding sequence fused to the cytochrome P450SU1 sequence to direct the protein into the chloroplasts. Such sequences may be engineered using coding regions of the transit peptide sequences, or coding regions of the transit peptide sequence plus a portion of the coding region of the mature polypeptide, of nuclear genes encoding proteins that are normally imported into the chloroplasts of plants. Good sources of sequences for these fusions are the ribulose bisphosphate carboxylase (SSU) (Dean et al. Mol. Gen. Genet. 206:465–474 (1987)) and the chlorophyll a/b binding protein (Dunsmuir, Nucleic Acid Res. 13:2503-2518 (1985)) both from petunia. Other sources would be similar, nuclear encoded genes from other plants that encode proteins that are transported into chloroplasts. Fusions that only add the amino terminal amino acid sequence that is normally removed upon transport into chloroplasts and fusions that contain the normally removed peptide sequence and up to at least 27 amino acids of the mature transported protein can be added onto the amino terminus of cytochrome P450SU1 and downstream from the promoter and ribosomal binding site without preventing the expression of functional P450SU1 protein.

This technique will work for introducing into plants any soluble cytochrome P450 enzyme for which chloroplast ferredoxin acts as a reductant.

Engineering plasmids with P450SU1 and FeS-B for the transformation of plants

Although chloroplast ferredoxins are a source of reductant for cytochrome P450SU1, an alternative source is the FeS-B protein from *S. griseolus* which is the natural reductant for P450SU1. Thus plasmids that upon introduction into plant cells can direct the expression of both cytochrome P450SU1 and FeS-B are useful. To express both proteins in plant cells, modifications similar to those used to express cytochrome P450SU1 can also be done, on the same plasmid, to express FeS-B protein. Such proteins can be directed either to the cytoplasm or to chloroplasts of plant cells.

Such a recombinant plasmid resulting in expression in the cytoplasm comprises A) the DNA encoding for the cytochrome P450 or the DNA encoding for the cytochrome P450 and the DNA encoding for the FeS protein, B) one or more,segments of the DNA sequence of a plant promoter upstream and operably linked to said encoding, C) one or more of a 5'-untranslated sequence including a ribosomal binding site upstream and operably linked to said encoding, and D) one or more of a DNA sequence downstream and operably linked to said encodings of a 3'-untranslated sequence which enables the mRNA transcribed from the plasmids to be polyadenylated on its 3' end.

Alternatively, a plasmid for targetting the proteins to the chloroplasts comprises A) the DNA encoding for the cytochrome P450 or the DNA encoding for the cytochrome P450 and the DNA encoding for the FeS protein, B) one or more segments of the DNA sequence of a plant promoter operably linked to said encoding in the upstream position; C) one or more of a 5'-untranslated sequence including a ribosomal binding site operably linked to said encoding in the upstream position; D) one or more of a DNA sequence operably linked to said encoding in the downstream position of a 3'-untranslated sequence which enables the mRNA transcribed from the plasmids to be polyadenylated on its 3' end; and E) one or more of a transit peptide coding sequence or a transit peptide encoding sequence and additionally mature coding sequence of nuclear genes that encode proteins that are normally imported into the chloroplasts of plants operably linked to the DNA encoding for the amino terminus of the cytochrome P450, or to the DNA encodings for the amino terminae of the cytochrome P450 and FeS protein, and downstream from the promoter and ribosomal binding site.

The preferred plasmids for expression of cytochrome P450SU1 along with FeS-B in the cytoplasm and chloroplasts of plant cells are described in Example 19.

Introduction of plasmids into plants

DNAs containing the cytochrome P450SU1, P450SU2, FeS-A or FeS-B coding sequences with promoters from plant genes can be subcloned into T-DNA plasmids that mediate the transfer of these DNAs from *Agrobacterium* to plants (R. T. Fraley et al. Proc. Natl. Acad. Sci. U.S.A. 80:4803–4807 (1983), H. Klee et al. Annual Rev. Plant Physiol. 38:476–486 (1987) and references therein). This subcloning can be performed by methods well known to those skilled in the art (T. Maniatis et al., Molecular Cloning:a Laboratory Manual, Cold Spring Harbor Press, Cold Spring Harbor, N.Y. (1982) and T. A. Kunkel Proc. Natl. Acad. Sci. U.S.A. 82:488–492 (1985)). Although several different T-DNA plasmids were used in the examples presented here, pAGS502 could have been used for all of them since it contains unique HindIII, BamHI and EcoRI sites in the T-DNA region. Other T-DNA plasmids could also be used too as long as suitable restriction sites (i.e., HindIII, BamHI, EcoRI) are present in the region of the plasmid that is mobilized into plant cells. Alternatively, the restriction sites on the DNA fragments to be inserted into the T-DNA plasmids could be changed (T. A. Kunkel Proc. Natl. Acad. Sci. U.S.A. 82:488–492 (1985)) to allow insertion into most any restriction endonuclease site in a T-DNA plasmid.

Plasmids are mobilized into Agrobaterium such as *A. tumifaciens* strain LBA4404 (Hoekema et al. Nature 303:179–180, 1983) using tri-parental matings (Ruvkin and Ausubel, Nature 289:85–88, 1981), or the freezethaw method (Plant Molec. Biol. Manual, S. B. Gelvin and R. A. Schilperoot, Eds., A3:1–19, 1988). The resulting Agrobacterium strains are then cocultivated with protoplasts as described by van der Elzen et al. Plant Mol. Biol. 5:149–154(1985) or leaf disks as described by Horsch et al. Science 227:1229–1231,(1985) of *Nicotiana tabacum* cv. Wisconsin 38 and kanamycin resistant transformants selected. Kanamycin resistant transformed tobacco plants are regenerated from the transformed protoplasts or leaf disks and the plants are allowed to flower. Seed is obtained from each plant following self pollination.

Plants other than *Nicotiana tabacum*, including plants of horticultural or agronomic utility, such as such as vegetable or other crops, can be transformed in ways known to those skilled in the art (Gasser and Fraley, Science 244:1293–1299 (1989)). Using the Agrobacterium mediated T-DNA transfer of DNA the plasmids pSU18, pSSU-SU111, pSSU-SU121, pCab-SU111, pCabSU121, pCab-SU131, pSiFe11, pSuFe21, pSuFe31 and pSuFe41 can be mobilized into plant species that include, but are not limited to *Lycopersicon esculentum*, (tomato), (McCormick et al., Plant Cell Rap., 5:81–84 (1986)), *Brassica napus*, (oilseed rape), (Pua et al., Bio/-Technology, 5:815–817 (1987)); *Gossypium hirsutum*, (cotton), (Umbeck et al., Bio/Technology 5:263–266 (1987)) *Glycine max*, (soybean) (Hinchee et al., Bio/-Technology, 6:915–921 (1988)), and *Arabidopsis thaliana* (Valvekens et al., Proc. Natl. Acad. Sci. USA 85:5536–5540 (1988)). The plasmids pSU18, pSSU-SU111, pSSU-SU121, pCab-SU111, pCab-SU121, pCab-SU131, pSUFe11, pSUFe21, pSUFe31 and pSU-Fe41 can be transformed into plant protoplasts as has been demonstrated for rice (*Oryza sativa*) (Toriyama et al., Bio/Technology, 6:1072–1074 (1988)) and maize (*Zea mays* L.) (Rhodes et al., Science, 140:204–207 (1988)). An additional alternative method to introduce the plasmids pSU18, pSSU-SU111, pSSU-SU121, pCab-SU111, pCab-SU121, pCab-SU131, pSUFe11, pSU-Fe21, pSUFe31 and pSUFe41 into plants is through the use of a "particle gun" (Klein et al., Nature, 327:70–73 (1987)). This method has been shown to work for *Nicotiana tabacum*, tobacco, (Klein et al., Proc. Natl. Acad. Sci., U.S.A., 85:8502–8505 (1988)) and *Glycine max*, soybeans, (McCabe et al., Bio/Technology, 6:923–926 (1988)) but is not necessarily limited to these species.

Following introduction of plasmids into plant cells by any of the above procedures, the plasmids or portions of these plasmids may be stably incorporated into the chromosomal DNA of the cell. In the case where plants are regenerated from single cells, all cells of the regenerated plant are expected to carry the integrated plasmid or plasmid parts. In the case where single cells within a regenerating multicellular structure are transformed, cells arising from the transformed cell(s) will give rise to sectors which carry the integrated plasmid or plasmid parts. In either case, the regenerated plants carrying the plasmid or plasmid parts are termed primary transformants. Depending on the species, the primary transformants can flower and give rise to gametes which fuse to form zygotes either by self pollination or by outcrossing with other plants of the same species.

Seed arising from either self pollination or outcrossing of a primary transformant contain embryos which are progeny of the primary transformant. A portion of the progeny plants may receive chromosomes which carry copies of the plasmid or plasmid parts, depending on the number of copies of the plasmid or plasmid parts stably incorporated in the primary transformant, patterns of mendelian segregation, linkage relationships between the plasmids or plasmid parts where multiple copies exist, and whether or not the gametes arose from sectors carrying the integrated plasmid or plasmid parts. In like fashion these progeny plants may flower and give rise to subsequent generations of seed and plants carrying the plasmid or plasmid parts incorporated into the original primary transformant.

A similar situation pertains to the endosperm tissue of seed in cases where the endosperm is formed by sexual means.

A male sterility system for hybrid seed production

A means of inducing male sterility in plants generating the female parent to be used in a cross to produce hybrid seed would be very useful. Hybrid seed production is an important means of introducing desirable traits into agronomically valuable crop plants. For instance, quality traits such as oil content, herbicide resistance, disease resistance, adaptability to environmental conditions, and the like, can be hybridized in offspring so that the latter are invested with the most desirable traits of its parents. In addition, progeny from a hybrid cross may possess new qualities resulting from the combination of the two parental types, such as yield enhancement resulting from the phenomenon known as heterosis. Controlled cross-fertilization to produce hybrid seeds has been difficult to achieve commercially due to competing self-fertilization, which occurs in most crop plants.

Currently, hybrid seed production is performed by one of the following means: (a) mechanically removing or covering the male organs to prevent self-fertilization followed by exposing the male-disabled plants to plants with male organs that contain the trait(s) desired for crossing; (b) growing genetically male-sterile plants in the presence of plants with fertile male organs that contain the trait that is desired for crossing; or (c) treating plants with chemical hybridizing agents (CHA) that selectively sterilize male organs followed by exposing the male-disabled plants to plants with fertile male organs that contain the trait that is desired for crossing. Some disadvantages to each of these methods include: (a) this is only possible for a few crops, such as corn; where the male and female organs are separate; and it is labor intensive and costly; (b) genetically male sterile lines are cumbersome to maintain, requiring crosses with restorer lines; (c) CHAs are not highly effective. The following method is applicable to a wide range of crops and allows selfing to maintain lines.

A plant is made to be receptive to male sterility induction by the introduction of the cytochrome p450SU1 or SU2 coding region under control of a suitable male organ-specific promoter. The resulting transgenic plant produces the cytochrome p450 enzyme only in its male organ. Such transgenic plants are male-fertile when grown normally. The p450-containing untreated fertile plant can be genetically crossed and propagated normally through seed production. Unlike normal plants, however, these plants can be rendered male-sterile by exposure to nontoxic chemical that is converted by the p450 enzyme into an active toxin. The toxin present in the male organ disrupts normal pollen development making the plant male sterile. The male sterility trait is only expressed when wanted, by contacting the plant with a selected protoxin; otherwise the transgenic plant behaves normally. Suitable protoxins include 10015 and other compounds that are sufficiently converted into 10014 by the cytochrome p450 enzyme.

EXAMPLES 1-3

Demonstration of constitutive expression of cytochrome P450SU1 in *S. lividans* strains that are transformed with pCAO400, pCAO401, pCAO200SU1-FeS-B#9 and pCAO200SU1#12

Cultures of *S. lividans* strains transformed with any one of the four plasmids pCAO400, pCAO401, pCAO200SU1-FeS-B#9 or pCAO200SU1#12 were grown in either sporulation broth or YEME broth media. The cultures were grown for approximately 24-36 hours at 30° C. An aliquot of cells was removed from the cultures at this time. If sulfonylurea induction of cytochrome P450SU1 was to be tested, a solution of the sulfonylurea 10001 that gave a final concentration in the culture of approximately 0.1-0.15 mg/ml was added to the culture remaining after the removal of the aliquots. Aliquots of cells were removed from the induced culture at various intervals up to 24 hours later and harvested and washed as described.

Western blot analyses for cytochrome P450SU1 was performed on cell extracts as described.

EXAMPLE 1

Figure 5:
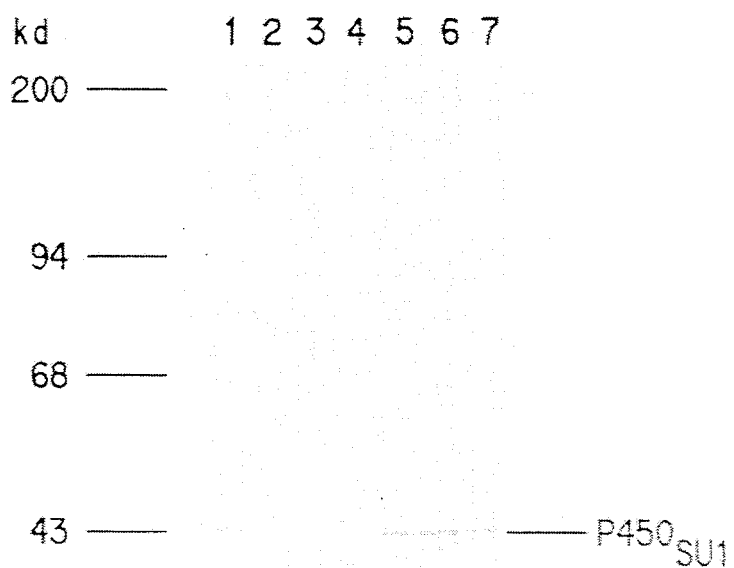
FIG. 5 shows Western blots as follows:
lane 1, 50 ng of purified cytochrome P450SU1;
lane 2, blank;
lane 3, protein from *S. lividans* C37 grown with no sulfonylurea;
lane 4, protein frem *S. lividans* C37 induced for six hours with 120 ppm of 10001;
lane 5, *S. lividans* transformed with pCAO400 grown with no sulfonylurea;
lane 6, *S. lividans* transformed with pCAO400 induced for six hours with 120 ppm of 10001;
lane 7, 500 ng of purified cytochrome P450SU1.

*S. lividans* transformed with pCAO400 and *S. lividans* C37 (Omer et. al., J. Bacteriol. 170:2174–2184, (1988), herein incorporated by reference), which contains the plasmid pCAO106 (from which pCAO170 the plasmid from which pCAO400 was derived), were grown as separate cultures in sporulation broth as described above. An aliquot of cells was removed from each culture before adding 10001 to a concentration of 0.12 mg/ml to the cells and another aliquot of cells was taken 24 hours after adding 10001. Western blots were run on approximately 25 μg of protein from each aliquot of cells and analyzed for the presence of cytochrome P450SU1 by means of antiserum to cytochrome P450SU1 as described. The data in FIG. 5 show that *S. lividans* C37 (which does not contain the gene for cytochrome P450SU1) made no cytochrome P450SU1 whether or not it was induced with 10001. It also shows that cytochrome P450SU1 was made by *S. lividans* transformed with pCAO400 whether or not it had been induced with 10001.

EXAMPLE 2

Figure 6:
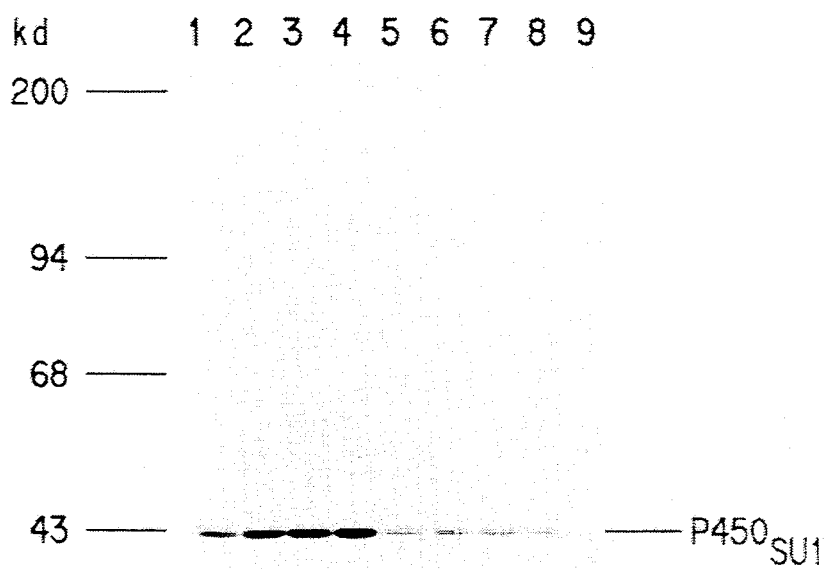
FIG. 6 shows Western blots as follows:
lanes 1, protein extract of *S. lividans* transformed with pCAO401 and induced with 120 ppm of 10001 or 24 hours.

*S. lividans* containing pCAO400 and *S. lividans* containing pCAO401 were used separately to inoculate 200 ml of sporulation broth and grown for approximately 36 hours. Fresh sporulation broth (100 ml) was added to each culture and a 30 ml aliquot was removed from each. At this time 36 mg of 10001 was added to each culture followed by the removal of 30 ml aliquots at 3, 6 and 24 hours. The cells in each aliquot were pelleted by means of centrifugation, washed and broken in a French pressure cell, as described. Approximately 25 μg of protein from each aliquot was used in a Western blot analysis for cytochrome P450SU1 by means of anti-P450SU1 antibody. The results shown in FIG. 6 indicate that cytochrome P450SU1 was produced by both S. lividans containing pCAO400 and S. lividans containing pCAO401, whether or not 10001 had been added.

EXAMPLE 3

S. lividans containing pCAO200, containing pCAO200SU1-FeS-B#9 and S. lividans containing pCAO200SU#112 were grown separately in 400 ml of YEME broth with-shaking at 30° C. for approximately 36 hours. S. griseolus ATCC 11796 was grown in 400 ml of sporulation broth for approximately 30 hours. Six hours before harvesting the cells from the cultures, 200 ml of YEME was added to the S. lividans cells. Six hours before harvesting, the S. griseolus culture was split into two 200 ml aliquots and 100 ml of fresh sporulation broth was added to each. At this time, 36 mg of 10001 was also added to one of the two S. griseolus cultures. The cells from each of the five cultures were harvested by means of centrifugation and washed twice with 50 mM MOPS pH 7.2 and an aliquot of the harvested cells was broken in a French pressure cell, as described. Approximately 30 μg of protein was used in a Western blot analysis for cytochrome P450SU1 using antiserum against cytochrome P450SU1. The results are shown in FIG. 7. No cytochrome P450SU1 was found in the S. lividans cells containing pCAO200 or in the S. griseolus culture not induced with 10001. Cytochrome P450SU1 was detected in the cultures of S. lividans transformed with either pCAO200SU1-FeS-B#9 or pCAO200SU1#12 and in the S. griseolus ATCC 11796 culture induced with 10001.

EXAMPLES 4–9

Metabolism of sulfonylurea compounds by S. lividans cells containing the genes for cytochrome P450SU1 and FeS-B

EXAMPLE 4

Separate cultures (50 ml) inoculated with S. lividans C37, S. lividans transformed with pCAO400 or S. lividans transformed with pCAO401 in sporulation broth containing 0.12 mg/ml of 10001 were grown with shaking at 30° C. Aliquots (1.5 ml) of each culture were removed at 24, 32, 48 and 56 hours after inoculation and the supernatant of each aliquot was analyzed by HPLC for its concentration of 10001 and its metabolites 10002 or 10003.

The concentration (μM) of each compound is presented in Table 1.

TABLE 1

| Strain | Time (hours) | 10001 | 10002 | 10003 |
|---|---|---|---|---|
| S. lividans pCAO401 | 0 | 284 | 0 | 0 |
|  | 24 | 230 | 32 | 26 |
|  | 32 | 203 | 44 | 36 |
|  | 48 | 123 | 63 | 46 |
|  | 56 | 105 | 71 | 48 |
| S. lividans pCAO400 | 0 | 300 | 0 | 0 |
|  | 24 | 269 | 17 | 16 |

TABLE 1-continued

| Strain | Time (hours) | 10001 | 10002 | 10003 |
|---|---|---|---|---|
|  | 32 | 240 | 25 | 22 |
|  | 48 | 184 | 39 | 28 |
|  | 56 | 137 | 47 | 29 |
| S. lividans C37 | 0 | 325 | 1 | 0 |
|  | 24 | 320 | 2 | 0 |
|  | 32 | 295 | 3 | 0 |
|  | 48 | 281 | 6 | 3 |
|  | 56 | 280 | 7 | 3 |

EXAMPLE 5

A 100 ml culture of S. griseolus ATCC 11796 in sporulation broth and a 50 ml culture of S. lividans transformed with pCAO400 in YEME broth were prepared and incubated for 24 hours as described. At that time, the S. griseolus culture was split into two 50 ml aliquots into two separate flasks and 25 ml of fresh sporulation broth was added to each and 9 mg of 10000 was added to one of these cultures to induce cytochrome P450SU1 expression. Fresh YEME broth (25 ml) was added to the S. lividans culture. After an additional 6 hours growth at 30° C., the cells in each culture were harvested as described above, washed twice with MOPS (50 mM, pH 7.2) and recentrifuged. The cell pellets were resuspended in four cell volumes of MOPS (50 mM, pH 7.2) containing 0.2% glucose and about 100 μg/ml of 10004. These cell suspensions were incubated at 30° C. with shaking and aliqouts were taken at 2 and 5.5 hours. The supernatant of each aliquot was analyzed by HPLC and the concentrations of the sulfonylurea compound 10004 and its metabolite 10005 were determined.

The concentration (μM) of 10004 and 10005 in the supernatant of each aliquot is shown in Table 2.

TABLE 2

| Cells | Time (hours) | 10004 | 10005 |
|---|---|---|---|
| none | 0 | 144 | 0 |
| S. griseolus uninduced | 2 | 55 | 72 |
|  | 5.5 | 12 | 114 |
| S. griseolus induced | 2 | 0 | 122 |
|  | 5.5 | 0 | 122 |
| S. lividans pCAO400 | 2 | 72 | 67 |
|  | 5.5 | 0 | 125 |

EXAMPLE 6

S. lividans transformed respectively with pCAO20-0SU1-FeS-B#9, pCAO200SU#112 and pCAO200 were cultured for 36 hours in 400 ml of YEME broth at 30° C. S. griseolus ATCC 11796 was similarly cultured in 400 ml of sporulation broth. Six hours before harvesting the cells, 150 ml of fresh YEME broth was added to the S. lividans cells, and the S. griseolus cells were split into two 200 ml cultures with 100 ml of fresh sporulation broth added to each. 10001 (36 mg) was added to one of the two S. griseolus cultures to induce cytochrome P450SU1. The cells were prepared as described above in Example 5 and the concentrations of the sulfonylurea compound 10006 and its metabolites 10007, 10008 or 10009 were determined.

The concentration (μM) of each compound is presented in Table 3.

TABLE 3

| Cells | Time (hours) | 10006 | 10007 | 10008 | 10009 |
|---|---|---|---|---|---|
| none | 0 | 362 | 0 | 0 | 0 |
| S. griseolus | 2 | 404 | 1 | 1 | 1 |
| ATCC 11796 | 4 | 394 | 2 | 1 | 1 |
| uninduced | 6 | 405 | 2 | 1 | 2 |
| S. griseolus | 2 | 369 | 4 | 3 | 4 |
| ATCC 11796 | 4 | 357 | 6 | 6 | 7 |
| induced | 6 | 355 | 8 | 5 | 9 |
| S. lividans | 2 | 326 | 12 | 18 | 15 |
| pCAO200 | 4 | 267 | 21 | 38 | 33 |
| SU1-FeS-B#9 | 6 | 232 | 30 | 55 | 49 |
| S. lividans | 2 | 376 | 2 | 1 | 0 |
| PCAO200SU1#12 | 4 | 384 | 2 | 1 | 1 |
|  | 6 | 386 | 2 | 1 | 1 |
| S. lividans | 2 | 381 | 4 | 0 | 0 |
| pCAO200 | 4 | 377 | 1 | 0 | 0 |
|  | 6 | 375 | 1 | 0 | 0 |

EXAMPLE 7

The cells were prepared as described above for Example 6 and it was determined to what extent the sulfonylurea compound 10010 was metabolized to compounds 10011 and 10012. The concentration (μM) of each compound is presented in Table 4.

TABLE 4

| Cells | Time (hours) | 10010 | 10011 | 10012 |
|---|---|---|---|---|
| none | 0 | 87 | 0 | 0 |
| S. griseolus | 2 | 70 | 12 | 0 |
| ATCC11796 | 4 | 49 | 20 | 2 |
| uninduced | 6 | 37 | 24 | 8 |
| S. griseolus | 2 | 40 | 32 | 2 |
| ATCC11796 | 4 | 8 | 46 | 11 |
| induced | 6 | 4 | 42 | 19 |
| S. lividans | 2 | 35 | 34 | 2 |
| pCAO200 | 4 | 11 | 37 | 12 |
| SU1-FeS-B#9 | 6 | 4 | 27 | 20 |
| S. lividans | 2 | 90 | 4 | 0 |
| pCAO200 | 4 | 85 | 7 | 0 |
| SU1#12 | 6 | 80 | 11 | 0 |
| S. lividans | 2 | 90 | 1 | 0 |
| pCAO200 | 4 | 89 | 2 | 0 |
|  | 6 | 89 | 3 | 0 |

EXAMPLE 8

The cells were prepared as described above for Example 6 and it was determined to what extent the sulfonylurea compound 10001 was metabolized to compounds 10002 and 10003, The concentration (μM) of each compound is presented in Table 5.

TABLE 5

| Cells | Time (hours) | 10001 | 10002 | 10003 |
|---|---|---|---|---|
| none | 0 | 291 | 0 | 0 |
| S. griseolus | 2 | 244 | 20 | 14 |
| ATCC 11796 | 4 | 167 | 54 | 37 |
| uninduced | 6 | 86 | 86 | 62 |
| S. griseolus | 2 | 220 | 127 | 76 |
| ATCC 11796 | 4 | 36 | 203 | 128 |
| induced | 6 | 3 | 218 | 142 |
| S. lividans | 2 | 28 | 105 | 86 |
| pCAO200 | 4 | 0 | 116 | 95 |
| SU1-FeS-B#9 | 6 | 0 | 112 | 94 |
| S. lividans | 2 | 281 | 2 | 2 |
| pCAO200 | 4 | 276 | 4 | 4 |
| SU1#12 | 6 | 276 | 6 | 5 |
| S. lividans | 2 | 301 | 2 | 1 |
| pCAO200 | 4 | 287 | 1 | 1 |
|  | 6 | 313 | 2 | 2 |

EXAMPLE 9

The cells were prepared as described above for Example 6 and it was determined to what extent the sulfonylurea compound 10004 was metabolized to compound 10005, The concentration (μM) of each compound is presented in Table 6.

TABLE 6

| Cells | Time (hours) | 10004 | 10005 |
|---|---|---|---|
| none | 0 | 114 | 0 |
| S. griseolus | 2 | 52 | 68 |
| ATCC 11796 | 4 | 0 | 114 |
| uninduced | 6 | 0 | 121 |
| S. griseolus | 2 | 0 | 122 |
| ATCC 11796 | 4 | 0 | 120 |
| induced | 6 | 2 | 118 |
| S. lividans | 2 | 2 | 35 |
| pCAO200 | 4 | 1 | 100 |
| SU1-FeS-B#9 | 6 | 2 | 100 |
| S. lividans | 2 | 81 | 43 |
| pCAO200 | 4 | 29 | 84 |
| SU1#12 | 6 | 0 | 109 |
| S. lividans | 2 | 97 | 22 |
| pCAO200 | 4 | 92 | 26 |
|  | 6 | 85 | 30 |

Examples 4–9 demonstrate that the genes for cytochrome P450SU1 and FeS-B when expressed in *S. livdans* can metabolize sulfonylurea compounds to the same products that are produced by *S. griseolus* ATCC 11796. Expression in *S. lividans* strains that have the gene(s) for cytochrome P450SU1 with or without FeS-B, however, is constitutive, not requiring induction by compounds like 10001. For optimal metabolic activity of *S. lividans* strains expressing cytochrome P450SU1, the gene for its electron donor FeS-B must be present as well. Examples 6–9 demonstrate that expressing the genes for both P450SU1 and FeS-B in *S. lividans* enables *S. lividans* to metabolize several sulfonylurea compounds more readily than *S. griseolus* cells that have not been previously induced with 10001. Such strains would be valuable for metabolizing sulfonylurea compounds that are poor inducers of cytochrome P450SU1 in *S. griseolus* ATCC 11796 since they can be metabolized by the *S. lividans* strains described without having to first induce with 10001 or some other sulfonylurea and later remove the inducing compound and its metabolites from the culture.

EXAMPLE 10

Constitutive expression of cytochrome, P450SU2 and FES-A in *S. lividans*

The plasmid made for the examples below was made by ligating the 2.0 kb BamHI fragment from pUC19-SU2-8 containing the genes for cytochrome P450SU2 and FeS-A into the BamHI site of pCAO200 which resulted in the plasmid pCAO200SU2-FeS-A#11. The plasmid pCAO200SU2-FeS-A#11 was transformed into *Streptomyces lividans* using methods selecting for resistance to the antibiotic thiostrepton encoded by the plasmid (Hopwood et al., Genetic Manipulation of Streptomyces. A Laboratory Manual, pp. 12–14 and 104–109, John Innes Foundation, Norwich, U. K., herein incorporated by reference). A restriction endonuclease map of pCAO200SU2-FeS-A#11 is shown in FIG. 8.

*S. lividans* containing the plasmid pCAO200SU2-FeS-A#11 was grown in YEME broth at 30° C. as described in Example 1 and the level of cytochrome P450SU2 was analyzed by Western blot as in Examples 1–3. The results are shown in FIG. 9. As can be seen, cytochrome P450SU2 is expressed in *S. lividans* transformed with pCAO200-SU2-FeS-A in the absence of sulfonylrurea induction. *S. lividans* cells transformed with pCAO200 do not produce cytochrome P450SU2.

EXAMPLES 11–12

Metabolism of sulfonylurea compounds by *S. lividans* cells containing the genes for cytochrome P450SU2 and FeS-A

EXAMPLE 11

*S. lividans* transformed with pCAO200SU2-FeS-A#11 and *S. lividans* transformed with pCAO200 were cultured for 36 hours in 400 ml of YEME broth at 30° C. *S. griseolus* PH2001 (mutant without SU1) was cultured in 400 ml of sporulation broth at 30° C. Nine hours before harvesting the cells, the *S. griseolus* PH2001 culture was divided into two 200 ml cultures. Both received 100 ml of fresh sporulation broth and one received 36 mg of 10001 to induce cytochrome P450SU2. The cells were prepared as described above in Example 6 and the concentrations of the sulfonylurea compound 10001 and its metabolites 10002 and 10003 were determined.

The concentration (μM) of each compound is presented in Table 7.

TABLE 7

| Strain | Time (hours) | 10001 | 10002 | 10003 |
|---|---|---|---|---|
| none | 0 | 279 | 0 | 0 |
| S. griseolus | 2 | 271 | 7 | 1 |
| PH2001 | 4 | 264 | 12 | 2 |
| uninduced | 6 | 244 | 23 | 3 |
| S. griseolus | 2 | 286 | 41 | 7 |
| PH2001 | 4 | 256 | 60 | 10 |
| induced | 6 | 234 | 71 | 13 |
| S. lividans | 2 | 279 | 7 | 1 |
| pCAO200SU2 | 4 | 273 | 12 | 2 |
| -FeS-A#11 | 6 | 251 | 15 | 3 |

EXAMPLE 12

The cells were prepared as described above for Example 11 and it was determined to what extent the sulfonylurea compound 10010 was metabolized to compound 10011.

The concentration (μM) of each compound is presented in Table 8.

TABLE 8

| Strain | Time (hours) | 10010 | 10011 |
|---|---|---|---|
| none | 0 | 88 | 0 |
| S. griseolus | 2 | 89 | 0 |
| PH2001 | 4 | 88 | 0 |
| uninduced | 6 | 89 | 1 |
| S. griseolus | 2 | 64 | 21 |
| PH2001 | 4 | 56 | 28 |
| induced | 6 | 50 | 32 |
| S. lividans | 2 | 90 | 1 |
| + pCAO200SU2 | 4 | 84 | 5 |
| -FeS-A#11 | 6 | 72 | 14 |

The results of Example 10 (the Western blot analysis) showed that bacteria containing the cytochrome P450SU2 gene produced cytochrome P450SU2 constitutively. This is in contrast to the case in *S. griseolus* strains in which P450SU2 is made in detectable amounts only with the addition of inducing sulfonylurea compounds such as 10001 (O'Keefe et al. Recent Adv. in Phytochemistry 21: 151–137, (1987)). Results from Examples 11 and 12 (the metabolism experiments) show that constitutive expression of the cytochrome P450SU2 and FeS-A genes in *S. lividans* enables *S. lividans* to metabolize sulfonylurea compounds nearly to the same extent as *S. griseolus* PH2001. Also, *S. lividans* transformed with pCAO200SU2-FeS-A#11 metabolizes the sulfonylurea 10010, which is a poor inducer of cytochrome P450SU2 in *S. griseolus*, more readily than uninduced *S. griseolus* PH2001.

EXAMPLE 13

Prevention of sulfonylurea inhibition of plant growth

A 2 liter culture of *S. lividans* pCAO200SU1-FeS-B#9 was grown in YEME medium at 30° C. until the culture was in lake log phase of growth and the absorbance in a spectrophotometer at a wavelength of 600 nM was between about 1.0 and 1.3. Tomato seedlings (*Lysopersicon esculentum* cv. "Pixie") were seeded directly into soiless media, Oasis Wedges® (Smithers-Oasis, Kent, Ohio), fertilized with 500 ppm Peters'® fertilizer (20:19:18); and 300 ppm of iron was added weekly. As the tomato plants develop, roots ramify through the Oasis Wedges®. The tomato plants were transplanted to pots when they were 4 inches tall as follows.

Five inch standard round pots (without holes) were filled with Sassafras sandy loam (pH 6.7, 0.8% OM) and an oasis cube. The contents of the each pot was sprayed, prior to transplanting the tomato plants, with either 10001, in 25% dry flowable composition (25 DF) or 10010, 75 DF at rates of 16, 32, 64, 125 or 250 grams of active ingredient per hectare (g ai/ha). The Oasis cube was then removed and replaced by another containing a transplant tomato plant dipped in either water (treatment A), YEME medium (treatment B)-or the culture of *S. lividans* pCAO200SU1-FeS-B#9 described above (treatment C). Six transplant tomato plants received each of the three treatments, and five transplant tomato plants (to serve as controls) received no treatment. The resulting tomato plants were grown in a greenhouse for 19 days and watered twice daily, after which they were evaluated for visual injury (100=complete kill, other numbers=percentage of injury relative to controls [subjectively determined], 0=no injury) with respect to the water dipped, no-herbicide control treatments. The plants were left in the greenhouse for one more week after which the fresh weights of the shoots of the plants were determined. The roots of the plants which received these treatments and controls were examined too.

Table 9 shows the visual injury ratings for the transplants which were determined by visual inspection 19 days after transplanting (DAT). Tomato plants which were planted into 10001 and 10010 showed different degrees of visual damage depending on which treatment they received. Tomato plants treated with treatment C were significantly less injured by 10001 when the latter was applied at rates of 64, 125, and 250 g ai/ha than were the tomato plants which received treatments A or B. Tomato plants which had been transplanted into 10010 were injured to similar extents regardless of the treatment they received.

Weights of the fresh shoots of those plants which received 16 and 32 g ai/ha of 10010 and of all those plants which received 10001 were determined (Table 10). The weights of the fresh shoots of tomatoes planted into 10010 receiving water, YEME or *S. lividans* treatments were not significantly different (p=0.05) from each other and were all considerably less than those which did not receive any herbicide. While the shoots of tomatoes planted into 10001 (at application rates of 64, 125, or 250 g ai/ha) weighed considerably less than those which did not receive herbicide, they weighed significantly more when they had been dipped in *S. lividans* than when they were treated with water or YEME. Shoot weights of the tomatoes dipped in the cultures of pCAO200SU1-FeS-B#9 were approximately 3-4 times greater at the concentration of 250 g ai/ha of 10001 and 2-3 times at the concentration of 125 g ai/ha of 10001. The differences between the weights of the shoots from plants which received 10001 at application rates of 16 or 32 g ai/ha were not significant regardless of which additional treatment they received.

Visual examination of the root systems of selected treatments showed no signs of injury when the plants were dipped in water, YEME or pCAO200SU1-FeS-B#9 and did not receive herbicide. Apparently *S. lividans* produced no gross signs of damage or aberrant morphology to the roots. When the plants received 10001, they all had roots with damage typical of that resulting from contact with sulfonylureas (stunted primary roots with poorly developed secondary roots). Presumably, dipping the plants in *S. lividans* depleted the level of 10001 in the soil solution in the vicinity of the roots to a low enough level to alleviate some shoot symptoms, but not enough to mitigate damage to the roots directly in contact with the soil.

TABLE 9

| Sulfonyl-urea | Dosage rate (g ai/ha) | Treatment A (water) | Treatment B (YEME) | Treatment C (pCAO200SU1-FeS-B#9) |
|---|---|---|---|---|
| Visual Injury Ratings of Transplanted Tomatoes* | | | | |
| 10010 | 250 | 100,80,100, 90,100,100 | 100,80,80, 100,80,80 | 70,80,80, 100,90,90 |
| | 125 | 80,100,80, 90,100,100 | 100,70,80, 100,80,70 | 80,80,80 60,80,80 |
| | 64 | 80,100,80, 80,100,100 | 50,60,80, 70,100,80 | 60,100,100 80,80,100 |
| | 32 | 80,100,80, 100,100,100 | 70,70,60, 80,60,60 | 60,50,60 50,60,60 |
| | 16 | 60,80,90, 60,50,80, | 60,80,70, 80,60,50 | 60,60,60 60,60,60 |
| 10001 | 250 | 100,80,100, 100,90,80 | 80,70,80, 80,100,80 | 50,50,50 50,50,50 |
| | 125 | 100,100,90, 90,80,80 | 70,70,70, 70,80,60 | 50,50,50 50,50,50 |
| | 64 | 70,50,80, 70,70,60 | 60,60,80, 60,60,60 | 40,50,50 40,40,40 |
| | 32 | 40,100,70, 60,80,60 | 50,60,50, 50,80,60 | 40,40,40 100,40,40 |
| | 16 | 40,40,40, 60,40,40 | 60,50,50, 50,50,50 | 40,40,40 40,40,40 |
| none | 0 | 0,0,0 0,0, | 0,0,0, 30,30 | 0,0,0 20,20 |
| Mean value of visual ratings | | | | |
| 10010 | 250 | 95.0 | 86.7 | 85 |
| | 125 | 91.7 | 83.3 | 76.7 |
| | 64 | 90.0 | 83.3 | 86.7 |
| | 32 | 93.3 | 66.7 | 56.7 |
| | 16 | 70.0 | 63.3 | 60 |
| 10001 | 250 | 91.7 | 81.7 | 50.0 |
| | 125 | 90 | 70 | 50 |
| | 64 | 66.7 | 63.3 | 43.3 |
| | 32 | 68.3 | 58.3 | 50 |
| | 16 | 43.3 | 51.7 | 40 |
| none | | 0 | 12 | 8 |

*Scale of 0 to 100 with 100 = complete kill, 0 = no injury.

TABLE 10

| Sulfonyl-urea | Dosage rate (g ai ha) | Treatment A (water) | Treatment B (YEME) | Treatment C (pCAO200SU1-FeS-B#9) |
|---|---|---|---|---|
| Shoot Fresh Weights of Selected Treatments (grams) | | | | |
| 10010 | 32 | 0.85,0.38,0.93 0.74,0.34,0.66 | 3.0,1.03,1.05 1.74,1.82,0.98 | 2.16,1.09,2.30 2.21,0.93,2.07 |
| | 16 | 0.56,1.45,2.54 2.14,0.78,0.18 | 1.42,3.10,1.65 1.56,1.49,0.28 | 2.86,1.19,3.27 2.70,1.62,0.95 |
| 10001 | 250 | 0.53,1.03,0.46 0.10,1.55,0.10 | 0.64,0.76,0.51 0.19,0.11,0.20 | 2.64,2.61,2.50 2.17,2.71,1.81 |
| | 125 | 1.86,0.73,1.88 0.1,0.10,0.10 | 1.13,1.24,1.68 0.63,1.11,0.58, | 3.06,3.69,4.00 1.41,1.55,2.60 |
| | 64 | 2.06,0.32,1.45 0.78,2.59,1.04 | 1.32,1.48,2.23 0.62,1.40,1.36 | 4.04,3.88,2.74 2.91,2.62,1.45 |
| | 32 | 2.43,3.30,1.16 5.36,0.80,1.90 | 0.53,2.82,1.86 1.26,1.84,2.26 | 4.02,2.19,3.22 4.10,3.10,3.59 |
| | 16 | 3.85,1.46,4.80 3.79,2.36,3.23 | 3.61,1.59,2.62 1.77,2.89,1.59 | 2.60,2.42,2,36 4.32,3.10,3.80 |
| none | | 14.8,17.1,12.6 16.28,14.77 | 16.9,15.0,5.0 11.4,16.5 | 11.2,12.09, 15.75,7.8,7.54 |
| Mean Shoot Fresh Weights (grams) | | | | |
| 10010 | 32 | 0.65 | 1.60 | 1.79 |
| | 16 | 1.28 | 1.58 | 2.10 |
| 10001 | 250 | 0.63 | 0.40 | 2.41 |
| | 125 | 0.80 | 1.06 | 2.72 |
| | 64 | 1.37 | 1.40 | 2.94 |
| | 32 | 2.49 | 1.76 | 3.37 |
| | 16 | 3.25 | 2.35 | 3.1 |
| None | | 15.11 | 12.96 | 10.88 |

EXAMPLE 14

Demonstration of metabolism of sulfonylurea compounds by *S. griseolus, S. griseus, S. ambofaciens,* and *S. lividans* strains that are transformed with pPAT108

*S. griseolus* PH2003, *S. griseus* PH4001, *S. ambofaciens* PH4002, and *S. lividans* J11326 were transformed with the plasmid pPAT108. The transformed *S. griseolus* strain, PH3826, was cultured for 24 hours in 150 mls of sporulation broth with 5 ug/ml thiostrepton. The transformed *S. griseus* strain, PH3832, and the transformed *S. ambofaciens* strain, PH3834, were cultured for 24 hours in 150 mls of trypticase soy broth with 5 ug/ml thiostrepton. The transformed *S. lividans* strain, PH3822, was similarly cultured in 150 mls of YEME broth with 5 ug/ml thiostrepton. Three hours before harvesting the cells, 50 mls of fresh medium of the same type with 5 ug/ml thiostrepton was added to each culture. The cells from each of the cultures were harvested by centrifugation, washed twice with 50 mMMOPS, pH7.2 and re-suspended in five cell volumes of MOPS containing 0.2% glucose and 120 ug/ml of the sulfonylurea 10001. The cell suspensions were incubated at 30° C. with shaking and aliquots were removed at 0.5, 1, 2 and 4 hours. The supernatant of each aliquot was analyzed by HPLC and the concentration of the sulfonylurea compound 10001 and its metabolites 10002 and 10003 were determined.

The concentration (uM) of each compound is presented in Table 11.

TABLE 11

| Strain | Time (hours) | 10001 | 10002 | 10003 |
|---|---|---|---|---|
| *S. griseolus* PH3826 | 0.5 | 222 | 41 | 22 |
| | 1.0 | 137 | 101 | 58 |
| | 2.0 | 19 | 171 | 97 |
| | 4.0 | 0 | 189 | 107 |
| *S. griseus* PH3832 | 0.5 | 281 | 18 | 9 |
| | 1.0 | 238 | 45 | 26 |
| | 2.0 | 177 | 82 | 46 |
| | 4.0 | 77 | 138 | 80 |

TABLE 11-continued

| Strain | Time (hours) | 10001 | 10002 | 10003 |
|---|---|---|---|---|
| S. ambofaciens PH3834 | 0.5 | 299 | 6 | 1 |
| | 1.0 | 278 | 11 | 6 |
| | 2.0 | 250 | 27 | 14 |
| | 4.0 | 191 | 64 | 33 |
| S. lividans PH3822 | 0.5 | 294 | 2 | 1 |
| | 1.0 | 284 | 5 | 3 |
| | 2.0 | 262 | 10 | 5 |
| | 4.0 | 232 | 25 | 15 |
| S. griseus PH4001 | 1.0 | 370 | 1 | 1 |
| | 4.0 | 377 | 2 | 4 |
| S. ambofaciens PH4002 | 1.0 | 406 | 0 | 0 |
| | 4.0 | 412 | 0 | 0 |

EXAMPLE 15

Demonstration of metabolism of sulfonylurea compounds of S. griseolus, S. grisens, S. ambofaciens, and S. lividans strains that are transformed pCS325

S. griseolus PH2003, S. griseus PH4001, S. ambofaciens PH4002, and S. lividans JI1326 were transformed with the plasmid pCS325. Cells of the transformed strains of S. griseolus PH3809, S. griseus PH3817, S. ambofaciens PH3818, and S. lividans PH3816, were grown and treated as described in Example 14, and the concentrations of the sulfonylurea compound 10001 and its metabolites 10002 and 10003 were determined.

The concentration (uM) of each compound is presented in Table 12.

TABLE 12

| Strain | Time (hours) | 10001 | 10002 | 10003 |
|---|---|---|---|---|
| S. griseolus PH3809 | 0.5 | 175 | 64 | 6 |
| | 1.0 | 108 | 155 | 16 |
| | 2.0 | 0 | 236 | 24 |
| | 4.0 | 0 | 238 | 25 |
| S. griseus PH3817 | 0.5 | 226 | 37 | 3 |
| | 1.0 | 181 | 73 | 7 |
| | 2.0 | 69 | 167 | 16 |
| | 4.0 | 0 | 220 | 23 |
| S. ambofaciens PH3818 | 0.5 | 286 | 16 | 1 |
| | 1.0 | 265 | 33 | 3 |
| | 2.0 | 210 | 67 | 7 |
| | 4.0 | 129 | 134 | 13 |
| S. lividans PH3816 | 0.5 | 331 | 19 | 1 |
| | 1.0 | 339 | 36 | 3 |
| | 2.0 | 299 | 68 | 7 |
| | 4.0 | 248 | 103 | 11 |

The results in Examples 14 and 15 showed that transformation of Streptomyces strains with broad host range plasmids containing the genes for P450SU1 and FeS-B or P450SU2 and FeS-A enabled these transformed strains to constitutively metabolize sulfonylurea compounds. The rate at which these transformed strains were able to carry out the metabolism of a sulfonylurea compound varied depending on the ability of endogenous reductases to provide reducing equivalents to the P450 as required for catalysis and on the copy number of the plasmid in the transformed strain.

EXAMPLE 16

Metabolism of Non-sulfonylurea Herbicides by Bacteria Containing the Genes for P450SU1 or P450SU2

Separate cultures (50 ml) inoculated with S. lividans C37, S. lividans transformed with pCAO200SU1-FeS-B#9, S. griseolus ATCC11796, S. griseolus PH2003 transformed with pIJ425, or S. ariseolus PH2003 transformed with pCS325 were cultured in sporulation broth for 18 hours at 30° C. with shaking. Each culture was then resuspended in 25 ml fresh sporulation broth and 3.0 mg herbicide added. In the case of cultures of S. griseolus ATCC11796, a second culture containing herbicide and 3.0 mg 10001 was also prepared. Each culture was reincubated for 24 hours, then an aliquot of the medium was withdrawn and analyzed by HPLC. The percent conversion of herbicide was determined.

The percent conversion of herbicide is presented in Table 13. The results in Table 13 show that bacteria containing constitutively expressed P450SU1 metabolized the nonsulfonylurea herbicides 10017, 10018, and 10019. In addition bacteria containing constitutively expressed P450SU2 metabolized the nonsulfonylurea herbicides 10020, 10021, 10017, 10022 and 10018.

TABLE 13

| Strain | Percent Conversion | | | | | | | |
|---|---|---|---|---|---|---|---|---|
| | 10020 | 10021 | 10017 | 10022 | 10018 | 10019 | 10023 | 10001 |
| S. griseolus ATCC 11796 | 12 | NT | 1 | 1 | NT* | 0 | 0 | 100 |
| S. griseolus ATCC 11796, 10001 added | 33 | NT | 35 | 30 | NT* | 80 | 0 | 100 |
| S. lividans C37 | 17 | 0 | 19 | 50 | 0 | 0 | 0 | 0 |
| S. lividans pCAO200 SU1-FeS-B#9 | 19 | 23 | 47 | 42 | 56 | 35 | 0 | 56 |
| S. griseolus PH2003 pIJ425 | 7 | 7 | 6 | 0 | 10 | 0 | NT* | 100 |
| S. griseolus PH2003 pCS325 | 89 | 93 | 98 | 96 | 72 | 9 | NT* | 100 |

*NT = Not tested

EXAMPLE 17

Metabolism of 10015 Analogs to 10014—Formulation of Phytotoxic Metabolites by P450OSU1

Cultures of S. griseolus ATCC11796 were cultivated in sporulation-broth (50ml) at 30° C. with shaking for 17 hours. Each culture was then resuspended in 25 ml fresh sporulation broth, 3.0 mg sulfonylurea was added, and the culture reincubated for 4 days. Aliquots of the medium were then analyzed by HPLC. Formation of 10014 was measured based on similarity of retention time and UV spectrum of the test metabolite to that formed by metabolism of 10015.

The percent conversion of sulfonylurea to 10014 is presented in Table 14. The results in Table 14 show that P450SU1 metabolized the nonphytotoxic sulfonylureas 10015, 10024, 10025, 10026, 10027 and 10028 to phytotoxic 10014.

TABLE 14

| Sulfonylurea | N-substitution | % Conversion to 10014 |
|---|---|---|
| 10029 | —CH$_3$ | 0 |
| 10024 | —CH$_2$CH$_3$ | 69 |
| 10027 | —CH$_2$CH$_2$CH$_3$ | <10 |
| 10004 | —CH$_2$CH$_2$CH$_2$CH$_3$ | 0 |
| 10015 | —CH(CH$_3$)$_2$ | 100 |
| 10030 | —CH$_2$CH(CH$_3$)$_2$ | 0 |
| 10025 | -benzyl | 50 |
| 10028 | —CH$_2$CH═CH$_2$ | 27 |
| 10031 | —COCH$_3$ | 0 |
| 10026 | —CH$_2$CH$_2$F | 18 |
| 10032 | —CH$_2$Si(CH$_3$)$_3$ | 0 |

EXAMPLE 18

Prevention of sulfonylurea inhibition of plant growth

One liter cultures of *S. griseolus* ATCC 11796, *S. lividans* pCAO200, *S. lividans* pCAO200-#9-SU1-FeS-B or *S. lividans* pCAO200-#12-SU1 were grown in YEME medium (sporulation broth for the *S. griseolus* culture) at 30° C. until the cultures were in late log phase of growth and the absorbance of each culture in a spectrophotometer at a wavelength of 600 nM was between 1.0 and 1.3. Tomato seedlings (*Lycopersicon esculentum* cv. "Pixie") were seeded directly into soiless media, Oasis Wedges ® (Smithers-Oasis, Kent, Ohio), fertilized with 500 ppm Peter's ® fertilizer (20:19:18); and 300 ppm of iron was added weekly. As the tomato plants develop, roots ramify through the Oasis Wedges ®. The tomato plants were transplanted to pots when they were 4 inches tall as follows.

Five inch standard round pots (without holes) were filled with Sassafras sandy loam (ph 6.7, 0.8% OM) and a single Oasis cube and then treated preemergence with either Classic ® (10001) 25 DF (16, 32, 64, 125 and 250 grams active ingredient/hectare [g ai/ha]) or Oust ® (10010) 75 DF at rates of 4, 8, 16, 32 and 64 g ai/ha), both herbicides available from E. I. du Pont de Nemours and Company, Wilmington, Del. The oasis cube was then removed and replaced by a transplant tomato dipped in either the cultures described above of *S. griseolus* ATCC 11796 (treatment A), *S. lividans* pCAO200 (treatment B), *S. lividans* pCAO200-#9-SU1-FeS-B (treatment C), *S. lividans* pCAO200-#12-SU1 (treatment D) or into water (treatment E). Five transplants were tested for each treatment at each dosage rate. The pots were placed on a greenhouse bench for 22 days and watered twice daily, after which shoot fresh weights of treatments were determined. Roots of these treatments and controls were examined too. Plants, soil and pots treated with bacterial cultures were double bagged and disposed by incineration.

Table 15 shows the weights of the fresh shoots for the transplants which were determined 22 days after transplanting. When fresh weights were compared, the safening by treatment C (*S. lividans*-#9-SU1-FeS-B) was clear (P=0.05). Treatment C permitted significantly greater fresh weights than the water controls (treatment E) at 10001 rates of 32, 64 and 125 g ai/ha and at 10010 rates of 16 and 32 g ai/ha. At these herbicide application rates, treatment C gave greater safening than treatments A, B and D as well, which demonstrated the need for the inclusion of the DNA encoding FeS-B for the best safening. Shoot fresh weight of the tomatoes in treatment C (*S. lividans* pCAO200-#9-SU1-Fes-B) were approximately 2-3 times greater than those from the other treatments when planted into soil with 32, 64 and 125 g ai/ha of 10001 or 16 and 32 g ai/ha of 10010. The differences between the weights of the shoots from plants receiving the other herbicide treatments were not significantly different from those treated with water.

Visual examination of the root systems of the plants treated with any of the five treatments showed no signs of injury when they did not receive herbicide. When the plants were treated with herbicide, all had roots with damage typical of that resulting from contact with sulfonylureas (stunted primary roots with poorly developed secondary roots). This pointed to *S. lividans* expressing the genes for cytochrome P450SU1 and FeS-B being able to deplete the level of herbicide within the transplanted cube, but since *S. lividans* probably did not colonize the roots of the transplant, damage still occurred when the roots came directly in contact with the treated soil.

TABLE 15

Shoot Fresh Weights of Tomatoes Transplanted into 10001 or 10010 after Various Treatments*

| Herbicide | Rate (g ai/ha) | Pretreatment** | | | | |
|---|---|---|---|---|---|---|
| | | A | B | C | D | E |
| 10001 | 16 | 0.88 | 0.67 | 1.63 | 0.62 | 1.67 |
| | | (0.16) | (0.09) | (0.18) | (0.13) | (0.48) |
| | 32 | 0.74 | 0.47 | 1.62 | 0.82 | 1.07 |
| | | (0.20) | (0.05) | (0.15) | (0.19) | (0.25) |
| | 64 | 0.21 | 0.53 | 1.24 | 0.47 | 0.46 |
| | | (0.04) | (0.07) | (0.08) | (0.04) | (0.16) |
| | 125 | 0.49 | 0.38 | 1.01 | 0.35 | 0.23 |
| | | (0.13) | (0.11) | (0.29) | (0.05) | (0.02) |
| | 250 | 0.44 | 0.25 | 0.55 | 0.26 | 0.21) |
| | | (0.12) | (0.07) | (0.24) | (0.03) | (0.04) |
| 10010 | 4 | 1.16 | 0.73 | 0.88 | 0.88 | 2.00 |
| | | (0.11) | (0.14) | (0.12) | (0.27) | (0.24) |
| | 8 | 0.58 | 0.69 | 1.02 | 0.75 | 0.65 |
| | | (0.17) | (0.3) | (0.32) | (0.15) | (0.32) |
| | 16 | 0.32 | 0.65 | 0.98 | 0.56 | 0.39 |
| | | (0.06) | (0.15) | (0.13) | (0.11) | (0.25) |
| | 32 | 0.33 | 0.42 | 1.01 | 0.62 | 0.28 |
| | | (0.03) | (0.09) | (0.15) | (0.10) | (0.04) |
| | 64 | 0.30 | 0.39 | 0.46 | 0.29 | 0.34 |
| | | (0.06) | (0.12) | (0.14) | (0.05) | (0.09) |
| None | — | 14.14 | 9.73 | 14.25 | 16.40 | 23.73 |
| | | (0.44) | (1.90) | (2.56) | (2.91) | (4.70) |

*The values in grams are the mean of five plants for each pretreatment and herbicide rate. The standard deviation in parentheses () is indicated below the mean weight value
**Key to Pretreatments:
A: *Streptomyces griseolus* ATCC11796
B: *Streptomyces lividans* pCAO200
C: *S. lividans* pCAO200-#9-SU1-FeS-B
D: *S. lividans* pCAO200-#12-SU1
E: water

EXAMPLE 19

Engineering plasmids with the P450SU1 and or FeS-B coding sequences for the transformation of plants Sequences must be added to 5'-end and 3'-end of the cytochrome P450SU1 and FeS-B coding sequence in order to get transcription and translation of the cytochrome P450SU1 and FeS-B genes in plants. We have done so in ten plasmids that are described below, General descriptions of these ten plasmids are given first followed by detailed descriptions of how these plasmids were made.

A. Plasmid for cytoplasmic expression of cytochrome P450SU1 with or without FeS-B The plasmid, pSU17, was prepared containing the P450SU1 coding sequence with the Cauliflower Mosaic Virus 35S promoter and the 5' untranslated region from the petunia chlorophyll a/b binding protein gene "Cab22L" (described in Harpster et al. Mol, Gen. Genet, 212:182–190 (1988) herein incorporated by reference) upstream of the P450SU1 coding sequence. The 3' untranslated region from the small subunit of ribulose bisphosphate carboxylase (SSU) gene "SSU301" from petunia (Dean et al, Mol, Gen, Genet,206:465–474 (1987)) was placed downstream of the P450SU1 coding sequence, For propagation in *E. coli* the pSU17 contained the sequences of the plasmid pUC118. A diagram of pSU17 is shown in FIG. 10A, The construct pSU17 when introduced into plant cells expressed cytochrome P450SU1 in the cytoplasm, The plasmid pSuFe1 contains two adjacent Cauliflower Mosaic Virus (CaMV) 35S promoters promoting transcription in opposite directions along with the 60 bp region from the 5'-untranslated region of the small subunit of ribulose bis-phosphate carboxylase (SSU) from petunia to constitutively express cytochrome P450SU1 and FeS-B in the cytoplasm of plants. The 3'-untranslated region used for expression of both genes is from the gene for hopaline synthetase(nos) derived from T-DNA of *Agrobacterium tumefaciens* (Depicker et al., J. Mol. Appl. Genet. 1:561–573 (1982)). A diagram of pSuFe1 is shown in FIG. 15A.

B. Plasmids that encode cytochrome P450SU1 and or FeS-B proteins that additionally contain peptides that can facilitate the transport of cytochrome P450SU1 or FeS-B into chloroplasts of plant cells In order to express the cytochrome P450SU1 or FeS-B proteins in the chloroplasts of plants, eight constructions were engineered using 5' promoter regions, coding regions of the transit peptide sequences and in some cases part of the mature coding sequences of genes encoding proteins normally imported into the chloroplasts of plants. The genes for normally imported proteins were those for ribulose bisphosphate carboxylase (SSU) and chlorophyll a/b binding protein (Cab) both from petunia. Plasmids that only added to the P450SU1 coding sequence the amino terminal amino acid sequence that is normally removed upon transport into chloroplasts and plasmids that added to the P450SU1 coding sequence the normally removed peptide and up to 27 amino acids of the mature transported protein were constructed. Plasmids that additionally contain the FeS-B coding sequence only added the DNA sequence that encodes the peptide normally removed upon transport into the chloroplast.

1. pSSU-SU11. This plasmid was prepared and contained the DNA encoding the first 69 amino acids of the SSU301 gene from petunia (Dean et al., Mol. Gen. Genet. 206:465–474 (1987) herein incorporated by reference) (57 amino acid chloroplast transit peptide and 12 amino acids of mature SSU301) added onto the NH2-terminus of the P450SU1 coding sequence. The SSU301 promoter and 5' and 3' untranslated sequences (Dean et al., Mol. Gen. Genet. 206:465–474 (1987)) of the SSU301 gene provided transcription and translation signals for expression of this protein in plants. For propagation in *E. coli* pSSU-SU11 included the sequences of the plasmid pUC11S. A diagram of pSSU-SU11 is shown in FIG. 10B.

2. pSSU-SU12. This plasmid was prepared like pSSU-SU11 except that it contained only the DNA encoding the 57 amino acid chloroplast transit peptide of the petunia SSU301 gene added onto the amino terminus of P450SU1. A diagram of pSSU-SU12 is shown in FIG. 10C.

3. pCab-SU13. This plasmid was prepared containing the DNA encoding the first 61 amino acids of the petunia Cab22L gene (Dunsmuir, Nucleic Acids Res. 13:2503–2518 (1985) herein incorporated by reference) (34 amino acids of the chloroplast transit peptide and 27 amino acids of the mature Cab22L protein) added onto the NH2-terminus of cytochrome P450SU1. The promoter and 5'-untranslated region of the petunia Cab22L gene (Gidoni et al. Mol. Gen. Genet. 211:507–514 (1988) herein incorporated by reference) and the 3'-untranslated region of the petunia SSU301 gene provided transcription and translation signals for expression in plant cells. For propagation in *E. coli* pCab-SU13 included the sequences of the plasmid pUC118. A diagram of pCab-SU13 is shown in FIG. 10F.

4. pCab-SU11. This plasmid is similar to pCab-SU13 except that it contains the DNA encoding first 48 amino acids of the petunia Cab22L gene (Dunsmuir, Nucleic Acids Res. 13:2503–2518(1985)) (34 amino acids of the chloroplast transit peptide and 14 amino acids of the mature Cab22L protein) added onto the NH2-terminus of cytochrome P450SU1. This plasmid can be prepared from pCab-SU13 by site-directed mutagenesis in which the 39 nucleotides encoding for the 13 additional amino acids of the Cab22L protein found in pCab-SU13 are removed from the plasmid using methods well known to those-skilled in the art (Kunkel, T. A., et al. Proc. Natl. Acad. Sci. U.S.A., 82:488–492 (1985)) knowing that the DNA sequence spanning this area in pCab-SU13 is:

ATG AGG AAG ACT GCT ACC AAG GCC AAG CCT
Met$_1$—Arg$_2$—Lys$_3$—Thr$_4$—Ala$_5$—Thr$_6$—Lys$_7$—Ala$_8$—Lys$_9$—Pro$_{10}$
Cab22L mature protein GTC TCT TCT GGC AGC CCA TGG TAT
Val$_{11}$—Ser$_{12}$—Ser$_{13}$—Gly$_{14}$—Ser$_{15}$—Pro$_{16}$—Trp$_{17}$—Tyr$_{18}$—

GGT CCT GAT CGT GTC AAG TAC TTG
Gly$_{19}$—Pro$_{20}$—Asp$_{21}$—Arg$_{22}$—Val$_{23}$—Lys$_{24}$—Tyr$_{25}$—Phe$_{26}$—

GGC AGT ACT GAT ACC GCC
Gly$_{17}$—Ser$_1$—Thr$_2$—Asp$_3$—Thr$_4$—Ala$_5$
Cytochrome P450SU1

A diagram of pCab-SU11 is shown in FIG. 10D.

5. pCab-SU12. This plasmid is similar to pCab-SU13 except that it contains the DNA encoding first 53 amino acids of the petunia Cab22L gene (Dunsmuir, Nucleic Acids Res. 13:2503–2518 (1985)) (34 amino acids of the chloroplast transit peptide and 19 amino acids of the mature Cab22L protein) added onto the NH2-terminus of cytochrome P450SU1. This plasmid can be prepared from pCab-SU13 by site-directed mutagenesis in which the 24 nucleotides encoding for the 8 additional amino acids of the Cab22L protein found in pCab-SU13 are removed from the plasmid using methods well known to those skilled in the art (Kunkel, T. A. et el., Proc. Natl. Aced. Sci. U.S.A., 82:488–492 (1985)) knowing that the DNA sequence spanning this area in pCab-SU13 is as shown above. A diagram of pCab-SU13 is shown in FIG. 10E.

6. The plasmid pSuFe2 contains two adjacent CaMV 35S promoters directing transcription in opposite directions along with the 60 bp region from the 5'-untranslated region of SSU from petunia. The cytochrome P450SU1 and FeS-B coding sequences, however, have sequences encoding the 57 amino acid chloroplast transit peptide from SSU added at the start of each coding sequence. The FeS-B gene contains the nos 3'-untranslated sequence while the P450SU1 gene contains the petunia SSU 3'-untranslated sequence. This construction constitutively expresses cytochrome P450SU1 end FeS-B and targets their resulting proteins to the chloroplasts or plastids plants and upon entry into the chloroplast and processing of the transit peptide the mature P450SU1 or FeS-B protein will be present without any additional sequences. A diagram of pSuFe2 is shown in FIG. 15B.

7. The plasmid pSuFe3 contains two adjacent SSU promoters from petunia directing transcription in opposite directions. These two promoters express cytochrome P450SU1 and FeS-B coding sequences that have had sequences encoding the 57 amino acid chloroplast transit peptide from SSU added at the start of each coding sequence. The FeS-B gene has the nos 3'-untranslated sequence while cytochrome P450SU1 has the petunia SSU 3'-untranslated sequence. This construction expresses both cytochrome P450SU1 and FeS-B in a light dependent fashion. The two proteins are also targeted to the chloroplast where, after proteolytic cleavage of the transit peptide, they exist without any additional sequences being added. A diagram of pSuFe3 is shown in FIG. 15C.

8. The plasmid pSuFe4 is similar to pSuFe3 except that instead of the two SSU promoters being adjacent to one another, the nos 3'-untranslated sequence and petunia SSU 3'-untranslated sequence are adjacent to one another. All of the components of the two plasmids are otherwise the same. A diagram of pSuFe4 is shown in FIG. 15D.

Seven of the plasmids described above, i.e., two for cytoplasmic expression and five for chloroplast expression, were deposited in the American Type Culture Collection under the following access numbers. pCab-SU11 and pCab-SU12 can be made from pCab-SU13 as described above by those skilled in the art. pSuFe4 can be made from pSuFe3 as described below by those skilled in the art.

| P450SU1 construction | ATCC accession number |
|---|---|
| pSU17 | 67995 |
| pSSU-SU11 | 67994 |
| pSSU-SU12 | 67993 |
| pCab-SU13 | 67992 |
| pSuFe1 | |
| pSuFe2 | |
| pSuFe3 | |

Plasmids for expression of cytochrome P450SU1 with or without FeS-B in the cytoplasm of plant cells 1. Construction of pSU17. Flow diagram is shown in FIGS. 17A to 17D.

Plasmids used in sequencing the genes for cytochrome P450SU1 and FeS-B were derived by exonuclease III deletion (Hemikoff, Gene 28:351-359, 1984) from either end of the 2.4 kb BamHI DNA fragment that contains these genes. One of these plasmids, pSU12-1.8, has an endpoint 6bp downstream from the translation termination codon for P450SU1 while still containing the entire coding sequence for cytochrome P450SU1. This plasmid, pSU12-1.8, was used as a starting place to develop DNA constructions that would express the P450SU1 protein in plant cells. Addition of sequences to the 3'-end of the P450SU1 coding sequence are required for translation in plants. pSU12-1.8 was digested with HindIII and the site was filled in using the Klenow fragment of DNA polymerase I (Maniatis et al., Molecular Cloning: a Laboratory Manual, Cold Spring Harbor Press, Cold Spring Harbor, N.Y.(1982)). This plasmid was cut with EcoRI and the approximately 1.3 kb EcoRI-blunt end DNA fragment containing the P450SU1 coding sequence was subcloned into EcoRI-HincII cut pUC118 creating pSU14. The 3' nontranslated sequence from the SSU301 gene (encoding the small subunit of ribulose bisphosphate carboxylase[SSU]from petunia) was fused to the 3'-end of the P450SU1 coding sequence as follows. pSSU3033, a plasmid containing the SSU301 gene with a BglII site at the TGA stop codon of the translational stop for SSU (C. Dean et al. The Plant Cell 1:201-208 (1989)) was cut with BglII and the ends blunted with the Klenow fragment of DNA polymerase I (Maniatis et al., Molecular Cloning: a Laboratory Manual, Cold Spring Harbor Press, Cold Spring Harbor, N.Y.(1982)) and then cut with BamHI. The resulting 1.45 kb blunt end-BamHI DNA fragment containing the 3'-end of the SSU301 gene was subcloned into BamHI-HincII cut pUC118 and the resulting plasmid called pSSU3040. A three component ligation consisting of 1. the P450SU1 coding region from pSU14 (a 1.3 kb EcoRI-PstI DNA fragment), 2. the 3'-untranslated region from the SSU301 gene (a 1.45 kb PstI-BamHI fragment from pSSU3040) and 3. BamHI-EcoRI cleaved pUC1118 was performed (Manjarls et al., Molecular Cloning: a Laboratory Manual, Cold Spring Harbor Press, Cold Spring Harbor, N.Y.(1982)) to create pSU15. A ScaI site was introduced at the ATG start codon:

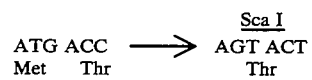

for P450SU1 in pSU15 by in vitro mutagenesis (Kunkel, T. A. PNAS 82: 488-492, (1985)) creating pSU16. This creates a P450SU1 "cassette" which was used in further constructions to express the P450SU1 gene in plants. A plasmid, p35S(J):Cab22L-CH, that contains the Cauliflower Mosaic Virus(CaMV) 35S promoter and the 5' untranslated region from the petunia chlorophyll a/b binding protein gene "Cab 22L" (Harpster et al. Molecular and General Genetics, 212: 182-190, 1988) was used to provide a promoter for expression of P450SU1 in plants. A 1.2 kb EcoRI-NcoI(blunted with the Klenow fragment of DNA polymerase I, (Maniatis et al., Molecular Cloning: a Laboratory Manual, Cold Spring Harbor Press, Cold Spring Harbor, N.Y.(1982))) from p35S(J):Cab22L-CH was ligated to ScaI(blunt)-EcoRI cleaved pSU16 to create pSU17. When the filled in NcoI site from p35S(J):Cab22L-CH and the ScaI site from pSU17 were fused together in this construction the ATG start codon for cytochrome P450SU1 was regenerated. This construction, pSU17, when introduced into plants expressed cytochrome P450SU1 in the cytoplasm of the plant cell.

In FIGS. 17A to 17 D the following steps are designated with letters at the arrows:

For FIG. 17A:
A 1) Hind III cut and fill in with Klenow
2) EcoRI cut
B EcoRI+HincII cut For FIG. 17C:
C EcoRI+PstI cut
D BamHI+EcoRI cut E BamHI+PstI cut
F 3 component ligation
For FIG. 17B:
  G 1) BglII and fill in with Klenow
    2) BamHI cut
  H BamHI+HincII
  I Ligate
For FIG. 17D:
  J Site directed mutation of P450SU1 ATG start site to ScaI site
  K 1) ScaI
    2) EcoRI cut
  L 1) NcoI cut and fill in with Klenow
    2) EcoRI cut
  M Ligate 2. Construction of plasmid pSUFel. Flow diagram is shown in FIGS. 18A to 18D.

Plasmids used in sequencing the genes for cytochrome P450SU1 and FeS-B were derived by exonuclease III deletion (Henikoff, Gene 28:351–359, 1984) from either end of the 2.4 kb BamHI DNA fragment that contains these genes. One of these plasmids, pSU12-2.04, has an endpoint several base pairs downstream of the stop codon of FeS-B. By site-directed mutagenesis (Munkel, T. A. PNAS 82: 488–492, (1985)) a ScaI site was introduced at the ATG initiation codon creating the plasmid pFeSB-1.02 and changing the sequence at the translation initiation site from

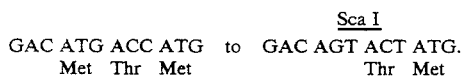

```
                        ScaI
GAC ATG ACC ATG   to   GAC AGT ACT ATG.
    Met Thr Met               Thr Met
```

A 0.24 kb ScaI-XbaI fragment, containing the FeS-B coding sequence from pFeSB-1.02 was cloned into p29593 that had been NcoI cut and the ends filled in with the Klenow fragment of DNA polymerase I (Maniatis et al., Molecular Cloning: a Laboratory Manual, Cold Spring Harbor Press, Cold Spring Harbor, N.Y.(1982)) and then subcut with XbaI creating pFeSB-3. The filled in NcoI site from p29593 recreates the ATG initiation codon for FeS-B. p29593 is a derivative of p35S(J):Cab22L CH (Harpstar et al. Mol. Gen. Genet. 212: 182–190 (1988)) that has had a BglII site introduced by site-directed mutagenesis (Kunkel, PNAS 82:488–492 (1985)) approximately 190 bp upstream of the transcription start point (using the DNA sequence of R. C. Gardner et al., Nucleic Acids Res. 9:2871–2888 (1981) nucleotide 7238 G changed to a C and nucleotide 7239 C changed to a T) of the CaMV 35S promoter (J. Odell et al. Nature 313:810–813 (1985)). p29593 contains the 35S promoter of Cauliflower Mosaic Virus (CaMV) and the 3' untranslated sequence of the hopaline synthase gene (nos) from T-DNA of *Agrobacterium tumefaciens* (Depicker et al. J. Mol. Appl. Genet. 1:561–573 (1982)). pSU17, from above, was digested with BamHI and partially digested with XhoI forming a 2.86 kb DNA fragment containing the cytochrome P450SU1 coding sequence and the 3' untranslated region of the petunia SSU gene. This was ligated with XhoI and BamHI digested p29593 to form pSU20. The 3'-untranslated region of the SSU gene was removed from pSU20 by partial PstI digestion and blunting the ends with T4 DNA polymerase (Maniatis et al., Molecular Cloning: a Laboratory Manual, Cold Spring Harbor Press, Cold Spring Harbor, N.Y.(1982)) and then digesting with BamHI and filling the ends with the Klenow fragment of DNA polymerase I (Maniatis et al., Molecular Cloning: a Laboratory Manual, Cold Spring Harbor Press, Cold Spring Harbor, N.Y.(1982)). The resulting DNA was intramolecularly ligated forming pSU21. A 2.6kb partially BglII digested and HindIII digested DNA fragment of pSU21 was isolated that contained the CaMV 35S promoter, P450SU1 coding sequence and the nos 3' untranslated sequence. This DNA fragment was ligated to a 0.76 kb HindIII-BglII DNA fragment of pFeSB-3 containing the CaMV 35S promoter, FeS-B coding sequence and nos gene 3' untranslated sequence forming pSUFel. pSUFel contains 2 CaMV 35S promoters one that transcribes the FeS-B coding sequence and nos gene 3' untranslated sequence and the other that transcribes the P450SU1 coding sequence and a nos gene 3' untranslated sequence. The plasmid pSUFel when transformed into plant cells drives expression of p450SU1 and FeS-B in the cytoplasm.

In FIGS. 18A to 18D the following steps are designated with letters at the arrows:
For FIG. 18A:
  A 1) XhoI partial cut
    2) BamHI cut
  B XhoI +BamHI cut
  C Ligate
For FIG. 18B:
  D 1) PstI partial, T4 blunt ends
    2) BamHI cut and fill in with Klenow
  E Recircularize
For FIG. 18C:
  F 1) NcoI and fill in with Klenow
    2) XbaI cut
  G Site directed mutagenesis of FeS-B ATG start to ScaI site
  H ScaI+XbaI cut
  I Ligate
For FIG. 18D:
  J BlII+HindIII cut
  K 1) BglII partial
    2) HindIII cut
  L Ligate with HindIII cut pUC118

Plasmids that direct the expression of cytochrome P450SU1 with or without FeS-B to the chloroplasts of plant cells In order to express the cytochrome P450SU1 protein or FeS-B in the chloroplasts of plants, plasmids were constructed using 5' promoter regions, coding regions of the transit peptide sequences, and in some cases the mature coding sequences of genes encoding proteins normally imported into the chloroplasts of plants. The naturally chloroplast imported genes used in these plasmids were those for ribulose hisphosphate carboxylase (SSU) and the chlorophyll a/b binding protein (Cab) both from petunia. Plasmids were made that added DNA encoding for amino terminal amino acid sequence that is normally removed upon transport into chloroplasts. Other plasmids were made that added DNA encoding the chloroplast transit peptide sequence and up to 27 amino acids of the mature transported protein onto the DNA encoding cytochrome P450SU1.

1. Construction of plasmids pSSU-SU11 and pSSU-SU12. Flow diagram is shown in FIGS. 19A and 19B.

A 1.8 kb ClaI(end blunted with Klenow fragment of DNA polymerase I)-BamHI DNA fragment from pSSU3019(Dean et al. The Plant Cell 1:201–208, (1989)) a clone that contains the 5' and 3' flanking regions but lacks the introns of the SSU301 gene was cloned into SmaI-BamHI cleaved pUC8 generating pSSU3043. The polylinker of pUC8 adds onto the SSU301 gene an EcoRI site to be used in the constructions. To make the fusion between the chloroplast transit peptide and P450SU1 an EcoRV site was introduced by site directed mutagenesis (Kunkel, PNAS 82: 488-492, (1985)) into the mature SSU301 coding sequence after amino acid 12 creating pSSU3044. A 1.4 kb EcoRI-EcoRV DNA fragment from pSSU3044 containing the SSU301 promoter and the DNA encoding the amino-terminus of the SSU301 protein was cloned into EcoRI-ScaI cleaved pSU16 creating pSSU-SU11. pSSU-SU11 encodes 12 extra amino acids in addition to the chloroplast transit peptide from the SSU301 protein added onto the DNA encoding the amino terminus of the P450SU11 protein. To create a precise fusion of the chloroplast transit peptide coding sequence with the P450SU1 coding sequence, an oligonucleotide directed site specific deletion (Kunkel, PNAS 82: 488-492, (1985)) was used to loop out the extra nucleotides between the transit peptide and the amino terminus of P450SU1. The resulting plasmid, pSSU-SU12, contains a perfect fusion between the transit peptide of the SSU301 gene and the amino terminus of P450SU1. The plasmids pSSU-SU11 and pSSU-SU12 express cytochrome P450SU1 in plant cells that is targeted to the chloroplasts.

In FIGS. 19A and 19B the following steps are designated with letters at the arrows:
For FIG. 19A:
  A 1) ClaI cut and fill in with Klenow
  2) BamHI cut
  B SmaI+BamHI
  C Ligate
  D Site directed mutagenesis creating EcoRV site at aa12 of mature SSU301 protein
For FIG. 19B:
  E EcoRI+EcoRV cue
  F ScaI+EcoRI
  G Ligate
  H Oligonucleotide loopout of sequences coding for 12aa of SSU mature peptide.

2. Construction of plasmids pCab-SU11, pCab-SU12 and pCab-SU13. Flow diagram is shown in FIGS. 20A to 20C To make the chlorophyll a/b binding protein fusion to P450SU1, a 950 bp BalI-SacI DNA fragment of the petunia Cab22L gene (Dunsmuir, Nucleic Acids Res. 13:2503-2518 (1985)) containing the Cab22L promoter, chloroplast transit pastime coding sequence and part of the mature Cab22L coding sequence was cloned into SmaI-SacI digested pBluescript KS+(Stratagene Inc. San Diego, Calif. 92121) creating pCab22LT. A ScaI site was created by site-directed mutagenesis after the codon for amino acid 14 of the mature Cab protein coding sequence of pCab22LT creating pCab22LT1. The Cab22L promoter, codons encoding the transit peptide and 14 amino acids of the mature Cab22L protein were subcloned as a 1.2 kb EcoRI-ScaI fragment of pCab22LT1 into EcoRI-ScaI cleaved pSU16 creating pCab-SU11. An oligonucleotide was made that looped in 39 nucleotides (Kunkel, PNAS 82: 488-492, (1985)) encoding amino acids 15-27 of the mature Cab22L protein into the junction between the Cab22L coding sequence and the P450SU1 coding sequence creating pCab-SU13. pCab-SU13 encodes a protein that contains the Cab22L chloroplast transit sequence, 27 amino acids of the mature Cab22L protein fused to the amino terminus of the P450SU1 protein. A SmaI site was created by site-directed mutagenesis (Kunkel, PNAS 82:488-492, (1985)) at amino acid 19 of pCab22LT creating pCab22LT2. The Cab22L promoter, codons encoding the transit peptide and 19 amino acids of the mature Cab22L protein were subcloned as a 1.2 kb EcoRI-SmaI DNA fragment of pCab22LT2 into EcoRI-ScaI cleaved pSU16 creating pCab-SU12. The plasmids pCab-SU11, pCab-SU12 and pCab-SU13 express cytochrome P450SU1 in plant cells that is targeted to the chloroplasts.

In FIGS. 20A to 20C the following steps are designated with letters at the arrows:
For FIG. 20A:
  A SmaI+SacI cut
  B Ligate
  C Site directed mutagenesis of Cab-M at amino acid 14 to ScaI site
  D Site directed mutagenesis of Cab-M at amino acid 19 to SmaI site
For FIG. 20B:
  E SmaI+EcoRI cut
  F EcoRI+ScaI cut
  G Ligate
For FIG. 20C:
  F EcoRI+ScaI cut
  H ScaI+EcoRI cut
  I Ligate
  J Use oligonucleotide to loop in 39 nucleotides coding for amino acid 15-27 of Cab mature at ScaI site 3. Construction of plasmids pSUFe3 and pSUFe4. Flow diagram is shown in FIGS. 21A to 21D p29593(see construction of pSUFe1) was cleaved with NcoI and XbaI and ligated with a 1 kb NcoI-XbaI DNA fragment from pFeSB-1.02 (see construction of pSUFe1) that contains the FeS-B coding sequence. This forms plasmid pFenos1 and puts the 3' untranslated sequence of the nos gene from p29593 downstream of the FeS-B coding sequence. pFenos1 was cleaved with BglII removing a 0.75 kb BglII DNA fragment and the remaining BglII DNA fragment was recircularized creating pFenos2. A 1.4 kb EcoRI-EcoRV DNA fragment from pSSU3044 (see construction of pSSU-SU11) that contains the promoter, sequences coding for the chloroplast transit sequence and the first 12 mature amino acids of the mature protein of the petunia SSU301 gene was isolated. This fragment was ligated with pSFenbs2 that had been partially digested with ScaI and completely digested with EcoRI creating pSFenos1. pSFenos1 contains the petunia SSU301 gene promoter with sequences encoding the chloroplast transit peptide and the first 12 amino acids of the mature SSU301 protein added onto the beginning of the FeS-B coding sequence. The nos 3' untranslated sequences are located after the termination codon of FeS-B. The DNA sequence that encodes the twelve amino acids of the mature SSU301 protein in pSFenos1 were removed by site directed mutagenesis (Kunkel) creating pFenos2. pFenos2 was partially digested with HindIII and ligated to HindIII cut pGEM7Zf(+)(Promega Corporation, Madison, Wis. 53711) to put a BamHI site downstream of the nos gene 3' untranslated sequences. This plasmid is named pSFenos3. pSFenos3 was cut with EcoRI and BamHI to give an ~1.9 kb BamHI-EcoRI DNA fragment containing the petunia SSU301 gene promoted FeS-B gene. A 4.25 kb EcoRI-BamHI DNA fragment was isolated from pSSU-SU12(see construction of pSSU-SU12 above) that contains the petunia SSU301 promoter, DNA encoding the chloroplast transit peptide and the 3' untranslated region flanking the cytochrome P450SU1 coding sequence. These two BamHI-EcoRI DNA fragments were ligated together along with EcoRI digested PUC118 to create pSUFe3. The same two BamHI-EcoRI DNA fragments were ligated together along with BamHI digested PUC118 to create pSUFe4.

Both pSUFe3 and pSUFe4 contain 1). the petunia SSU301 promoter such that-in plants it will transcribe sequences encoding the SSU301 chloroplast transit peptide linked to the coding sequence for FeS-B and the nos gene 3' untranslated sequence and 2). a second petunia SSU301 promoter such that in plants it will transcribe sequences encoding the SSU301 chloroplast transit peptide linked to the coding sequence for cytochrome P450SU1 and the SSU301 gene 3' untranslated sequence. pSUFe3 has these two segments oriented such that the two SSU301 promoters are adjacent to one another. pSUFe4 has these two segments oriented such that the nos geyne 3' untranslated sequence and the SSU301 3' untranslated sequence are adjacent to one another.

In FIGS. 21A to 21D the following steps are designated with letters at the arrows:

For FIG. 21A:
A. NcoI+XbaI digestion of pFeSB-1.02
B. NcoI+XbaI digestion of p29593
C. 1) BglII digestion and
   2) Recircularization of pFenos1

For FIG. 21B:
D. ScaI partial digestion and EcoRI digestion of pFenos2
E. EcoRI+EcoRV digestion of pSSU3044
F. Site specific oligonucleotide directed deletion of nucleotides encoding SSU mature sequence For FIG. 21C:
G. Partial HindIII digestion of pSFenos2
H. HindIII digestion of pGEM7ZF(+)

For FIG. 21D:
I. EcoRI+BamHI digestion of pSFenos3
J. EcoRI+BamHI digestion of pSSU-SU12
K. EcoRI digestion of PUC118
L. BamHI digestion of PUC118
M. 3 component ligation
N. 3 component ligation 4. Construction of pSUFe2. Flow diagram shown in FIGS. 22A and 22B p29593 can be cut with BamHI and ligated to an EcoRI-BamHI adaptor (New England Biolabs Inc., Beverly, Mass.) with subsequent recircularization forming p29593-1. This puts an EcoRI site in p29593-1 at the position of the BamHI site in p29593. An ~2.2 kb EcoRI-BglII DNA fragment of p29593-1 containing the CaMV 35 S promoter and petunia Cab 22L 5' untranslated sequence can be ligated to p29593 cut with EcoRI and partially digested with BglII forming p29593-2. p29593-2 contains two adjacent CaMV 35S promoters and petunia Cab 22L 5' untranslated sequences arranged such that transcription from the two promoters would be in opposite directions. A 1.3 kb NcoI fragment from p29593-2 containing the two CaMV 35S promoters and Cab22L 5' untranslated sequences can then be ligated to pSUFe3 that has its two petunia SSU301 promoters removed by partial NcoI digestion to form pSUFe2. pSUFe2 is similar to pSUFe1 except that both the cytochrome P450SU1 and FeS-B coding sequences have sequences for the petunia SSU301 gene chloroplast transit peptide fused to them.

In FIGS. 22A and 22B the following steps are designated with letters at the arrows:

For FIG. 22A:
A. 1) BamHI digestion and addition of BamHI-EcoRI adapters to p29593 and
   2) Recircularization
B. BglII partial digestion and EcoRI digestion of p29593
C. BglII+EcoRI digestion of p29593-1

For FIG. 22B:
D. NcoI digestion of p29593-2
E. NcoI partial digestion of pSUFe3

C. Introduction of constructs into T-DNA plasmids

Six of the constructs (i.e., pSU17, pSSU-SU11, pSSU-SU12, pCabSU11, pCabSU12 and pCab-SU13) containing the P450SU1 coding sequence with promoters from plant genes were digested with BamHI and inserted into the plasmid pAGS135 at its unique BamHI site. Plasmid pAGS135 was derived from pAGS112 (P. van den Elzen et al. Plant Mol. Biol. 5:149-154, 1985, herein incorporated by reference,) by removal of the XhoI site outside of the T-DNA right border following digestion of pAGS112 DNA with XhoI, treatment with the Klenow fragment of DNA polymerase I to blunt the ends and then self ligating. The plasmid pAGS112 was derived from the wide host-range vector pLAFR (Friedman et al. Gene 18:289-296, herein incorporated by reference) by insertion of an EcoRI fragment in which the T-DNA borders flank a gene for expressing kanamycin resistance in plants and multiple cloning sites. pAGS501, pAGS502 and pZS96 are similar to pAGS135 in that they are T-DNA border containing plasmids expressing kanamycin resistance in plants.

A summary of how pAGS501, pAGS502 and pZS96 were made is described below.

pAGS501 and 502 were constructed as follows. pRK$_{290}$ (G. Ditta et al., Proc. Natl. Acad. Sci. U.S.A., 77:7347-7351, (1980)) was cut with EcoRI and tile ends filled in with the Klenow fragment of DNA polymerase I (T. Maniatis et al., Molecular Cloning:a Laboratory Manual, Cold Spring Harbor, N.Y. (1982)). pAGS111 (P. J. van den Elzen et al., Plant Mol. Biol. 5:149-154, (1985)) was cut with EcoRI and HindIII and the ends filled in with the Klenow fragment of DNA polymerase I (T. Maniatis et al., (1982)). The 6.7 kb DNA fragment from pAGS111 containing the left and right borders of T-DNA and the kanamycin nucleotidyl phosphotransferase gene under the control of the hopaline synthetase promoter was ligated to the cleaved pRK290 DNA creating p1881. p1881 was cut with XhoI, the ends blunted with the Klenow fragment of DNA polymerase I and circularly ligated creating p1882. p1882 was cut with BamHI and ligated to a double stranded oligonucleotide containing XbaI, HindIII, XhoI, EcoRI and HpaI sites. The ends of the double stranded oligonucleotide are such that when ligated to BamHI cut p1882 one end recreates a BamHI site while the other end does not. Plasmids pAGS501 and pAGS502 are the two possible results of such a ligation. Both plasmids contain BamHI, HindIII and EcoRI sites between the T-DNA borders that can be used as cloning sites for DNA to be mobilized into plants.

In FIGS. 23A and 23B, the following steps are designated with letters at the arrows:

A. 1) HindIII+EcoRI digestion of pAGS111
   2) fill in of restriction endocunlease ends with the Klenow fragment of DNA polymeraseI B. 1) EcoRI digestion of pRK290
   2) fill in of restriction endonuclease ends of pRK290
   3) ligation of pRK290 with the ~6.7 kb T-DNA fragment of pAGS111
C. 1) XhoI digestion of p1881
   2) fill in of restriction endocunlease ends of p1881
   3) intramolecular ligation of p1881
D. 1) BamHI digestion of p1882
   2) ligation of HpaI, EcoRI, HindIII, XbaI, BamHI oligonucleotide with p1882.

pZS96 was constructed as follows. This plasmid utilizes the replication and stability functions of pvS1 for use in Agrobacterium (Itoh et al., Plasmid, 11:206-220 (1984)). A derivative of pVS1, pGV910 (J. Lemans et al., Gene, 19:361-364 (1982)) was cut with BamHI and SalI and the 8.0 kb HamHI-SalI DNA fragment containing the replication origin and stability functions was ligated to a 4.1 kb BamHI-SalI fragment from pBR322 (Bolivar et al., Gene, 2:95-113 (1977)) creating pZS67. pZS67 was cut with SacI and PvuII and the ends blunted with T4 DNA polymerase (T. Maniatis et al., 1982) creating the 8.6 kb plasmid pZS68. pZS68 was cut with BamHI and the ends filled in with the Klenow fragment of DNA polymerase I (T. Manjarls et al., 1982) and recircularized creating pZS69. The unique PstI site in pZS69 was removed by exchanging the 222 bp AvaII-AvaII fragment within the ampicillin resistance gene containing the PstI site with a similar fragment from pUC19 (C. Yanisch-Peron et al. Gene 33:103-119, (1985)) that does not contain a PstI site creating pZS71. The T-DNA region of pAGS111 (P. J. can den Elzen et al., (1985)) was cut out as a 5.7 kb EcoRI-HindIII fragment and cloned into EcoRI-HindIII cleaved pZS71 creating pZS73 (12.3 kb). pZS73 was cut with EcoRI, the ends filled in with the Klenow fragment of DNA polymerase I (T. Maniatis et al., 1982) and the plasmid recircularized to form pZS74. pZS74 was cut with HindIII, the ends filled in with the Klenow fragment of DNA polymerase I (T. Manjarls et al. 1982) and the plasmid recircularized to form pZS75. A 444 bp HaeII-HaeII DNA fragment from pUC19 containing the polylinker region whose ends had been blunted with T4 DNA polymerase (T. Manjarls et al., 1982) was cloned into pZS75 that had been cut with BamHI sites that are not within the polylinker region. This was accomplished through sequential steps of,- separate partial digestions with KpnI, SalI or BamHI, filling the ends with either the Klenow fragment of DNA polymerase I or T4 DNA polymerase (T. Manjarls et al, 1982) and recircularizing the plasmid.

In FIG. 24A the following steps are designated with letters at the arrows:

A. 1) BamHI+SalI digestion of pGV910 and pBR322
   2) ligation of 4.1 kb BamHI-SalI pBR322 fragment with the 8.0 kb BamHI-SalI pGV910 fragment
B. 1) PvuII+SacII digestion of pZS67
   2) blunt restriction endonuclease ends with T4 DNA polymerase
   3) intramolecular ligation.

In FIG. 24B the following steps are designated with letters at the arrows.

C. 1> BamHI digestion of pZS68
   2) fill in of restriction endonuclease ends with the Klenow fragment of DNA polymerase I
   3) intramolecular ligation
D. AvaII digestion of pUC19
E. 1) AvaII digestion of pZS69
   2) ligation of the 222 bp AvaII fragment of pUC19 with the 11.9 kb AvaII fragment of pZS69.

In FIG. 24C the following steps are designated with letters at the arrows.

F. HindIII+EcoRI digestion of pAGS111
G. 1) EcoRI+HindIII digestion of pZS71
   2) Ligation of the ~5.7 kb HindIII-EcoRI fragment of pAGS111 with HindIII-EcoRI cut pZS71
H. 1) HindIII digestion of pZS73 and fill in restriction ends
   2) intramolecular ligation
   3) EcoRI digestion of plasmid from 2)
   4) intramolecular ligation.

In FIG. 24D the following steps are designated with letters at the arrows.

I. 1) HaeII digestion of pUC19 and blunt ends with T4 DNA polymerase
   2) BamHI digestion of pZS75 and fill in restriction ends
   3) ligate digested pZS75 with ~440 bp HaeII fragment of pUC19
J. 1) KpnI digestion, blunt ends with T4 DNA polymerase
   2) intramolecular ligation
   3) SalI partial digestion of plasmid from 2), blunt ends with Klenow fragment of DNA polymerase I
   4) intramolecular ligation
   5) BamHI partial digestion of plasmid from 4), blunt ends with Klenow fragment of DNA polymerase I
   6) intramolecular ligation.

These plasmids were used as follows to clone the segments of pSUFe1, pSUFe2, pSUFe3 and pSUFe4 that enable expression of cytochrome P450SU1 and FeS-B in plants. The ~3.4 kb HindIII fragment of pSUFe1 containing the two CaMV 35S promoters and nos 3' untranslated sequences along with the cytochrome P450SU1 and FeS-B coding sequences was cloned into HindIII cut pAGS502 creating pSUFe11. The ~4.75 kb BamHI fragment of pSUFe2 containing two CaMV 35S promoters, nos 3' untranslated sequence, SSU301 3' untranslated sequence and the coding sequences of P450SU1 and FeS-B each linked to sequences encoding the chloroplast transit peptide of the SSU301 gene was cloned into BamHI cut pAGS501 creating pSUFe21. The 6.3 kb BamHI fragment of pSUFe3 containing two petunia SSU301 promoters, nos 3' untranslated sequence, SSU301 3' untranslated sequence and the coding sequences of P450SU1 and FeS-B each linked to sequences encoding the chloroplast transit peptide of the SSU301 gene was cloned into BamHI cut pZS96 DNA creating pSUFe31. The 6.3 kb EcoRI fragment of pSUFe4 containing two petunia SSU301 promoters, nos 3' untranslated sequence, SSU301 3' untranslated sequence and the coding sequences of P450SU1 and FeS-B each linked to sequences encoding the chloroplast transit peptide of the SSU301 gene was cloned into EcoRI cut pZS96 DNA creating pSUFe41. Below is a list indicating the expression constructs described above and the name for the plasmid made from each when cloned into pAGS135, pAGS501, pAGS502 or pZS96.

| P450SU1 construction | Plasmids |
|---|---|
| pSU17 | pSU18 |
| pSSU-SU11 | pSSU-SU111 |
| pSSU-SU12 | pSSU-SU121 |

| P450SU1 construction | Plasmids |
| --- | --- |
| pCab-SU11 | pCab-SU111 |
| PCab-SU12 | pCab-SU121 |
| pCab-SU13 | pCab-SU131 |
| pSuFe1 | pSuFe11 |
| pSuFe2 | pSuFe21 |
| pSuFe3 | pSuFe31 |
| pSuFe4 | pSuFe41 |

D. Transfer to Agrobacterium and into tobacco

The plasmids listed above were mobilized into the Agrobacterium strain LBA4404/pAL4404(Hoekema et al. Nature 303:179–180, 1983, herein incorporated by reference) using tri-parental matings (Ruvkin and Ausubel, Nature 289:85–88, 1981, herein incorporated by reference). The resulting Agrobacterium strains were then cocultivated with protoplasts (van den Elzen et al. Plant Mol. Biol. 5:149–154) or leaf disks (Horsch et al. Science 227:1229–1231, 1985) of *Nicotiana tabacum* cv. Wisconsin 38 and kanamycin resistant transformants were selected.

Kanamycin resistant transformed tobacco plants were regenerated from the transformed protoplasts or leaf disks and the leaves of plants were tested for mRNA expression of the P450SU1 and FeS-B coding sequences by primer extension. Those plants that showed moderate to high levels of mRNA were allowed to flower, were self-pollinated and seed obtained from each. Several different independent transformed plants originating from each P450SU1 expression construction were isolated. The following Table 16 lists the parent construct, promoter used and additions to the P450SU1 coding sequence for each plant line used.

TABLE 16

| Plant Line | Parent plasmid | Promoter | Amino Terminal Additions |
| --- | --- | --- | --- |
| A. Plants Expressing Cytochrome P450SU1 | | | |
| W38 | none | none | |
| AGS112 | pAGS112 | none (no P450 gene) | |
| SU18.8 | pSU18 | CaMV | none |
| SU18.14 | " | " | " |
| SU18.15 | " | " | " |
| SSU-SU111.5 | pSSU-SU111 | SSU | SSU transit sequence + 12 extra amino acids of mature SSU |
| SSU-SU121.3 | pSSU-SU121 | SSU | SSU Transit Sequence |
| Cab-SU111.8 | pCab-SU111 | Cab | Cab transit sequence + 14 amino acids of mature Cab |
| Cab-SU121.5 | pCab-SU121 | Cab | Cab transit sequence + 19 amino acids of mature Cab |
| Cab-SU131.5 | pCab-SU131 | Cab | Cab transit sequence + 27 amino acids of mature Cab |

TABLE 16 -continued

| Plant Line | Parent plasmid | Promoter | Amino Terminal Additions |
| --- | --- | --- | --- |
| B. Plants Expressing Cytochrome P450SU1 and FeS-B | | | |
| SuFe11.1 | pSuFe11 | CaMv | None |
| SuFe11.3 | pSuFe11 | 35S | None |
| SuFe11.4 | pSuFe11 | 35S | None |
| SuFe11.7 | pSuFe11 | 35S | None |
| SuFe11.8 | pSuFe11 | 35S | None |
| SuFe11.1 | pSuFe11 | 35S | None |
| SuFe21.2 | pSuFe21 | 35S | SSU Transit Sequence |
| SuFe21.5 | pSuFe21 | 35S | SSU Transit Sequence |
| SuFe21.6 | pSuFe21 | 35S | SSU Transit Sequence |
| SuFe21.7 | pSuFe21 | 35S | SSU Transit Sequence |
| SuFe21.8 | pSuFe21 | 35S | SSU Transit Sequence |
| SuFe31.13 | pSuFe31 | SSU | SSU Transit Sequence |
| SuFe31.28 | pSuFe31 | SSU | SSU Transit Sequence |
| SuFe41.34 | pSuFe41 | SSU | SSU Transit Sequence |
| SuFe41.37 | pSuFe41 | SSU | SSU Transit Sequence |
| SuFe41.56 | pSuFe41 | SSU | SSU Transit Sequence |
| SuFe41.60 | pSuFe41 | SSU | SSU Transit Sequence |

EXAMPLE 20

P450 enzyme activity in tissues of transformed tobacco

A. Experimental methods

Plants were grown from tobacco seed produced by self-pollinated transformed plants in Metro-Mix ® 350 under 16 hour light (light intensity of 400 μEinsteins per second per square meter at pot level, 22° C. and 80% relative humidity) followed by 8 hours of dark (18° C. and 70 to 80% relative humidity) and watered three times daily with half strength Hoagland's solution. The presence of the cytochrome P450 protein in individual plants was confirmed by Western blot analysis before testing for sulfonylurea metabolism.

During growth, the tobacco plants produced leaves attached to the main stalk, none of which were of the same age or size. Removal of leaves attached to the main stalk of each plant forced the growth of lateral shoots which in turn produced the many leaves of similar size and age needed for the experiments. The leaves were excised under water with a scalpel. These leaves were transferred to cups with the uptake solution (20 ppm sulfonylurea in 1 mM potassium phosphate buffer, pH 7.0) and allowed to take up the solution through the cut leaf base for 2 hours in the light (200 μEinsteins per second per sq. meter) at 22° C. and 86% relative humidity. At the end of the uptake period, sample leaves were either frozen in liquid nitrogen and stored at −20° C. (designated '0 hour post-uptake samples') or transferred to cups with phosphate buffer alone for an additional 5 hours of incubation in the light before freezing (designated 5 hour post-uptake samples'). In the 10001 experiments some leaves were incubated for 21 hours post-uptake under continuous light (200 µEinsteins per second per square meter, 22° C., and 63% relative humidity).

Individual leaves were extracted with 30 ml acetone/water (80%/20% by volume) for 1 minute in a Sorvall ® Omni-Mixer. The brei was centrifuged to remove the tissue debris. Acetone in the supernatant was removed under a stream of nitrogen. The resulting aqueous extract was acidified to pH 2 to 3 with sulfuric acid and then extracted three times with methylene chloride. The combined methylene chloride extracts were reduced to dryness by rotary evaporation at 30° to 40° C. The dry residue was dissolved in acetone for transfer to a vial. Once transferred the acetone was removed by evaporation under a stream of nitrogen. Before HPLC analysis the dry sample was redissolved in 1.0 ml of acetonitrile/water (25%/75%). HPLC separations were carried out on a Zorbax ® ODS column (4.6 mm×250 man) at 45° C. with a flow rate of 1.4 ml per minute. Separation of extract components was achieved with a 5 to 80% acetonitrile gradient (with 0.1% formic acid; the balance was water) and a run time of 25 minutes. 10015 and its metabolites were detected at 254 nm while $^{14}C$-10001 and its metabolites were detected with a Radiomatic Flo-One ® detector. A diode array detector was used in separate experiments to obtain the absorbance spectra of the 10015 metabolite and an 10014 standard in the HPLC analysis of several extracts (HPLC method is described in Romesser et al., Biochem. Biophys. Res. Comm., 140:650–659 (1986)). Comparison of the metabolite absorbance spectrum with that of the 10014 confirmed the metabolite's identity.

B. Metabolism of 10015

Leaf tissues only from progeny of the transformed tobacco plants (SSU-SU111.5, SSU-SU121.3 and CAB-SU131.5) which received plasmids engineered to direct the *S. griseolus* cytochrome P450 (SU1) to the chloroplast N-dealkylated 10015 to 10014 (FIG. 11). The results are shown in Table 17.

TABLE 17

| Metabolism of 10015 to 10014 in Tobacco Leaves | | | |
|---|---|---|---|
| Plant Family construction | 10014 levels at 0 hour* | (µg/leaf) at 5 hour* | No. of Leaves |
| W38 | 0 | 0 | 6 (3 from each of 2 plants) |
| AGS112** | 0 | 0 | 4 (4 from one plant) |
| SSU-SU111.5# | 2.1 (+/− 1.4) | 1.8 (+/− 1.4) | 6 (2 from each of 3 plants) |
| SSU-SU121.3# | 1.2 (+/− 0.5) | 1.7 (+/− 1.1) | 4 (2 from each of 2 plants) |
| Cab-SU131.5# | 1.3 (+/− 1.0) | 2.9 (+/− 1.3) | 8 (4 from each of 2 plants) |
| SU18.8@ | 0 | 0 | 8 (4 from each of 2 plants) |
| SU18.15@ | 0 | 0 | 2 (2 from one plant) |

*Post-uptake incubation time
**Control (there is no P450SU1 sequence in this plasmid)
The P450 sequence is chloroplast directed.
@The P450 sequence is cytoplasm directed.

The metabolite (10014) was identified by its comigration with an 10014 standard on HPLC analysis (detection at 254 nm) and by comparison of the absorbance spectrum of the metabolite with that of the 10014 standard. The absorbance spectra were identical (FIGS. 12A and 12B). The levels of 10014 in the leaves (Table 17) represent metabolic conversion of 10 to 20% of the 10015 loaded into the leaves during the 2 hour uptake period (based on calculations from the volume of 10015 solution taken up). The 0 and 5 hour post-uptake incubations were included to look at the kinetics of metabolism. Because of the variability in 10014 production a reaction rate constant was not calculated.

Leaf tissues from the progenitor plant type, Wisconsin 38 tobacco, and progeny of tobacco transformed with the pAGS112 plasmid (a plasmid without the bacterial cytochrome P450SU1 gene) were unable to produce any detectable 10014 from 10015 (Table 17). This showed that the transgenic tobacco's ability to metabolize 10015 to 10014 was due to the expression of the bacterial gene in the plants and not to any native ability of the tobacco.

Leaf tissues from progeny of plants transformed with the plasmid pSU18 (i.e., plant lines SU18.14 and SU18.15), also, were tested for their ability to metabolize 10015 to 10014. Under the conditions of the experiment no conversion of 10015 to 10014 was detected (Table 17).

Transit sequences from the small subunit of carboxylase (the SSU transformants) or from the chlorophyll a/b protein (the Cab transformants) were included in the engineered plasmids to direct the cytochrome p450SU1 protein to the chloroplast after synthesis in the cytoplasm. The mature cytochrome P450SU1 protein for the SSU-SU111.5 transformant included a 14 amino acid fragment of the small subunit of RuBP carboxylase. The SSU-SU121.3 transformant's mature cytochrome had no additional amino acid additions. The mature cytochrome protein for the Cab-SU131.5 transformant had an additional 27 amino acids from the chlorophyll a/b protein. Inspection of the levels of 10014 produced in the transformants (Table 17) showed that the 14 or 27 amino acids added to the cytochrome P450SU1 did not prevent the metabolism of 10015 to 10014 in the transgenic tobacco leaf tissues.

C. Metabolism of 10001

Leaf tissues from a plant transformed with pAGS112, a plasmid not containing DNA encoding cytochrome P450SU1, metabolized 10001 to 10002 and 10003 through O-demethylation and de-esterification, respectively (FIG. 13A). The metabolism of 10001 was assumed to be a native metabolic ability of tobacco. However, it complicated the assessment of the metabolic activity of 10001 of the tissues from plants transformed with cytochrome P450SU1 containing plasmids (pSU18, pSSU-SU111. pSSU-SU121, and pCab-SU131). Although a limited number of samples were tested (each time point represents the average of two leaves tested), the results (FIGS. 13A, 13B and 13C) showed that after 21 hours, 10001 was metabolized to a significantly greater extent and more 10002 was produced in the leaf tissues from those plants transformed with plasmids pSSU-SU111 and pCab-SU131 than in leaf tissues from plants transformed with pAGS112. The results indicated that the cytochrome P450SU1 was actively metabolizing 10001 in the transgenic tobacco.

Leaf tissues from progeny of the transformants, SU18.8 and SU18.14, were tested for the ability to metabolize 10001 to 10002 and 10003. Because of the native ability of the tobacco to metabolize 10001, it was difficult to determine whether there was a contribution of the bacterial enzyme to metabolism.

EXAMPLE 21

Metabolism of 10015 by tobacco plants with P450SU1

Sulfonylurea compound 10015 exhibits low phytotoxicity to a wide variety of plant species. This compound is an excellent substrate for P450SU1, which rapidly converts it to into the highly phytotoxic compound 10014 (FIG. 11). Thus, tobacco plants transformed to contain P450SU1 and sprayed with normally subtoxic rates of 10015 would be severely damaged if they contained functional P450SU1 in sufficient quantity to allow the accumulation of toxic compound 10014 within plant tissues.

Tobacco plants (Nicotiana tabactum cv. Wisconsin 38) transformed with plasmids pAGS112, pSU18, pSSU-SU111, pCab-SU121 or pCab-SU131 (singly) and accumulating the P450SU1 protein were identified by Western blot analysis. Seed arising from the self pollination of individual primary transformants designated AGS112, SU18.8, SU18.14, SSU-SU111.5, Cab-SU111.8, and Cab-SU131.5 gave rise to the plants described in this Example. The progeny of primary AGS112 and Cab-SU121.5 transformants segregated for single copy kanamycin resistance. In contrast, the progeny of the plants transformed with plasmids containing P450SU1 (other than Cab-SU121.5) segregated for multicopy kanamycin resistance. Thus, most plants containing the gene encoding P450SU1 and sprayed with 10015 in this Example likely contained at least one, and in many cases multiple, copies of P450SU1, while very few individuals likely carried no copies of the gene encoding P450SU1.

Seed from transformed and nontransformed tobacco plants was germinated in a commercial potting mix Metro-Mix® 350 for 25 days. Individual plants were then transferred to 4 inch×4 inch pots containing Metro Mix® 350 and were allowed to grow in the greenhouse for an additional 22 days at which time most plants contained 4–5 fully expanded leaves. A developmentally uniform population of plants was selected from among these transplants and the individual plants were then sprayed with a carrier solution of AGWT (90.2% Acetone: 4.8% Glycerol: 4.8% Water: 0.24% Tween 20 by volume) containing sulfonylurea compound 10015 at concentrations of 1,4, or 16 grams/hectare (g/ha). The sprayed plants were returned to the greenhouse and rated for injury 22 days later.

One to two days before spraying one leaf from each plant was frozen and stored at −80° C. for analysis of P450SU1 content. At assay thawed leaves were ground in a buffer containing 0.1M sodium tricine pH 7.8, 10 mM sodium chloride, and 5 mM magnesium chloride. The extracts were clarified by centrifugation at 28,000 to 33,000×g for one hour and protein in the supernatant fraction was concentrated. The relative P450SU1 content of the supernatant fraction from each leaf was estimated by "immuno slot blots" where the extract from each leaf was placed in a template which deposited the extract onto individual "slots" or narrow lanes on nitrocellulose paper. The protein bound to the nitrocellulose was incubated with a P450SU1 specific antibody and subsequently treated as described for the Western Blot procedure.

Foliar application of 10015 at a rate of 1 g/ha (Table 18) resulted in minimal damage to nontransformed plants (W38) and the progeny of plants transformed with plasmid pAGS112. In contrast, plants transformed with constructions directing P450SU1 to the chloroplast (SSU-SU111.5, Cab-SU111.8, Cab-SU121.5 and Cab-SU131.5) were severely injured by application of compound 10015 at 1 g/ha. As shown in FIG. 14 damage to the plants containing P450SU1 was indeed dramatic, resulting not only in a severe inhibition of plant growth but also in leaf chlorosis and gross-morphological deformation of new leaves arising near the shoot apex. The difference in height between the progeny of untransformed (W38) plants and plants transformed with pAGS112 in FIG. 14 was within the range of normal variation expected following growout of untreated, transplanted tobacco plants.

Immuno slot blot analysis confirmed that injured plants contained the P450SU1 protein at the time of spraying. Two "exceptional" plants which showed lower than expected levels of injury contained either no (Cab-SU121.5-19) or lower (Cab-SU131.5-15) levels of P450SU1 than severely injured plants in the same family. These plants may be segregants containing no or single copies, respectively, of the gene encoding P450SU1. Control plants arising from pAGS112 primary transformants were not individually typed for kanamycin resistance. However, since these plants segregated 3 resistant:1 sensitive for the ability to germinate on kanamycin, there is a >98% probability that at least one plant transformed with pAGS112 was sampled at the optimal discriminatory rate of 1 g/ha 10015.

When this experiment was repeated at a higher application rate of 4 g/ha of compound 10015, most plants transformed with constructions directing P450 SU1 to the chloroplast were again severely injured (Table 19). Nontransformed plants and progeny plants from a primary AGS112 transformant showed some background damage at this higher application rate, but this damage was clearly less than that experienced by plants transformed to contain chloroplast localized P450SU1. In this experiment two exceptional plants containing P450SU1 (Cab-SU111.8-10; Cab-SU131.5-21) exhibited lower than expected phytotoxic damage. Given that plants transformed with these plasmids and expressing P450SU1 were severely damaged at the lower application rate of 1 g/ha of compound 10015 (Table 18), it is likely that these two exceptional plants received a reduced dose of 10015 during treatment or were mistyped during immuno slot analysis.

Several transformants containing cytoplasmically directed P450SU1 (SU18.8, SU18.14) were damaged more severely than nontransformed plants, but to a lesser extent than transformants containing chloroplast localized P450SU1. This was especially evident at the treatment rate of 4 g/ha of compound 10015 (Table 19). The difference in activity between cytoplasmically localized and chloroplast localized P450SU1 does not always reflect a higher accumulation of P450SU1 in the chloroplast directed constructions (compare SU18.8, SU18.14 with Cab-SU111.8 and Cab-SU121.5, Table 19). This suggests that P450SU1 functions more efficiently in the chloroplast than in the cytoplasm.

When 10015 was applied at a concentration of 16 g/ha both transformed and non-transformed plants were extensively injured and no useful information was obtained.

These data demonstrate that P450SU1 is functionally active in the progeny of transformed plants at the whole plant level. In the case of constructions designed to direct the P450SU1 protein to the chloroplast the inclusion of amino terminal extensions to P450SU1 as described in Example 19 did not prevent the activity of P450SU1 in intact plants.

TABLE 18

Response of P450SU1 Transformed Tobacco to Sulfonylurea Compound 10015 (1 g/ha)

| Family/ Construction | Plant I.D. No. | % Damage | Protein (ug/slot) | Blot Rating |
|---|---|---|---|---|
| W38 | | 0 | | NT |
| W38 | | 0 | | NT |
| W38 | | 10 | | NT |
| AGS 112 | | 0 | 10 | (−) |
| AGS 112 | | 0 | 10 | (−) |
| AGS 112 | | 10 | | NT |
| SU18.8 | 14 | 10 | 6 | (++) |
| SU18.14 | 11 | 40 | 5 | (++) |
| SSU-SU111.5 | 10 | 95 | 11 | (++++) |
| SSU-SU111.5 | 22 | 95 | 10 | (+++) |
| SSU-SU111.5 | 24 | 95 | | NT |
| Cab-SU111.8 | 12 | 90 | 9 | (+) |
| Cab-SU111.8 | 14 | 95 | 4 | (+) |
| Cab-SU111.8 | 17 | 95 | | NT |
| Cab-SU121.5 | 11 | 85 | | NT |
| Cab-SU121.5 | 13 | 95 | 7 | (+) |
| Cab-SU121.5 | 18 | 95 | | NT |
| Cab-SU121.5 | 19 | 20 | 5 | (−) |
| Cab-SU131.5 | 15 | 50 | 4 | (+) |
| Cab-SU131.5 | 18 | 95 | 13 | (++½) |
| Cab-SU131.5 | 27 | 90 | 11 | (++) |

NT = Not Tested
(+), (++), (+++), (++++) = relative amount of immunologically detected P450SU1

TABLE 19

Response of P450SU1 Transformed Tobacco to Sulfonylurea Compound 10015 (4 g/ha)

| Family/ Construction | Plant I.D. No. | % Damage | Protein (ug/slot) | Blot Rating |
|---|---|---|---|---|
| W38 | | 0 | | |
| W38 | | 10 | | |
| W38 | | 20 | | NT |
| W38 | | 30 | | NT |
| AGS 112 | | 0 | | NT |
| AGS 112 | | 40 | | NT |
| SU18.8 | 11 | 60 | 6 | (++) |
| SU18.14 | 15 | 70 | 6 | (++) |
| SSU-SU111.5 | 11 | 100 | 13 | (++++) |
| SSU-SU111.5 | 12 | 100 | 2 | (+++) |
| SSU-SU111.5 | 13 | 100 | | NT |
| Cab-SU111.8 | 10 | 0 | 6 | (+) |
| Cab-SU111.8 | 15 | 99 | 5 | (+) |
| Cab-SU121.5 | 12 | 90 | 5 | (+) |
| Cab-SU121.5 | 22 | 100 | 9 | (+) |
| Cab-SU121.5 | 28 | 95 | | NT |
| Cab-SU131.5 | 21 | 40 | 12 | (++) |
| Cab-SU131.5 | 28 | 100 | 13 | (++) |
| Cab-SU131.5 | 29 | 100 | | NT |

NT = Not Tested
(+), (++), (+++), (++++) = relative amount of immulogically detected P450SU1

EXAMPLES 22-25

Tissue Culture Growth of Transformed Tobacco Seed

Growth medium was prepared from Murishige minimal organics medium (Gibco Laboratories, Grand Island, N.Y.), 8 g/l agar, supplemented with T vitamins (50 ppb biotin, 0.5 ppm pyridoxine HCl, 0.5 ppm thiamine HCl, 5 ppm nicotinic acid, 0.5 ppm folic acid, 2 ppm glycine, 100 ppm myo-inositol), sterilized and placed into sterile PlantCon plant tissue culture containers (Flow Laboratories, McLean, Va.). Tobacco seed obtained from the self-pollination of the primary transformants was surface sterilized by a treatment of not more than 30 min in 20% chlorine bleach, 0.1% sodium dodecyl sulfate, followed by rinsing in distilled water, and placed on the surface of the medium in the sterile containers. Following this treatment, the seed was allowed to germinate and grow under illumination (100 microeinsteins·m$^{-2}$·s$^{-1}$), at 22° C.

Determination of the number of genetic loci of the transformed tobacco

The number of loci where t-DNA was incorporated into the genome of the tobacco was determined by segregation analysis of kanamycin resistance in the next generation of progeny. Seed from the self pollination of the primary transformants was grown as described above on medium supplemented with 200 ppm kanamycin sulfate (Sigma). After 21 days, resistant (transformed) plants were unaffected compared to control plants, whereas sensitive plants were smaller, partially chlorotic, and poorly rooted. Determination of the number of genetic loci of the primary transformants was based on the segregation of the kanamycin resistance trait.

EXAMPLE 22

Detection of the P-450 phenotype by sulfonylurea treatment

Because of the increased phytotoxicity of 10014 over that of 10015, plants grown in media containing 10015 should be growth inhibited if they contain an active cytochrome P450SU1. To test this, seeds of tobacco were grown in tissue culture media supplemented with 50 nM compound 10015, and the results are shown in Table 20.

TABLE 20

| Plant Line | Number of genetic loci[a] | Inhibition[b] |
|---|---|---|
| AGS112 (Control) | 1 | 1 |
| SU18.8 | >2 | 1 |
| SU18.14 | 2 | 2 |
| SU18.15 | >2 | 2 |
| SSU-SU111.5 | ≧3 | 3 |
| Cab-SU111.8 | >2 | 3 |
| Cab-SU121.5 | 2 | 3 |
| Cab-SU131.5 | N.D.[c] | 3 |

[a]Number of genetic loci was determined by segregation analysis of >100 seed
[b]Inhibition of growth of 6 individuals was visually rated. 1 = little or no inhibition; 2 = moderate inhibition; 3 = severe inhibition, cotyledons expand but no growth occurs.
[c]Number of genetic loci could not be determined.

The data in this table showed that plants containing the P450 gene, especially those where the mature protein is directed to the chloroplast, were sensitive to inhibition by compound 10015. The high (>1) number of genetic loci of most of the parents of these plants insures a high likelihood that all of the six plants sampled have the P450 gene.

Sulfonylurea Selection of P450+FeS containing plants

The results above demonstrated that it was possible to use the P450 gene as a selectable marker by growing the plants in the presence of 50 nM of compound 10015. This technique was used to analyze the progeny of plants transformed with both the gene for SU1 and FeS-B, and the results are shown in Table 21.

TABLE 21

| Plant Line | Kanamycin Resistant | Copy No. | Compound 10015 Sensitive |
|---|---|---|---|
| AGS502 (Control) | 6/9 | 1 | 0/9 |
| SuFeII.1 | 7/9 | ≧4 | 2/9 |
| SuFeII.3 | 5/10 | 1 | 0/8 |
| SuFeII.4 | 7/10 | 1 | 0/10 |
| SuFeII.7 | 9/10 | 1 | 0/9 |
| SuFeII.8 | 10/10 | 2 | 1/10 |
| SuFeII.11 | 7/8 | 2 | 0/9 |

TABLE 21-continued

| Plant Line | Kanamycin Resistant | Copy No. | Compound 10015 Sensitive |
|---|---|---|---|
| SuFe21.2 | 7/10 | 1 | 7/9 |
| SuFe21.5 | 8/10 | 1 | 8/9 |
| SuFe21.6 | 9/10 | 1 | 7/9 |
| SuFe21.7 | 7/10 | 1 | 5/7 |
| SuFe21.8 | 8/9 | 1 | 10/10 |

Results for kanamycin resistance and compound 10015 sensitivity are expressed as plants demonstrating result/total plants. Copy number determination is from kanamycin sensitive segregation analysis of about 100 seed.

Plants exhibiting sensitivity to compound 10015 could be rescued from this treatment by plucking the seedlings from the surface of the medium and placing them in fresh medium containing no 10015. After several weeks growth, leaf tissue from the plants was collected, homogenized and analyzed for presence of the cytochrome P450SU1 antigen by Western blot analysis. Analysis of both 10015 resistant and 10015 sensitive plants from lines SuFe21.2, SuFe21.5, SuFe21.6, SuFe21.7, and SuFe21.8 revealed that of 8 plants characterized as 10015 resistant none had detectable levels of P450SU1 on a Western blot, while 18 out of 21 plants sensitive to 10015 had Western blot detectable levels of P450SU1.

These results demonstrated that the expression of P450SU1 leads to a negative selectable phenotype. When the mature protein was targeted to the chloroplast, this selection was comparable to the positive selection by kanamycin.

EXAMPLE 23

Sulfonylurea Selection of Transgenic Tobacco Lines SuFe31 and SuFe41

Plants transformed With the plasmids pSuFe31 and pSuFe41 were selected for high expression of P450SU1 and FeS-B mRNA by primer extension analysis as described in Example 19, and self pollinated to produce seed. This seed was germinated on medium containing 50 nM of compound 10015 and analyzed for sensitivity to this compound (indicating the presence of an active cytochrome P450SU1 enzyme) as in Example 22.

TABLE 22

| Plant Line | Number 10015 Resistant | Number 10015 Sensitive | Ratio Sensitive/Resistant |
|---|---|---|---|
| AGS502 (Control) | 32 | 0 | 0 |
| SuFe31.13 | 4 | 12 | 3.0 |
| SuFe31.28 | 5 | 10 | 2.0 |
| SuFe41.34 | 32 | 0 | 0 |
| SuFe41.37 | 8 | 24 | 3.0 |
| SuFe41.56 | 32 | 0 | 0 |
| SuFe41.60 | 15 | 0 | 0 |

Segregation of the compound 10015 sensitivity trait in SuFe31.13, SuFe31.38 and SuFe41.37 demonstrates that the sensitive plants are expressing an enzymatically active cytochrome P450SU1, and these plants are progeny of a heterozygous plant transformed at a single locus.

EXAMPLE 24

Transformed Tobacco Detoxification of Sulfonylurea

Tobacco seed from plants transformed with several P450SU1 and P450SU1+FeS-B constructions were tested for their ability to grow on tissue culture medium supplemented with compound 10001. Seed was placed on medium containing: 0, 5, 10, 20, and 40 nM of compound 10001. After 100 days, the plants were visually rated for their resistance (due to herbicide detoxification) to the herbicide treatment. All plants grown in the absence of herbicide and those treated with the lowest levels (5 nM and 10 nM) of 10001 had grown so large that no comparative rating was possible. The severely growth inhibited plants (those grown in the presence of 20 nM and 40 nM of compound 10001) were scored by comparing them to AGS502 plants (transformed without P450 gene) in Table 23.

TABLE 23

| Plant Line | 10001 Concentration (nM) | Individual Scores |
|---|---|---|
| SuFe21.5 | 20 | 2,0,0,0,0,0 |
| SuFe21.5 | 40 | 3,3,3,2,1 |
| SuFe21.8 | 20 | 3,3,0,0,0 |
| SuFe11.8 | 20 | 0,0,0,0,0 |
| SuFe11.8 | 40 | 0,0,0,0,0,0 |
| SuFe11.4 | 20 | 3,3,2,0,0 |
| SuFe11.4 | 40 | 0,0,0,0,0,0 |
| SSU-SU111.5 | 20 | 0,0,0,0,0 |
| SSU-SU111.5 | 40 | 0,0,0,0 |

SCORING SYSTEM: Visual comparison to AGS502 plants which uniformly appeared:

20 nM ∼1 cm tall, 6 leaves ∼1 cm diameter
40 nM ∼0.5 cm tall, 6 leaves ∼0.3 cm diameter, chlorotic
Ratings: 0 = essentially identical to AGS 502 controls;
1 = marginally larger (>1.2×) than AGS502;
2 = clearly larger (1.2 to 2×) than AGS502;
3 = substantially larger (>2×) than AGS502.

EXAMPLE 25

Interchangeability of FeS-A and FeS-B

The ability of both FeS-A or FeS-B to transfer reducing equivalents to either P450SU1 or P450SU2 was examined. Mixtures of the purified proteins were tested to see if FeS-A and/or FeS-B carried out the transfer of electrons from NADPH and Spinach ferredoxin:-NADP oxidoreductase to cytochromes P450SU1 or P450SU2. The ability for these FeS proteins to transfer reducing equivalents is a prerequisite for their involvement in the catalytic activity of the cytochromes P450.

The experiment was carried out at room temperature, in a buffer consisting of 0.1M MOPS-NaOH (pH 7.0), 0.2M NaCl, 10 mM compound 10013 (chlorsulfuron), and 50 nM ferredoxin:NADP oxidoreductase (purified from spinach leaves according to the method of Zanetti and Curti, Methods in Enzymology, 1980, Vol 69 pp250–255, herein incorporated by reference). To this mixture was added either FeS-A or FeS-B (as indicated in Table 24, 0.03 mM NADPH, and incubated for 10 min. The absorption spectrum was measured (Hewlett-Packard Model 8450A uv/vis spectrophotometer), P450 protein added, the sample bubbled with CO for 30 seconds, and the absorption measured again after 1 min and 5 min. The appearance of an absorption band at about 450 nm indicated the reduction of the cytochrome by the FeS protein.

TABLE 24

| Additions[a] | Fraction P450 Reduced 1 min | Fraction P450 Reduced 5 min |
|---|---|---|
| P450SU1 | <0.05 | <0.05 |
| P450SU1 + FeS-A | 0.51 | 0.81 |

TABLE 24-continued

| Additions[a] | Fraction P450 Reduced 1 min | Fraction P450 Reduced 5 min |
| --- | --- | --- |
| P450SU1 + FeS-B | 0.10 | 0.46 |
| P-450SU2 | <0.05 | <0.05 |
| P450SU2 + FeS-A | 0.98 | 1.0 |
| P450SU2 + FeS-B | 0.91 | 1.0 |

[a]Proteins were added at concentrations defined by their absorption spectra: SU1 (A418 = 0.017), SU2 (A418 = 0.027), FeS-A (A410 = 0.066), FeS-B (A410 = 0.071).

The data in Table 24 demonstrated that the FeS proteins participate in the transfer of electrons to the cytochromes P450, and that they may be used interchangeably, either FeS-A or FeS-B with SU1, or either FeS-A or FeS-B with SU2.

EXAMPLE 26

A negative selection system in transgenic Arabidopsis

Shoot growth of Arabidopsia seedlings that carry the cytochrome P450SU1 coding region was arrested when seeds were germinated on medium containing the sulfonylurea 10015 at concentrations which have no visible effect on seedlings lacking the coding region, thus providing a negative selection system for plants expressing the introduced gene. Plants lacking expression of the gene survived, while shoot growth of those expressing the gene was stunted.

The plasmids pSU18, pSSU-SU111, and pCab-SU111, as described in Example 19, Section C, were transformed directly into the Agrobacterium strain LBA4404/pAL4404 (Hoekema et al. Nature 303:179–180, 1983) using the freeze-thaw method (Plant Molec. Biol. Manual, S. B. Gelvin and R. A. Schilperoot, editors, A3:1–19, 1988, herein incorporated by reference) and selected on YEP medium (Table 25) with 50 mg/l rifampicin and 5 mg/l tetracycline. The presence of the plasmid DNA in selected clones was verified by restrictlob digests.

Standard aseptic techniques for the manipulation of sterile media and axenic plant/bacterial cultures were followed, including the use of a laminar flow hood for all transfers. Compositions of the culture media are listed in Table 25. Unless otherwise indicated, 25×100 mm petri plates were used for plant tissue cultures. Incubation of plant tissue cultures was at 23° C. under constant illumination with mixed fluorescent and "Gro and Sho" plant lights (General Electric) unless otherwise noted.

The source of explants was in vitro grown plants of Arabidopsis thaliana (L.) Heynh, geographic race Wassilewskija. Seeds were sterilized for 10 min in a solution of 50% chlorine bleach with 0.1% sodium dodecylsulfate, rinsed three to five times with sterile distilled H2O, dried thoroughly on sterile filter paper, and then sown on GM medium. The plates were sealed with filter tape (Carolina Biologicals, Burlington, N.C. USA) and incubated for seven days as described above. Seedlings were transferred to GM medium in 25×150 mm petri dishes, 36–40 per plate. Plates were sealed with filter tape and incubated for 2–3 weeks.

Prior to inoculation with Agrobacterium, root tissues were cultured on callus induction medium (MSKig) for four days. Whole root systems were harvested by pulling plantlets out of the agar using forceps, laying the roots-on MSKig medium, and then cutting off the shoot with a scalpel. Petri dishes were sealed with filter tape and incubated for four days.

Cultures of Agrobacterium cells containing each of the plasmids were grown in 5 ml of YEP broth containing 2 mg/l tetracycline. The cultures were grown for approximately 17–20 hours in glass culture tubes in a New Brunswick platform shaker (225 rpm) maintained at 28° C. Pre-cultured whole roots were cut into 0.5 cm segments and placed in a 100 µm filter, made from a Tri-Pour beaker (VWR Scientific, San Francisco, Calif. USA) and 100 µm wire mesh, which is set in a petri dish. Root segments were inoculated for several minutes in 30–50 ml of a 1:20 dilution of an overnight Agrobacterium culture with periodic gentle mixing. Inoculated roots were transferred to sterile filter paper to draw off most of the liquid. Small bundles of roots, consisting of several root segments, were placed on MSKig medium containing 100 µM acetosyringone (3′,5′-dimethoxy-4′-hydroxyacetophenone, Aldrich Chemical Co., Milwaukee, Wis., USA). Petri plates were sealed with parafilm or filter tape and incubated for two to three days.

After inoculation, root segments were rinsed and transferred to shoot induction medium containing antibiotics. Root bundles were placed in a 100 µm filter unit (described above) and rinsed with 30–50 ml liquid MSKig medium. The filter was vigorously shaken in the solution to help remove the Agrobacterium, transferred to a clean petri dish, and rinsed again. Roots were blotted on sterile filter paper and bundles of roots were placed on MSg medium containing 500 mg/l vancomycin with and without 50 mg/l kanamycin. Plates were sealed with filter tape and incubated for 12 to 21 days.

Green nodules and small shoot primordia were visible at about 2 weeks. The explants were either left intact or were broken into numerous pieces and placed on GM medium containing 200–300 mg/l vancomycin for further shoot development. Plates were either sealed with two pieces of tape or with filter tape. As they developed, individual shoots were isolated from the callus and were placed on MSRg medium containing 100 mg/l vancomycin. Dishes were sealed as described above and incubated for four to seven days. Shoots were then transferred to GM medium containing 100–200 mg/l vancomycin in 25×100 mm petri dishes or PlantCon containers (Flow Laboratories, McLean, Va.). Many primary transformants (T1) which were transferred to individual containers set seed (T2).

T2 seed was harvested from selected putative transformants and sown on GM medium containing 50 mg/l kanamycin and that containing 5 ppb 10015. Plates were sealed with filter tape, cold treated for 2 or more days at 4° C., and then incubated for 10 to 20 days at 23° C. under constant illumination as described above. Seedlings were scored as resistant (green, true leaves develop) and sensitive (no true leaves develop). Table 26 shows the number and percent of seedlings that are resistant and sensitive to kanamycin and 10015. The percent of resistant seedlings is inversely proportional with the two selections. Kanamycin is a positive selection for those seedlings that carry the foreign DNA. Therefore, this inverse relationship indicated that 10015 negatively selected, that is arrested shoot growth of, seedling expressing the P450SU1 gene, while those seedlings that do not express the P450SU1 gene survived.

Selected T2 seedlings that were kanamycin resistant were transplanted to soil and were grown to maturity at 21° C. daytime (14 hours) 18° C. nighttime (10 hours) at 65–80% relative humidity. T3 seed was collected, sterilized, and germinated on GM medium containing 50 mg/l kanamycin and that containing 5 ppb 10015. Plates were sealed with filter tape, cold treated for 2 or more days at 4° C., and then incubated for 10 to 20 days at 23° C. under constant illumination as described above. Seedlings were scored as resistant and sensitive and results are shown in Table 27. Two of the six plants produced seed that was 100% resistant to kanamycin and 100% sensitive to 10015; they are homozygous for the inserted DNA. The other four parents are heterozygous and show an inverse proportion of kanamycin and 10015 resistant seedlings. Thus, growth of seedlings which carry the heterologous genes was arrested when grown on medium containing 10015, while growth of seedlings which do not carry the genes was not affected. Therefore, seedlings expressing the P450SU1 gene can be negatively selected.

Selective destruction of plant tissues was exhibited in seedlings grown on medium containing 10015. Expression of the P450SU1 gene was controlled by the tissue-specific promoter from the cab gene which is expressed in the green tissues of plants. T3 seedlings grown on 5 ppb 10015, as described above, exhibited root growth but shoot growth was inhibited. Thus, only the shoot, which expresses P450SU1 was destroyed by the application of 10015.

Germination assays of homozygous seed on various concentrations of 10015 were performed to assay the relative sensitivity to 10015 produced by the three different promoters and between independent transformants. Seed was sterilized, sown on GM medium with 0, 0.5, 1, 2, 5, 10 and 20 ppb 10015, incubated, and scored as described above. In addition, seedlings are rated on a scale of one to three for the amount of growth. Results are shown in Table 27A. These results show that independent transformants exhibit different sensitivity to 10015.

To test if seedlings that do not carry the cytochrome P450SU1 coding region or those that exhibit lower activity of the gene product can be selected, wild type seeds were placed in specified areas on GM medium containing 10 ppb 10015. Over 500 seed that are homozygous for the P450SU1 coding region were sown on the same plates. The plates were sealed, cold-treated, and incubated as previously described. Plates were observed to determine if differentiation exists between the wild type seeds, and those exhibiting activation of 10015. Wild type seedlings were unaffected by the dying transformed seedlings. In addition, when greater than 10,000 seed of a homozygous Cab-SU111 plant was sown on GM medium with 10 ppb 10015, then cold-treated and incubated as described above, eighteen seedlings were resistant to 10015 and were unaffected by neighboring seedlings.

Integration of the coding region is confirmed by Southern blot analysis of selected progeny exhibiting kanamycin resistance and 10015 sensitivity. Southern blots are performed as described in Sambrook et al., *Molecular Cloning: A Laboratory Manual* 2nd edition (Cold Spring Harbor Laboratory, N.Y., 1989) hereby incorporated by reference. Plant DNA is digested with an enzyme appropriate for producing a DNA fragment containing DNA sequence from the introduced DNA, and an appropriate probe is used to detect this fragment.

TABLE 25

| Medium Composition | |
|---|---|
| YEP MEDIUM | Per Liter |
| Bacto Yeast Extract | 10.0 g |
| Bacto Peptone | 10.0 g |
| NaCl | 5.0 g |
| Agar (optional) | 15.0 g |
| pH 7.0 | |
| BASIC MEDIUM | |
| 1 pkg. Murashige and Skoog Minimal Organics Medium without Sucrose (Gibco #510-3118 or Sigma # M6899) | |
| 10 ml Vitamin Supplement | |
| 0.05% MES | |
| 0.8% agar | |
| pH 5.8 | |
| VITAMIN SUPPLEMENT - 100 X Stock | |
| 10 mg/l thiamine | |
| 50 mg/l pyridoxine | |
| 50 mg/l nicotinic acid | |
| GM = Germination Medium | |
| Basic Medium | |
| 1% sucrose | |
| MSKig = Callus Induction Medium | |
| Basic Medium | |
| 2% glucose | |
| 0.5 mg/l 2,4-D | |
| 0.3 mg/l Kinetin | |
| 5 mg/l IAA | |
| MSg = Shoot Induction Medium | |
| Basic Medium | |
| 2% glucose | 20 g/l |
| 0.15 mg/l IAA | 0.86 μM |
| 5.0 mg/l 2iP | 24.6 μM |
| MSRg = Shoot Induction Medium | |
| Basic medium | |
| 2% glucose | 20 g/l |
| 12 mg/l IBA | 58.8 μM |
| 0.1 mg/l Kinetin | 0.46 μM |

TABLE 26

Seed Germination Assay

| | | Kanamycin (50 mg/l) | | | 10015 (5 ppb) | | |
|---|---|---|---|---|---|---|---|
| ID | Plasmid | #R[a] | #S[b] | % R[c] | #R[a] | #S[b] | %R[c] |
| 12-1 | pCab-SU111 | 11 | 6 | 65 | 3 | 10 | 23 |
| 12-2 | pCab-SU111 | 0 | 12 | 0 | 13 | 0 | 100 |
| 12-4 | pCab-SU111 | 13 | 18 | 42 | 12 | 8 | 60 |
| 12-5 | pCab-SU111 | 0 | 20 | 0 | 15 | 0 | 100 |
| 12-6 | pCab-SU111 | 15 | 9 | 62 | 5 | 9 | 36 |
| 12-7 | pCab-SU111 | 21 | 7 | 75 | 9 | 13 | 40 |
| 12-8 | pCab-SU111 | 6 | 5 | 55 | 1 | 7 | 13 |
| 12-9 | pCab-SU111 | 13 | 3 | 81 | 3 | 9 | 25 |
| 12-10 | pCab-SU111 | 0 | 21 | 0 | 9 | 0 | 100 |
| 12-11 | pCab-SU111 | 0 | 9 | 0 | 4 | 0 | 100 |

[a] = number of resistant seedlings
[b] = number of sensitive seedlings
[c] = percent of seedlings which are resistant

TABLE 27

T3 Seed Germination Assay

| | | Kanamycin (50 mg/l) | | | 10015 (5 ppb) | | |
|---|---|---|---|---|---|---|---|
| ID | Plasmid | #R[a] | #S[b] | % R[c] | #R[a] | #S[b] | % R[c] |
| 12-1-1 | pCab-SU111 | 184 | 0 | 100 | 0 | 196 | 0 |
| 12-1-2 | pCab-SU111 | 191 | 0 | 100 | 0 | 191 | 0 |
| 12-1-3 | pCab-SU111 | 136 | 41 | 77 | 42 | 90 | 32 |
| 12-1-4 | pCab-SU111 | 98 | 39 | 72 | 80 | 129 | 37 |
| 12-1-5 | pCab-SU111 | 161 | 56 | 74 | 99 | 177 | 36 |
| 12-1-6 | pCab-SU111 | 254 | 75 | 77 | 83 | 152 | 35 |

TABLE 27-continued

| | | T3 Seed Germination Assay | | | | | |
|---|---|---|---|---|---|---|---|
| | | Kanamycin (50 mg/l) | | | 10015 (5 ppb) | | |
| ID | Plasmid | #R[a] | #S[b] | % R[c] | #R[a] | #S[b] | % R[c] |
| WT | — | 0 | 77 | 0 | 58 | 5 | 92 |

[a] = number of resistant seedlings
[b] = number of sensitive seedlings
[c] = percent of seedlings which are resistant

TABLE 27A

| | | Visual Inhibition Ratings of Seedlings* ppb 10015 | | | | | |
|---|---|---|---|---|---|---|---|
| ID | Construct | 0 | 1 | 2 | 5 | 10 | 20 |
| Wild type | | 1 | 1 | 1 | 1 | 1 | 1 |
| 12.20.5 | Cab-SU111 | 1 | 1 | 2 | 3 | 4 | 4 |
| 12.1.1 | Cab-SU111 | 1 | 1 | 1 | 2 | 4 | 4 |
| 12.16.2 | Cab-SU111 | 1 | 1 | 1 | 1 | 1 | 1 |
| 17.74.4 | SSU-SU111 | 1 | 1 | 1 | 2 | 3 | 3 |
| 13.4.6 | SSU-SU111 | 1 | 1 | 1 | 3 | 4 | 4 |
| 17.92.3 | SSU-SU111 | 1 | 1 | 1 | 1 | 1 | 1 |
| 17.17.3 | SU18 | 1 | 1 | — | 1 | 2 | 4 |
| 13.3.1 | SU18 | 1 | 1 | 1 | 2 | 4 | 4 |
| 17.1.10 | SU18 | 1 | 1 | 1 | 3 | 4 | 4 |

*Scale of 1 to 4 with 4 = complete inhibition, and 1 = no inhibition.

EXAMPLE 27

Cytochrome D450SU1 metabolism of sulfonylureas supported by various FeS proteins The purpose of this example was to define the combination of cytochrome p450SU1 and other proteins which results in optimal metabolism of sulfonylureas, based on conclusions from in vitro experiments. In these experiments, the rate of metabolism of 10015 to 10014, mediated by purified cytochrome p450SU1, was tested to find which FeS protein functions as the best direct electron donor.

Assays were carried out in 0.025 ml of buffer containing 0.1M MOPS—NaOH (pH 7.0), 0.2M NaCl, 0.2 mM 10015, 2 μM purified cytochrome p450SU1, Spinach ferredoxin:NADP oxidoreductase (FNR) as indicated in Table 28, various FeS proteins as indicated in Table 8, and an NADPH regenerating system consisting of 5 mM glucose-6-phosphate, and 2 Units/ml *Leuconostoc mesenteroides* glucose-6-phosphate dehydrogenase. The reaction was initiated by the addition of NADPH to a final concentration of 0.03 mM. After 15 min the reaction was terminated by the addition of 0.25 ml $H_2O$:acetonitrile:$H_3PO_4^-$(80:19:1). After filtering this mixture through a 0.2 μm filter, the amount of metabolite (10014) formed was analyzed by HPLC.

TABLE 28

| FES Addition | FNR concentration (mM) | Rate (nmol 10014) · (nmol p450) − 1 · (min) − 1 |
|---|---|---|
| 4 mM FeS-B | 0.2 | 0.3 |
| 4 mM FeS-B | 2.0 | 0.3 |
| 20 mM FeS-B | 2.0 | 0.4 |
| 4 mM FeS-A | 0.2 | 1.0 |
| 4 mM FeS-A | 2.0 | 2.6 |
| 20 mM Fes-A | 2.0 | 5.1 |
| 4 mM spinach Fd | 0.2 | 0.2 |
| 4 mM spinach Fd | 2.0 | 0.2 |
| 20 mM spinach Fd | 2.0 | 0.4 |
| none | 0.2 | <0.03 |
| none | 2.0 | 0.06 |

These results demonstrated that FeS-A, FeS-B, and spinach ferredoxin (an FeS protein) functioned as the direct reductant of P450SU1 during 10015 metabolism. Because a 10-fold increase in the FNR concentration did not increase the rate of metabolism with FeS-B or spinach ferredoxin, it was apparent that FNR was not rate limiting for those reactions, and the overall rate of metabolism was determined by FeS reduction of the P450. At 2 μM FNR, although somewhat rate limited by FNR, the rate of metabolism when 4 μM FeS-A was present was still at least 8-fold faster than with the same concentration of FeS-B.

It is not known if this differential ability of the two *S. griseolus* FeS proteins to support sulfonylurea metabolism was a result of some damage to FeS-B occuring during purification, or if the same differential ability occurs in vivo with the endogenous reductase proteins. Nonetheless, these in vitro results suggested that p450SU1 and FeS-A were the optimal combination for maximal p450SU1 metabolic activity, and supported claims for combinations of DNA resulting in coordinated expression of these two proteins as preferred constructions.

EXAMPLE 28

The cytochrome p450SU1 coding region was expressed specifically in the anther tissue of tobacco plants. The promoter region derived from the tobacco TA29 gene, which is a gene expressed naturally only in the tapetal tissue of the tobacco anther, was used. The tobacco TA29 gene has been described by Goldberg in Science 240, pp. 1460–1467 (1988) and in EPA 89-344029. The TA29 promoter fragment was prepared from the TA29 gene by isolating a 1500 bp ClaI-HindIII fragment from the TA29 gene clone, during which the ClaI end was filled in, and cloning this into the HindIII (blunt) and HindIII sites of M13mp19. The sequence of DNA surrounding the translation initiation ATG was determined by sequencing in from the HindIII end of the fragment according to the method of Sanger et al., Proc. Natl. Acad. Sci. USA 74:5463–5467 (1977) using a U.S. Biochemical Corporation Seguenase DNA sequencing kit and following the manufacturer's protocol. It was then altered to create an NcoI site at this ATG by using site-directed mutagenesis, as described in Viitanen et al., J. Biol. Chem. 263:15000–15007 (1988). The mutagenesis was carried out using the oligonucleotide of sequence AGAAATTAGCTACCATGGTAGCT-CCAAAAT that was synthesized using an Applied Biosystems DNA synthesizer and following the manufacturer's procedure. The TA29 promoter fragment containing the new NcoI site was then moved as a SmaI-HindIII fragment, the SmaI site being derived from the M13mp19 polylinker, into SmaI and HindII digested pTZ19 (Pharmacia) creating pTZAL.

Two chimeric genes were constructed that contain the TA-29 promoter and the SU1 coding region followed by the petunia Rubisco small subunit gene untranslated and polyadenylation region ("SSU301 3'"). One chimetic gene also contained the Rubisco small subunit chloroplast transit sequence and the other did not. These chimeric genes were called A-T-SU1 and A-SU1, respectively. To construct A-SU1 a ScaI-BamHI fragment was isolated that contains the same SU1 coding region and "SSU301" polyadenylation region that was present in the clone pSU17 which has been deposited with the ATCC and bears accession number 67995. The ScaI end of the fragment was joined to the filled in NcoI site at the 3' end of the TA29 promoter. The plasmid containing the TA29 promoter fragment was also digested with BamHI to accommodate the 3' end of the SU1 fragment. The resulting plasmid was called pTZA-SU1.

In constructing A-T-SU1 the source of the SU1 coding region adjacent to the transit sequence was the SSu-SU11 gene which has been deposited with the ATCC as pSSU-SU11 and bears the accession number 67994. An NcoI fragment containing the transit sequence and the 5' region of SU1 was purified as well as an NcoI-HindIII fragment containing the 3' region of SU1 and some polyadenylation region from the SSU301 gene. The NcoI-HindIII 3' fragment was first ligated with NcoI and HindIII cut pTZAL that was described above Next the NcoI fragment was ligated into the NcoI site of the resulting plasmid and a clone containing this fragment in the correct orientation was identified by digestion with SphI. From the resulting clone a SmaI-DraI fragment containing the TA29 promoter transit sequence and part of the SU1 coding region was cloned into SmaI and DraI digested pTZA-SU1, the SmaI site in both being present in the pTZ19 polylinker. This step was carried out to place the promoter, transit, and 5' SU1 sequences adjacent to a complete SSU301 polyadenylation region. The resulting plasmid was called pTZA-T-SU1.

The SU1 chimeric genes were each isolated as Asp718-BamHI fragments, the Asp718 site coming from the polylinker of pTZ19. They were ligated into Asp718 and BamIII digested pZS96. pZS96 was prepared as described in Example 19. The resulting plasmid with the A-SU1 chimeric gene residing in the pZS96 plasmid was pZ6A-SU1 and is shown in FIG. 25A. The resulting plasmid with the A-T-SU1 chimeric gene residing in the pZS96 plasmid was called pZ6A-T-SU1 and is shown in FIG. 25B.

pZ6A-SU1 and pZ6A-T-SU1 were each transformed into Agrobacterium tumefaciens strain LBA4404 by direct DNA uptake following the procedure described in Plant Molecular Biology Manual, SB Gelvin et al., ads. Kluwer Academic Press PMAN-A3/7, 1988, herein incorporated by reference. The presence of each intact vector in Agrobacterium colonies selected on mina medium with sucrose containing 100 µg/ml kanamycin and 100 µg/ml carbenicillin was verified by restriction enzyme digests of miniprep DNA. Leaf disks of Nicotiana tabacum cv. Xanthi were inoculated with Agrobacterium carrying the constructed plasmids and kanamycin resistant plants were obtained as described previously.

Twenty-one plants transformed with the A-T-SU1 gene and 15 plants transformed with the A-SU1 gene were grown to maturity. From each plant, anthers were dissected from five early developmental stage buds in which the petals had not yet separated and they were frozen in liquid nitrogen. RNA was prepared following the procedure of Verwoerd et al., Nucleic Acids Research 17:2362, 1989, and analyzed on Northern blots for the presence of messenger RNA (mRNA) produced by the chimeric SU1 gene that was introduced into the plant. Northern blots were prepared according to Rave et al. Nucleic Acids Research 6:3559-3569, 1979, and probed as described in Maniatis et al. Molecular Cloning:a Laboratory Manual, Cold Spring Harbor, N.Y., each herein incorporated by reference. The probe fragment used was a PstI fragment isolated from SSU-SU114 containing part of the transit sequence and the SU1 coding region. This probe detected the A-SU1 and A-T-Su1 mRNAs as well as the Rubisco small subunit mRNA (due to homology with the transit sequence).

In several plants no SU1 mRNA was detected in the anthers and these plants were not analyzed further. Plants showing expression of the SU1 mRNA in the anthers were analyzed further to determine whether the SU1 mRNA expression was anther-specific. Leaf RNA was prepared from each plant and compared to the anther RNA isolated from the same plant on Northern blots. The levels of SU1 mRNA in the leaf and anther RNA samples from each plant were compared to distinguish those plants in which the anther SU1 mRNA was in greater abundance than the leaf SU1 mRNA, indicating anther-specific expression. "Anther-specific" as used herein means expression of the gene regulated by the anther-specific promoter is predominantly in the desired anther tissue. Out of 14 plants expressing the A-T-SU1 mRNA in the anther, 71% showed anther-specific expression. The term "anther" refers to the part of the flower that physically contains pollen. Pollen grains, at all stages of development, are considered a part of the anther. For the sake of simplicity, the term is intended to include gamete as well. By "gamete" is meant a mature gem cell capable of forming a new individual by fusion with another gamete. Out of 12 plants expressing the A-SU1 mRNA in the anther, 42% showed anther-specific expression. Thus there was some variability among plants receiving the SU1 coding region regulated by the TA29 promoter, but plants with anther-specific expression of the p450SU1 gene were created.

The resulting data was as follows:

| A denotes anther, L denotes leaf | |
| --- | --- |
| A-T-SU1 plants: | A >> L: 17A, 33A, 41A, 43A, 56A |
| | A > L: 13A, 24A, 28A, 31B, 38A |
| | A = L: 61A, 63A, 64B |
| | A < L: 52B |
| | no A: 7A, 12A, 23A, 37A, 59A, 62B |
| | plant 65A produced no buds |
| A-SU1 plants: | A >> L: 19A, 31A, 34A |
| | A > L: 26A, 56A |
| | A = L: 36C, 52A, 59A |
| | A < L: 11B, 32A, 40A, 64B |
| | no A: 3A, 8A |
| | plant 14A produced no buds |

Application of compound 10015 was as follows. The tapetal cells of the anther surround the developing pollen and are instrumental in supporting the development of mature pollen. Thus production of a toxin in the tapetal cells was expected to disrupt the development of normal mature pollen. The nontoxic compound 10015 was sprayed onto flowering transgenic plants that had anther-specific expression of P450SU1 mRNA. Plants were hand sprayed with rates between 4 and 128 g/hectare, which consisted of 14-25 ml of 5.3-95 μg/ml of 10015. The 10015 was first dissolved in up to 0.8 ml of 0.01 N ammonium hydroxide and then diluted into AGWT (90.2% Acetone:4.8% Glycerol:4.8% Water:0.24% Tween 20 by volume). Little effect was seen when rates of less than 32 g/ha were applied. At 32 g/ha and above, effects were seen on the ability of pollen to germinate in vitro. Newly opened buds were collected at time intervals between four and 23 days after spraying. The anthers were removed and pollen was brushed into Brewbaker and Kwak medium (15% sucrose, 200 ppm calcium nitrate, 100 ppm boric acid).

Growth of tubes from the pollen, indicating germination, was assessed after four hours of incubation by microscopic observation.

Pollen from some of the transgenic plants collected following application of 10015 showed reduced ability to germinate in vitro. Germination of pollen from two plants with anther-specific expression of the A-T-SU1 gene (41A and 56 A) was reduced to 0% at 7 to 11 days after application of 32 g/ha of 10015 (0.59 mg in 20 ml). The germination stayed at less than 0.1% through 18 days on one of these plants and through 13 days on the other plant. Three other plants (31B, 43A, 24A) also had reduced pollen germination rates varying between 0 and 2% for time periods of a few days to a week. Pollen from the control untransformed plant with the same application of 10015 germinated at a rate of 50% to 90% (varying between buds) over this same time period. Two other transgenic plants sprayed with 100 g/ha (1.85 mg in 24 ml) were greatly affected: one (plant 28A) had no pollen germination at 7–14 days after treatment and less than 0.1% germination at 21 days, the other (plant 38A) had no pollen germination at 7–11 days, but increased to 1–25% (varying between buds) at 14 days. Thus seven plants out of the 10 plants tested that had anther-specific expression of A-T-SU1 showed reduced pollen viability in vitro following application of 10015, and three plants showed almost complete absence of pollen viability for a week or more.

The transgenic plants expressing the A-SU1 gene were not as affected by 10015 application: two plants showed only slight reduction in pollen viability.

Thus it has been demonstrated by an in vitro pollen germination assay that application of 10015 to transgenic plants, that express the p450SU1 gene from the TA29 promoter and show anther-specific expression of the p450SU1 mRNA, substantially reduced the viability of the pollen. The ability of pollen from treated plants to function in vivo is being tested by using it to cross fertilize emasculated flowers on control untreated plants. The female fertility of treated plants is being tested by cross-fertilizing emasculated flowers of these plants with pollen from untreated control plants. It is expected that the three plants that were most affected by the 10015 application as described above will behave as male sterile, female fertile plants in the time period when the in vitro pollen germination is lowest.

EXAMPLE 29

Metabolism of Non-sulfonylurea Herbicides by Bacteria Containing the Genes for p450SU1

This experiment was performed as in Example 17 with the following changes. Separate cultures (50 ml) inoculated with *S. lividans* C37, *S. lividans* transformed with pCAO200SU1-FeS-B#9, or *S. griseolus* ATCC11796 were cultured in sporulation broth for 18 hours at 30° C. with shaking. Each culture was then resuspended in 25 ml fresh sporulation broth and 3.0 mg herbicide added. Each culture was reincubated for 18 hours, then an aliquot of the medium was withdrawn and analyzed by HPLC. The percent conversion of herbicide was determined.

The percent conversion of herbicide is presented in Table 29. The results in Table 29 show that bacteria containing constitutively expressed P450SU1 metabolized the nonsulfonylurea herbicides 0033, 10034, 10035, and 10036.

TABLE 29

| | Percent Conversion | | | |
|---|---|---|---|---|
| Strain | 10033 | 10034 | 10035 | 10036 |
| *S. griseolus* ATCC11796 | 100 | 13 | 21 | 100 |
| *S. lividans* C37 | 5 | 10 | 22 | 8 |
| *S. lividans* pCAO200 SU1-FeS-B#9 | 88 | 69 | 96 | 100 |

What is claimed is:

1. A recombinant plasmid comprising

A) segments selected from the group consisting of i) the DNA sequence encoding cytochrome P450 enzyme P450SU1 comprising:

```
130                     150
ATGACCGATACCGCCACGACGCC
--+----------+----------+
TACTGGCTATGGCGGTGCTGCGG
Met Thr Asp Thr Ala Thr Thr Pr

170
 CCAGACCACGGACGCACCCGCCTTCCCGAG
 ---------+----------+----------+
 GGTCTGGTGCCTGCGTGGGCGGAAGGGCTC
 o Gln Thr Thr Asp Ala Pro Ala Phe Pro Se 190                   210
CAACCGGAGCTGTCCCTACCAGTTACCGGA
---------+----------+----------+
GTTCGCCTCGACAGGGATGGTCAATGGCCT
r Asn Arg Ser Cys Pro Tyr Gln Leu Pro As

230
 CGGCTACGCCCAGCTCCGGGACACCCCCGG
 ---------+----------+----------+
 GCCGATGCGGGTCGAGGCCCTGTGGGGGCC
 p Gly Tyr Ala Gln Leu Arg Asp Thr Pro Gl 250                   270
CCCCCTGCACCGGGTGACGCTCTACGACGG
---------+----------+----------+
GGGGGACGTGGCCCACTGCGAGATGCTGCC
y Pro Leu His Arg Val Thr Leu Tyr Asp Gl

290
 CCGTCAGGCGTGGGTGGTGACCAAGCACGA
 ---------+----------+----------+
 GGCAGTCCGCACCCACCACTGGTTCGTGCT
 y Arg Gln Ala Trp Val Val Thr Lys His Gl 310                   330
GGCCGCGCGCAAACTGCTCGGCGACCCCCG
---------+----------+----------+
CCGGCGCGCGTTTGACGAGCCGCTGGGGGC
u Ala Ala Arg Lys Leu Leu Gly Asp Pro Ar

350
 GCTGTCCTCCAACCGGACGGACGACAACTT
 ---------+----------+----------+
 CGACAGGAGGTTGGCCTGCCTGCTGTTGAA
 g Leu Ser Ser Asn Arg Thr Asp Asp Asn Ph 370                   390
CCCCGCCACGTCACCGCGCTTCGAGGCCGT
---------+----------+----------+
GGGGCGGTGCAGTGGCGCGAAGCTCCGGCA
e Pro Ala Thr Ser Pro Arg Phe Glu Ala Va

410
 CCGGGAGAGCCCGCAGGCGTTCATCGGCCT
 ---------+----------+----------+
 GGCCCTCTCGGGCGTCCGCAAGTAGCCGGA
 l Arg Glu Ser Pro Gln Ala Phe Ile Gly Le 430                   450
GGACCCGCCCGAGCACGGCACCCGGCGGCG
---------+----------+----------+
```

-continued

```
CCT GGGC GGGC T CGT GCC GT GGGC CGC CGC
u  Asp Pro  Pro Glu His Gly Thr Arg Arg Ar

470
    GAT GAC GAT CAG CGA GTT CAC CGT CAA GCG
    ---------+----------+----------+
    CTA CTG CTA GTC GCT CAA GTG GCA GTT CGC
  g Met Thr Ile Ser Glu Phe Thr Val Lys Ar 490                510
    GAT CAA GGG CAT GCG CCC CGA GGT CGA GGA
    ---------+----------+----------+
    CTA GTT CCC GTA CGC GGG GCT CCA GCT CCT
  g Ile Lys Gly Met Arg Pro Glu Val Glu Gl

530
    GGT GGT GCA CGG CTT CCT CGA CGA GAT GCT
    ---------+----------+----------+
    CCA CCA CGT GCC GAA GGA GCT GCT CTA CGA
  u Val Val His Gly Phe Leu Asp Glu Met Le 550                570
    GGC CGC CGG CCC GAC CGC CGA CCT GGT CAG
    ---------+----------+----------+
    CCG GCG GCC GGG CTG GCG GCT GGA CCA GTC
  u Ala Ala Gly Pro Thr Ala Asp Leu Val Se

590
    TCA GTT CGC GCT GCC GGT GCC CTC CAT GGT
    ---------+----------+----------+
    AGT CAA GCG CGA CGG CCA CGG GAG GTA CCA
  r Gln Phe Ala Leu Pro Val Pro Ser Met Va 610                630
    GAT CTG CCG ACT CCT CGG CGT GCC CTA CGC
    ---------+----------+----------+
    CTA GAC GGC TGA GGA GCC GCA CGG GAT GCG
  l Ile Cys Arg Leu Leu Gly Val Pro Tyr Al

650
    CGA CCA CGA GTT CTT CCA GGA CGC GAG CAA
    ---------+----------+----------+
    GCT GGT GCT CAA GAA GGT CCT GCG CTC GTT
  a Asp His Glu Phe Phe Gln Asp Ala Ser Ly 670                690
    GCG GCT GGT GCA GTC CAC GGA CGC GCA GAG
    ---------+----------+----------+
    CGC CGA CCA CGT CAG GTG CCT GCG CGT CTC
  s Arg Leu Val Gln Ser Thr Asp Ala Gln Se

710
    CGC GCT CAC CGC GCG GAA CGA CCT CGC GGG
    ---------+----------+----------+
    GCG CGA GTG GCG CGC CTT GCT GGA GCG CCC
  r Ala Leu Thr Ala Arg Asn Asp Leu Ala Gl 730                750
    TTA CCT GGA CGG CCT CAT CAC CCA GTT CCA
    ---------+----------+----------+
    AAT GGA CCT GCC GGA GTA GTG GGT CAA GGT
  y Tyr Leu Asp Gly Leu Ile Thr Gln Phe Gl

770
    GAC CGA ACC GGG CGC GGG CCT GGT GGG CGC
    ---------+----------+----------+
    CTG GCT TGG CCC GCG CCC GGA CCA CCC GCG
  n Thr Gln Pro Gly Ala Gly Leu Val Gly Al
        790                810
    TCT GGT CGC CGA CCA GCT GGC CAA CGG CGA
    ---------+----------+----------+
    AGA CCA GCG GCT GGT CGA CCG GTT GCC GCT
  a Leu Val Ala Asp Gln Leu Ala Asn Gly Gl

830
    GAT CGA CCG TGA GGA ACT GAT CTC CAC CGC
    ---------+----------+----------+
    CTA GCT GGC ACT CCT TGA CTA GAG GTG GCG
  u Ile Asp Arg Glu Glu Leu Ile Ser Thr Al 850                870
    GAT GCT GCT CCT CAT CGC CGG CCA CGA GAC
```

```
    ---------+----------+----------+
    CTA CGA CGA GGA GTA GCG GCC GGT GCT CTG
  a Met Leu Leu Leu Ile Ala Gly His Glu Th

890
    CAC GGC CTC GAT GAC CTC CCT CAG CGT GAT
    ---------+----------+----------+
    GTG CCG GAG CTA CTG GAG GGA GTC GCA CTA
  r Thr Ala Ser Met Thr Ser Leu Ser Val Il 910                930
    CAC CCT GCT GGA CCA CCC CGA GCA GTA CGC
    ---------+----------+----------+
    GTG GGA CGA CCT GGT GGG GCT CGT CAT GCG
  e Thr Leu Leu Asp His Pro Glu Gln Tyr Al

950
    CGC CCT GCG CGC CGA CCG CAG CCT CGT GCC
    ---------+----------+----------+
    GCG GGA CGC GCG GCT GGC GTC GGA GCA CGG
  a Ala Leu Arg Ala Asp Arg Ser Leu Val Pr 970                990
    CGG CGC GGT GGA GGA ACT GCT CCG CTA CCT
    ---------+----------+----------+
    GCC GCG CCA CCT CCT TGA CGA GGC GAT GGA
  o Gly Ala Val Glu Glu Leu Leu Arg Tyr Le

1010
    CGC CAT CGC CGA CAT CGC GGG CGG CCG CGT
    ---------+----------+----------+
    GCG GTA GCG GCT GTA GCG CCC GCC GGC GCA
  u Ala Ile Ala Asp Ile Ala Gly Gly Arg Va 1030                1050
    CGC CAC GGC CGG ACA TCG AGG TCG AGG GGCA
    ---------+----------+----------+
    GCG GTG CCG CCT GTA GCT CCA GCT CCC CGT
  l Ala Thr Ala Asp Ile GlU Val Glu Gly Hi

1070
    CCT CAT CCG GGC CGG CGA GGG CGT GAT CGT
    ---------+----------+----------+
    GGA GTA GGC CCG GCC GCT CCC GCA CTA GCA
  s Leu Ile Arg Ala Gly Glu Gly Val Ile Va 1090                1110
    CGT CAA CTC GAT AGC CAA CCG GGA CGG CAC
    ---------+----------+----------+
    GCA GTT GAG CTA TCG GTT GGC CCT GCC GTG
  l Val Asn Ser Ile Ala Asn Arg Asp Gly Th

1130
    GGT GTA CGA GGA CCC GGA CGC CCT CGA CAT
    ---------+----------+----------+
    CCA CAT GCT CCT GGG CCT GCG GGA GCT GTA
  r Val Tyr Glu Asp Pro Asp Ala Leu Asp Il 1150                1170
    CCA CCG CTC CGC GCG CCA CCA CCT CGC CTT
    ---------+----------+----------+
    GGT GGC GAG GCG CGC GGT GGT GGA GCG GAA
  e His Arg Ser Ala Arg His His Leu Ala Ph

1190
    CGG CTT CGG CGT GCA CCA GTG CCT GGG CCA
    ---------+----------+----------+
    GCC GAA GCC GCA CGT GGT CAC GGA CCC GGT
  e Gly Phe Gly Val His Gln Cys Leu Gly Gl 1210                1230
    GAA CCT CGC CCG GCT GGA GCT GGA GGT CAT
    ---------+----------+----------+
    CTT GGA GCG GGC CGA CCT CGA CCT CCA GTA
  n Asn Leu Ala Arg Leu Glu Leu Glu Val Il

1250
    CCT CAA CGC CCT CAT GGA CCG CGT CCC GAC
    ---------+----------+----------+
    GGA GTT GCG GGA GTA CCT GGC GCA GGG CTG
  e Leu Asn Ala Leu Met Asp Arg Val Pro Th
```

-continued

```
        1270               1290
GCTGCACTGGCCGTCCCCGTCGAGCAGTT
--------+---------+---------+
CGACGCTGACCGGCAGGGGCAGCTCGTCAA
 r  Leu Arg Leu Ala Val Pro Val Glu Gln Le

1310
    GGTGCTGCGGCCGGGTACGACGATCCAGGG
    ---------+---------+---------+
    CCACGACGCCGGCCCATGCTGCTAGGTCCC
    u  Val Leu Arg Pro Gly Thr Thr Ile Gln Gl 1330              1350
CGTCAACGAACTCCCGGTCACCTGGTGA
--------+---------+---------
GCAGTTGCTTGAGGGCCAGTGGACCACT
 y Val Asn Glu Leu Pro Val Thr Trp End;
``` ii) the DNA sequence encoding cytochrome P450 enzyme P450SU2 comprising:

```
             210
        ATGACGACCGCAGAAC
        -----+---------+
        TACTGCTGGCGTCTTG
            Met Thr Thr Ala Glu A

230
   GCACCGCTCCCCCCGACGCCCTCACCGTCC
   ---------+---------+---------+
   CGTGGCGAGGGGGGCTGCGGGAGTGGCAGG
    rg Thr Ala Pro Pro Asp Ala Leu Thr Val P 250              270
CGGCCAGCCGCGCCCCGGCTGCCCCTTCG
---------+---------+---------+
GCCGGTCGGCGCGGGGGCCGACGGGGAAGC
 ro Ala Ser Arg Ala Pro Gly Cys Pro Phe A

290
   ACCCCGCGCCCGACGTCACCGAGGCGGCCC
   ---------+---------+---------+
   TGGGGCGCGGGCTGCAGTGGCTCCGCCGGG
    sp Pro Ala Pro Asp Val Thr Glu Ala Ala A 310              330
GCACCGAACCGGTCACCCGGGCCACCCTCT
---------+---------+---------+
CGTGGCTTGGCCAGTGGGCCCGGTGGGAGA
 rg Thr Glu Pro Val Thr Arg Ala Thr Leu T

350
   GGGACGGCTCCTCCTGCTGGCTGGTGACGC
   ---------+---------+---------+
   CCCTGCCGAGGAGGACGACCGACCACTGCG
    rp Asp Gly Ser Ser Cys Trp Leu Val Thr A 370              390
GCCATCAGGACGTCCGCGCGGTCCTCGGCG
---------+---------+---------+
CGGTAGTCCTGCAGGCGCGCCAGGAGCCGC
 rg His Gln Asp Val Arg Ala Val Leu Gly A

410
   ACCCGCGCTTCAGCGCCGACGCCCACCGCA
   ---------+---------+---------+
   TGGGCGCGAAGTCGCGGCTGCGGGTGGCGT
    sp Pro Arg Phe Ser Ala Asp Ala His Arg T 430              450
CCGGCTTCCCCTTCCTGACCGCCGGCGGCC
---------+---------+---------+
GGCCGAAGGGGAAGGACTGGCGGCCGCCGG
 hr Gly Phe Pro Phe Leu Thr Ala Gly Gly A

470
    GCGAGATCATCGGCACCAACCCGACCTTCC
    ---------+---------+---------+
    CGCTCTAGTAGCCGTGGTTGGGCTGGAAGG
     rg Glu Ile Ile Gly Thr Asn Pro Thr Phe L
```

```
              490              510
    TGCGCATGGACGACCCGGAGCACGCCCGAC
    ---------+---------+---------+
    ACGCGTACCTGCTGGGCCTCGTGCGGGCTG
     eu Arg Met Asp Asp Pro Glu His Ala Arg L

530
    TGCGCCGGATGCTCACCGCCGACTTCATCG
    ---------+---------+---------+
    ACGCGGCCTACGAGTGGCGGCTGAAGTAGC
     eu Arg Arg Met Leu Thr Ala Asp Phe Ile V 550              570
    TCAAGAAGGTCGAGGCGATGCGCCCCGAGG
    ---------+---------+---------+
    AGTTCTTCCAGCTCCGCTACGCGGGGCTCC
     al Lys Lys Val Glu Ala Met Arg Pro Glu V

590
    TGCAGCGCCTCGCCGACGACCTGGTCGACC
    ---------+---------+---------+
    ACGTCGCGGAGCGGCTGCTGGACCAGCTGG
     al Gln Arg Leu Ala Asp Asp Leu Val Asp A 610              630
    GGATGACCACCGGACGCACCTCCGCCGACC
    ---------+---------+---------+
    CCTACTGGTGGCCTGCGTGGAGGCGGCTGG
     rg Met Thr Thr Gly Arg Thr Ser Ala Asp L

650
    TGGTCACCGAGTTCGCGCTGCCGCTGCCGT
    ---------+---------+---------+
    ACCAGTGGCTCAAGCGCGACGGCGACGGCA
     eu Val Thr Glu Phe Ala Leu Pro Leu Pro S 670              690
    CCCTGGTGATCTGCCTGCTGCTCGGCGTCC
    ---------+---------+---------+
    GGGACCACTAGACGGACGACGAGCCGCAGG
     er Leu Val Ile Cys Leu Leu Leu Gly Val P

710
    CCTACGAGGACCACGCGTTCTTCCAGGAGC
    ---------+---------+---------+
    GGATGCTCCTGGTGCGCAAGAAGGTCCTCG
     ro Tyr Glu Asp His Ala Phe Phe Gln Glu A 730              750
    GCAGCCGGGTCCTGCTCACCCTGCGGTCCA
    ---------+---------+---------+
    CGTCGGCCCAGGACGAGTGGGACGCCAGGT
     rg Ser Arg Val Leu Leu Thr Leu Arg Ser T

770
    CTCCCGAGGAAGTCCGGGCCGCCCAGGACG
    ---------+---------+---------+
    GAGGGCTCCTTCAGGCCCGGCGGGTCCTGC
     hr Pro Glu Glu Val Arg Ala Ala Gln Asp G 790              810
    AGTTGCTGGAGTACCTCGCCCGGCTCGCCC
    ---------+---------+---------+
    TCAACGACCTCATGGAGCGGGCCGAGCGGG
     lu Leu Leu Glu Tyr Leu Ala Arg Leu Ala A

830
    GGACCAAGCGGGAGCGGCCGGACGACGCCA
    ---------+---------+---------+
    CCTGGTTCGCCCTCGCCGGCCTGCTGCGGT
     rg Thr Lys Arg Glu Arg Pro Asp Asp Ala I 850              870
    TCATCAGCCGCCTGGTCGCCCGCGGCGAGC
    ---------+---------+---------+
    AGTAGTCGGCGGACCAGCGGGCGCCGCTCG
     le Ile Ser Arg Leu Val Ala Arg Gly Glu L

890
    TCGACGACACCCAGATCGCCACCATGGGAC
    ---------+---------+---------+
```

-continued

```
            AGCTGCTGTGGGTCTAGCGGTGGTACCCTG
            eu  Asp Asp Thr Gln Ile Ala Thr Met Gly  A
              910                     930
            GCCTGTTGCTGGTCGCCGGCCACGAGACGA
            ----------+----------+----------+
            CGGACAACGACCAGCGGCCGGTGCTCTGCT
            rg  Leu Leu Leu Val Ala Gly His Glu Thr  T
                         950
            CCGCCAACATGACCGCGCTCTCCACCCTCG
            ----------+----------+----------+
            GGCGGTTGTACTGGCGCGAGAGGTGGGAGC
            hr  Ala Asn Met Thr Ala Leu Ser Thr Leu  V
              970                     990
            TGCTGCTGCGCAACCCCGACCAACTCGCCC
            ----------+----------+----------+
            ACGACGACGCGTTGGGGCTGGTTGAGCGGG
            al  Leu Leu Arg Asn Pro Asp Gln Leu Ala  A
                        1010
            GGCTGCGCGCCGAACCCGCGCTCGTCAAGG
            ----------+----------+----------+
            CCGACGCGCGGCTTGGGCGCGAGCAGTTCC
            rg  Leu Arg Ala Glu Pro Ala Leu Val Lys  G
              1030                    1050
            GCGCCGTCGAGGAGCTGCTGCGCTACCTGA
            ----------+----------+----------+
            CGCGGCAGCTCCTCGACGACGCGATGGACT
            ly  Ala Val Glu Glu Leu Leu Arg Tyr Leu  T
                        1070
            CGATCGTGCACAACGGCGTTCCCCGGATCG
            ----------+----------+----------+
            GCTAGCACGTGTTGCCGCAAGGGGCCTAGC
            hr  Ile Val His Asn Gly Val Pro Arg Ile  A
              1090                    1110
            CCACCGAGGACGTGCTCATCGGCGGCCGCA
            ----------+----------+----------+
            GGTGGCTCCTGCACGAGTAGCCGCCGGCGT
            la  Thr Glu Asp Val Leu Ile Gly Gly Arg  T
                        1130
            CCATCGCCGCCGGCGAGGGCGTCCTGTGCA
            ----------+----------+----------+
            GGTAGCGGCGGCCGCTCCCGCAGGACACGT
            hr  Ile Ala Ala Gly Glu Gly Val Leu Cys  M
              1150                    1170
            TGATCAGCTCCGCCAACCGGGACGCCGAGG
            ----------+----------+----------+
            ACTAGTCGAGGCGGTTGGCCCTGCGGCTCC
            et  Ile Ser Ser Ala Asn Arg Asp Ala Glu  V
                        1190
            TGTTCCCCGGCGGCGACGACCTCGACGTGG
            ----------+----------+----------+
            ACAAGGGGCCGCCGCTGCTGGAGCTGCACC
            al  Phe Pro Gly Gly Asp Asp Leu Asp Val  A
              1210                    1230
            CCCGCGACGCCCGCCGCCACGTGGCCTTCG
            ----------+----------+----------+
            GGGCGCTGCGGGCGGCGGTGCACCGGAAGC
            la  Arg Asp Ala Arg Arg His Val Ala Phe  G
                        1250
            GCTTCGGCGTCCACCAGTGCCTGGGACAGC
            ----------+----------+----------+
            CGAAGCCGCAGGTGGTCACGGACCCTGTCG
            ly  Phe Gly Val His Gln Cys Leu Gly Gln  P
              1270                    1290
            CGTTGGCCAGGGTGGAGCTCCAGATCGCCA
            ----------+----------+----------+
            GCAACCGGTCCCACCTCGAGGTCTAGCGGT
            ro  Leu Ala Arg Val Glu Leu Gln Ile Ala  I
                        1310
            TCGAAACGCTGCTGCGCCGCCTGCCGGACC
```

```
            ----------+----------+----------+
            AGCTTTGCGACGACGCGGCGGACGGCCTGG
            le  Glu Thr Leu Leu Arg Arg Leu Pro Asp  L
              1330                    1350
            TGCGGCTGGCCGTGCCCCACGAGGAGATCC
            ----------+----------+----------+
            ACGCCGACCGGCACGGGGTGCTCCTCTAGG
            eu  Arg Leu Ala Val Pro His Glu Glu Ile  P
                        1370
            CGTTCCGCGGCGACATGGCCGATCTACGGGG
            ----------+----------+----------+
            GCAAGGCGCCGCTGTACCGCTAGATGCCCC
            ro  Phe Arg Gly Asp Met Ala Ile Tyr Gly  V
                        1390
            TCCACTCGCTGCCGATCGCCTGGTAG
            ----------+----------+------
            AGGTGAGCGACGGCTAGCGGACCATC
            al  His Ser Leu Pro Ile Ala Trp End  ;
``` iii) either of the DNA sequence encoding cytochrome P450 enzyme P450SU1 of i) or the DNA sequence encoding cytochrome P450 enzyme P450SU2 of ii) in combination with the DNA sequence encoding iron sulfur protein FeS-B comprising:

```
                        1370
                     ATGACCATGCGG
                    -+----------+
                     TACTGGTACGCC
                     Met Thr Met Arg
              1390                    1410
            GTGAGTGCGGATCGGACGGTCTGCGTCGGT
            ----------+----------+----------+
            CACTCACGCCTAGCCTGCCAGACGCAGCCA
            Val Ser Ala Asp Arg Thr Val Cys Val Gly
                        1430
            GCCGGGCTGTGTGCGCTGACGGCGCCGGGC
            ----------+----------+----------+
            CGGCCCGACACACGCGACTGCCGCGGCCCG
            Ala Gly Leu Cys Ala Leu Thr Ala Pro Gly
              1450                    1470
            GTCTTCGACCAGGACGACGACGGGATCGTC
            ----------+----------+----------+
            CAGAAGCTGGTCCTGCTGCTGCCCTAGCAG
            Val Phe Asp Gln Asp Asp Asp Gly Ile Val
                        1490
            ACGGTGCTGACGGCCGAACCCGCCGCCGAC
            ----------+----------+----------+
            TGCCACGACTGCCGGCTTGGGCGGCGGCTG
            Thr Val Leu Thr Ala Gly Pro Ala Ala Asp
              1510                    1530
            GACGACCGGCGCACCGCGCGCGAGGCCGGC
            ----------+----------+----------+
            CTGCTGGCCGCGTGGCGCGCGCTCCGGCCG
            Asp Asp Arg Arg Thr Ala Arg Glu Ala Gly
                        1550
            CATCTCTGTCCGTCCGGTGCGGTCCGCGTC
            ----------+----------+----------+
            GTAGAGACAGGCAGGCCACGCCAGGCGCAG
            His Leu Cys Pro Ser Gly Ala Val Arg Val
                        1570
            GTCGAGGACACGGAA
            ----------+-----
            CAGCTCCTGTGCCTT
            Val Glu Asp Thr Glu  ;
``` and iv) either of the DNA sequence encoding cytochrome P450 enzyme P450SU1 of i) or the DNA sequence encoding cytochrome P450 enzyme P450SU2 of ii) in combination with the DNA sequence encoding iron sulfur protein FeS-A comprising:

```
                    1470
         ATGCGCATCCACGTCGACCAGGACAAGTGC
         --------+----------+----------+-
         TACGCGTAGGTGCAGCTGGTCCTGTTCACG
         Met Arg Ile His Val Asp Gln Asp Lys Cys

1490
                  TGCGGCGCCGGCAGTTGCG
                  ---------+----------+
                  ACGCCGCGGCCGTCAACGC
                  Cys Gly Ala Gly Ser Cys V 1510                  1530
         TCCTCGCCGCGCCCGACGTCTTCGACCAGC
         ---------+----------+----------+
         AGGAGCGGCGCGGGCTGCAGAAGCTGGTCG
         al Leu Ala Ala Pro Asp Val Phe Asp Gln A

1550
         GGGAGGAGGACGGCATCGTGGTCCTCCTCG
         ---------+----------+----------+
         CCCTCCTCCTGCCGTAGCACCAGGAGGAGC
         rg Glu Glu Asp Gly Ile Val Val Leu Leu A 1570                  1590
         ACACCGCGCCGCCCGCCGCGCTGCACGACG
         ---------+----------+----------+
         TGTGGCGCGGCGGGCGGCGCGACGTGCTGC
         sp Thr Ala Pro Pro Ala Ala Leu His Asp A

1610
         CGGTCCGTGAGGCGGCGACCATCTGCCCCG
         ---------+----------+----------+
         GCCAGGCACTCCGCCGCTGGTAGACGGGGC
         la Val Arg Glu Ala Ala Thr Ile Cys Pro A

1630
         CCGCCGCGATCACGGTGACCGAC
         ---------+----------+---
         GGCGGCGCTAGTGCCACTGGCTG
         la Ala Ala Ile Thr Val Thr Asp ;
```

B) a plant promoter sequence upstream and operably linked to each said DNA sequence, C) a 5'-untranslated sequence upstream and operably linked to each said DNA sequence, and D) a 3'-untranslated sequence which enables the mRNA transcribed from the plasmids to be polyadenylated on its 3' end downstream and operably linked to each said DNA sequence.

2. A plasmid of claim 1 wherein the promoter is selected from the group consisting of the 35S promoter from the Cauliflower Mosaic Virus, the promoter from the SSU301 gene from petunia, and the promoter from the Cab22L gene from petunia.

3. A plasmid of claim 1 wherein the 3'-untranslated sequence is selected from the group consisting of those of the SSU301 gene from petunia, and of the gene for nopaline synthetase derived from T-DNA of *Agrobacterium tumefaciens*.

4. A plasmid of claim 1 wherein the promoter and 5'-untranslated sequences are those of the 35S promoter from the Cauliflower Mosaic Virus, the promoter from the SSU301 gene from petunia, or the promoter from the Cab22L gene from petunia and the 3'-untranslated sequences are those of the SSU301 gene from petunia.

5. A plasmid of claim 1 wherein the promoter is a tissue specific promoter.

6. A plasmid of claim 1 comprising pSU17 of FIG. 10A.

7. A plasmid of claim 1 comprising pSuFe1 of FIG. 15A.

8. A recombinant plasmid comprising
  A) segments selected from the group consisting of
    i) the DNA sequence encoding cytochrome P450 enzyme P450SU1 comprising:

```
              130                  150
         ATGACCGATACCGCCACGACGCC
         --+----------+----------+
         TACTGGCTATGGCGGTGCTGCGG
         Met Thr Asp Thr Ala Thr Thr Pr

170
         CCAGACCACGGACGCACCCGCCTTCCCGAG
         ---------+----------+----------+
         GGTCTGGTGCCTGCGTGGGCGGAAGGGCTC
         o Gln Thr Thr Asp Ala Pro Ala Phe Pro Se 190                  210
         CAACCGGAGCTGTCCCTACCAGTTACCGGA
         ---------+----------+----------+
         GTTCGCCTCGACAGGGATGGTCAATGGCCT
         r Asn Arg Ser Cys Pro Tyr Gln Leu Pro As

230
         CGGCTACGCCCAGCTCCGGGACACCCCCGG
         ---------+----------+----------+
         GCCGATGCGGGTCGAGGCCCTGTGGGGGCC
         p Gly Tyr Ala Gln Leu Arg Asp Thr Pro Gl 250                  270
         CCCCCTGCACCGGGTGACGCTCTACGACGG
         ---------+----------+----------+
         GGGGGACGTGGCCCACTGCGAGATGCTGCC
         y Pro Leu His Arg Val Thr Leu Tyr Asp Gl

290
         CCGTCAGGCGTGGGTGGTGACCAAGCACGA
         ---------+----------+----------+
         GGCAGTCCGCACCCACCACTGGTTCGTGCT
         y Arg Gln Ala Trp Val Val Thr Lys His Gl 310                  330
         GGCCGCGCGCAAACTGCTCGGCGACCCCCG
         ---------+----------+----------+
         CCGGCGCGCGTTTGACGAGCCGCTGGGGGC
         u Ala Ala Arg Lys Leu Leu Gly Asp Pro Ar

350
         GCTGTCCTCCAACCGGACGGACGACAACTT
         ---------+----------+----------+
         CGACAGGAGGTTGGCCTGCCTGCTGTTGAA
         g Leu Ser Ser Asn Arg Thr Asp Asp Asn Ph 370                  390
         CCCCGCCACGTCACCGCGCTTCGAGGCCGT
         ---------+----------+----------+
         GGGGCGGTGCAGTGGCGCGAAGCTCCGGCA
         e Pro Ala Thr Ser Pro Arg Phe Glu Ala Va

410
         CCGGGAGAGCCCGCAGGCGTTCATCGGCCT
         ---------+----------+----------+
         GGCCCTCTCGGGCGTCCGCAAGTAGCCGGA
         l Arg Glu Ser Pro Gln Ala Phe Ile Gly Le 430                  450
         GGACCCGCCCGAGCACGGCACCCGGCGGCG
         ---------+----------+----------+
         CCTGGGCGGGCTCGTGCCGTGGGCCGCCGC
         u Asp Pro Pro Glu His Gly Thr Arg Arg Ar

470
         GATGACGATCAGCGAGTTCACCGTCAAGCG
         ---------+----------+----------+
         CTACTGCTAGTCGCTCAAGTGGCAGTTCGC
         g Met Thr Ile Ser Glu Phe Thr Val Lys Ar 490                  510
         GATCAAGGGCATGCGCCCCGAGGTCGAGGA
         ---------+----------+----------+
```

-continued
```
CTAGTTCCCGTACGCGGGGCTCCAGCTCCT
---------+---------+---------+
g  Ile Lys Gly Met Arg Pro Glu Val Glu Gl
              530
     GGTGGTGCACGGCTTCCTCGACGAGATGCT
     ---------+---------+---------+
     CCACCACGTGCCGAAGGAGCTGCTCTACGA
     u Val Val His Gly Phe Leu Asp Glu Met Le
         550            570
GGCCGCCGGCCCGACCGCCGACCTGGTCAG
---------+---------+---------+
CCGGCGGCCGGGCTGGCGGCTGGACCAGTC
u Ala Ala Gly Pro Thr Ala Asp Leu Val Se
              590
     TCAGTTCGCGCTGCCGGTGCCCTCCATGGT
     ---------+---------+---------+
     AGTCAAGCGCGACGGCCACGGGAGGTACCA
     r Gln Phe Ala Leu Pro Val Pro Ser Met Va
         610            630
GATCTGCCGACTCCTCGGCGTGCCCTACGC
---------+---------+---------+
CTAGACGGCTGAGGAGCCGCACGGGATGCG
l Ile Cys Arg Leu Leu Gly Val Pro Tyr Al
              650
     CGACCACGAGTTCTTCCAGGACGCGAGCAA
     ---------+---------+---------+
     GCTGGTGCTCAAGAAGGTCCTGCGCTCGTT
     a Asp His Glu Phe Phe Gln Asp Ala Ser Ly
         670            690
GCGGCTGGTGCAGTCCACGGACGCGCAGAG
---------+---------+---------+
CGCCGACCACGTCAGGTGCCTGCGCGTCTC
s Arg Leu Val Gln Ser Thr Asp Ala Gln Se
              710
     CGCGCTCACCGCGCGGAACGACCTCGCGGG
     ---------+---------+---------+
     GCGCGAGTGGCGCGCCTTGCTGGAGCGCCC
     r Ala Leu Thr Ala Arg Asn Asp Leu Ala Gl
         730            750
TTACCTGGACGGCCTCATCACCCAGTTCCA
---------+---------+---------+
AATGGACCTGCCGGAGTAGTGGGTCAAGGT
y Tyr Leu Asp Gly Leu Ile Thr Gln Phe Gl
              770
     GACCGAACCGGGCGCGGGGCCTGGTGGGCGC
     ---------+---------+---------+
     CTGGCTTGGCCCGCGCCCGGACCACCCGCG
     n Thr Gln Pro Gly Ala Gly Leu Val Gly Al
         790            810
TCTGGTCGCCGACCAGCTGGCCAACGGCGA
---------+---------+---------+
AGACCAGCGGCTGGTCGACCGGTTGCCGCT
a Leu Val Ala Asp Gln Leu Ala Asn Gly Gl
              830
     GATCGACCGTGAGGAACTGATCTCCACCGC
     ---------+---------+---------+
     CTAGCTGGCACTCCTTGACTAGAGGTGGCG
     u Ile Asp Arg Glu Glu Leu Ile Ser Thr Al
         850            870
GATGCTGCTCCTCATCGCCGGCCACGAGAC
---------+---------+---------+
CTACGACGAGGAGTAGCGGCCGGTGCTCTG
a Met Leu Leu Leu Ile Ala Gly His Glu Th
              890
     CACGGCCTCGATGACCTCCCTCAGCGTGAT
     ---------+---------+---------+
     GTGCCGGAGCTACTGGAGGGAGTCGCACTA
     r Thr Ala Ser Met Thr Ser Leu Ser Val Il
         910            930
CACCCTGCTGGACCACCCCGAGCAGTACGC
```
```
---------+---------+---------+
GTGGGACGACCTGGTGGGGCTCGTCATGCG
e Thr Leu Leu Asp His Pro Glu Gln Tyr Al
              950
     CGCCCTGCGCGCCGACCGCAGCCTCGTGCC
     ---------+---------+---------+
     GCGGGACGCGCGGCTGGCGTCGGAGCACGG
     a Ala Leu Arg Ala Asp Arg Ser Leu Val Pr
         970            990
CGGCGCGGTGGAGGAACTGCTCCGCTACCT
---------+---------+---------+
GCCGCGCCACCTCCTTGACGAGGCGATGGA
o Gly Ala Val Glu Glu Leu Leu Arg Tyr Le
              1010
     CGCCATCGCCGACATCGCGGGCGGCCGCGT
     ---------+---------+---------+
     GCGGTAGCGGCTGTAGCGCCCGCCGGCGCA
     u Ala Ile Ala Asp Ile Ala Gly Gly Arg Va
         1030           1050
CGCCACGGCGGACATCGAGGTCGAGGGGCA
---------+---------+---------+
GCGGTGCCGCCTGTAGCTCCAGCTCCCCGT
l Ala Thr Ala Asp Ile GlU Val Glu Gly Hi
              1070
     CCTCATCCGGGCCGGCGAGGGCGTGATCGT
     ---------+---------+---------+
     GGAGTAGGCCCGGCCGCTCCCGCACTAGCA
     s Leu Ile Arg Ala Gly Glu Gly Val Ile Va
         1090           1110
CGTCAACTCGATAGCCAACCGGGACGGCAC
---------+---------+---------+
GCAGTTGAGCTATCGGTTGGCCCTGCCGTG
l Val Asn Ser Ile Ala Asn Arg Asp Gly Th
              1130
     GGTGTACGAGGACCCGGACGCCCTCGACAT
     ---------+---------+---------+
     CCACATGCTCCTGGGCCTGCGGGAGCTGTA
     r Val Tyr Glu Asp Pro Asp Ala Leu Asp Il
         1150           1170
CCACCGCTCCGCGCGCCACCACCTCGCCTT
---------+---------+---------+
GGTGGCGAGGCGCGCGGTGGTGGAGCGGAA
e His Arg Ser Ala Arg His His Leu Ala Ph
              1190
     CGGCTTCGGCGTGCACCAGTGCCTGGGCCA
     ---------+---------+---------+
     GCCGAAGCCGCACGTGGTCACGGACCCGGT
     e Gly Phe Gly Val His Gln Cys Leu Gly Gl
         1210           1230
GAACCTCGCCCGGCTGGAGCTGGAGGTCAT
---------+---------+---------+
CTTGGAGCGGGCCGACCTCGACCTCCAGTA
n Asn Leu Ala Arg Leu Glu Leu Glu Val Il
              1250
     CCTCAACGCCCTCATGGACCGCGTCCCGAC
     ---------+---------+---------+
     GGAGTTGCGGGAGTACCTGGCGCAGGGCTG
     e Leu Asn Ala Leu Met Asp Arg Val Pro Th
         1270           1290
GCTGCGACTGGCCGTCCCCGTCGAGCAGTT
---------+---------+---------+
CGACGCTGACCGGCAGGGGCAGCTCGTCAA
r Leu Arg Leu Ala Val Pro Val Glu Gln Le
              1310
     GGTGCTGCGGCCGGGTACGACGATCCAGGG
     ---------+---------+---------+
     CCACGACGCCGGCCCATGCTGCTAGGTCCC
     u Val Leu Arg Pro Gly Thr Thr Ile Gln Gl
```

```
                    1330              1350
        CGTCAACGAACTCCCGGTCACCTGGTGA
        ---------+----------+---------
        GCAGTTGCTTGAGGGCCAGTGGACCACT
      y Val Asn Glu Leu Pro Val Thr Trp End;
``` ii) the DNA sequence encoding cytochrome P450 enzyme P450SU2 comprising:

```
                         210
              ATGACGACCGCAGAAC
              -----+----------+
              TACTGCTGGCGTCTTG
              Met Thr Thr Ala Glu A

230
        GCACCGCTCCCCCCGACGCCCTCACCGTCC
        ---------+----------+----------+
        CGTGGCGAGGGGGGCTGCGGGAGTGGCAGG
        rg Thr Ala Pro Pro Asp Ala Leu Thr Val P 250                  270
        CGGCCAGCCGCGCCCCGGCTGCCCCTTCG
        ---------+----------+---------+
        GCCGGTCGGCGCGGGGCCGACGGGGAAGC
        ro Ala Ser Arg Ala Pro Gly Cys Pro Phe A

290
        ACCCCGCGCCCGACGTCACCGAGGCGGCCC
        ---------+----------+----------+
        TGGGGCGCGGGCTGCAGTGGCTCCGCCGGG
        sp Pro Ala Pro Asp Val Thr Glu Ala Ala A 310                  330
        GCACCGAACCGGTCACCCGGGCCACCCTCT
        ---------+----------+----------+
        CGTGGCTTGGCCAGTGGGCCCGGTGGGAGA
        rg Thr Glu Pro Val Thr Arg Ala Thr Leu T

350
        GGGACGGCTCCTCCTGCTGGCTGGTGACGC
        ---------+----------+----------+
        CCCTGCCGAGGAGGACGACCGACCACTGCG
        rp Asp Gly Ser Ser Cys Trp Leu Val Thr A 370                  390
        GCCATCAGGACGTCCGCGCGGTCCTCGGCG
        ---------+----------+----------+
        CGGTAGTCCTGCAGGCGCGCCAGGAGCCGC
        rg His Gln Asp Val Arg Ala Val Leu Gly A

410
        ACCCGCGCTTCAGCGCCGACGCCCACCGCA
        ---------+----------+----------+
        TGGGCGCGAAGTCGCGGCTGCGGGTGGCGT
        sp Pro Arg Phe Ser Ala Asp Ala His Arg T 430                  450
        CCGGCTTCCCCTTCCTGACCGCCGGCGGCC
        ---------+----------+----------+
        GGCCGAAGGGGAAGGACTGGCGGCCGCCGG
        hr Gly Phe Pro Phe Leu Thr Ala Gly Gly A

470
        GCGAGATCATCGGCACCAACCCGACCTTCC
        ---------+----------+----------+
        CGCTCTAGTAGCCGTGGTTGGGCTGGAAGG
        rg Glu Ile Ile Gly Thr Asn Pro Thr Phe L 490                  510
        TGCGCATGGACGACCCGGAGCACGCCCGAC
        ---------+----------+---------+
        ACGCGTACCTGCTGGGCCTCGTGCGGGCTG
        eu Arg Met Asp Asp Pro Glu His Ala Arg L

530
        TGCGCCGGATGCTCACCGCCGACTTCATCG
        ---------+----------+----------+
        ACGCGGCCTACGAGTGGCGGCTGAAGTAGC
        eu Arg Arg Met Leu Thr Ala Asp Phe Ile V
```

```
              550                  570
        TCAAGAAGGTCGAGGCGATGCGCCCCGAGG
        ---------+----------+----------+
        AGTTCTTCCAGCTCCGCTACGCGGGGCTCC
        al Lys Lys Val Glu Ala Met Arg Pro Glu V

590
        TGCAGCGCCTCGCCGACGACCTGGTCGACC
        ---------+----------+----------+
        ACGTCGCGGAGCGGCTGCTGGACCAGCTGG
        al Gln Arg Leu Ala Asp Asp Leu Val Asp A 610                  630
        GGATGACCACCGGACGCACCTCCGCCGACC
        ---------+----------+----------+
        CCTACTGGTGGCCTGCGTGGAGGCGGCTGG
        rg Met Thr Thr Gly Arg Thr Ser Ala Asp L

650
        TGGTCACCGAGTTCGCGCTGCCGCTGCCGT
        ---------+----------+----------+
        ACCAGTGGCTCAAGCGCGACGGCGACGGCA
        eu Val Thr Glu Phe Ala Leu Pro Leu Pro S 670                  690
        CCCTGGTGATCTGCCTGCTGCTCGGCGTCC
        ---------+----------+---------+
        GGGACCACTAGACGGACGACGAGCCGCAGG
        er Leu Val Ile Cys Leu Leu Leu Gly Val P

710
        CCTACGAGGACCACGCCGTTCTTCCAGGAGC
        ---------+----------+----------+
        GGATGCTCCTGGTGCGCAAGAAGGTCCTCG
        ro Tyr Glu Asp His Ala Phe Phe Gln Glu A 730                  750
        GCAGCCGGGTCCTGCTCACCCTGCGGTCCA
        ---------+----------+----------+
        CGTCGGCCCAGGACGAGTGGGACGCCAGGT
        rg Ser Arg Val Leu Leu Thr Leu Arg Ser T

770
        CTCCCGAGGAAGTCCGGGCCGCCCAGGACG
        ---------+----------+----------+
        GAGGGCTCCTTCAGGCCCGGCGGGTCCTGC
        hr Pro Glu Glu Val Arg Ala Ala Gln Asp G 790                  810
        AGTTGCTGGAGTACCTCGCCCGGCTCGCCC
        ---------+----------+----------+
        TCAACGACCTCATGGAGCGGGCCGAGCGGG
        lu Leu Leu Glu Tyr Leu Ala Arg Leu Ala A

830
        GGACCAAGCGGGAGCGGCCGGACGACGCCA
        ---------+----------+----------+
        CCTGGTTCGCCCTCGCCGGCCTGCTGCGGT
        rg Thr Lys Arg Glu Arg Pro Asp Asp Ala I 850                  870
        TCATCAGCCGCCTGGTCGCCCGCGGCGAGC
        ---------+----------+----------+
        AGTAGTCGGCGGACCAGCGGGCGCCGCTCG
        le Ile Ser Arg Leu Val Ala Arg Gly Glu L

890
        TCGACGACACCCAGATCGCCACCATGGGAC
        ---------+----------+----------+
        AGCTGCTGTGGGTCTAGCGGTGGTACCCTG
        eu Asp Asp Thr Gln Ile Ala Thr Met Gly A 910                  930
        GCCTGTTGCTGGTCGCCGGCCACGAGACGA
        ---------+----------+----------+
        CGGACAACGACCAGCGGCCGGTGCTCTGCT
        rg Leu Leu Leu Val Ala Gly His Glu Thr T

950
        CCGCCAACATGACCGCGCTCTCCACCCTCG
        ---------+----------+---------+
```

-continued
```
            GGCGGT T GT ACT GGCGCGAGAGGT GGGAGC
               hr Ala Asn Met Thr Ala Leu Ser Thr Leu V
           970                          990
           T GCT GCT GCGCAACCCCGACCAACT CGCCC
           ---------+----------+----------+
           ACGACGACGCGT T GGGGCT GGT T GAGCGGG
             al Leu Leu Arg Asn Pro Asp Gln Leu Ala A
                          1010
           GGCT GCGCGCCGAACCCGCGCT CGT CAAGG
           ---------+----------+----------+
           CCGACGCGCGGCT T GGGCGCGAGCAGT T CC
             rg Leu Arg Ala Glu Pro Ala Leu Val Lys G
                  1030                  1050
           GCGCCGT CGAGGAGCT GCT GCGCT ACCT GA
           ---------+----------+----------+
           CGCGGCAGCT CCT CGACGACGCGAT GGACT
             ly Ala Val Glu Glu Leu Leu Arg Tyr Leu T
                          1070
           CGAT CGT GCACAACGGCGT T CCCCGGAT CG
           ---------+----------+----------+
           GCT AGCACGT GT T GCCGCAAGGGGCCT AGC
             hr Ile Val His Asn Gly Val Pro Arg Ile A
                  1090                  1110
           CCACCGAGGACGT GCT CAT CGGCGGCCGCA
           ---------+----------+----------+
           GGT GGCT CCT GCACGAGT AGCCGCCGGCGT
             la Thr Glu Asp Val Leu Ile Gly Gly Arg T
                          1130
           CCAT CGCCGCCGGCGAGGGCGT CCT GT GCA
           ---------+----------+----------+
           GGT AGCGGCGGCCGCT CCCGCAGGACACGT
             hr Ile Ala Ala Gly Glu Gly Val Leu Cys M
                  1150                  1170
           T GAT CAGCT CCGCCAACCGGGACGCCGAGG
           ---------+----------+----------+
           ACT AGT CGAGGCGGT T GGCCCT GCGGCT CC
             et Ile Ser Ser Ala Asn Arg Asp Ala Glu V
                          1190
           T GT T CCCCGGCGGCGACGACCT CGACGT GG
           ---------+----------+----------+
           ACAAGGGGCCGCCGCT GCT GGAGCT GCACC
             al Phe Pro Gly Gly Asp Asp Leu Asp Val A
                  1210                  1230
           CCCGCGACGCCCGCCGCCACGT GGCCT T CG
           ---------+----------+----------+
           GGGCGCT GCGGGCGGCGGT GCACCGGAAGC
             la Arg Asp Ala Arg Arg His Val Ala Phe G
                          1250
           GCT T CGGCGT CCACCAGT GCCT GGGACAGC
           ---------+----------+----------+
           CGAAGCCGCAGGT GGT CACGGACCCT GT CG
             ly Phe Gly Val His Gln Cys Leu Gly Gln P
                  1270                  1290
           CGT T GGCCAGGGT GGAGCT CCAGAT CGCCA
           ---------+----------+----------+
           GCAACCGGT CCCACCT CGAGGT CT AGCGGT
             ro Leu Ala Arg Val Glu Leu Gln Ile Ala I
                          1310
           T CGAAACGCT GCT GCGCCGCCT GCCGGACC
           ---------+----------+----------+
           AGCT T T GCGACGACGCGGCGGACGGCCT GG
             le Glu Thr Leu Leu Arg Arg Leu Pro Asp L
                  1330                  1350
           T GCGGCT GGCCGT GCCCCACGAGGAGAT CC
           ---------+----------+----------+
           ACGCCGACCGGCACGGGGT GCT CCT CT AGG
             eu Arg Leu Ala Val Pro His Glu Glu Ile P
                          1370
           CGT T CCGCGGCGACAT GGCGAT CT ACGGGG
```
```
           ---------+----------+----------+
           GCAAGGCGCCGCT GT ACCGCT AGAT GCCCC
             ro Phe Arg Gly Asp Met Ala Ile Tyr Gly V
                          1390
           T CCACT CGCT GCCGAT CGCCT GGT AG
           ---------+----------+------
           AGGT GAGCGACGGCT AGCGGACCAT C
             al His Ser Leu Pro Ile Ala Trp End ;
``` iii) either of the DNA sequence encoding cytochrome P450 enzyme P450SU1 of i) or the DNA sequence P450 enzyme P450SU2 of ii) in combination with the DNA sequence encoding iron sulfur protein FeS-B comprising:

```
                          1370
                      AT GACCAT GCGG
                    -+----------+
                      T ACT GGT ACGCC
                       Met Thr Met Arg
                  1390                  1410
           GT GAGT GCGGAT CGGACGGT CT GCGT CGGT
           ---------+----------+----------+
           CACT CACGCCT AGCCT GCCAGACGCAGCCA
             Val Ser Ala Asp Arg Thr Val Cys Val Gly
                          1430
           GCCGGGCT GT GT GCGCT GACGGCGCCGGGC
           ---------+----------+----------+
           CGGCCCGACACACGCGACT GCCGCGGCCCG
             Ala Gly Leu Cys Ala Leu Thr Ala Pro Gly
                  1450                  1470
           GT CT T CGACCAGGACGACGACGGGAT CGT C
           ---------+----------+----------+
           CAGAAGCT GGT CCT GCT GCT GCCCT AGCAG
             Val Phe Asp Gln Asp Asp Asp Gly Ile Val
                          1490
           ACGGT GCT GACGGCCGAACCCGCCGCCGAC
           ---------+----------+----------+
           T GCCACGACT GCCGGCT T GGGCGGCGGCT G
             Thr Val Leu Thr Ala Gly Pro Ala Ala Asp
                  1510                  1530
           GACGACCGGCGCACCGCGCGCGAGGCCGGC
           ---------+----------+----------+
           CT GCT GGCCGCGT GGCGCGCGCT CCGGCCG
             Asp Asp Arg Arg Thr Ala Arg Glu Ala Gly
                          1550
           CAT CT CT GT CCGT CCGGT GCGGT CCGCGT C
           ---------+----------+----------+
           GT AGAGACAGGCAGGCCACGCCAGGCGCAG
             His Leu Cys Pro Ser Gly Ala Val Arg Val
                          1570
           GT CGAGGACACGGAA
           ---------+-----
           CAGCT CCT GT GCCT T
             Val Glu Asp Thr Glu ;
``` and iv) either of the DNA sequence encoding cytochrome P450 enzyme P450SU1 of i) or the DNA sequence encoding cytochrome P450SU2 of ii) in combination with the DNA sequence encoding iron sulfur protein FeS-A comprising:

```
                          1470
           AT GCGCAT CCACGT CGACCAGGACAAGT GC
           ---------+----------+----------+-
           T ACGCGT AGGT GCAGCT GGT CCT GT T CACG
             Met Arg Ile His Val Asp Gln Asp Lys Cys
                          1490
                   T GCGGCGCCGGCAGT T GCG
```

-continued

```
                    ---------+----------+
                    ACGCCGCGGCCGTCAACGC
                    Cys Gly Ala Gly Ser Cys  V 1510                          1530
TCCTCGCCGCGCCCGACGTCTTCGACCAGC
----------+----------+----------+
AGGAGCGGCGCGGGCTGCAGAAGCTGGTCG
al Leu Ala Ala Pro Asp Val Phe Asp Gln  A

1550
        GGGAGGAGGACGGCATCGTGGTCCTCCTCG
        ----------+----------+----------+
        CCCTCCTCCTGCCGTAGCACCAGGAGGAGC
        rg Glu Glu Asp Gly Ile Val Val Leu Leu  A 1570                          1590
ACACCGCGCCGCCCGCCGCGCTGCACGACG
----------+----------+----------+
TGTGGCGCGGCGGGCGGCGCGACGTGCTGC
sp Thr Ala Pro Pro Ala Ala Leu His Asp  A

1610
    CGGTCCGTGAGGCGGCGACCATCTGCCCCG
    ----------+----------+----------+
    GCCAGGCACTCCGCCGCTGGTAGACGGGGC
    la Val Arg Glu Ala Ala Thr Ile Cys Pro  A

1630
CCGCCGCGATCACGGTGACCGAC
----------+----------+---
GGCGGCGCTAGTGCCACTGGCTG
la Ala Ala Ile Thr Val Thr Asp  ;
```

B) a plant promoter sequence operably linked to each said DNA sequence in the upstream position;

C) a 5'-untranslated sequence operably linked to each said DNA sequence in the upstream position;

D) a 3'-untranslated sequence which enables the mRNA transcribed from the plasmids to be polyadenylated on its 3' end operably linked to each said DNA sequence in the downstream position; and E) a transit peptide coding sequence or a transit peptide coding sequence plus additionally mature coding sequence of nuclear genes that encode proteins that are normally imported into the chloroplasts of plants operably linked to the DNA encoding for the amino terminus of the cytochrome P450, or to the DNA encoding for the amino terminae of the cytochrome P450 and the FeS protein, and downstream from the promoter.

9. A plasmid of claim 8 wherein the promoter is a tissue specific promoter.

10. A plasmid of claim 8 wherein the transit peptide coding sequence is selected from the group consisting of that from ribulose bisphosphate carboxylase gene of petunia or that from the chlorophyll a/b binding protein gene of petunia.

11. A plasmid of claim 8 wherein the promoter is selected from the group consisting of the 35S promoter from Cauliflower Mosaic Virus, the promoter from the SSU301 gene from petunia, and the promoter from the Cab22L gene from petunia.

12. A plasmid of claim 8 wherein the 3'-untranslated sequence is selected from the group consisting of those of the SSU301 gene from petunia, and the gene for nopaline synthetase derived from T-DNA of *Agrobacterium tumefaciens*.

13. A plasmid of claim 8 wherein the promoter and 5'-untranslated sequences are of the 35S promoter from Cauliflower Mosaic Virus, the promoter from the SSU301 gene from petunia, or the promoter from the Cab22L gene from petunia and the 3'-untranslated sequences are those of the SSU301 gene from petunia.

14. The plasmid of claim 8 comprising pSSU-SU11 of FIG. 10B.

15. The plasmid of claim 8 comprising pSSU-SU12 of FIG. 10C.

16. The plasmid of claim 8 comprising pCab-SU11 of FIG. 10D.

17. The plasmid of claim 8 comprising pCab-SU12 of FIG. 10E.

18. The plasmid of claim 8 comprising pCab-SU13 of FIG. 10F.

19. The plasmid of claim 8 comprising pSuFe2 of FIG. 15B.

20. The plasmid of claim 8 comprising pSuFe3 of FIG. 15C.

21. The plasmid of claim 8 comprising pSuFe4 of FIG. 15D.

22. A plasmid of claim 1 comprising pSU18.

23. A plasmid of claim 1 comprising pSuFe11.

24. A plasmid of claim 8 comprising pSSU-SU111.

25. A plasmid of claim 8 comprising pSSU-SU121.

26. A plasmid of claim 8 comprising pCAB-SU111.

27. A plasmid of claim 8 comprising pCAB-SU121.

28. A plasmid of claim 8 comprising pCAB-SU131.

29. A plasmid of claim 8 comprising pSuFe21.

30. A plasmid of claim 8 comprising pSuFe31.

31. A plasmid of claim 8 comprising pSuFe41.

32. A transformed plant containing the
   A) DNA sequence encoding cytochrome P450 enzyme P450SU1 and iron sulfur protein FeS-B comprising:

```
           10                  30
GCGGACAGGGGGACTCCTGAAGATGTCTGATAGAGGCCGTTGCGTTCTCTACGGGGGCAA
----------+----------+----------+----------+----------+----------+
CGCCTGTCCCCCTGAGGACTTCTACAGACTATCTCCGGCAACGCAAGAGATGCCCCCGTT 70              90                  110
GTCTATGCTCCGAAATAGAGAACATGGCGTTCTTTAAAGGTGAGAATTCTTGAATCGGAG
----------+----------+----------+----------+----------+----------+
CAGATACGAGGCTTTATCTCTTGTACCGCAAGAAATTTCCACTCTTAAGAACTTAGCCTC
                                                         EcoRI 130                150                170
TGGACCGATGACCGATACCGCCACGACGCCCCAGACCACGGACGCACCCGCCTTCCCGAG
----------+----------+----------+----------+----------+----------+
ACCTGGCTACTGGCTATGGCGGTGCTGCGGGGTCTGGTGCCTGCGTGGGCGGAAGGGCTC
P450SU1    Met Thr Asp Thr Ala Thr Thr Pro Gln Thr Thr Asp Ala Pro Ala Phe Pro Se
Start
```

```
                190                      210                      230
CAACCGGAGCTGTCCCTACCAGTTACCGGACGGCTACGCCCAGCTCCGGGACACCCCGG
---------+---------+---------+---------+---------+---------+
GTTGGCCTCGACAGGGATGGTCAATGGCCTGCCGATGCGGGTCGAGGCCCTGTGGGGCC
r Asn Arg Ser Cys Pro Tyr Gln Leu Pro Asp Gly Tyr Ala Gln Leu Arg Asp Thr Pro Gl 250                      270                      290
CCCCCTGCACCGGGTGACGCTCTACGACGGCCGTCAGGCGTGGGTGGTGACCAAGCACGA
---------+---------+---------+---------+---------+---------+
GGGGGACGTGGCCCACTGCGAGATGCTGCCGGCAGTCCGCACCCACCACTGGTTCGTGCT
y Pro Leu His Arg Val Thr Leu Tyr Asp Gly Arg Gln Ala Trp Val Val Thr Lys His Gl 310                      330                      350
GGCCGCGCGCAAACTGCTCGGCGACCCCGGCTGTCCTCCAACCGGACGGACGACAACTT
---------+---------+---------+---------+---------+---------+
CCGGCGCGCGTTTGACGAGCCGCTGGGGGCCGACAGGAGGTTGGCCTGCCTGCTGTTGAA
u Ala Ala Arg Lys Leu Leu Gly Asp Pro Arg Leu Ser Ser Asn Arg Thr Asp Asp Asn Ph 370                      390                      410
CCCCGCCACGTCACCGCGCTTCGAGGCCGTCCGGGAGAGCCCGCAGGCGTTCATCGGCCT
---------+---------+---------+---------+---------+---------+
GGGGCGGTGCAGTGGCGCGAAGCTCCGGCAGGCCCTCTCGGGCGTCCGCAAGTAGCCGGA
e Pro Ala Thr Ser Pro Arg Phe Glu Ala Val Arg Glu Ser Pro Gln Ala Phe Ile Gly Le 430                      450                      470
GGACCCGCCCGAGCACGGCACCCGGCGGCGGATGACGATCAGCGAGTTCACCGTCAAGCG
---------+---------+---------+---------+---------+---------+
CCTGGGCGGGCTCGTGCCGTGGGCCGCCGCCTACTGCTAGTCGCTCAAGTGGCAGTTCGC
u Asp Pro Pro Glu His Gly Thr Arg Arg Arg Met Thr Ile Ser Glu Phe Thr Val Lys Ar 490                      510                      530
GATCAAGGGCATGCGCCCCGAGGTCGAGGAGGTGGTGCACGGCTTCCTCGACGAGATGCT
---------+---------+---------+---------+---------+---------+
CTAGTTCCCGTACGCGGGGCTCCAGCTCCTCCACCACGTGCCGAAGGAGCTGCTCTACGA
g Ile Lys Gly Met Arg Pro Glu Val Glu Glu Val Val His Gly Phe Leu Asp Glu Met Le 550                      570                      590
GGCCGCCGGCCCGACCGCCGACCTGGTCAGTCAGTTCGCGCTGCCGGTGCCCTCCATGGT
---------+---------+---------+---------+---------+---------+
CCGGCGGCCGGGCTGGCGGCTGGACCAGTCAGTCAAGCGCGACGGCCACGGGAGGTACCA
u Ala Ala Gly Pro Thr Ala Asp Leu Val Ser Gln Phe Ala Leu Pro Val Pro Ser Met Va 610                      630                      650
GATCTGCCGACTCCTCGGCGTGCCCTACGCCGACCACGAGTTCTTCCAGGACGCGAGCAA
---------+---------+---------+---------+---------+---------+
CTAGACGGCTGAGGAGCCGCACGGGATGCGGCTGGTGCTCAAGAAGGTCCTGCGCTCGTT
l Ile Cys Arg Leu Leu Gly Val Pro Tyr Ala Asp His Glu Phe Phe Gln Asp Ala Ser Ly 670                      690                      710
GCGGCTGGTGCAGTCCACGGACGCGCAGAGCGCGCTCACCGCGCGGAACGACCTCGCGGG
---------+---------+---------+---------+---------+---------+
CGCCGACCACGTCAGGTGCCTGCGCGTCTCGCGCGAGTGGCGCGCCTTGCTGGAGCGCCC
s Arg Leu Val Gln Ser Thr Asp Ala Gln Ser Ala Leu Thr Ala Arg Asn Asp Leu Ala Gl 730                      750                      770
TTACCTGGACGGCCTCATCACCCAGTTCCAGACCGAACCGGGCGCGGGCCTGGTGGGCGC
---------+---------+---------+---------+---------+---------+
AATGGACCTGCCGGAGTAGTGGGTCAAGGTCTGGCTTGGCCCGCGCCCGGACCACCCGCG
y Tyr Leu Asp Gly Leu Ile Thr Gln Phe Gln Thr Glu Pro Gly Ala Gly Leu Val Gly Al 790                      810                      830
TCTGGTCGCCGACCAGCTGGCCAACGGCGAGATCGACCGTGAGGAACTGATCTCCACCGC
---------+---------+---------+---------+---------+---------+
AGACCAGCGGCTGGTCGACCGGTTGCCGCTCTAGCTGGCACTCCTTGACTAGAGGTGGCG
a Leu Val Ala Asp Gln Leu Ala Asn Gly Glu Ile Asp Arg Glu Glu Leu Ile Ser Thr Al 850                      870                      890
GATGCTGCTCCTCATCGCCGGCCACGAGACCACGGCCTCGATGACCTCCCTCAGCGTGAT
---------+---------+---------+---------+---------+---------+
CTACGACGAGGAGTAGCGGCCGGTGCTCTGGTGCCGGAGCTACTGGAGGGAGTCGCACTA
a Met Leu Leu Leu Ile Ala Gly His Glu Thr Thr Ala Ser Met Thr Ser Leu Ser Val Il 910                      930                      950
CACCCTGCTGGACCACCCCGAGCAGTACGCCGCCCTGCGCGCCGACCGCAGCCTCGTGCC
---------+---------+---------+---------+---------+---------+
GTGGGACGACCTGGTGGGGCTCGTCATGCGGCGGGACGCGCGGCTGGCGTCGGAGCACGG
e Thr Leu Leu Asp His Pro Glu Gln Tyr Ala Ala Leu Arg Ala Asp Arg Ser Leu Val Pr 970                      990                      1010
CGGCGCGGTGGAGGAACTGCTCCGCTACCTCGCCATCGCCGACATCGCGGGCGGCCGCGT
```

```
                    ---------+----------+----------+----------+----------+----------+
GCCGCGCCACCTCCTTGACGAGGCGATGGAGCGGTAGCGGCTGTAGCGCCCGCCGGCGCA
o Gly Ala Val Glu Glu Leu Leu Arg Tyr Leu Ala Ile Ala Asp Ile Ala Gly Gly Arg Va
          1030               1050                1070
CGCCACGGCGGACATCGAGGTCGAGGGGCACCTCATCCGGGCCGGCGAGGGCGTGATCGT
        ---------+----------+----------+----------+----------+----------+
GCGGTGCCGCCTGTAGCTCCAGCTCCCCGTGGAGTAGGCCCGGCCGCTCCCGCACTAGCA
l Ala Thr Ala Asp Ile Glu Val Glu Gly His Leu Ile Arg Ala Gly Glu Gly Val Ile Va
          1090               1110                1130
CGTCAACTCGATAGCCAACCGGGACGGCACGGTGTACGAGGACCCGGACGCCCTCGACAT
        ---------+----------+----------+----------+----------+----------+
GCAGTTGAGCTATCGGTTGGCCCTGCCGTGCCACATGCTCCTGGGCCTGCGGGAGCTGTA
l Val Asn Ser Ile Ala Asn Arg Asp Gly Thr Val Tyr Glu Asp Pro Asp Ala Leu Asp Il
          1150               1170                1190
CCACCGCTCCGCGCGCCACCACCTCGCCTTCGGCTTCGGCGTGCACCAGTGCCTGGGCCA
        ---------+----------+----------+----------+----------+----------+
GGTGGCGAGGCGCGCGGTGGTGGAGCGGAAGCCGAAGCCGCACGTGGTCACGGACCCGGT
e His Arg Ser Ala Arg His His Leu Ala Phe Gly Phe Gly Val His Gln Cys Leu Gly Gl
          1210               1230                1250
GAACCTCGCCCGGCTGGAGCTGGAGGTCATCCTCAACGCCCTCATGGACCGCGTCCCGAC
        ---------+----------+----------+----------+----------+----------+
CTTGGAGCGGGCCGACCTCGACCTCCAGTAGGAGTTGCGGGAGTACCTGGCGCAGGGCTG
n Asn Leu Ala Arg Leu Glu Leu Glu Val Ile Leu Asn Ala Leu Met Asp Arg Val Pro Th
          1270               1290                1310
GCTGCGACTGGCCGTCCCCGTCGAGCAGTTGGTGCTGCGGCCGGGTACGACGATCCAGGG
        ---------+----------+----------+----------+----------+----------+
CGACGCTGACCGGCAGGGGCAGCTCGTCAACCACGACGCCGGCCCATGCTGCTAGGTCCC
r Leu Arg Leu Ala Val Pro Val Glu Gln Leu Val Leu Arg Pro Gly Thr Thr Ile Gln Gl
          1330               1350                1370
CGTCAACGAACTCCCGGTCACCTGGTGACGGGGGAGAGGGGCAAGGACATGACCATGCGG
        ---------+----------+----------+----------+----------+----------+
GCAGTTGCTTGAGGGCCAGTGGACCACTGCCCCCTCTCCCCGTTCCTGTACTGGTAGGCC
y Val Asn Glu Leu Pro Val Thr Trp End          FeS-B   Start   Met Thr Met Arg
          1390               1410                1430
GTGAGTGCGGATCGGACGGTCTGCGTCGGTGCCGGGCTGTGTGCGCTGACGGCGCCGGGC
        ---------+----------+----------+----------+----------+----------+
CACTCACGCCTAGCCTGCCAGACGCAGCCACGGCCCGACACACGCGACTGCCGCGGCCCG
Val Ser Ala Asp Arg Thr Val Cys Val Gly Ala Gly Leu Cys Ala Leu Thr Ala Pro Gly
          1450               1470                1490
GTCTTCGACCAGGACGACGACGGGATCGTCACGGTGCTGACGGCCGAACCCGCCGCCGAC
        ---------+----------+----------+----------+----------+----------+
CAGAAGCTGGTCCTGCTGCTGCCCTAGCAGTGCCACGACTGCCGGCTTGGGCGGCGGCTG
Val Phe Asp Gln Asp Asp Asp Gly Ile Val Thr Val Leu Thr Ala Glu Pro Ala Ala Asp
          1510               1530                1550
GACGACCGGCGCACCGCGCGCGAGGCCGGCCATCTCTGTCCGTCCGGTGCGGTCCGCGTC
        ---------+----------+----------+----------+----------+----------+
CTGCTGGCCGCGTGGCGCGCGCTCCGGCCGGTAGAGACAGGCAGGCCACGCCAGGCGCAG
Asp Asp Arg Arg Thr Ala Arg Glu Ala Gly His Leu Cys Pro Ser Gly Ala Val Arg Val
          1570               1590                1610
GTCGAGGACACGGAATAGGGTCAAGGACACGGAACAGGCGAGCGGGGATTCCGGCCGTCG
        ---------+----------+----------+----------+----------+----------+
CAGCTCCTGTGCCTTATCCCAGTTCCTGTGCCTTGTCCGCTCGCCCCTAAGGCCGGCAGC
Val Glu Asp Thr Glu End
          1630               1650                1670
GCCGGGGCGGTCTCCGGCCGACGGGCTGGGGCCGCCCGCGGTGCCGCCGCGCAGGCGAGG
        ---------+----------+----------+----------+----------+----------+
CGGCCCCGCCAGAGGCCGGCTGCCCGACCCCGGCGGGCGCCACGGCGGCGCGTCCGCTCC
          1690               1710                1730
CCGCCGGTGGCGCCCGGCACCCGCGGCGGCCGTCAGATCCACCCCTTCCGCGCCGCGTAC
        ---------+----------+----------+----------+----------+----------+
GGCGGCCACCGCGGGCCGTGGGCGCCGCCGGCAGTCTAGGTGGGGAAGGCGCGGCGCATG
          1750               1770                1790
AGAGCGAGTTGGAAACGGGTGGTGGCGTCGGCGGCGCGGTTGAGCTGCTCCAACTGGCGG
        ---------+----------+----------+----------+----------+----------+
TCTCGCTCAACCTTTGCCCACCACCGCAGCCGCCGCGCCAACTCGACGAGGTTGACCGCC
          1810               1830                1850
GAGAGGGTGCGTCGACTGATGCCGAGCAGTTCGGCGATGGTCTCGTCCGTGACGCCGCTC
        ---------+----------+----------+----------+----------+----------+
```

-continued

```
CTCTCCCACGCAGCTGACTACGGCTCGTCAAGCCGCTACCAGAGCAGGCACTGCGGCGAG
     1870
CCCAGCAGCTCCAGGATCC
---------+---------
GGGTCGTCGAGGTCCTAGG
         BamHI;
``` or B) the DNA sequence encoding cytochrome P450 enzyme P450SU2 and iron sulfur protein FeS-A comprising;

```
         10                  30                  50
GGATCCGGCCACCGCCCGACCCGTCCGCACTCCGCCCCGCCGACCGTCGTCCATCCGCCC
---------+---------+---------+---------+---------+---------+
CCTAGGCCGGTGGCGGGCTGGGCAGGCGTGAGGCGGGGCGGCTGGCAGCAGGTAGGCGGG
BamHI 70                  90                 110
CTGCGGCCATGCGGTTTGAGCCAACCTCGGTGCTGCCGCGATCTGCCCTTCCCTCCCCCG
---------+---------+---------+---------+---------+---------+
GACGCCGGTACGCCAAACTCGGTTGGAGCCACGACGGCGCTAGACGGGAAGGGAGGGGGC 130                 150                 170
CCGGGCCTGCGTTAGCGTGACGACATCTTAATTACCTAAGTTAGGTAATTAGCTCACGCG
---------+---------+---------+---------+---------+---------+
GGCCCGGACGCAATCGCACTGCTGTAGAATTAATGGATTCAATCCATTAATCGAGTGCGC 190                 210                 230
GAAGGACCGGCCGCATGACGACCGCAGAACGCACCGCTCCCCCCGACGCCCTCACCGTCC
---------+---------+---------+---------+---------+---------+
CTTCCTGGCCGGCGTACTGCTGGCGTCTTGCGTGGCGAGGGGGCTGCGGGAGTGGCAGG
P450SU2      Met Thr Thr Ala Glu Arg Thr Ala Pro Pro Asp Ala Leu Thr Val P
Start 250                 270                 290
CGGCCAGCCGCGCCCCCGGCTGCCCCTTCGACCCCGCGCCCGACGTCACCGAGGCGGCCC
---------+---------+---------+---------+---------+---------+
GCCGGTCGGCGCGGGGGCCGACGGGGAAGCTGGGGCGCGGGCTGCAGTGGCTCCGCCGGG
or  Ala Ser Arg Ala Pro Gly Cys Pro Phe Asp Pro Ala Pro Asp Val Thr Glu Ala Ala A 310                 330                 350
GCACCGAACCGGTCACCCGGGCCACCCTCTGGGACGGCTCCTCCTGCTGGCTGGTGACGC
---------+---------+---------+---------+---------+---------+
CGTGGCTTGGCCAGTGGGCCCGGTGGGAGACCCTGCCGAGGAGGACGACCGACCACTGCG
rg  Thr Glu Pro Val Thr Arg Ala Thr Leu Trp Asp Gly Ser Ser Cys Trp Leu Val Thr A 370                 390                 410
GCCATCAGGACGTCCGCGCGGTCCTCGGCGACCCGCGCTTCAGCGCCGACGCCCACCGCA
---------+---------+---------+---------+---------+---------+
CGGTAGTCCTGCAGGCGCGCCAGGAGCCGCTGGGCGCGAAGTCGCGGCTGCGGGTGGCGT
rg  His Gln Asp Val Arg Ala Val Leu Gly Asp Pro Arg Phe Ser Ala Asp Ala His Arg T 430                 450                 470
CCGGCTTCCCCTTCCTGACCGCCGGCGGCCGCGAGATCATCGGCACCAACCCGACCTTCC
---------+---------+---------+---------+---------+---------+
GGCCGAAGGGGAAGGACTGGCGGCCGCCGGCGCTCTAGTAGCCGTGGTTGGGCTGGAAGG
hr  Gly Phe Pro Phe Leu Thr Ala Gly Gly Arg Glu Ile Ile Gly Thr Asn Pro Thr Phe L 490                 510                 530
TGCGCATGGACGACCCGGAGCACGCCCGACTGCGCCGGATGCTCACCGCCGACTTCATCG
---------+---------+---------+---------+---------+---------+
ACGCGTACCTGCTGGGCCTCGTGCGGGCTGACGCGGCCTACGAGTGGCGGCTGAAGTAGC
eu  Arg Met Asp Asp Pro Glu His Ala Arg Leu Arg Arg Met Leu Thr Ala Asp Phe Ile V 550                 570                 590
TCAAGAAGGTCGAGGCGATGCGCCCCGAGGTGCAGCGCCTCGCCGACGACCTGGTCGACC
---------+---------+---------+---------+---------+---------+
AGTTCTTCCAGCTCCGCTACGCGGGGCTCCACGTCGCGGAGCGGCTGCTGGACCAGCTGG
al  Lys Lys Val Glu Ala Met Arg Pro Glu Val Gln Arg Leu Ala Asp Asp Leu Val Asp A
```

```
                    610                      630                            650
GGATGACCACCGGACGCACCTCCGCCGACCTGGTCACCGAGTTCGCGCTGCCGCTGCCGT
--------+---------+---------+---------+---------+---------+
CCTACTGGTGGCCTGCGTGGAGGCGGCTGGACCAGTGGCTCAAGCGCGACGGCGACGGCA
rg  Met Thr Thr Gly Arg Thr Ser Ala Asp Leu Val Thr Glu Phe Ala Leu Pro Leu Pro  S 670                      690                            710
CCCTGGTGATCTGCCTGCTGCTCGGCGTCCCCTACGAGGACCACGCGTTCTTCCAGGAGC
--------+---------+---------+---------+---------+---------+
GGGACCACTAGACGGACGACGAGCCGCAGGGGATGCTCCTGGTGCGCAAGAAGGTCCTCG
er  Leu Val Ile Cys Leu Leu Leu Gly Val Pro Tyr Glu Asp His Ala Phe Phe Gln Glu  A 730                      750                            770
GCAGCCGGGTCCTGCTCACCCTGCGGTCCACTCCCGAGGAAGTCCGGGCCGCCCAGGACG
--------+---------+---------+---------+---------+---------+
CGTCGGCCCAGGACGAGTGGGACGCCAGGTGAGGGCTCCTTCAGGCCCGGCGGGTCCTGC
rg  Ser Arg Val Leu Leu Thr Leu Arg Ser Thr Pro Glu Glu Val Arg Ala Ala Gln Asp  G 790                      810                            830
AGTTGCTGGAGTACCTCGCCCGGCTCGCCCGGACCAAGCGGGAGCGGCCGGACGACGCCA
--------+---------+---------+---------+---------+---------+
TCAACGACCTCATGGAGCGGGCCGAGCGGGCCTGGTTCGCCCTCGCCGGCCTGCTGCGGT
lu  Leu Leu Glu Tyr Leu Ala Arg Leu Ala Arg Thr Lys Arg Glu Arg Pro Asp Asp Ala  I 850                      870                            890
TCATCAGCCGCCTGGTCGCCCGCGGCGAGCTCGACGACACCCAGATCGCCACCATGGGAC
--------+---------+---------+---------+---------+---------+
AGTAGTCGGCGGACCAGCGGGCGCCGCTCGAGCTGCTGTGGGTCTAGCGGTGGTACCCTG
le  Ile Ser Arg Leu Val Ala Arg Gly Glu Leu Asp Asp Thr Gln Ile Ala Thr Met Gly  A 910                      930                            950
GCCTGTTGCTGGTCGCCGGCCACGAGACGACCGCCAACATGACCGCGCTCTCCACCCTCG
--------+---------+---------+---------+---------+---------+
CGGACAACGACCAGCGGCCGGTGCTCTGCTGGCGGTTGTACTGGCGCGAGAGGTGGGAGC
rg  Leu Leu Leu Val Ala Gly His Glu Thr Thr Ala Asn Met Thr Ala Leu Ser Thr Leu  V 970                      990                            1010
TGCTGCTGCGCAACCCCGACCAACTCGCCCGGCTGCGCGCCGAACCCGCGCTCGTCAAGG
--------+---------+---------+---------+---------+---------+
ACGACGACGCGTTGGGGCTGGTTGAGCGGGCCGACGCGCGGCTTGGGCGCGAGCAGTTCC
al  Leu Leu Arg Asn Pro Asp Gln Leu Ala Arg Leu Arg Ala Glu Pro Ala Leu Val Lys  G 1030                     1050                           1070
GCGCCGTCGAGGAGCTGCTGCGCTACCTGACGATCGTGCACAACGGCGTTCCCCGGATCG
--------+---------+---------+---------+---------+---------+
CGCGGCAGCTCCTCGACGACGCGATGGACTGCTAGCACGTGTTGCCGCAAGGGGCCTAGC
ly  Ala Val Glu Glu Leu Leu Arg Tyr Leu Thr Ile Val His Asn Gly Val Pro Arg Ile  A 1090                     1110                           1130
CCACCGAGGACGTGCTCATCGGCGGCCGCACCATCGCCGCCGGCGAGGGCGTCCTGTGCA
--------+---------+---------+---------+---------+---------+
GGTGGCTCCTGCACGAGTAGCCGCCGGCGTGGTAGCGGCGGCCGCTCCCGCAGGACACGT
la  Thr Glu Asp Val Leu Ile Gly Gly Arg Thr Ile Ala Ala Gly Glu Gly Val Leu Cys  M 1150                     1170                           1190
TGATCAGCTCCGCCAACCGGGACGCCGAGGTGTTCCCCGGCGGCGACGACCTCGACGTGG
--------+---------+---------+---------+---------+---------+
ACTAGTCGAGGCGGTTGGCCCTGCGGCTCCACAAGGGGCCGCCGCTGCTGGAGCTGCACC
et  Ile Ser Ser Ala Asn Arg Asp Ala Glu Val Phe Pro Gly Gly Asp Asp Leu Asp Val  A 1210                     1230                           1250
CCCGCGACGCCCGCCGCCACGTGGCCTTCGGCTTCGGCGTCCACCAGTGCCTGGGACAGC
--------+---------+---------+---------+---------+---------+
GGGCGCTGCGGGCGGCGGTGCACCGGAAGCCGAAGCCGCAGGTGGTCACGGACCCTGTCG
la  Arg Asp Ala Arg Arg His Val ALa Phe Gly Phe Gly Val His Gln CYs Leu Gly Gln  P 1270                     1290                           1310
CGTTGGCCAGGGTGGAGCTCCAGATCGCCATCGAAACGCTGCTGCGCCGCCTGCCGGACC
--------+---------+---------+---------+---------+---------+
GCAACCGGTCCCACCTCGAGGTCTAGCGGTAGCTTTGCGACGACGCGGCGGACGGCCTGG
ro  Leu Ala Arg Val Glu Leu Gln Ile Ala Ile Glu Thr Leu Leu Arg Arg Leu Pro Asp  L
```

```
             1330                    1350                    1370
T GC GGC T GGC CGT GCC CC AC GAG GAG AT C CC GT T CC GC GGC GAC AT GGC GAT CT AC GGGG
---------+---------+---------+---------+---------+---------+
GC AAC C GGT CCC AC CT C GAG GT CT AGC GGT AGC TTT GC GAC GAC GC GGC GGA CGG CCT GG
eu  Arg Leu Ala Val Pro His Glu Glu Ile Pro Phe Arg Gly Asp Met Ala Ile Tyr Gly  V 1390                    1410                    1430
T GC GGC T GGC CGT GCC CC AC GAG GAG AT C CC GT T CC GC GGC GAC AT GGC GAT CT AC GGGG
---------+---------+---------+---------+---------+---------+
AC GCC GAC CGG CAC GGG GT GCT CCT CT AGG GC AAG GC GCC GCT GT AC CGC T AGA T GCCC C
al  His Ser Leu Pro Ile Ala Trp End 1450                    1470                    1490
T CC ACT C GCT GCC GAT CGC CT GGT AGC CC GGG CGC CCC CAC CAC CGA CC AC CAC GC ACC C
---------+---------+---------+---------+---------+---------+
AGGT GAGC GAC GGC T AGC GGA CC AT CGG GCC CGC GGG GGT GGT GGC T GGT GGT GC GT GGG
FeS-A        Met Arg Ile His Val Asp Gln Asp Lys Cys Cys Gly Ala Gly Ser Cys  V 1510                    1530                    1550
TT GGGA GC ACC AT GCG CAT CC AC GT CGA CC AGG AC AAG T GCT GC GGC GCC GGC AGT T GCG
---------+---------+---------+---------+---------+---------+
AA CCCT CGT GGT AC GCG T AGG T GC AGC T GGT CCT GTT CAC GAC GCC GC GGC CGT CAA CGC
al  Leu Ala Ala Pro Asp Val Phe Asp Gln Arg Glu Glu Asp Gly Ile Val Val Leu Leu  A 1570                    1590                    1610
T CCT CGC CGC GCC CGA CGT CT T C GAC CAG CGG GAG GAG GAC GGC AT C GT GGT CCT CCT CG
---------+---------+---------+---------+---------+---------+
AGGA GC GGC GC GGG CT GC AGA AGC T GGT C GCC CT CCT CCT GCC GT AGC ACC AGG AGG AGC
sp  Thr Ala Pro Pro Ala Ala Leu His Asp Ala Val Arg Glu Ala Ala Thr Ile Cys Pro A 1630                    1650                    1670
AC AC CGC GCC GCC CGC CGC GCT GCA C GAC GC GGT CCG T GAG GC GGC GAC CAT CT GCCC CG
---------+---------+---------+---------+---------+---------+
T GT GGC GC GGC GGG CGG CGC GAC GT GCT GC GCC AGG CAC T CC GCC GCT GGT AGA CGG GGC
la  Ala Ala Ile Thr Val Thr Asp End 1690                    1710                    1730
CC GCC GCG AT CAC GGT GAC CGA CT GAG CC ACC GGC CGC CCC GCC CGC CCG CGC CCC GGT C
---------+---------+---------+---------+---------+---------+
GGC GGC GCT AGT GCC ACT GGC T GAC T CGG T GGC C GGC GGG GC GGG CGG GC GC GGG GCC AG 1750                    1770                    1790
CCC GCA T CCC CCC GCG GCC CGG GGC GC GCC CCT AAC CCG CCG CCC CGC ACG CC GT CGC GC
---------+---------+---------+---------+---------+---------+
GGG CGT AGG GGG GC GCC GGG CCC CGC GCG GGG ATT GGG CGG CGG GGC GT GC GGC AGC GCG 1810                    1830                    1850
GC GCC GCC AGT GCC CGC AGC GCC GCC T CGG AC GAC GAA CCC GGC ACG GCG T GGT GGG TC A
---------+---------+---------+---------+---------+---------+
CGC GGC GGT CAC GGG CGT CGC GGC GGA GCC T GCT GCT T GGG CCG T GCC GCA CCA CCC AGT 1870                    1890                    1910
CC AGC GT CT GCC CCG GTT CGG CCG CCA CGC GCA GCG T CCC GT AGG T CAG GGT CAG CGG GC
---------+---------+---------+---------+---------+---------+
GGT CGC AGA CGG GGC CAA GCC GGC GGT GCG CGT CGC AGG GCA T CCA GT CCC AGT CGC CCG 1930                    1950                    1970
CC ACC ACC GGG T GGT CCA GCT GCT T CGT CCC GAA ACC CTT GT CCT T GAT GT CGT GCC GGG
---------+---------+---------+---------+---------+---------+
GGT GGT GGC CCA CCA GGT CGA CGA AGC AGG GCT TTT GGG AAC AGG AAC T ACA GCA CGG CCC

1990
CCC AGA AGC GCC GGA ACT CCT CGC TCT GCA CGG T CAG TT CGG T GAT CCG CGC GGT CAG CG
---------+---------+---------+---------+---------+---------+
GGG T CTT CGC GGC CTT GAG GAG CGA GAC GT GCC AGT CAA GCC ACT AGG CGC GCC AGT CGC
            BamHI
```

33. A plant transformed with
A) the DNA sequence encoding cytochrome P450 enzyme P450SU1 comprising:

```
                130                                150
AT GAC CGA T AC C GCC ACG ACG CC
```

```
                                -continued
--+---------+---------+
TACTGGCTATGGCGGTGCTGCGG
Met Thr Asp Thr Ala Thr Thr Pr 170
CCAGACCACGGACGCACCCGCCTTCCCGAG
---------+---------+---------+
GGTCTGGTGCCTGCGTGGGCGGAAGGGCTC
o Gln Thr Thr Asp Ala Pro Ala Phe Pro Se 190              210
CAACCGGAGCTGTCCCTACCAGTTACCGGA
---------+---------+---------+
GTTCGCCTCGACAGGGATGGTCAATGGCCT
r Asn Arg Ser Cys Pro Tyr Gln Leu Pro As 230
CGGCTACGCCCAGCTCCGGGACACCCCGG
---------+---------+---------+
GCCGATGCGGGTCGAGGCCCTGTGGGGGCC
p Gly Tyr Ala Gln Leu Arg Asp Thr Pro Gl 250              270
CCCCCTGCACCGGGTGACGCTCTACGACGG
---------+---------+---------+
GGGGGACGTGGCCCACTGCGAGATGCTGCC
y Pro Leu His Arg Val Thr Leu Tyr Asp Gl 290
CCGTCAGGCGTGGGTGGTGACCAAGCACGA
---------+---------+---------+
GGCAGTCCGCACCCACCACTGGTTCGTGCT
y Arg Gln Ala Trp Val Val Thr Lys His Gl 310              330
GGCCGCGCGCAAACTGCTCGGCGACCCCCG
---------+---------+---------+
CCGGCGCGCGTTTGACGAGCCGCTGGGGGC
u Ala Ala Arg Lys Leu Leu Gly Asp Pro Ar 350
GCTGTCCTCCAACCGGACGGACGACAACTT
---------+---------+---------+
CGACAGGAGGTTGGCCTGCCTGCTGTTGAA
g Leu Ser Ser Asn Arg Thr Asp Asp Asn Ph 370              390
CCCCGCCACGTCACCGCGCTTCGAGGCCGT
---------+---------+---------+
GGGGCGGTGCAGTGGCGCGAAGCTCCGGCA
e Pro Ala Thr Ser Pro Arg Phe Glu Ala Va 410
CCGGGAGAGCCCGCAGGCGTTCATCGGCCT
---------+---------+---------+
GGCCCTCTCGGGCGTCCGCAAGTAGCCGGA
l Arg Glu Ser Pro Gln Ala Phe Ile Gly Le 430              450
GGACCCGCCCGAGCACGGCACCCGGCGGCG
---------+---------+---------+
CCTGGGCGGGCTCGTGCCGTGGGCCGCCGC
u Asp Pro Pro Glu His Gly Thr Arg Arg Ar 470
GATGACGATCAGCGAGTTCACCGTCAAGCG
---------+---------+---------+
CTACTGCTAGTCGCTCAAGTGGCAGTTCGC
g Met Thr Ile Ser Glu Phe Thr Val Lys Ar 490              510
GATCAAGGGCATGCGCCCCGAGGTCGAGGA
---------+---------+---------+
CTAGTTCCCGTACGCGGGGCTCCAGCTCCT
g Ile Lys Gly Met Arg Pro Glu Val Glu Gl 530
GGTGGTGCACGGCTTCCTCGACGAGATGCT
---------+---------+---------+
CCACCACGTGCCGAAGGAGCTGCTCTACGA
u Val Val His Gly Phe Leu Asp Glu Met Le 550              570
GGCCGCCGGCCCGACCGCCGACCTGGTCAG
---------+---------+---------+
CCGGCGGCCGGGCTGGCGGCTGGACCAGTC
u Ala Ala Gly Pro Thr Ala Asp Leu Val Se 590
TCAGTTCGCGCTGCCGGTGCCCTCCATGGT
---------+---------+---------+
AGTCAAGCGCGACGGCCACGGGAGGTACCA
r Gln Phe Ala Leu Pro Val Pro Ser Met Va 610              630
GATCTGCCGACTCCTCGGCGTGCCCTACGC
---------+---------+---------+
CTAGACGGCTGAGGAGCCGCACGGGATGCG
l Ile Cys Arg Leu Leu Gly Val Pro Tyr Al 650
CGACCACGAGTTCTTCCAGGACGCGAGCAA
---------+---------+---------+
GCTGGTGCTCAAGAAGGTCCTGCGCTCGTT
a Asp His Glu Phe Phe Gln Asp Ala Ser Ly 670              690
GCGGCTGGTGCAGTCCACGGACGCGCAGAG
---------+---------+---------+
CGCCGACCACGTCAGGTGCCTGCGCGTCTC
s Arg Leu Val Gln Ser Thr Asp Ala Gln Se 710
CGCGCTCACCGCGCGGAACGACCTCGCGGG
---------+---------+---------+
GCGCGAGTGGCGCGCCTTGCTGGAGCGCCC
r Ala Leu Thr Ala Arg Asn Asp Leu Ala Gl 730              750
TTACCTGGACGGCCTCATCACCCAGTTCCA
---------+---------+---------+
AATGGACCTGCCGGAGTAGTGGGTCAAGGT
y Tyr Leu Asp Gly Leu Ile Thr Gln Phe Gl 770
GACCGAACCGGGCGCGGGCCTGGTGGGCGC
---------+---------+---------+
CTGGCTTGGCCCGCGCCCGGACCACCCGCG
n Thr Gln Pro Gly Ala Gly Leu Val Gly Al
              790              810
TCTGGTCGCCGACCAGCTGGCCAACGGCGA
---------+---------+---------+
AGACCAGCGGCTGGTCGACCGGTTGCCGCT
a Leu Val Ala Asp Gln Leu Ala Asn Gly Gl 830
GATCGACCGTGAGGAACTGATCTCCACCGC
---------+---------+---------+
CTAGCTGGCACTCCTTGACTAGAGGTGGCG
u Ile Asp Arg Glu Glu Leu Ile Ser Thr Al 850              870
GATGCTGCTCCTCATCGCCGGCCACGAGAC
---------+---------+---------+
CTACGACGAGGAGTAGCGGCCGGTGCTCTG
a Met Leu Leu Leu Ile Ala Gly His Glu Th 890
CACGGCCTCGATGACCTCCCTCAGCGTGAT
---------+---------+---------+
GTGCCGGAGCTACTGGAGGGAGTCGCACTA
r Thr Ala Ser Met Thr Ser Leu Ser Val Il 910              930
CACCCTGCTGGACCACCCCGAGCAGTACGC
---------+---------+---------+
GTGGGACGACCTGGTGGGGCTCGTCATGCG
e Thr Leu Leu Asp His Pro Glu Gln Tyr Al 950
CGCCCTGCGCGCCGACCGCAGCCTCGTGCC
---------+---------+---------+
GCGGGACGCGCGGCTGGCGTCGGAGCACGG
a Ala Leu Arg Ala Asp Arg Ser Leu Val Pr
```

```
       970              990
CGGCGCGGTGGAGGAACTGCTCCGCTACCT
---------+----------+---------+
GCCGCGCCACCTCCTTGACGAGGCGATGGA
o Gly Ala Val Glu Glu Leu Leu Arg Tyr Le

1010
CGCCATCGCCGACATCGCGGGCGGCCGCGT
---------+----------+---------+
GCGGTAGCGGCTGTAGCGCCCGCCGGCGCA
u Ala Ile Ala Asp Ile Ala Gly Gly Arg Va 1030              1050
CGCCACGGCGGACATCGAGGTCGAGGGGCA
---------+----------+---------+
GCGGTGCCGCCTGTAGCTCCAGCTCCCCGT
l Ala Thr Ala Asp Ile Glu Val Glu Gly Hi

1070
CCTCATCCGGGCCGGCGAGGGCGTGATCGT
---------+----------+---------+
GGAGTAGGCCCGGCCGCTCCCGCACTAGCA
s Leu Ile Arg Ala Gly Glu Gly Val Ile Va 1090              1110
CGTCAACTCGATAGCCAACCGGGACGGCAC
---------+----------+---------+
GCAGTTGAGCTATCGGTTGGCCCTGCCGTG
l Val Asn Ser Ile Ala Asn Arg Asp Gly Th

1130
GGTGTACGAGGACCCGGACGCCCTCGACAT
---------+----------+---------+
CCACATGCTCCTGGGCCTGCGGGAGCTGTA
r Val Tyr Glu Asp Pro Asp Ala Leu Asp Il 1150              1170
CCACCGCTCCGCGCGCCACCACCTCGCCTT
---------+----------+---------+
GGTGGCGAGGCGCGCGGTGGTGGAGCGGAA
e His Arg Ser Ala Arg His His Leu Ala Ph

1190
CGGCTTCGGCGTGCACCAGTGCCTGGGCCA
---------+----------+---------+
GCCGAAGCCGCACGTGGTCACGGACCCGGT
e Gly Phe Gly Val His Gln Cys Leu Gly Gl 1210              1230
GAACCTCGCCCGGCTGGAGCTGGAGGTCAT
---------+----------+---------+
CTTGGAGCGGGCCGACCTCGACCTCCAGTA
n Asn Leu Ala Arg Leu Glu Leu Glu Val Il

1250
CCTCAACGCCCTCATGGACCGCGTCCCGAC
---------+----------+---------+
GGAGTTGCGGGAGTACCTGGCGCAGGGCTG
e Leu Asn Ala Leu Met Asp Arg Val Pro Th 1270              1290
GCTGCGACTGGCCGTCCCCGTCGAGCAGTT
---------+----------+---------+
CGACGCTGACCGGCAGGGGCAGCTCGTCAA
r Leu Arg Leu Ala Val Pro Val Glu Gln Le

1310
GGTGCTGCGGCCGGGTACGACGATCCAGGG
---------+----------+---------+
CCACGACGCCGGCCCATGCTGCTAGGTCCC
u Val Leu Arg Pro Gly Thr Thr Ile Gln Gl 1330              1350
CGTCAACGAACTCCCGGTCACCTGGTGA
---------+----------+---------
GCAGTTGCTTGAGGGCCAGTGGACCACT
y Val Asn Glu Leu Pro Val Thr Trp End;
``` in combination with the DNA sequence encoding iron sulfur protein FeS-A comprising:

```
              1470
ATGCGCATCCACGTCGACCAGGACAAGTGC
---------+----------+----------+-
TACGCGTAGGTGCAGCTGGTCCTGTTCACG
Met Arg Ile His Val Asp Gln Asp Lys Cys

1490
TGCGGCGCCGGCAGTTGCG
---------+----------+
ACGCCGCGGCCGTCAACGC
Cys Gly Ala Gly Ser Cys V 1510              1530
TCCTCGCCGCGCCCGACGTCTTCGACCAGC
---------+----------+----------+
AGGAGCGGCGCGGGCTGCAGAAGCTGGTCG
al Leu Ala Ala Pro Asp Val Phe Asp Gln A

1550
GGGAGGAGGACGGCATCGTGGTCCTCCTCG
---------+----------+----------+
CCCTCCTCCTGCCGTAGCACCAGGAGGAGC
rg Glu Glu Asp Gly Ile Val Val Leu Leu A 1570              1590
ACACCGCGCCCGCCCGCCGCGCTGCACGACG
---------+----------+----------+
TGTGGCGCGGCGGGCGGCGCGACGTGCTGC
sp Thr Ala Pro Pro Ala Ala Leu His Asp A

1610
CGGTCCGTGAGGCGGCGACCATCTGCCCCG
---------+----------+----------+
GCCAGGCACTCCGCCGCTGGTAGACGGGGC
la Val Arg Glu Ala Ala Thr Ile Cys Pro A

1630
CCGCCGCGATCACGGTGACCGAC
---------+----------+---
GGCGGCGCTAGTGCCACTGGCTG
la Ala Ala Ile Thr Val Thr Asp ;
```

B) the DNA sequence encoding cytochrome P450 enzyme P450SU2 comprising:

```
                        210
            ATGACGACCGCAGAAC
            -----+----------+
            TACTGCTGGCGTCTTG
            Met Thr Thr Ala Glu A

230
GCACCGCTCCCCCCGACGCCCTCACCGTCC
---------+----------+----------+
CGTGGCGAGGGGGGCTGCGGGAGTGGCAGG
rg Thr Ala Pro Pro Asp Ala Leu Thr Val P 250              270
CGGCCAGCCGCGCCCCCGGCTGCCCCTTCG
---------+----------+----------+
GCCGGTCGGCGCGGGGGCCGACGGGGAAGC
ro Ala Ser Arg Ala Pro Gly Cys Pro Phe A

290
ACCCCGCGCCCGACGTCACCGAGGCGGCCC
---------+----------+----------+
TGGGGCGCGGGCTGCAGTGGCTCCGCCGGG
sp Pro Ala Pro Asp Val Thr Glu Ala Ala A 310              330
GCACCGAACCGGTCACCCGGGCCACCCTCT
---------+----------+----------+
CGTGGCTTGGCCAGTGGGCCCGGTGGGAGA
rg Thr Glu Pro Val Thr Arg Ala Thr Leu T

350
GGGACGGCTCCTCCTGCTGGCTGGTGACGC
---------+----------+----------+
CCCTGCCGAGGAGGACGACCGACCACTGCG
rp Asp Gly Ser Ser Cys Trp Leu Val Thr A
```

-continued

```
            370                390
GCCATCAGGACGTCCGCGCGGTCCTCGGCG
---------+---------+---------+
CGGTAGTCCTGCAGGCGCGCCAGGAGCCGC
rg  His Gln Asp Val Arg Ala Val Leu Gly A

410
ACCCGCGCTTCAGCGCCGACGCCCACCGCA
---------+---------+---------+
TGGGCGCGAAGTCGCGGCTGCGGGTGGCGT
sp  Pro Arg Phe Ser Ala Asp Ala His Arg T 430                450
CCGGCTTCCCCTTCCTGACCGCCGGCGGCC
---------+---------+---------+
GGCCGAAGGGGAAGGACTGGCGGCCGCCGG
hr  Gly Phe Pro Phe Leu Thr Ala Gly Gly A

470
GCGAGATCATCGGCACCAACCCGACCTTCC
---------+---------+---------+
CGCTCTAGTAGCCGTGGTTGGGCTGGAAGG
rg  Glu Ile Ile Gly Thr Asn Pro Thr Phe L 490                510
TGCGCATGGACGACCCGGAGCACGCCCGAC
---------+---------+---------+
ACGCGTACCTGCTGGGCCTCGTGCGGGCTG
eu  Arg Met Asp Asp Pro Glu His Ala Arg L

530
TGCGCCGGATGCTCACCGCCGACTTCATCG
---------+---------+---------+
ACGCGGCCTACGAGTGGCGGCTGAAGTAGC
eu  Arg Arg Met Leu Thr Ala Asp Phe Ile V 550                570
TCAAGAAGGTCGAGGCGATGCGCCCCGAGG
---------+---------+---------+
AGTTCTTCCAGCTCCGCTACGCGGGGCTCC
al  Lys Lys Val Glu Ala Met Arg Pro Glu V

590
TGCAGCGCCTCGCCGACGACCTGGTCGACC
---------+---------+---------+
ACGTCGCGGAGCGGCTGCTGGACCAGCTGG
al  Gln Arg Leu Ala Asp Asp Leu Val Asp A 610                630
GGATGACCACCGGACGCACCTCCGCCGACC
---------+---------+---------+
CCTACTGGTGGCCTGCGTGGAGGCGGCTGG
rg  Met Thr Thr Gly Arg Thr Ser Ala Asp L

650
TGGTCACCGAGTTCGCGCTGCCGCTGCCGT
---------+---------+---------+
ACCAGTGGCTCAAGCGCGACGGCGACGGCA
eu  Val Thr Glu Phe Ala Leu Pro Leu Pro S 670                690
CCCTGGTGATCTGCCTGCTGCTCGGCGTCC
---------+---------+---------+
GGGACCACTAGACGGACGACGAGCCGCAGG
er  Leu Val Ile Cys Leu Leu Leu Gly Val P

710
CCTACGAGGACCACGCGTTCTTCCAGGAGC
---------+---------+---------+
GGATGCTCCTGGTGCGCAAGAAGGTCCTCG
ro  Tyr Glu Asp His Ala Phe Phe Gln Glu A 730                750
GCAGCCGGGTCCTGCTCACCCTGCGGTCCA
---------+---------+---------+
CGTCGGCCCAGGACGAGTGGGACGCCAGGT
rg  Ser Arg Val Leu Leu Thr Leu Arg Ser T

770
CTCCCGAGGAAGTCCGGGCCGCCCAGGACG
---------+---------+---------+
```

-continued

```
GAGGGCTCCTTCAGGCCCGGCGGGTCCTGC
hr  Pro Glu Glu Val Arg Ala Ala Gln Asp G 790                810
AGTTGCTGGAGTACCTCGCCCGGCTCGCCC
---------+---------+---------+
TCAACGACCTCATGGAGCGGGCCGAGCGGG
lu  Leu Leu Glu Tyr Leu Ala Arg Leu Ala A

830
GGACCAAGCGGGAGCGGCCGGACGACGCCA
---------+---------+---------+
CCTGGTTCGCCCTCGCCGGCCTGCTGCGGT
rg  Thr Lys Arg Glu Arg Pro Asp Asp Ala I 850                870
TCATCAGCCGCCTGGTCGCCCGCGGCGAGC
---------+---------+---------+
AGTAGTCGGCGGACCAGCGGGCGCCGCTCG
le  Ile Ser Arg Leu Val Ala Arg Gly Glu L

890
TCGACGACACCCAGATCGCCACCATGGGAC
---------+---------+---------+
AGCTGCTGTGGGTCTAGCGGTGGTACCCTG
eu  Asp Asp Thr Gln Ile Ala Thr Met Gly A 910                930
GCCTGTTGCTGGTCGCCGGCCACGAGACGA
---------+---------+---------+
CGGACAACGACCAGCGGCCGGTGCTCTGCT
rg  Leu Leu Leu Val Ala Gly His Glu Thr T

950
CCGCCAACATGACCGCGCTCTCCACCCTCG
---------+---------+---------+
GGCGGTTGTACTGGCGCGAGAGGTGGGAGC
hr  Ala Asn Met Thr Ala Leu Ser Thr Leu V 970                990
TGCTGCTGCGCAACCCCGACCAACTCGCCC
---------+---------+---------+
ACGACGACGCGTTGGGGCTGGTTGAGCGGG
al  Leu Leu Arg Asn Pro Asp Gln Leu Ala A

1010
GGCTGCGCGCCGAACCCGCGCTCGTCAAGG
---------+---------+---------+
CCGACGCGCGGCTTGGGCGCGAGCAGTTCC
rg  Leu Arg Ala Glu Pro Ala Leu Val Lys G 1030               1050
GCGCCGTCGAGGAGCTGCTGCGCTACCTGA
---------+---------+---------+
CGCGGCAGCTCCTCGACGACGCGATGGACT
ly  Ala Val Glu Glu Leu Leu Arg Tyr Leu T

1070
CGATCGTGCACAACGGCGTTCCCCGGATCG
---------+---------+---------+
GCTAGCACGTGTTGCCGCAAGGGGCCTAGC
hr  Ile Val His Asn Gly Val Pro Arg Ile A
            1090               1110
CCACCGAGGACGTGCTCATCGGCGGCCGCA
---------+---------+---------+
GGTGGCTCCTGCACGAGTAGCCGCCGGCGT
la  Thr Glu Asp Val Leu Ile Gly Gly Arg T

1130
CCATCGCCGCCGGCGAGGGCGTCCTGTGCA
---------+---------+---------+
GGTAGCGGCGGCCGCTCCCGCAGGACACGT
hr  Ile Ala Ala Gly Glu Gly Val Leu Cys M 1150               1170
TGATCAGCTCCGCCAACCGGGACGCCGAGG
---------+---------+---------+
ACTAGTCGAGGCGGTTGGCCCTGCGGCTCC
et  Ile Ser Ser Ala Asn Arg Asp Ala Glu V

1190
TGTTCCCCGGCGGCGACGACCTCGACGTGG
```

```
                                                      -continued
---------+----------+----------+
ACAAGGGGCCGCCGCTGCTGGAGCTGCACC
al  Phe Pro Gly Gly Asp Asp Leu Asp Val  A 1210                1230
CCCGCGACGCCCGCCGCCACGTGGCCTTCG
---------+----------+----------+
GGGCGCTGCGGGCGGCGGTGCACCGGAAGC
la  Arg Asp Ala Arg Arg His Val Ala Phe  G 1250
GCTTCGGCGTCCACCAGTGCCTGGGACAGC
---------+----------+----------+
CGAAGCCGCAGGTGGTCACGGACCCTGTCG
ly  Phe Gly Val His Gln Cys Leu Gly Gln  P 1270                1290
CGTTGGCCAGGGTGGAGCTCCAGATCGCCA
---------+----------+----------+
GCAACCGGTCCCACCTCGAGGTCTAGCGGT
ro  Leu Ala Arg Val Glu Leu Gln Ile Ala  I 1310
TCGAAACGCTGCTGCGCCGCCTGCCGGACC
---------+----------+----------+
AGCTTTGCGACGACGCGGCGGACGGCCTGG
le  Glu Thr Leu Leu Arg Arg Leu Pro Asp  L 1330                1350
TGCGGCTGGCCGTGCCCCACGAGGAGATCC
---------+----------+----------+
ACGCCGACCGGCACGGGGTGCTCCTCTAGG
eu  Arg Leu Ala Val Pro His Glu Glu Ile  P 1370
CGTTCCGCGGCGACATGGCGATCTACGGGG
---------+----------+----------+
GCAAGGCGCCGCTGTACCGCTAGATGCCCC
ro  Phe Arg Gly Asp Met Ala Ile Tyr Gly  V 1390
TCCACTCGCTGCCGATCGCCTGGTAG
---------+----------+------
AGGTGAGCGACGGCTAGCGGACCATC
al  His Ser Leu Pro Ile Ala Trp End ;
``` in combination with the DNA sequence encoding iron sulfur protein FeS-B comprising:

```
                    1370
               ATGACCATGCGG
               -+----------+
               TACTGGTACGCC
               Met Thr Met Arg 1390                1410
GTGAGTGCGGATCGGACGGTCTGCGTCGGT
---------+----------+----------+
CACTCACGCCTAGCCTGCCAGACGCAGCCA
Val Ser Ala Asp Arg Thr Val Cys Val Gly

1430
GCCGGGCTGTGTGCGCTGACGGCGCCGGGC
---------+----------+----------+
CGGCCCGACACACGCGACTGCCGCGGCCCG
Ala Gly Leu Cys Ala Leu Thr Ala Pro Gly 1450                1470
GTCTTCGACCAGGACGACGACGGGATCGTC
---------+----------+----------+
CAGAAGCTGGTCCTGCTGCTGCCCTAGCAG
Val Phe Asp Gln Asp Asp Asp Gly Ile Val

1490
ACGGTGCTGACGGCCGAACCCGCCGCCGAC
---------+----------+----------+
TGCCACGACTGCCGGCTTGGGCGGCGGCTG
Thr Val Leu Thr Ala Gly Pro Ala Ala Asp 1510                1530
GACGACCGGCGCACCGCGCGCGAGGCCGGC
```

```
                                                      -continued
---------+----------+----------+
CTGCTGGCCGCGTGGCGCGCGCTCCGGCCG
Asp Asp Arg Arg Thr Ala Arg Glu Ala Gly 1550
CATCTCTGTCCGTCCGGTGCGGTCCGCGTC
---------+----------+----------+
GTAGAGACAGGCAGGCCACGCCAGGCGCAG
His Leu Cys Pro Ser Gly Ala Val Arg Val 1570
GTCGAGGACACGGAA
---------+-----
CAGCTCCTGTGCCTT
Val Glu Asp Thr Glu ;
```

34. A plant transformed with a plasmid of claim 1.

35. A plant transformed with the DNA sequence of claim 5.

36. A plant transformed with a plasmid of claim 8.

37. A plant transformed with a plasmid of claim 9.

38. Seed and progeny which has inherited said DNA sequence from a plant of claim 32.

39. Seed and progeny which has inherited said DNA sequence from a plant of claim 33.

40. Seed and progeny which has inherited said DNA sequence from a plant of claim 34.

41. Seed and progeny which has inherited said DNA sequence from a plant of claim 36.

42. A tobacco plant transformed with a plasmid of claim 1.

43. A tobacco plant transformed with a plasmid of claim 8.

44. A tomato plant transformed with a plasmid of claim 1.

45. A tomato plant containing a plasmid of claim 8.

46. A corn plant transformed with a plasmid of claim 1.

47. A corn plant transformed with a plasmid of claim 8.

48. A soybean plant transformed with a plasmid of claim 1.

49. A soybean plant transformed with a plasmid of claim 8.

50. A Brassica species transformed with a plasmid of claim 1.

51. A Brassica species transformed with a plasmid of claim 8.

52. A rice plant transformed with a plasmid of claim 1.

53. A rice plant transformed with a plasmid of claim 8.

54. A cotton plant transformed with a plasmid of claim 1.

55. A cotton plant transformed with a plasmid of claim 8.

56. A vegetable plant transformed with a plasmid of claim 1.

57. A vegetable plant transformed with a plasmid of claim 8.

58. A method of transforming a plant to metabolize herbicide compounds comprising introducing into the plant a plasmid of claim 1 and selecting plants capable of metabolizing herbicide compounds.

59. A method of transforming a plant to metabolize herbicide compounds comprising introducing into the plant a plasmid of claim 8 and selecting plants capable of metabolizing herbicide compounds.

60. The method of claim 58 wherein the herbicide is a sulfonylurea.

61. The method of claim 59 wherein the herbicide is a sulfonylurea.

62. A method to reduce herbicide residues in plants, progeny, and seeds comprising transforming the parent plants with the plasmid of claim 1 to produce progeny plants expressing P450SU1 enzyme which metabolizes said herbicide compounds.

63. A method to reduce herbicide residues in plants, progeny and seeds comprising transforming the parent plants with the plasmid of claim 8 to produce progeny plants expressing P450SU1 enzyme which metabolizes said herbicide compounds.

64. The method of claim 62 wherein the herbicide is a sulfonylurea.

65. The method of claim 63 wherein the herbicide is a sulfonylurea.

66. A transformed plant containing a DNA sequence selected from the group consisting of
A) the DNA sequence encoding cytochrome P450 enzyme P450SU1 comprising:

```
130                          150
ATGACCGATACCGCCACGACGCC
--+----------+-----------+
TACTGGCTATGGCGGTGCTGCGG
Met Thr Asp Thr Ala Thr Thr Pr

170
CCAGACCACGGACGCACCCGCCTTCCCGAG
---------+-----------+----------+
GGTCTGGTGCCTGCGTGGGCGGAAGGGCTC
o Gln Thr Thr Asp Ala Pro Ala Phe Pro Se 190                    210
CAACCGGAGCTGTCCCTACCAGTTACCGGA
---------+-----------+----------+
GTTCGCCTCGACAGGGATGGTCAATGGCCT
r Asn Arg Ser Cys Pro Tyr Gln Leu Pro As

230
CGGCTACGCCCAGCTCCGGGACACCCCGG
----------+-----------+----------+
GCCGATGCGGGTCGAGGCCCTGTGGGGCC
p Gly Tyr Ala Gln Leu Arg Asp Thr Pro Gl 250                    270
CCCCCTGCACCGGGTGACGCTCTACGACGG
----------+-----------+----------+
GGGGGACGTGGCCCACTGCGAGATGCTGCC
y Pro Leu His Arg Val Thr Leu Tyr Asp Gl

290
CCGTCAGGCGTGGGTGGTGACCAAGCACGA
----------+-----------+----------+
GGCAGTCCGCACCCACCACTGGTTCGTGCT
y Arg Gln Ala Trp Val Val Thr Lys His Gl 310                    330
GGCCGCGCGCAAACTGCTCGGCGACCCCCG
----------+-----------+----------+
CCGGCGCGCGTTTGACGAGCCGCTGGGGGC
u Ala Ala Arg Lys Leu Leu Gly Asp Pro Ar

350
GCTGTCCTCCAACCGGACGGACGACAACTT
----------+-----------+----------+
CGACAGGAGGTTGGCCTGCCTGCTGTTGAA
g Leu Ser Ser Asn Arg Thr Asp Asp Asn Ph 370                    390
CCCCGCCACGTCACCGCGCTTCGAGGCCGT
----------+-----------+----------+
GGGGCGGTGCAGTGGCGCGAAGCTCCGGCA
e Pro Ala Thr Ser Pro Arg Phe Glu Ala Va
```

```
            410
CCGGGAGAGCCCGCAGGCGTTCATCGGCCT
----------+-----------+----------+
GGCCCTCTCGGGCGTCCGCAAGTAGCCGGA
l Arg Glu Ser Pro Gln Ala Phe Ile Gly Le 430                    450
GGACCCGCCCGAGCACGGCACCCGGCGGCG
----------+-----------+----------+
CCTGGGCGGGCTCGTGCCGTGGGCCGCCGC
u Asp Pro Pro Glu His Gly Thr Arg Arg Ar

470
GATGACGATCAGCGAGTTCACCGTCAAGCG
----------+-----------+----------+
CTACTGCTAGTCGCTCAAGTGGCAGTTCGC
g Met Thr Ile Ser Glu Phe Thr Val Lys Ar 490                    510
GATCAAGGGCATGCGCCCCGAGGTCGAGGA
----------+-----------+----------+
CTAGTTCCCGTACGCGGGGCTCCAGCTCCT
g Ile Lys Gly Met Arg Pro Glu Val Glu Gl

530
GGTGGTGCACGGCTTCCTCGACGAGATGCT
----------+-----------+----------+
CCACCACGTGCCGAAGGAGCTGCTCTACGA
u Val Val His Gly Phe Leu Asp Glu Met Le 550                    570
GGCCGCCGGCCCGACCGCCGACCTGGTCAG
----------+-----------+----------+
CCGGCGGCCGGGCTGGCGGCTGGACCAGTC
u Ala Ala Gly Pro Thr Ala Asp Leu Val Se

590
TCAGTTCGCGCTGCCGGTGCCCTCCATGGT
----------+-----------+----------+
AGTCAAGCGCGACGGCCACGGGAGGTACCA
r Gln Phe Ala Leu Pro Val Pro Ser Met Va 610                    630
GATCTGCCGACTCCTCGGCGTGCCCTACGC
----------+-----------+----------+
CTAGACGGCTGAGGAGCCGCACGGGATGCG
l Ile Cys Arg Leu Leu Gly Val Pro Tyr Al

650
CGACCACGAGTTCTTCCAGGACGCGAGCAA
----------+-----------+----------+
GCTGGTGCTCAAGAAGGTCCTGCGCTCGTT
a Asp His Glu Phe Phe Gln Asp Ala Ser Ly 670                    690
GCGGCTGGTGCAGTCCACGGACGCGCAGAG
----------+-----------+----------+
CGCCGACCACGTCAGGTGCCTGCGCGTCTC
s Arg Leu Val Gln Ser Thr Asp Ala Gln Se

710
CGCGCTCACCGCGCGGAACGACCTCGCGGG
----------+-----------+----------+
GCGCGAGTGGCGCGCCTTGCTGGAGCGCCC
r Ala Leu Thr Ala Arg Asn Asp Leu Ala Gl 730                    750
TTACCTGGACGGCCTCATCACCCAGTTCCA
----------+-----------+----------+
AATGGACCTGCCGGAGTAGTGGGTCAAGGT
y Tyr Leu Asp Gly Leu Ile Thr Gln Phe Gl

770
GACCGAACCGGGCGCGGGCCTGGTGGGCGC
----------+-----------+----------+
CTGGCTTGGCCCGCGCCCGGACCACCCGCG
n Thr Gln Pro Gly Ala Gly Leu Val Gly Al
       790                    810
TCTGGTCGCCGACCAGCTGGCCAACGGCGA
----------+-----------+----------+
AGACCAGCGGCTGGTCGACCGGTTGCCGCT
a Leu Val Ala Asp Gln Leu Ala Asn Gly Gl
```

```
                        830
GATCGACCGTGAGGAACTGATCTCCACCGC
---------+---------+---------+
CTAGCTGGCACTCCTTGACTAGAGGTGGCG
u  Ile Asp Arg Glu Glu Leu Ile Ser Thr Al 850                 870
GATGCTGCTCCTCATCGCCGGCCACGAGAC
---------+---------+---------+
CTACGACGAGGAGTAGCGGCCGGTGCTCTG
a  Met Leu Leu Leu Ile Ala Gly His Glu Th

890
CACGGCCTCGATGACCTCCCTCAGCGTGAT
---------+---------+---------+
GTGCCGGAGCTACTGGAGGGAGTCGCACTA
r  Thr Ala Ser Met Thr Ser Leu Ser Val Il 910                 930
CACCCTGCTGGACCACCCCGAGCAGTACGC
---------+---------+---------+
GTGGGACGACCTGGTGGGGCTCGTCATGCG
e  Thr Leu Leu Asp His Pro Glu Gln Tyr Al

950
CGCCCTGCGCGCCGACCGCAGCCTCGTGCC
---------+---------+---------+
GCGGGACGCGCGGCTGGCGTCGGAGCACGG
a  Ala Leu Arg Ala Asp Arg Ser Leu Val Pr 970                 990
CGGCGCGGTGGAGGAACTGCTCCGCTACCT
---------+---------+---------+
GCCGCGCCACCTCCTTGACGAGGCGATGGA
o  Gly Ala Val Glu Glu Leu Leu Arg Tyr Le

1010
CGCCATCGCCGACATCGCGGGCGGCCGCGT
---------+---------+---------+
GCGGTAGCGGCTGTAGCGCCCGCCGGCGCA
u  Ala Ile Ala Asp Ile Ala Gly Gly Arg Va 1030                1050
CGCCACGGCGGACATCGAGGTCGAGGGGCA
---------+---------+---------+
GCGGTGCCGCCTGTAGCTCCAGCTCCCCGT
l  Ala Thr Ala Asp Ile Glu Val Glu Gly Hi

1070
CCTCATCCGGGCCGGCGAGGGCGTGATCGT
---------+---------+---------+
GGAGTAGGCCCGGCCGCTCCCGCACTAGCA
s  Leu Ile Arg Ala Gly Glu Gly Val Ile Va 1090                1110
CGTCAACTCGATAGCCAACCGGGACGGCAC
---------+---------+---------+
GCAGTTGAGCTATCGGTTGGCCCTGCCGTG
l  Val Asn Ser Ile Ala Asn Arg Asp Gly Th

1130
GGTGTACGAGGACCCGGACGCCCTCGACAT
---------+---------+---------+
CCACATGCTCCTGGGCCTGCGGGAGCTGTA
r  Val Tyr Glu Asp Pro Asp Ala Leu Asp Il 1150                1170
CCACCGCTCCGCGCGCCACCACCTCGCCTT
---------+---------+---------+
GGTGGCGAGGCGCGCGGTGGTGGAGCGGAA
e  His Arg Ser Ala Arg His His Leu Ala Ph

1190
CGGCTTCGGCGTGCACCAGTGCCTGGGCCA
---------+---------+---------+
GCCGAAGCCGCACGTGGTCACGGACCCGGT
e  Gly Phe Gly Val His Gln Cys Leu Gly Gl 1210                1230
GAACCTCGCCCGGCTGGAGCTGGAGGTCAT
---------+---------+---------+
```

```
CTTGGAGCGGGCCGACCTCGACCTCCAGTA
n  Asn Leu Ala Arg Leu Glu Leu Glu Val Il

1250
CCTCAACGCCCTCATGGACCGCGTCCCGAC
---------+---------+---------+
GGAGTTGCGGGAGTACCTGGCGCAGGGCTG
e  Leu Asn Ala Leu Met Asp Arg Val Pro Th 1270                1290
GCTGCGACTGGCCGTCCCCGTCGAGCAGTT
---------+---------+---------+
CGACGCTGACCGGCAGGGGCAGCTCGTCAA
r  Leu Arg Leu Ala Val Pro Val Glu Gln Le

1310
GGTGCTGCGGCCGGGTACGACGATCCAGGG
---------+---------+---------+
CCACGACGCCGGCCCATGCTGCTAGGTCCC
u  Val Leu Arg Pro Gly Thr Thr Ile Gln Gl 1330                1350
CGTCAACGAACTCCCGGTCACCTGGTGA
---------+---------+---------
GCAGTTGCTTGAGGGCCAGTGGACCACT
y  Val Asn Glu Leu Pro Val Thr Trp End;
```

B) the DNA sequence encoding cytochrome P450 enzyme P450SU2 comprising:

```
                        210
             ATGACGACCGCAGAAC
             -----+---------+
             TACTGCTGGCGTCTTG
             Met Thr Thr Ala Glu A

230
GCACCGCTCCCCCCGACGCCCTCACCGTCC
---------+---------+---------+
CGTGGCGAGGGGGGCTGCGGGAGTGGCAGG
rg Thr Ala Pro Pro Asp Ala Leu Thr Val P 250                 270
CGGCCAGCCGCGCCCCCGGCTGCCCCTTCG
---------+---------+---------+
GCCGGTCGGCGCGGGGGCCGACGGGGAAGC
ro Ala Ser Arg Ala Pro Gly Cys Pro Phe A

290
ACCCCGCGCCCGACGTCACCGAGGCGGCCC
---------+---------+---------+
TGGGGCGCGGGCTGCAGTGGCTCCGCCGGG
sp Pro Ala Pro Asp Val Thr Glu Ala Ala A 310                 330
GCACCGAACCGGTCACCCGGGCCACCCTCT
---------+---------+---------+
CGTGGCTTGGCCAGTGGGCCCGGTGGGAGA
rg Thr Glu Pro Val Thr Arg Ala Thr Leu T

350
GGGACGGCTCCTCCTGCTGGCTGGTGACGC
---------+---------+---------+
CCCTGCCGAGGAGGACGACCGACCACTGCG
rp Asp Gly Ser Ser Cys Trp Leu Val Thr A 370                 390
GCCATCAGGACGTCCGCGCGGTCCTCGGCG
---------+---------+---------+
CGGTAGTCCTGCAGGCGCGCCAGGAGCCGC
rg His Gln Asp Val Arg Ala Val Leu Gly A

410
ACCCGCGCTTCAGCGCCGACGCCCACCGCA
---------+---------+---------+
TGGGCGCGAAGTCGCGGCTGCGGGTGGCGT
sp Pro Arg Phe Ser Ala Asp Ala His Arg T 430                 450
CCGGCTTCCCCCTTCCTGACCGCCGGCGGCC
---------+---------+---------+
```

-continued

```
                GGCCGAAGGGGAAGGACTGGCGGCCGCCGG
              hr Gly Phe Pro Phe Leu Thr Ala Gly Gly A

470
           GCGAGATCATCGGCACCAACCCGACCTTCC
         ---------+----------+----------+
           CGCTCTAGTAGCCGTGGTTGGGCTGGAAGG
           rg Glu Ile Ile Gly Thr Asn Pro Thr Phe L 490                  510
         TGCGCATGGACGACCCGGAGCACGCCCGAC
         ---------+----------+----------+
         ACGCGTACCTGCTGGGCCTCGTGCGGGCTG
         eu Arg Met Asp Asp Pro Glu His Ala Arg L

530
              TGCGCCGGATGCTCACCGCCGACTTCATCG
            ---------+----------+----------+
              ACGCGGCCTACGAGTGGCGGCTGAAGTAGC
              eu Arg Arg Met Leu Thr Ala Asp Phe Ile V 550                  570
         TCAAGAAGGTCGAGGCGATGCGCCCCGAGG
         ---------+----------+----------+
         AGTTCTTCCAGCTCCGCTACGCGGGGCTCC
         al Lys Lys Val Glu Ala Met Arg Pro Glu V

590
              TGCAGCGCCTCGCCGACGACCTGGTCGACC
            ---------+----------+----------+
              ACGTCGCGGAGCGGCTGCTGGACCAGCTGG
              al Gln Arg Leu Ala Asp Asp Leu Val Asp A 610                  630
         GGATGACCACCGGACGCACCTCCGCCGACC
         ---------+----------+----------+
         CCTACTGGTGGCCTGCGTGGAGGCGGCTGG
         rg Met Thr Thr Gly Arg Thr Ser Ala Asp L

650
              TGGTCACCGAGTTCGCGCTGCCGCTGCCGT
            ---------+----------+----------+
              ACCAGTGGCTCAAGCGCGACGGCGACGGCA
              eu Val Thr Glu Phe Ala Leu Pro Leu Pro S 670                  690
         CCCTGGTGATCTGCCTGCTGCTCGGCGTCC
         ---------+----------+----------+
         GGGACCACTAGACGGACGACGAGCCGCAGG
         er Leu Val Ile Cys Leu Leu Leu Gly Val P

710
              CCTACGAGGACCACGCGTTCTTCCAGGAGC
            ---------+----------+----------+
              GGATGCTCCTGGTGCGCAAGAAGGTCCTCG
              ro Tyr Glu Asp His Ala Phe Phe Gln Glu A 730                  750
         GCAGCCGGGTCCTGCTCACCCTGCGGTCCA
         ---------+----------+----------+
         CGTCGGCCCAGGACGAGTGGGACGCCAGGT
         rg Ser Arg Val Leu Leu Thr Leu Arg Ser T

770
              CTCCCGAGGAAGTCCGGGCCGCCCAGGACG
            ---------+----------+----------+
              GAGGGCTCCTTCAGGCCCGGCGGGTCCTGC
              hr Pro Glu Glu Val Arg Ala Ala Gln Asp G 790                  810
         AGTTGCTGGAGTACCTCGCCCGGCTCGCCC
         ---------+----------+----------+
         TCAACGACCTCATGGAGCGGGCCGAGCGGG
         lu Leu Leu Glu Tyr Leu Ala Arg Leu Ala A

830
              GGACCAAGCGGGAGCGGCCGGACGACGCCA
            ---------+----------+----------+
              CCTGGTTCGCCCTCGCCGGCCTGCTGCGGT
              rg Thr Lys Arg Glu Arg Pro Asp Asp Ala I
```

```
                850                  870
         TCATCAGCCGCCTGGTCGCCCGCGGCGAGC
         ---------+----------+----------+
         AGTAGTCGGCGGACCAGCGGGCGCCGCTCG
         le Ile Ser Arg Leu Val Ala Arg Gly Glu L

890
              TCGACGACACCCAGATCGCCACCATGGGAC
            ---------+----------+----------+
              AGCTGCTGTGGGTCTAGCGGTGGTACCCTG
              eu Asp Asp Thr Gln Ile Ala Thr Met Gly A 910                  930
         GCCTGTTGCTGGTCGCCGGCCACGAGACGA
         ---------+----------+----------+
         CGGACAACGACCAGCGGCCGGTGCTCTGCT
         rg Leu Leu Leu Val Ala Gly His Glu Thr T

950
              CCGCCAACATGACCGCGCTCTCCACCCTCG
            ---------+----------+----------+
              GGCGGTTGTACTGGCGCGAGAGGTGGGAGC
              hr Ala Asn Met Thr Ala Leu Ser Thr Leu V 970                  990
         TGCTGCTGCGCAACCCCGACCAACTCGCCC
         ---------+----------+----------+
         ACGACGACGCGTTGGGGCTGGTTGAGCGGG
         al Leu Leu Arg Asn Pro Asp Gln Leu Ala A

1010
              GGCTGCGCGCCGAACCCGCGCTCGTCAAGG
            ---------+----------+----------+
              CCGACGCGCGGCTTGGGCGCGAGCAGTTCC
              rg Leu Arg Ala Glu Pro Ala Leu Val Lys G 1030                 1050
         GCGCCGTCGAGGAGCTGCTGCGCTACCTGA
         ---------+----------+----------+
         CGCGGCAGCTCCTCGACGACGCGATGGACT
         ly Ala Val Glu Glu Leu Leu Arg Tyr Leu T

1070
              CGATCGTGCACAACGGCGTTCCCCGGATCG
            ---------+----------+----------+
              GCTAGCACGTGTTGCCGCAAGGGGCCTAGC
              hr Ile Val His Asn Gly Val Pro Arg Ile A 1090                 1110
         CCACCGAGGACGTGCTCATCGGCGGCCGCA
         ---------+----------+----------+
         GGTGGCTCCTGCACGAGTAGCCGCCGGCGT
         la Thr Glu Asp Val Leu Ile Gly Gly Arg T

1130
              CCATCGCCGCCGGCGAGGGCGTCCTGTGCA
            ---------+----------+----------+
              GGTAGCGGCGGCCGCTCCCGCAGGACACGT
              hr Ile Ala Ala Gly Glu Gly Val Leu Cys M 1150                 1170
         TGATCAGCTCCGCCAACCGGGACGCCGAGG
         ---------+----------+----------+
         ACTAGTCGAGGCGGTTGGCCCTGCGGCTCC
         et Ile Ser Ser Ala Asn Arg Asp Ala Glu V

1190
              TGTTCCCCGGCGGCGACGACCTCGACGTGG
            ---------+----------+----------+
              ACAAGGGGCCGCCGCTGCTGGAGCTGCACC
              al Phe Pro Gly Gly Asp Asp Leu Asp Val A 1210                 1230
         CCCGCGACGCCCGCCGCCACGTGGCCTTCG
         ---------+----------+----------+
         GGGCGCTGCGGGCGGCGGTGCACCGGAAGC
         la Arg Asp Ala Arg Arg His Val Ala Phe G

1250
              GCTTCGGCGTCCACCAGTGCCTGGGACAGC
            ---------+----------+----------+
              CGAAGCCGCAGGTGGTCACGGACCCTGTCG
              ly Phe Gly Val His Gln Cys Leu Gly Gln P
```

```
              1270                     1290
    CGTTGGCCAGGGTGGAGCTCCAGATCGCCA
    ----------+----------+----------+
    GCAACCGGTCCCACCTCGAGGTCTAGCGGT
ro  Leu Ala Arg Val Glu Leu Gln Ile Ala I

1310
    TCGAAACGCTGCTGCGCCGCCTGCCGGACC
    ----------+----------+----------+
    AGCTTTGCGACGACGCGGCGGACGGCCTGG
le  Glu Thr Leu Leu Arg Arg Leu Pro Asp L 1330                     1350
    TGCGGCTGGCCGTGCCCCACGAGGAGATCC
    ----------+----------+----------+
    ACGCCGACCGGCACGGGGTGCTCCTCTAGG
eu  Arg Leu Ala Val Pro His Glu Glu Ile  P

1370
    CGTTCCGCGGCGACATGGCGATCTACGGGG
    ----------+----------+----------+
    GCAAGGCGCCGCTGTACCGCTAGATGCCCC
ro  Phe Arg Gly Asp Met Ala Ile Tyr Gly V

1390
    TCCACTCGCTGCCGATCGCCTGGTAG
    ----------+----------+------
    AGGTGAGCGACGGCTAGCGGACCATC
al  His Ser Leu Pro Ile Ala Trp End ;
```

C) either of the DNA sequence encoding cytochrome P450 enzyme P450SU1 of A) or the DNA sequence encoding cytochrome P450 enzyme P450SU2 of B) in combination with the DNA sequence encoding iron sulfur protein FeS-B comprising:

```
              1370
              ATGACCATGCGG
              -+----------+
              TACTGGTACGCC
              Met Thr Met Arg 1390                1410
    GTGAGTGCGGATCGGACGGTCTGCGTCGGT
    ----------+----------+----------+
    CACTCACGCCTAGCCTGCCAGACGCAGCCA
    Val Ser Ala Asp Arg Thr Val Cys Val Gly

1430
    GCCGGGCTGTGTGCGCTGACGGCGCCGGGC
    ----------+----------+----------+
    CGGCCCGACACACGCGACTGCCGCGGCCCG
    Ala Gly Leu Cys Ala Leu Thr Ala Pro Gly 1450                1470
    GTCTTCGACCAGGACGACGACGGGATCGTC
    ----------+----------+----------+
    CAGAAGCTGGTCCTGCTGCTGCCCTAGCAG
    Val Phe Asp Gln Asp Asp Asp Gly Ile Val

1490
    ACGGTGCTGACGGCCGAACCCGCCGCCGAC
    ----------+----------+----------+
    TGCCACGACTGCCGGCTTGGGCGGCGGCTG
    Thr Val Leu Thr Ala Gly Pro Ala Ala Asp
```

```
              1510                1530
    GACGACCGGCGCACCGCGCGCGAGGCCGGC
    ----------+----------+----------+
    CTGCTGGCCGCGTGGCGCGCGCTCCGGCCG
    Asp Asp Arg Arg Thr Ala Arg Glu Ala Gly

1550
    CATCTCTGTCCGTCCGGTGCGGTCCGCGTC
    ----------+----------+----------+
    GTAGAGACAGGCAGGCCACGCCAGGCGCAG
    His Leu Cys Pro Ser Gly Ala Val Arg Val

1570
    GTCGAGGACACGGAA
    ----------+-----
    CAGCTCCTGTGCCTT
    Val Glu Asp Thr Glu ;
``` or D) either of the DNA sequence encoding cytochrome P450 enzyme P450SU1 of A) or the DNA sequence encoding cytochrome P450 enzyme P450SU2 of B) in combination with the DNA sequence encoding iron sulfur protein FeS-A comprising:

```
                       1470
    ATGCGCATCCACGTCGACCAGGACAAGTGC
    --------+----------+----------+-
    TACGCGTAGGTGCAGCTGGTCCTGTTCACG
    Met Arg Ile His Val Asp Gln Asp Lys Cys

1490
              TGCGGCGCCGGCAGTTGCG
              ---------+----------+
              ACGCCGCGGCCGTCAACGC
              Cys Gly Ala Gly Ser Cys V 1510                1530
    TCCTCGCCGCGCCCGACGTCTTCGACCAGC
    ----------+----------+----------+
    AGGAGCGGCGCGGGCTGCAGAAGCTGGTCG
    al Leu Ala Ala Pro Asp Val Phe Asp Gln A

1550
    GGGAGGAGGACGGCATCGTGGTCCTCCTCG
    ----------+----------+----------+
    CCCTCCTCCTGCCGTAGCACCAGGAGGAGC
    rg Glu Glu Asp Gly Ile Val Val Leu Leu A 1570                1590
    ACACCGCGCCGCCCGCCGCGCTGCACGACG
    ----------+----------+----------+
    TGTGGCGCGGCGGGCGGCGCGACGTGCTGC
    sp Thr Ala Pro Pro Ala Ala Leu His Asp A

1610
    CGGTCCGTGAGGCGGCGACCATCTGCCCCG
    ----------+----------+----------+
    GCCAGGCACTCCGCCGCTGGTAGACGGGGC
    la Val Arg Glu Ala Ala Thr Ile Cys Pro A

1630
    CCGCCGCGATCACGGTGACCGAC
    ----------+----------+---
    GGCGGCGCTAGTGCCACTGGCTG
    la Ala Ala Ile Thr Val Thr Asp ;
``` which can metabolize herbicides.

* * * * *